(12) United States Patent
Young et al.

(10) Patent No.: US 6,380,249 B1
(45) Date of Patent: *Apr. 30, 2002

(54) HIV INTEGRASE INHIBITORS

(75) Inventors: Steven D. Young, Lansdale; Melissa Egbertson, Ambler; Linda S. Payne, Lansdale; John S. Wai, Harleysville; Thorsten E. Fisher, Hatfield; James P. Guare, Jr., Quakertown; Mark W. Embrey, North Wales; Lekhanh Tran, Norristown; Linghang Zhuang, Conshohocken; Joseph P. Vacca, Telford; H. Marie Langford, Lansdale; Jeffrey Melamed, Warminster, all of PA (US); Juan C. Jaen, Burlingame, CA (US); David L. Clark, Albany, CA (US); Julio C. Medina, Belmont, CA (US)

(73) Assignees: Merck & Co., Inc., Rahway, NJ (US); Tularik Inc., S. San Francisco, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 1 day.

(21) Appl. No.: 09/323,417

(22) Filed: Jun. 1, 1999

Related U.S. Application Data

(60) Provisional application No. 60/087,820, filed on Jun. 3, 1998.

(51) Int. Cl.[7] .................... A61K 31/215; A61K 31/24; C07C 229/00; C07C 321/00; C07C 323/00

(52) U.S. Cl. ................... 514/530; 514/530; 514/531; 514/538; 514/539; 514/541; 560/19; 560/48; 560/51; 560/53; 562/426; 562/433; 562/441; 562/451; 562/452; 562/457; 562/459; 562/462; 562/463

(58) Field of Search .................. 514/238.8, 237.2, 514/255, 256, 247, 317, 366, 374, 381, 383, 406, 415, 438, 450, 452, 467, 530, 531, 538, 539, 541; 544/105, 1 H, 224, 318, 336, 397; 546/221, 301, 335, 342; 548/233, 253, 255, 268.6, 376.1, 510; 549/79, 10, 15, 436, 438; 560/19, 48, 51, 53; 562/433, 426, 441, 451, 452, 457, 459, 463, 462

(56) References Cited

U.S. PATENT DOCUMENTS

| | | | |
|---|---|---|---|
| 3,772,336 A | | 11/1973 | Wright et al. .................. 549/57 |
| 3,899,508 A | * | 8/1975 | Wikel .......................... 260/310 |
| 4,336,397 A | | 6/1982 | Cragoe, Jr. et al. ............ 560/51 |
| 4,377,258 A | | 3/1983 | Kipp, Jr. ...................... 241/27 |
| 4,386,092 A | | 5/1983 | Oe et al. ...................... 424/256 |
| 4,423,063 A | * | 12/1983 | Rooney et al. ............... 424/278 |
| 5,134,142 A | | 7/1992 | Matsuo et al. ................ 514/255 |
| 5,516,797 A | | 5/1996 | Armistead et al. ........... 514/548 |
| 5,618,830 A | | 4/1997 | Selnick et al. ............... 514/358 |

FOREIGN PATENT DOCUMENTS

| | | | |
|---|---|---|---|
| EP | 418 845 | | 3/1991 |
| JP | 61-134346 | * | 3/1984 |
| WO | WO 95/13262 | * | 5/1995 |
| WO | WO 97/17316 | | 5/1997 |
| WO | WO 97/17317 | | 5/1997 |
| WO | WO 99/30699 | | 6/1999 |
| WO | WO 00/06529 | | 2/2000 |
| WO | WO 00/39086 | | 7/2000 |

OTHER PUBLICATIONS

Andreichekov et al, Synthesis of 4–Aroyltetrahydro–1, 5–diphenyl–2,3–pyrrolediones and Their Reaction with Amines and Hydrazine. Chem Abstracts 107:39766, pp. 697–698, 1986.*

Murray et al., A Simple Regioselective Synthesis of Ethyl 1,5–Diarylpyrazole–3–carboxylates, J. Heterocyclic Chem., pp. 1389–1392, 1989.*

Oka et al., Studies on the Syntheses of N–Heterocyclic Compounds. XXVI. Syntheses of Pyrido[3,4–d]pyridazine Derivatives., Chem. Pharm. Bull. 23(10), pp. 2306–2317, 1975.*

Oka et al., Studies on the Sytheses of N–Heterocyclic Compounds. XXV. Syntheses of Pyrido[3,4–d]pyridazine Derivatives., Chem. Pharm. Bull. 23(10), pp. 2239–2250, 1975.*

Witiak et al., Synthesis of Ethyl 6–Sustituted–Chroman and–Chromone–2–carboxylates. A Comparative Structure–Activity Study Employing the 6–Phenyl and Phenoxy Analogs in the Triton Hyperlipidemic Rat Model., J. Med. Chem., 18(9), pp. 934–942, 1975.*

Cooke et al., Colouring Matters of Australian Plants. XXIII A New Synthesis of Arylphenalenones and Napthoxanthenones, Aust. J. Chem. 33, pp. 2317–2324, 1980.*

Seki et al., 3–Phenacylidene–3,4–dihydro–1H–pyrido[2, 3–b]pyrazin–2–ones and 2–Phenacylidene–1, 2–dihydro–4H–pyrido[2,3–b]pyrazin–3–ones, J. Heterocyclic Chem., 32, pp. 347–348, 1995.*

(List continued on next page.)

*Primary Examiner*—Mukund J. Shah
*Assistant Examiner*—Deepak Rao
(74) *Attorney, Agent, or Firm*—Kenneth R. Walton; Melvin Winokur; Catherine D. Fitch

(57) ABSTRACT

Certain six-membered aromatic and heteroaromatic-dioxobutyric acid derivatives are described as inhibitors of HIV integrase and inhibitors of HIV replication. These compounds are useful in the prevention or treatment of infection by HIV and the treatment of AIDS, either as compounds, pharmaceutically acceptable salts, pharmaceutical composition ingredients, whether or not in combination with other antivirals, immunomodulators, antibiotics or vaccines. Methods of treating AIDS and methods of preventing or treating infection by HIV are also described.

21 Claims, No Drawings-

OTHER PUBLICATIONS

Sweeny et al., Synthesis of Anthocyanidins–III Total Synthesis of Apigeninidin and Luteolinidin Chlorides, Tetrahedron, 37, pp. 1481–1483, 1981.*

Schummer et al., Polyfunctional (R)–2–Hydroxycarboxylic Acids by Reduction of 2–Oxo acis with Hydrogen Gas or Formate and Resting Cells of *Proteus vulgaris*, Tetrahedron, 47 (43), pp. 9019–9034, 1991.*

Gomber et al. Computer–assisted structure –activity relationship analysis: pattern recognition studies on hypolipidemic arylpropionic acid derivatives(Quant. Struct. Act. Relat., 7(4), pp 225–234), 1988.*

Williams et al Inhibitors of glycolic acid axidase. 4–Substituted–2,4–dioxobutanoic acid derivatives. (J. Med. Chem., 26(8), pp 1196–1200), 1983.*

Kawamatsu et al Studies on antihyperlipidemic agents. I Synthesis and hypolidemic activities of phenoxy pheny acid derivatives. (Arzneim Forsch.., 30(3), pp. 454–459), 1980.*

Zhao, et al., Hydrazide–Containing Inhibitors of HIV–1 Integrase, J. Med. Chem., (1997), vol. 40, No. 8, pp. 937–941.

Zhao, et al., Arylamide Inhibitors of HIV–1 Integrase, J. Med. Chem., (1997), vol. 40, No. 8 pp. 1186–1194.

Williams, et al., Inhibitors of Glycolic Acid Oxidase. 4–Substituted 2,4–Dioxobutanoic Acid Derivatives, J. Med. Chem., (1983), vol. 26, pp. 1196–1200.

Tomassini, et al., Inhibition of Cap (m7 GpppXm)–Dependent Endonuclease of Influenza Virus by 4–Substituted 2,4–Dioxobutanoic Acid Compounds, Antimicrobial Agents & Chemotherapy, (1994), vol. 38, No. 12, pp. 2827–2837.

Ratner, et al., Complete nucleotide sequence of the AIDS virus, HTLV–III, Nature, (1985) vol. 313, pp. 277–284.

Toh, et al., Close structural resemblance between putative polymerase of a Drosophila transposable genetic element 17.6 and pol gene product of Moloney murine leukaemia vuris, The EMBO Journal, (1985), vol. 4, No. 5, pp. 1267–1272.

Power, et al., Nucleotide sequence of SRV–1, a Type D Simian Acquired Immune Deficiency Syndrome Retrovirus, Science, (1986) , vol. 231, pp. 1567–1572.

Pearl, et al., A structural model for the retroviral proteases, Nature, (1987), vol. 329, pp. 351–354.

LaFemina, et al., Inhibition of Human Immunodeficiency Virus Integrase by Bis–Catechols, Antimicrobial Agents & Chemotherapy, (1995), vol. 39, No. 2, pp. 320–324.

Giordani, et al., 4–Phenyl–4–oxo–butanoic Acid Derivatives Inhibitors of Kynurenine 3–Hydroxylase, Bioorganic & Medicinal Chemistry Letters , (1998) , vol. 8, pp. 2907–2912.

Hastings, et al., Anti–Influenza Virus Activities of 4–Substituted 2,4–Dioxobutanoic Acid Inhibitors, Antimicrobial Agents and Chemotherapy, (May 1996) vol. 40, No. 5, pp. 1304–1307.

Howarth et al., J.C.S. Perkins Trans, 1, Pyrolles and related compounds . . . , (1974), vol. 4, pp. 490–501.

Tanaka et al., Bull. Chem. Soc. JPN., Studies on Aromatic Sesquiterpenes . . . (1989), vol. 62, No. 6, pp. 2102–2104.

Freri, Variations in the Claisen condensation reaction, 1938, Chemical Abstracts No. 33:2488.

Lin et al., Substituted pyrazolyl compounds and methods employing these compounds, 1996, Chemical Abstracts No. 124: 202242 (HCAPLUS).

R.M. Saleh, Use of ethyl 2–thenoylpyruvate in the synthesis of heterocycles and their derivatives, 1991, Chemical Abstracts No. 114: No. 228839 (HCAPLUS).

Yanborisov, et al., Synthesis and pharmacological activity of heteroylpyruvic acids and their derivatives, 1998, Chemical Abstracts No. 130:153601 (HCAPLUS).

Burch, et al., "Acylpyruvates as potential antifungal agents", 1972, Chemical Abstracts No. 77:14833 (HCAPLUS).

Munakata, et al., "Pyrazole derivatives", 1980, Chemical Abstracts No. 93:550250 (HCAPLUS).

Derwent Abstract No. 1999–580735/49, "New indole derivatives are integrase inhibitors useful as antiviral and anti–HIV agents", abstract of WO 99/50245 (Shionogi & Co., Ltd.).

Derwent Abstract No. 2000–465713, "New and known di–heterocyclyl hydroxypropenone derivatives are integrase inhibitors for treating retroviral infections, including HIV and AIDS", abstract of WO 00/39086 (Shionogi & Co., Ltd.).

Y. Goldgur et al., "Structure of the HIV–1 integrase catalytic domain complexed with an inhibitor: A platform for antiviral drug design", Proc. Nat'l Acad. Science USA, vol. 96, No. 23, pp. 13040–13043 ( Nov. 9, 1999).

* cited by examiner

HIV INTEGRASE INHIBITORS

CROSS-REFERENCE TO RELATED APPLICATIONS

The present application claims priority to U.S. provisional application Ser. No. 60/087,820, filed Jun. 3, 1998.

BACKGROUND OF THE INVENTION

A retrovirus designated human immunodeficiency virus (HIV) is the etiological agent of the complex disease that includes progressive destruction of the immune system (acquired immune deficiency syndrome; AIDS) and degeneration of the central and peripheral nervous system. This virus was previously known as LAV, HTLV-III, or ARV. A common feature of retrovirus replication is the insertion by virally-encoded integrase of proviral DNA into the host cell genome, a required step in HIV replication in human T-lymphoid and monocytoid cells. Integration is believed to be mediated by integrase in three steps: assembly of a stable nucleoprotein complex with viral DNA sequences; cleavage of two nucleotides from the 3' termini of the linear proviral DNA; covalent joining of the recessed 3' OH termini of the proviral DNA at a staggered cut made at the host target site. The fourth step in the process, repair synthesis of the resultant gap, may be accomplished by cellular enzymes.

Nucleotide sequencing of HIV shows the presence of a pol gene in one open reading frame [Ratner, L. et al., Nature, 313, 277 (1985)]. Amino acid sequence homology provides evidence that the pol sequence encodes reverse transcriptase, integrase and an HIV protease [Toh, H. et al., EMBO J. 4, 1267 (1985); Power, M. D. et al., Science, 231, 1567 (1986); Pearl, L. H. et al., Nature, 329, 351 (1987)]. All three enzymes have been shown to be essential for the replication of HIV.

It is known that some antiviral compounds which act as inhibitors of HIV replication are effective agents in the treatment of AIDS and similar diseases, e.g., azidothymidine or AZT. Applicants demonstrate that the compounds of this invention are inhibitors of HIV integrase and inhibitors of HIV replication. The applicants additionally demonstrate that inhibition of integrase in vitro and HIV replication in cells is a direct result of inhibiting the strand transfer reaction catalyzed by the recombinant integrase in vitro and integrase as a component of the preintegration complex in HIV infected cells. The particular advantage of the present invention is highly specific inhibition of HIV integrase and HIV replication. The compounds of the present invention inhibit integrases of closely related lentiviruses such as HIV 2 and SIV, but not integrases from more distantly related retroviruses, for example RSV. These compounds do not inhibit binding or catalysis of other nucleic acid binding proteins, including enzymatic reactions such as those catalyzed by HIV reverse transcriptase, HIV Rnase H, Influenza transcriptase, Hepatitis C polymerase, Yeast DNA polymerase, DNase I, Eco RI endonuclease, or mammalian polymerase II.

Zhao et al., (J. Med Chem. vol. 40, pp. 937–941 and 1186–1194 (1997)) describe hydrazide and arylamide HIV integrase inhibitors. Bis-catechols useful for inhibiting HIV integrase are described in LaFemina et al. (Antimicrobial Agents & Chemotherapy, vol. 39, no. 2, pp. 320–324, February 1995).

U.S. Pat. Nos. 4,377,258; 4,336,397; and 4,423,063 as well as Williams and Rooney (J. Med. Chem. vol 26, pp. 1196–1200, 1983) disclose 2,4-dioxo-4-substituted-1-butanoic acid derivatives useful intreating urinary tract calcium oxalate lithiasis. 4-substituted 2,4-dioxobutanoic acid compounds useful for inhibiting an influenza virus endonuclease are described in Tomassini et al. (Antimicrobial Agents & Chemotherapy, vol. 38, no. 12, pp. 2827–2837, December, 1994). 4-phenyl-4-oxo-butenoic acid derivatives are disclosed as useful as kynurenine-3-hydroxylase inhibitors for the prevention and/or treatment of neurodegenerative diseases in PCT/EP96/04517, which published as WO 97/17316 and in PCT/EP96/04518, which published as WO 97/17317.

Applicants have discovered that certain six-membered aromatic and heteroaromatic diketo acid derivatives are potent inhibitors of HIV integrase. These compounds are useful in the treatment of AIDS or HIV infection.

SUMMARY OF THE INVENTION

Compounds of formula I, as herein defined, are disclosed. These compounds are useful in the inhibition of HIV integrase, the prevention of infection by HIV, the treatment of infection by HIV and in the treatment of AIDS and/or ARC, either as compounds, pharmaceutically acceptable salts or hydrates (when appropriate), pharmaceutical composition ingredients, whether or not in combination with other antivirals, anti-infectives, immunomodulators, antibiotics or vaccines. Methods of treating AIDS, methods of preventing infection by HIV, and methods of treating infection by HIV are also disclosed.

DETAILED DESCRIPTION OF THE INVENTION

This invention is concerned with compounds of formula I, combinations thereof, or pharmaceutically acceptable salts thereof, in the inhibition of HIV integrase, the prevention or treatment of infection by HIV and in the treatment of the resulting acquired immune deficiency syndrome (AIDS). Compounds of formula I are defined as follows:

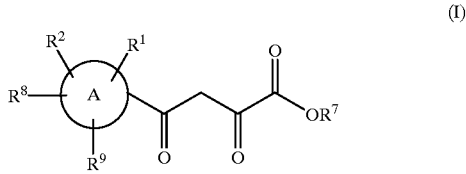

and tautomers and pharmaceutically acceptable salts thereof, wherein:

A is a six-membered aromatic or heteroaromatic ring containing 0, 1, or 2 nitrogen heteroatoms substituted on carbon or nitrogen by $R^1$, $R^2$, $R^8$, and $R^9$;

optionally the aromatic ring may be fused with another ring system to form:

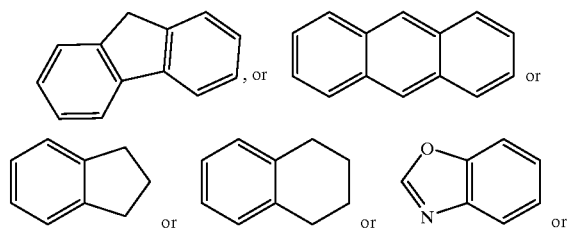

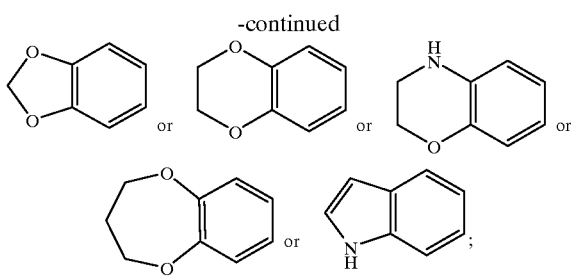

R¹ is selected from:
(1) —H,
(2) —$C_{1-5}$ alkyl,
(3) —$C_{1-6}$ alkyl-OR⁷,
(4) —O—$C_{1-6}$ alkyl-OR⁷,
(5) —O—$C_{1-6}$ alkyl-SR⁷,
(6) —$CF_3$ or —$CH_2CF_3$,
(7) -halo,
(8) —$NO_2$,
(9) —$C_{0-3}$ alkyl-N(R⁴)(R⁵),
(10) —R⁶,
(11) —$C_{2-5}$ alkenyl-R³,
(12) —$C_{2-5}$ alkynyl-R³,
(13) —O—R⁶,
(14) —O—$C_{1-6}$ alkyl, wherein one or more of the hydrogen atoms may be replaced with fluorine atoms,
(15) —O—$C_{1-6}$ alkyl-NH—C(O)—OR⁷;
(16) —O—$C_{2-6}$ alkyl-N(R⁴)(R⁵);
(17) —S—$C_{1-3}$ alkyl;
(18) —C(O)$CH_2$C(O)C(O)OR⁷;
(19) —$CH_2$—CH(OH)—$CH_2$O—R⁷; and
(20) —C(OH)(CH₃)—$CH_2$N(R⁴)(R⁵);

R² is selected from:
(1) —H,
(2) —R³,
(3) —$C_{1-6}$ alkyl,
(4) —$C_{1-6}$ alkyl substituted with R³, wherein one or more of the hydrogen atoms on $C_{1-6}$ alkyl may be replaced with a fluorine atom,
(5) —$C_{2-6}$ alkenyl,
(6) —O—R⁶,
(7) —O—$C_{1-6}$ alkyl-OR⁶,
(8) —O—$C_{1-6}$ alkyl-SR⁶,
(9) —S(O)$_n$—R⁶,
(10) —$C_{1-6}$ alkyl (OR⁶)(R⁴),
(11) —$C_{0-6}$ alkyl-N(R⁴)(R⁶),
(12) —$C_{1-6}$ alkyl S(O)$_n$—R⁶,
(13) —$C_{0-6}$ alkyl C(O)R⁶,
(14) —$C_{0-6}$ alkyl C(O)$CH_2$—C(O)—OH,
(15) —$C_{1-6}$ alkyl C(S)—R⁶,
(16) —$C_{1-6}$ alkyl NR⁴C(O)—R⁶,
(17) —$C_{1-6}$ alkyl-C(O)N(R⁴)(R⁵), and
(18) —$CH_2$(OR⁷)—R⁶;

each R³ is independently selected from:
(1) a 5 or 6 membered aromatic or heteroaromatic ring, containing 0, 1, 2, 3, or 4 heteroatoms selected from oxygen, nitrogen and sulfur, unsubstituted or substituted on nitrogen or carbon by 1 to 5 substituents selected from:
(a) halogen,
(b) $C_{1-6}$ alkyl, wherein one or more of the hydrogen atoms may be replaced with a fluorine atom,
(c) $C_{1-6}$ alkyloxy- wherein one or more of the hydrogen atoms may be replaced with a fluorine atom,
(d) phenyl,
(e) —$C_{1-6}$ alkyl,
(f) —CN,
(g) hydroxy,
(h) phenyloxy,
(i) —$C_{0-6}$ alkyl-N(R⁷)₂,

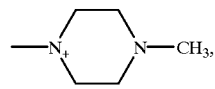

(k) oxo, and
(l) substituted phenyloxy with 1, 2, or 3 substituents selected from:
(i) halogen,
(ii) $C_{1-6}$ alkyl,
(iii) —$CF_3$, and
(iv) hydroxy;
(2) a 3 to 6 membered saturated ring containing 0, 1 or 2 heteroatoms selected from oxygen, nitrogen or sulfur, unsubstituted or substituted with 1 to 5 substituents selected from:
(a) halogen,
(b) $C_{1-6}$ alkyl,
(c) $C_{1-6}$ alkyloxy-,
(d) —$CF_3$,
(e) —$OCF_3$,
(f) —CN,
(g) =O,
(h) benzyl, and
(i) hydroxy;
(3) unsubstituted or substituted hexahydrothieno[3,4-d]imidazolyl with one or two substituents selected from:
(a) oxo,
(b) halogen,
(c) $C_{1-6}$ alkyl,
(d) $C_{1-6}$ alkyloxy-,
(e) —$CF_3$,
(f) —$OCF_3$,
(g) —CN, and
(h) hydroxy;
(4) a 5 or 6 membered aromatic or heteroaromatic ring, containing 0, 1, 2 or 3 heteroatoms selected from oxygen, nitrogen and sulfur, fused with a phenyl ring; wherein the ring system is unsubstituted or substituted on a nitrogen or carbon atom by 1 to 3 substituents selected from:
(a) -halogen,
(b) —$C_{1-6}$ alkyl,
(c) —$C_{1-6}$ alkyloxy-,
(d) —$CF_3$,
(e) —$CF_3$,
(f) —CN, and
(g) -hydroxy;
(5) a 3 to 6 membered saturated ring containing 0, 1 or 2 heteroatoms selected from oxygen, nitrogen or sulfur, fused with a phenyl ring, unsubstituted or substituted with 1 or 2 substituents selected from:
(a) halogen,
(b) $C_{1-6}$ alkyl,
(c) $C_{1-6}$ alkyloxy-,
(d) —$CF_3$,
(e) —$OCF_3$,
(f) —CN, (g) =O, and
(h) hydroxy;
(6) a 5 to 6 membered ring containing 0, 1 or 2 heteroatoms selected from oxygen, nitrogen or sulfur, containing 2 or 3 double bonds, unsubstituted or substituted with 1 or 2 substituents selected from:
(a) halogen,
(b) $C_{1-6}$ alkyl,
(c) $C_{1-6}$ alkyloxy-,
(d) —$CF_3$,
(e) —$OCF_3$,
(f) —CN,
(g) =O, and
(h) hydroxy; and
(7) a 5 to 6 membered ring containing 0, 1 or 2 heteroatoms selected from oxygen, nitrogen or sulfur, containing 2 or 3 double bonds, fused with a phenyl ring, unsubstituted or substituted with 1 or 2 substituents selected from:
(a) halogen,
(b) $C_{1-6}$ alkyl,
(c) $C_{1-6}$ alkyloxy-,
(d) —$CF_3$,
(e) —$OCF_3$,
(f) —CN,
(g) =O, and
(h) hydroxy; and each $R^4$ is independently selected from:
(1) —H,
(2) —$C_{1-4}$ alkyl,
(3) —$CF_3$,
(4) —$R^3$,
(5) —$C_{2-3}$ alkenyl,
(6) —$C_{1-3}$ alkyl-$R^3$,
(7) —$C_{2-3}$ alkenyl-$R^3$,
(8) —$S(O)_n$—$R^3$, and
(9) —C(O)—$R^3$;

each $R^5$ is independently selected from:
(1) —H,
(2) —$C_{1-3}$ alkyl,
(3) —$CF_3$,
(4) —$R^3$,
(5) —$C_{2-3}$ alkenyl,
(6) —$C_{1-3}$ alkyl-$R^3$,
(7) —$C_{2-3}$ alkenyl-$R^3$,
(8) —$S(O)_n$—$R^3$,
(9) —C(O)—$R^3$,
(10) —C(O)O$R^4$, and
(11) —C(O)C(O)OH;

each $R^6$ is independently selected from:
(1) —$C_{1-3}$ alkyl-$R^3$, and
(2) —$R^3$;

each $R^7$ is independently selected from:
(1) —H, and
(2) —$C_{1-6}$ alkyl;

$R^8$ is selected from:
(1) —H,
(2) —O—$C_{1-6}$ alkyl and
(3) $C_{1-6}$ alkyl;

$R^9$ is selected from:
(1) —H,
(2) —O—$C_{1-3}$ alkyl,
(3) —OH, and
(4) oxo; and each n is independently selected from 0, 1 and 2.

Also provided for by the present invention are compounds of structural formula (I) wherein:

when A is phenyl:
(1) $R^1$ is not $R^6$ para to the dioxobutyric acid/ester moiety; and
(2) $R^2$ is not selected from:
(a) phenyl para to the dioxobutyric acid/ester moiety,
(b) substituted phenyl para to the dioxobutyric acid/ester moiety,
(c) —$C_{1-6}$ alkyl phenyl para to the dioxobutyric acid/ester moiety, and
(d) substituted —$C_{1-6}$ alkyl phenyl para to the dioxobutyric acid/ester moiety; and
(3) at least one of $R^1$, $R^2$, and $R^8$ is not:
(a) —H,
(b) $C_{1-6}$ alkyl, or
(c) $R^3$ wherein $R^3$ is cycloalkyl; and
(4) and when $R^2$ is $S(O)_nR^6$, and $R^6$ is $CH_2$—$R^3$ or $R^3$, then $R^3$ is not unsubstituted phenyl.

Also provided for by the present invention are compounds of formula (I) wherein:
WHEN A is phenyl and $R^1$ is:
(a) H,
(b) $C_{1-5}$ alkyl,
(c) halo,
(d) $NO_2$,
(e) $R^6$ when $R^6$ is $CH_2R^3$ or $R^3$ and when $R^3$ is unsubstituted phenyl,
(f) —O—$C_{1-6}$ alkyl, or
(g) —$SC_{1-3}$ alkyl;
THEN $R^2$ is not selected from:
(a) H,
(b) $R^3$ when $R^3$ is unsubstituted phenyl,
(c) $C_{1-6}$ alkyl,
(d) $CH_2R^3$ when $R^3$ is unsubstituted phenyl, and
(e) $SOR^6$ when $R^6$ is $CH_2R^3$ or $R^3$ and when $R^3$ is unsubstituted phenyl.

Also provided for by the present invention are compounds of formula (I) wherein at least one of $R^1$, $R^2$, $R^8$ and $R^9$ is not hydrogen.

Also provided for by the present invention are compounds of formula (I) wherein: when A is a fused ring system, the six-membered aromatic ring is substituted by the dioxobutyric acid/ester moiety Applicants hereby incorporate by reference the disclosure of U.S. provisional application Serial No. 60/087,820, filed Jun. 3, 1998.

Also provided are compounds of formula Ia, which are defined as follows:

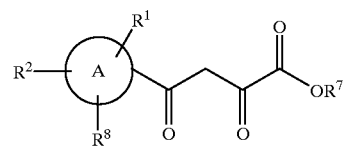

(Ia)

and tautomers and pharmaceutically acceptable salts thereof, wherein:
A is a six-membered aromatic or heteroaromatic ring containing 0, 1, or 2 heteroatoms selected from nitrogen and substituted on carbon or nitrogen by $R^1$, $R^2$ and $R^8$; the aromatic or heteroaromatic ring may optionally be fused with a 5- or 6-membered aromatic or heteroaromatic ring to form a fused ring system, provided that when A is a fused ring system, the six-membered aromatic or heteroaromatic ring is substituted by the dioxobutyric acid/ester moiety;

optionally the aromatic or heteroaromatic ring may be fused with another ring system to form:

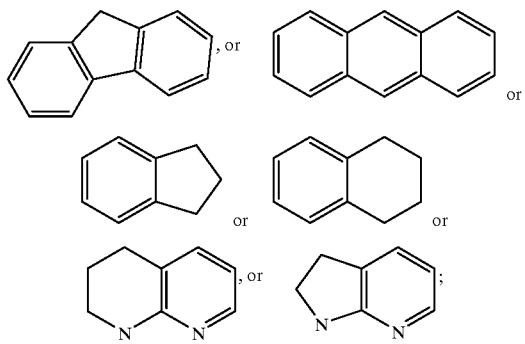

R¹ is selected from:
(1) —H,
(2) —$C_{1-5}$ alkyl,
(3) —$CF_3$,
(4) -halo,
(5) —$NO_2$,
(6) —$N(R^4)(R^5)$,
(7) —$R^6$,
(8) —$C_{2-5}$ alkenyl-$R^3$,
(9) —$C_{2-5}$ alkynyl-$R^3$,
(10) —O—$R^6$,
(11) —O—$C_{1-6}$ alkyl, and
(12) —$C(O)CH_2C(O)C(O)OR^7$;

R² is selected from:
(1) —H,
(2) —$R^3$,
(3) —$C_{1-6}$ alkyl,
(4) —$C_{1-6}$ alkyl substituted with $R^3$,
(5) —O—$R^6$,
(6) —O—$C_{1-6}$ alkyl-$OR^6$,
(7) —$S(O)_n$—$R^6$,
(8) —$C_{1-6}$ alkyl $(OR^6)(R^4)$,
(9) —$C_{0-6}$ alkyl-$N(R^4)(R^6)$,
(10) —$C_{1-6}$ alkyl $S(O)_n$—$R^6$,
(11) —$C_{1-6}$ alkyl $C(O)$—$R^6$,
(12) —$C_{1-6}$ alkyl $C(S)$—$R^6$,
(13) —$C_{1-6}$ alkyl $NR^4C(O)$—$R^6$, and
(14) —$C_{1-6}$ alkyl-$C(O)N(R^4)(R^5)$;

each R³ is independently selected from:
(1) a 5 or 6 membered aromatic or heteroaromatic ring, containing 0, 1, 2, 3, or 4 heteroatoms selected from oxygen, nitrogen and sulfur, unsubstituted or substituted on a nitrogen or carbon atom by 1 to 5 substituents selected from:
(a) halogen,
(b) $C_{1-6}$ alkyl,
(c) $C_{1-6}$ alkyloxy-,
(d) phenyl,
(e) —$CF_3$,
(f) —$OCF_3$,
(g) —CN,
(h) hydroxy,
(i) phenyloxy, and
(j) substituted phenyloxy with 1, 2, or 3 substituents selected from:
 (i) halogen,
 (ii) $C_{1-6}$ alkyl,
 (iii) —$CF_3$, and
 (iv) hydroxy;

(2) a 3 to 6 membered saturated ring containing 0 or 1 heteroatoms selected from oxygen, nitrogen or sulfur, unsubstituted or substituted with 1 to 5 substituents selected from:
(a) halogen,
(b) $C_{1-6}$ alkyl,
(c) $C_{1-6}$ alkyloxy-,
(d) —$CF_3$,
(e) —$OCF_3$,
(f) —CN,
(g) =O,
(h) hydroxy;

(3) unsubstituted or substituted hexahydrothieno[3,4-d]imidazolyl with one or two substituents selected from:
(a) oxo,
(b) halogen,
(c) $C_{1-6}$ alkyl,
(d) $C_{1-6}$ alkyloxy-,
(e) —$CF_3$,
(f) —$OCF_3$,
(g) —CN, and
(h) hydroxy;

(4) a 5 or 6 membered aromatic or heteroaromatic ring, containing 0, 1, or 2 heteroatoms selected from oxygen, nitrogen and sulfur, fused with a phenyl ring; wherein the ring system is unsubstituted or substituted on a nitrogen or carbon atom by 1 to 3 substituents selected from:
(a) -halogen,
(b) —$C_{1-6}$ alkyl,
(c) —$C_{1-6}$ alkyloxy-,
(d) —$CF_3$,
(e) —$OCF_3$,
(f) —CN, and
(g) -hydroxy;

(5) a 3 to 6 membered saturated ring containing 0 or 1 heteroatoms selected from oxygen, nitrogen or sulfur, fused with a phenyl ring, unsubstituted or substituted with 1 or 2 substituents selected from:
(a) halogen,
(b) $C_{1-6}$ alkyl,
(c) $C_{1-6}$ alkyloxy-,
(d) —$CF_3$,
(e) —$OCF_3$,
(f) —CN,
(g) =O,
(h) hydroxy;

(6) a 5 to 6 membered ring containing 0, 1 or 2 heteroatoms selected from oxygen, nitrogen or sulfur, containing 2 or 3 double bonds, unsubstituted or substituted with 1 or 2 substituents selected from:
(a) halogen,
(b) $C_{1-6}$ alkyl,
(c) $C_{1-6}$ alkyloxy-,
(d) —$CF_3$,
(e) —$OCF_3$,
(f) —CN,
(g) =O,
(h) hydroxy;

each R⁴ is independently selected from:
(1) —H,
(2) —$C_{1-3}$ alkyl,
(3) —$CF_3$,
(4) —$R^3$,
(5) —$C_{2-3}$ alkenyl,
(6) —$C_{1-3}$ alkyl-$R^3$, (7) —C$_{2-3}$ alkenyl-R$^3$,
(8) —S(O)$_n$—R$^3$, and
(9) —C(O)—R$^3$;

each R$^5$ is independently selected from:
(1) —H,
(2) —C$_{1-3}$ alkyl,
(3) —CF$_3$,
(4) —R$^3$,
(5) —C$_{2-3}$ alkenyl,
(6) —C$_{1-3}$ alkyl-R$^3$,
(7) —C$_{2-3}$ alkenyl-R$^3$,
(8) —S(O)$_n$—R$^3$, and
(9) —C(O)—R$^3$;

each R$^6$ is independently selected from:
(1) —C$_{1-3}$ alkyl-R$^3$, and
(2) —R$^3$;

R$^7$ is selected from:
(1) —H, and
(2) C$_{1-6}$ alkyl;

R$^8$ is selected from:.
(1) —H,
(2) —O—C$_{1-6}$ alkyl, and
(3) C$_{1-6}$ alkyl; and each n is independently selected from 0, 1 and 2.

Also provided by the present invention are compounds of structural formula (Ia) wherein:
when A is phenyl,
(1) R$^1$ is not:
(a) phenyl para to the dioxobutyric acid/ester moiety,
(b) substituted phenyl para to the dioxobutyric acid/ester moiety,
(c) C$_{1-3}$ alkyl phenyl para to the dioxobutyric acid/ester moiety, or
(d) substituted —C$_{1-3}$ alkyl phenyl para to the dioxobutyric acid/ester moiety; and
(2) R$^2$ is not selected from:
(a) phenyl para to the dioxobutyric acid/ester moiety,
(b) substituted phenyl para to the dioxobutyric acid/ester moiety,
(c) —C$_{1-6}$ alkyl phenyl para to the dioxobutyric acid/ester moiety, and
(d) substituted —C$_{1-6}$ alkyl phenyl para to the dioxobutyric acid/ester moiety; and
(3) at least one of R$^1$, R$^2$, and R$^8$ is not:
(a) —H,
(b) C$_{1-6}$ alkyl, or
(c) R$_3$ wherein R$_3$ is cycloalkyl; and
(4) and when R$^1$ or R$^2$ is S(O)$_n$R$^6$, R$^6$ is R$^3$.

Particular compounds of structural formula Ia include:
(1) 3-biphenyl-4-yl-2,4-dioxobutanoic acid,
(2) 4-(3,5-bis-benzyloxyphenyl)-2-hydroxy-4-oxo-but-2-enoic acid,
(3) 4-[3-(3,4-difluorobenzyl)oxyphenyl]-2-hydroxy-4-oxobut-2-enoic acid,
(4) 4-[3-(4-methylbenzyl)oxyphenyl]-2-hydroxy-4-oxobut-2-enoic acid,
(5) 4-(3-benzyloxy-5-methoxyphenyl)-2-hydroxy-4-oxobut-2-enoic acid,
(6) 4-(3-benzyloxyphenyl)-2-hydroxy-4-oxobut-2-enoic acid,
(7) 4-[3-(4-chlorobenzyl)oxyphenyl]-2-hydroxy-4-oxobut-2-enoic acid,
(8) 4-[3-(3,4-dichlorobenzyl)oxyphenyl]-2-hydroxy-4-oxobut-2-enoic acid,
(9) 4-[3-(4-fluorobenzyl)oxyphenyl]-2-hydroxy-4-oxobut-2-enoic acid,
(10) 4-[3-(3-chlorobenzyl)oxyphenyl]-2-hydroxy-4-oxobut-2-enoic acid,
(11) 4-[3-benzyloxy-5-(6-tert-butoxycarbonylaminohexyloxy)phenyl]-2-hydroxy-4-oxobut-2-enoic acid,
(12) 4-(3-(4-methoxybenzyloxy)phenyl)-4-oxo-2-butenoic acid,
(13) 4-(3-benzyloxy-5-hydroxyphenyl)-2-hydroxy-4-oxobut-2-enoic acid,
(14) 4-(3-(1-phenylethoxy)phenyl)-4-oxo-2-butenoic acid,
(15) 4-[3-benzyloxy-5-(6-[5-(2-oxohexahydrothieno[3,4-d]imidazol-4-yl)pentanoylamino]hexyloxy)-phenyl]-2-hydroxy-4-oxobut-2-enoic acid,
(16) 4-[3-(6-aminohexyloxy)-5-benzyloxyphenyl]-2-hydroxy-4-oxobut-2-enoic acid,
(17) 4-(3-dibenzylaminophenyl)-2-hydroxy-4-oxobut-2-enoic acid,
(18) 4-(3-chloro-phenyl)-2,4-dioxo-butanoic acid, and
(19) 4-(3-benzyl-phenyl)-2,4-dioxo-butanoic acid,
(20) 4-(4-dibenzylaminophenyl)-2-hydroxy-4-oxobut-2-enoic acid,
(21) 4-(4-benzylaminophenyl)-2-hydroxy-4-oxobut-2-enoic acid,
(22) 4-(2-benzyloxyphenyl)-2-hydroxy-4-oxobut-2-enoic acid,
(23) 4-naphthalen-1-yl-2,4-dioxobutanoic acid, and
(24) 4-naphthalen-2-yl-2,4-dioxobutanoic acid,
(25) 4-(6-benzyloxy-2-oxo-1,2-dihydropyridin-4-yl)-2-hydroxy-4-oxobut-2-enoic acid, and
(26) 4-(2,6-Bis benzyloxypyridin-4-yl)-2,4-dioxobutanoic acid,
(27) 4-[1-(4-fluorobenzyl)-5-indolyl]-2-hydroxy-4-oxo-2-butenoic acid,
(28) 4-[1-(4-fluorobenzyl)-4-indolyl]-2-hydroxy-4-oxo-2-butenoic acid,
(29) 4-(4-benzyloxyphenyl)-2-hydroxy-4-oxobut-2-enoic acid,
(30) 4-[1-(4-fluorobenzyl)-6-indolyl]-2-hydroxy-4-oxo-2-butenoic acid, and
(31) 4-biphenyl-4-yl-2,4-dioxobutanoic acid, and tautomers and pharmaceutically acceptable salts thereof.

Particular compounds of structural formula (I) include:
(1) 4-(3,5-Bis-benzyloxy-phenyl)-2,4-dioxobutanoic acid,
(2) 4-[3-Benzyloxy-5-(2-morpholin-4-yl-ethoxy)-phenyl]-2,4-dioxobutanoic acid,
(3) 4-[3-Benzyloxy-5-(6-tert-butoxycarbonylaminohexyloxy)phenyl]-2,4-dioxobutanoic acid,
(4) 4-(3-Benzylphenyl)-2,4-dioxobutanoic acid,
(5) 4-[3-(2-chlorobenzyl)phenyl]-2,4-dioxobutanoic acid,
(6) 4-(4-Dibenzylaminophenyl)-2,4-dioxobutanoic acid,
(7) 4-(3-Dibenzylaminophenyl)-2,4-dioxobutanoic acid,
(8) 1-(3-benzyloxy-5-methoxyphenyl)-2,4-dioxobutanoic acid,
(9) 1-(3-Benzyloxyphenyl)-2,4-dioxobutanoic acid,
(10) 1-(2-Benzyloxyphenyl)-2,4-dioxobutanoic acid,
(11) 1-[3-(4-Fluorobenzyloxy)phenyl]-2,4-dioxobutanoic acid,
(12) 1-[3-(3,4-Difluorobenzyloxy)phenyl]-2,4-dioxobutanoic acid,

(13) 4-[3-(5-methyl-thiophen-2-ylmethyl)-phenyl]-2,4-dioxobutyric acid,
(14) 4-{3-[(methyl-phenyl-amino)-methyl]-phenyl}-2,4-dioxobutyric acid,
(15) 4-(3-benzyl-5-pyrazin-2-yl-phenyl)-2,4-dioxobutyric acid,
(16) 2,4-dioxo-4-[3-(1,2,3,4-tetrahydronaphthalen-1-yl)-phenyl]butyric acid,
(17) 2,4-Dioxo-4-(3-phenylsulfanyl-phenyl)-butyric acid,
(18) 4-[3-(2,4-Difluoro-benzyl)-phenyl]-2,4-dioxobutyric acid,
(19) 4-[5-(4-Fluoro-benzyl)-2,3-dimethoxy-phenyl]-2,4-dioxobutyric acid,
(20) 4-(5-Benzyl-2-isopropoxyphenyl)-2,4-dioxobutyric acid,
(21) 4-[5-Benzyl-2-(2-N,N-dimethylaminoethoxy)phenyl]-2,4-dioxobutyric acid,
(22) 4-[5-Benzyl-2-(pyridin-2-yloxy)phenyl]-2,4-dioxobutyric acid,
(23) 4-(5-Benzyl-2-isopropoxy-3-methoxyphenyl)-2,4-dioxo-butyric acid,
(24) 4-(5-Benzyl-2,3-dimethoxyphenyl)-2,4-dioxobutyric acid,
(25) 4-(5-Benzyl-3-dimethylamino-2-methoxyphenyl)-2,4-dioxobutyric acid,
(26) 4-[5-Benzyl-2-N,N-dimethylaminobenzoxazol-7-yl]-2,4-dioxobutyric acid,
(27) 4-(3-Benzyl-5-pyrazin-2-ylmethylphenyl)-2,4-dioxobutyric acid,
(28) 4-(3-Benzyl-5-[1,2,3]triazol-2-ylmethylphenyl)-2,4-dioxobutyric acid,
(29) 4-[3-(3-Chloropyridin-2-ylmethyl)phenyl]-2,4-dioxobutyric acid,
(30) 4-[5-Benzyl-2-methoxy-3-(N,N-dimethylaminomethyl) phenyl]-2,4-dioxo-butyric acid,
(31) 4-(5-benzyl-3-methoxy-2-methoxyethoxyphenyl)-2,4-dioxobutyric acid,
(32) 4-(3-Benzyl-4-methoxyphenyl)-2,4-dioxobutyric acid,
(33) 4-(5-Benzyl-2-methoxyphenyl)-2,4-dioxobutyric acid,
(34) 4-(3-Benzyl-4-fluorophenyl)-2,4-dioxobutyric acid,
(35) 4-(3-Benzyl-4-N,N-dimethylaminophenyl)-2,4-dioxobutyric acid,
(36) 4-[5-(2-Methylbenzyl)-2,3-dimethoxyphenyl]-2,4-dioxobutyric acid,
(37) 2,4-Dioxo-4-(3-pyridin-2-ylmethylphenyl)butyric acid,
(38) 4-(5-Benzyl-3-N,N-dimethylaminophenyl)-2,4-dioxobutyric acid,
(39) 4-(5-Benzyl-3-methoxyphenyl)-2,4-dioxobutyric acid,
(40) 4-(5-Benzyl-2-benzyloxy-3-methoxyphenyl)-2,4-dioxobutyric acid,
(41) 4-[5-(3-Methylbenzyl)-2,3-dimethoxyphenyl]-2,4-dioxobutyric acid,
(42) 4-(5-Benzyl-3-benzyloxyphenyl)-2,4-dioxobutyric acid,
(43) 4-[5-Benzyl-2-(2-hydroxy)ethoxyphenyl]-2,4-dioxo-2-butanoic acid,
(44) 2,4-Dioxo-4-(3-pyridin-3-ylmethylphenyl)butyric acid,
(45) 4-[3-(3-Methyl-pyridin-2-ylmethyl)phenyl]-2,4-dioxo-butyric acid,
(46) 4-(5-Benzyl-2-methylsulfanylphenyl)-2,4-dioxobutyric acid,
(47) 4-(5-Benzyl-3-N-morpholinophenyl)-2,4-dioxobutyric acid,
(48) 4-(8-Benzyl-4-methyl-3,4-dihydro-2h-benzo[1,4]oxazin-6-yl)-2,4-dioxobutyric acid,
(49) 4-[5-(2-Chlorobenzyl)-3-N,N-dimethylaminophenyl]-2,4-dioxobutyric acid,
(50) 4-[5-(3-Chlorobenzyl)-3-N,N-dimethylaminophenyl]-2,4-dioxobutyric acid,
(51) 4-(5-Benzyl-2,3,4-trimethoxyphenyl)-2,4-dioxobutyric acid,
(52) 4-(6-Benzylbenzo[1,3]dioxol-4-yl)-2,4-dioxobutyric acid,
(53) 4-[3-Benzyl-5-(morpholine-4-carbonyl)phenyl]-2,4-dioxobutyric acid,
(54) 4-(3-Benzyl-5-pyridine-2-ylmethylphenyl)-2,4-dioxobutyric acid,
(55) 4-[3-Benzyl-5-(morpholinomethyl)phenyl]-2,4-dioxobutyric acid,
(56) 4-(3-Benzyl-5-pyridine-3-ylmethylphenyl)-2,4-dioxobutyric acid,
(57) 4-[3-Benzyl-5-(2-dimethylamino-1-hydroxy-1-methylethyl)phenyl]-2,4-dioxobutyric acid,
(58) 4-(5-Benzyl-2-N,N-dimethylaminophenyl)-2,4-dioxobutyric acid,
(59) 4-(5-Benzyl-2-fluorophenyl)-2,4-dioxobutyric acid,
(60) 4-(5-Benzyl-3-hydroxymethyl-2-methoxyphenyl)-2,4-dioxobutyric acid,
(61) 4-[5-Benzyl-2-(pyrazin-2-yloxy)phenyl]-2,4-dioxobutyric acid,
(62) 4-[3-Benzyl-5-(2-oxopiperidin-1-ylmethyl)phenyl]-2,4-dioxobutyric acid,
(63) 4-[5-Benzyl-2-methoxy-3-(morpholinomethyl)phenyl]-2,4-dioxobutyric acid,
(64) 4-[3-(2-Chlorobenzyl)-5-pyridin-2-ylmethylphenyl]-2,4-dioxobutyric acid,
(65) 4-[5-Benzyl-2-methoxy-3-(4-methylpiperazin-1-ylmethyl)phenyl]-2,4-dioxobutyric acid,
(66) 4-(5-Benzyl-2-methoxymethylphenyl)-2,4-dioxobutyric acid,
(67) 4-[3-(2-Fluorobenzyl)-5-morpholinomethylphenyl]-2,4-dioxobutyric acid,
(68) 4-[3-(4-Fluorobenzyl)-5-morpholinomethylphenyl]-2,4-dioxobutyric acid,
(69) 4-[3-(3-Fluorobenzyl)-5-morpholinomethylphenyl]-2,4-dioxobutyric acid,
(70) 4-[5-Benzyl-2-methoxy-3-(tert-butylcarbamoyl)phenyl]-2,4-dioxobutyric acid,
(71) 4-(3-Benzyl-5-[1,2,3]triazol-1-ylmethylphenyl)-2,4-dioxobutyric acid,
(72) 4-[5-Benzyl-3-(N'-methyl-N-piperazinyl)phenyl]-2,4-dioxobutyric acid,
(73) 4-(3-Benzyl-5-[1,2,4]triazol-1-ylmethylphenyl)-2,4-dioxobutyric acid,
(74) 4-(6-Benzyl-3-oxo-3,4-dihydro-2—H-benzo[1,4]oxazin-8-yl)-2,4-dioxobutyric acid,
(75) 4-[5-Benzyl-2-(pyrimidin-2-yloxy)phenyl]-2,4-dioxobutyric acid,

(76) 4-(5-Benzyl-3-amino-2-methoxyphenyl)-2,4-dioxobutyric acid,
(77) 4-(5-Benzyl-2-ethoxyphenyl)-2,4-dioxobutyric acid,
(78) 4-[5-Benzyl-2-(2-morpholin-4-yl-ethoxy)phenyl]-2,4-dioxobutyric acid,
(79) 4-(5-Benzyl-2-trifluoroethoxyphenyl)-2,4-dioxobutyric acid,
(80) 4-(5-Benzyl-2-cyclobutyloxyphenyl)-2,4-dioxobutyric acid,
(81) 4-(5-Benzyl-2-cyclopentyloxyphenyl)-2,4-dioxobutyric acid,
(82) 4-(3-Benzyl-5-tetrazol-2-ylmethylphenyl)-2,4-dioxobutyric acid,
(83) 4-(5-Benzyl-2,3-diisopropoxyphenyl)-2,4-dioxobutyric acid,
(84) 4-(5-Benzyl-2-isopropoxy-3-N-methylaminophenyl)-2,4-dioxobutyric acid,
(85) 4-(5-Benzyl-2-isopropoxy-3-N,N-dimethylaminophenyl)-2,4-dioxo-butyric acid,
(86) 4-[5-Benzyl-2-isopropoxy-3-(2-N,N-dimethylaminoethoxy)phenyl]-2,4-dioxobutyric acid,
(87) 4-[5-Benzyl-2-isopropoxy-3-(morpholinomethyl)phenyl]-2,4-dioxo-butyric acid,
(88) 4-(5-Benzyl-2-isopropoxy-3-N,N-dimethylaminomethylphenyl)-2,4-dioxo-butyric acid,
(89) 4-(7-Benzylbenzo[1,3]dioxol-5-yl)-2-hydroxy-4-oxobut-2-enoic acid,
(90) 2—Hydroxy-4-oxo-4-(3-phenylindan-5-yl)but-2-enoic acid,
(91) 4-(Dibenzylaminophenyl)-2-hydroxy-4-oxobut-2-enoic acid,
(92) 3-(3-Benzyl-5-carboxyacetylphenyl)-3-oxopropionic acid,
(93) 4-(4-Dibenzylaminophenyl)-2-hydroxy-4-oxobut-2-enoic acid,
(94) 4-(5-Benzyl-3-methoxy-2-methylthioethoxyphenyl)-2,4-dioxobutyric acid,
(95) 4-(7-Benzyl-2,3-dihydrobenzo[1,4]dioxin-5-yl)-2,4-dioxobutyric acid,
(96) (+/−) 4-(8-Benzyl-3-hydroxy-3,4-dihydro-2H-benzo[B][1,4]dioxepin-6-yl)-2,4-dioxobutyric acid,
(97) 4-(2,3-Dimethoxy-5-pent-4-enylphenyl)-2,4-dioxobutyric acid,
(98) 4-(5-Cyclopropylmethyl-2,3-dimethoxyphenyl)-2,4-dioxobutyric acid,
(99) (6-Benzyloxy-1-oxo-indan-2-ylidene)-hydroxyacetic acid,
(100) 4-(5-Benzyl-2-isopropoxy-3-[1,2,3]triazol-1-ylmethylphenyl)-2,4-dioxobutyric acid,
(101) 4-(5-Benzyl-2-isopropoxy-3-[1,2,4]triazol-1-ylmethylphenyl)-2,4-dioxobutyric acid,
(102) 4-[5-Benzyl-2-(3-N,N-dimethylaminopropoxy)-3-methoxyphenyl]-2,4-dioxobutyric acid,
(103) 4-[3-(Phenyldifluoromethyl)phenyl]-2,4-dioxobutyric acid,
(104) 4-(5-Benzyl-2-cyclopropyloxyphenyl)-2,4-dioxobutyric acid,
(105) 4-[5-Benzyl-2-isopropoxy-3-(1-piperidinylmethyl)phenyl]-2,4-dioxo-butyric acid,
(106) 4-[5-Benzyl-2-(2-dimethylamino-1-methylethoxy)phenyl]-2,4-dioxo-butyric acid,
(107) 4-[5-Benzyl-2-(1-methylpiperidin-4-yloxy)phenyl]-2,4-dioxo-butyric acid,
(108) 4-[3-Benzyl-5-(4-benzylpiperazin-1-yl)phenyl]-2,4-dioxo-butyric acid,
(109) 4-[5-Benzyl-2-isopropoxy-3-(pyridin-2-ylaminomethyl)phenyl]-2,4-dioxo-butyric acid,
(110) 4-[1-(2,6-Difluorobenzyl)-1H-indol-6-yl]-2,4-dioxobutyric acid,
(111) 4-(1-Benzyl-1H-indol-6-yl)-2,4-dioxobutyric acid,
(112) 1-[1-(4-Fluorobenzyl)-6-indolyl]-2,4-dioxobutanoic acid,
(113) 1-[1-(4-Fluorobenzyl)-4-indolyl]-2,4-dioxobutanoic acid,
(114) 4-[3-(2,4-Difluoro-benzyl)-phenyl]-2,4-dioxo-butyric acid,
(115) 2,4-Dioxo-4-[3-(2,6-difluoro-benzyl)-phenyl]-butyric acid,
(116) 2,4-Dioxo-4-[3-(2-4-6-trifluoro-benzyl)-phenyl]-butyric acid,
(117) 2,4-Dioxo-4-[3-(2-fluoro-3-chloro-benzyl)-phenyl]-butyric acid,
(118) 2,4-Dioxo-4-[3-(2-methyl-4-fluoro-benzyl)-phenyl]-butyric acid,
(119) 4-[3-(2,3-Dichloro-benzyl)-phenyl]-2,4-dioxo-butyric acid,
(120) 4-[3-(2-Chloro-3-methylbenzyl)phenyl]-2,4-dioxobutyric acid,
(121) 2,4-Dioxo-4-[3-(2,6-dichloro-benzyl)-phenyl]-butyric acid,
(122) 2,4-Dioxo-4-[3-(2,3,4,5,6-penta-fluoro-benzyl)-phenyl]-butyric acid,
(123) 4-[3-(2-Fluorobenzyl)phenyl]-2,4-dioxobutyric acid,
(124) 2,4-Dioxo-4-[3-(2-chloro-4-fluoro-benzyl)-phenyl]-butyric acid,
(125) 4-[3-(2-Methylbenzyl)phenyl]-2,4-dioxobutyric acid,
(126) 2,4-Dioxo-4-[3-(2-methoxybenzyl)phenyl]butyric acid,
(127) 4-[3-(2-Chlorobenzyl)phenyl]-2,4-dioxobutyric acid,
(128) 4-[3-(2-Bromobenzyl)phenyl]-2,4-dioxobutyric acid,
(129) 4-[5-(4-Fluoro-benzyl)-2,3-dimethoxy-phenyl]-2,4-dioxobutyric acid,
(130) 4-[3-(3-Chloro-2-methyl-benzyl)phenyl]-2,4-dioxobutyric acid,
(131) 4-[3-(2,3-Difluoro-benzyl)-phenyl]-2,4-dioxo-butyric acid,
(132) 4-(3,5-Dibenzylphenyl)-2,4-dioxo-butyric acid,
(133) 2,4-Dioxo-4-[3-(2-trifluoromethylbenzyl)phenyl]butyric acid,
(134) 4-[3-(4-Fluorobenzyl)phenyl]-2,4-dioxobutyric acid,
(135) 4-[3-(3-Chlorobenzyl)phenyl]-2,4-dioxobutyric acid,
(136) 2,4-Dioxo-4-[3-(2-bromo-3-chloro-benzyl)-phenyl]-butyric acid,
(137) 4-(3-Benzylphenyl)-2,4-dioxo-butyric acid,
(138) 4-[3-(2-Fluoro-3-methyl-benzyl)-phenyl]-2,4-dioxo-butyric acid, (139) 4-[3-(3-Chloro-4-fluoro-benzyl)-phenyl]-2,4-dioxo-butyric acid,
(140) 2,4-Dioxo-4-[3-(2-bromo-4-fluoro-benzyl)-phenyl]-butyric acid,
(141) 4-[3-(3-Bromobenzyl)phenyl]-2,4-dioxobutyric acid,
(142) 4-[3-(2,5-Difluoro-benzyl)-phenyl]-2,4-dioxobutyric acid,
(143) 4-[3-(5-Chloro-2-fluoro-benzyl)phenyl]-2,4-dioxobutyric acid,
(144) 4-[3-(3-Methylbenzyl)phenyl]-2,4-dioxobutyric acid,
(145) 4-(3-Benzyl-4-methyl-phenyl)-2,4-dioxo-butyric acid,
(146) 4-[3-(3,4-Difluoro-benzyl)-phenyl]-2,4-dioxobutyric acid,
(147) 4-[3-(2,5-Dichloro-benzyl)-phenyl]-2,4-dioxobutyric acid,
(148) 4-[3-(2-Chloro-6-methyl-benzyl)phenyl]-2,4-dioxobutyric acid,
(149) 2,4-Dioxo-4-[3-(2-trifluoromethyl-4-chloro-benzyl)-phenyl]-butyric acid,
(150) 4-[3-(2-Bromo-5-chloro-benzyl)-phenyl]-2,4-dioxo-butyric acid,
(151) 4-(3-Naphthalen-1-ylmethyl-phenyl)-2,4-dioxobutyric acid,
(152) 2,4-Dioxo-4-[3-(3-fluorobenzyl)phenyl]butyric acid,
(153) 2,4-Dioxo-4-(3-phenylsulfanyl-phenyl)-butyric acid,
(154) 2,4-Dioxo-4-[3-(1-phenylethyl)phenyl]butyric acid,
(155) 4-(3-Benzyl-4,5-dimethylphenyl)-2,4-dioxobutyric acid,
(156) 2,4-Dioxo-4-[3-(3-methoxybenzyl)phenyl]butyric acid,
(157) 4-[3-(5-Methyl-thiophen-2-ylmethyl)phenyl]-2,4-dioxo-butyric acid,
(158) 4-[3-(5-Chloro-thiophen-2-ylmethyl)phenyl]-2,4-dioxo-butyric acid,
(159) 4-(3-Benzyl-5-methylphenyl)-2,4-dioxo-butyric acid,
(160) 4-[3-(2-Cyanobenzyl)phenyl]-2,4-dioxo-butyric acid,
(161) 4-[3-Benzylphenyl]-2,4-dioxobutyric acid,
(162) 4-[3-(3,5-Dichloro-benzyl)-phenyl]-2,4-dioxobutyric acid,
(163) 4-(5-Benzyl-2,4-dimethylphenyl)-2,4-dioxobutyric acid,
(164) 4-(5-Benzyl-2-methylphenyl)-2,4-dioxo-butyric acid,
(165) 4-(3-Cyclohexylmethyl-phenyl)-2,4-dioxo-butyric acid,
(166) 4-{3-[(Methyl-phenyl-amino)-methyl]-phenyl}-2,4-dioxobutyric acid,
(167) 4-[3-Benzyl-5-(5-hydroxy-pentyl)-phenyl]-2,4-dioxo-butyric acid,
(168) 4-(3-Benzyl-5-pyrazin-2-yl-phenyl)-2,4-dioxobutyric acid,
(169) 4-[3-(3-tert-Butoxy-2-hydroxy-propyl)-5-(2-methyl-benzyl)-phenyl]-2,4-dioxo-butyric acid,
(170) 2,4-Dioxo-4-[3-(2,3-dimethoxy-benzyl)-phenyl]-butyric acid,
(171) 4-[3-(Methoxyphenylmethyl)phenyl]-2,4-dioxobutyric acid,
(172) 4-[3-[Hydroxy-(tetrahydro-furan-3-yl)-methyl]-5-(2-methylbenzyl)-phenyl]--2,4-dioxo-butyric acid,
(173) 2,4-Dioxo-4-(3-phenoxymethyl-phenyl)-butyric acid,
(174) 2,4-Dioxo-4-(3-phenoxymethyl-phenyl)-butyric acid
(175) 4-[3-Benzyl-5-(cyclopropylcarboxamido)-phenyl]-2,4-dioxobutyric acid,
(176) 4-[3-Benzyl-5-(t-butoxycarbamoyl)phenyl]-2,4-dioxobutyric acid,
(177) 4-[3-(Hydroxy-phenyl-methyl)-phenyl]-2,4-dioxo-butyric acid,
(178) 4-(5-Benzyl-2,3-dimethylphenyl)-2,4-dioxobutyric acid,
(179) n-[3-(3,5-Dibromobenzyl)phenyl]-2,4-dioxobutyric acid,
(180) 4-[3-(2-Methyl-benzyl)-5-pyrimidin-2-yl-phenyl]-2,4-dioxobutyric acid,
(181) 4-[3-Benzyl-2-(pyrimidin-2-ylamino)-phenyl]-2,4-dioxobutyric acid
(182) 4-[3-Benzoimidazol-1-ylmethyl-5-(2-methyl-benzyl)-phenyl]-2,4-dioxo-butyric acid,
(183) 2,4-Dioxo-4-[3-(3-trifluoromethylbenzyl)phenyl]butyric acid,
(184) 4-(4-Phenoxy-phenyl)-2,4-dioxo-butyric acid,
(185) 2,4-Dioxo-4-(3-[1,2,3]triazol-2-ylmethyl-phenyl)-butyric acid,
(186) 4-[3-Benzyl-5-(6-methoxy-pyridin-2-yl)-phenyl]-2,4-dioxobutyric acid,
(187) 4-(3-Benzotriazol-2-ylmethyl-phenyl)-2,4-dioxobutyric acid,
(188) 4-[3-Benzyl-5-(2-(4-methylpiperazin-1-yl)-pyrazin-6-yl)phenyl]-2,4-dioxobutyric acid,
(189) 4-[4-(3-Phenethyl)phenyl]-2,4-dioxobutyric acid,
(190) 4-[4-(3-Chlorobenzyl)phenyl]-2,4-dioxobutyric acid,
(191) 4-(3-Benzoimidazol-1-ylmethyl-phenyl)-2,4-dioxo-butyric acid,
(192) 4-[3-Benzyloxy-5-(6-tert-butoxycarbonylaminohexyloxy)phenyl]-2-hydroxy-4-oxo-but-2-enoic acid,
(193) 4-(3-Benzotriazol-1-ylmethyl-phenyl)-2,4-dioxobutyric acid,
(194) 4-[3-(3,5-Dimethyl-pyrazol-1-ylmethyl)-phenyl]-2,4-dioxobutyric acid,
(195) 4-[3-Benzyloxy-5-(2-morpholin-4-yl-ethoxy)phenyl]-2-hydroxy-4-oxo-but-2-enoic acid,
(196) 4-(4-Methyl-3-phenoxy-phenyl)-2,4-dioxo-butyric acid
(197) 4-[3-(2—Hydroxy-benzyl)-phenyl]-2,4-dioxobutyric acid,
(198) 4-[3-Benzyl-5-(6-dimethylamino-pyrazin-2-yl)-phenyl]-2,4-dioxo-butyric acid, and
(199) 4-(5-Benzyl-2-methoxypyridin-3-yl)-2,4-dioxobutyric acid;
and tautomers and pharmaceutically acceptable salts thereof.
One class of compounds of structural formula (I) includes:
(1) 4-(3-Benzylphenyl)-2,4-dioxobutanoic acid,
(2) 4-[3-(5-methyl-thiophen-2-ylmethyl)-phenyl]-2,4-dioxo-butyric acid, (3) 4-{3-[(methyl-phenyl-amino)-methyl]-phenyl}-2,4-dioxobutyric acid,
(4) 4-(3-benzyl-5-pyrazin-2-yl-phenyl)-2,4-dioxo-butyric acid,
(5) 2,4-dioxo-4-[3-(1,2,3,4-tetrahydronaphthalen-1-yl)-phenyl]butyric acid,
(6) 2,4-Dioxo-4-(3-phenylsulfanyl-phenyl)-butyric acid,
(7) 4-[3-(2,4-Difluoro-benzyl)-phenyl]-2,4-dioxo-butyric acid,
(8) 4-[5-(4-Fluoro-benzyl)-2,3-dimethoxy-phenyl]-2,4-dioxobutyric acid,
(9) 4-(5-Benzyl-2-isopropoxyphenyl)-2,4-dioxobutyric acid,
(10) 4-[5-Benzyl-2-(2-N,N-dimethylaminoethoxy)phenyl]-2,4-dioxobutyric acid,
(11) 4-[5-Benzyl-2-(pyridin-2-yloxy)phenyl]-2,4-dioxo-butyric acid,
(12) 4-(5-Benzyl-2-isopropoxy-3-methoxyphenyl)-2,4-dioxo-butyric acid,
(13) 4-(5-Benzyl-2,3-dimethoxyphenyl)-2,4-dioxobutyric acid,
(14) 4-(5-Benzyl-3-dimethylamino-2-methoxyphenyl)-2,4-dioxobutyric acid,
(15) 4-[5-Benzyl-2-N,N-dimethylaminobenzoxazol-7-yl]-2,4-dioxobutyric acid,
(16) 4-(3-Benzyl-5-pyrazin-2-ylmethylphenyl)-2,4-dioxobutyric acid,
(17) 4-(3-Benzyl-5-[1,2,3]triazol-2-ylmethylphenyl)-2,4-dioxobutyric acid,
(18) 4-[3-(3-Chloropyridin-2-ylmethyl)phenyl]-2,4-dioxobutyric acid,
(19) 4-[5-Benzyl-2-methoxy-3-(N,N-dimethylaminomethyl) phenyl]-2,4-dioxo-butyric acid,
(20) 4-(5-benzyl-3-methoxy-2-methoxyethoxyphenyl)-2,4-dioxobutyric acid,
(21) 4-(5-Benzyl-2-isopropoxy-3-[1,2,3]triazol-1-ylmethylphenyl)-2,4-dioxobutyric acid,
(22) 4-(5-Benzyl-2-isopropoxy-3-[1,2,4]triazol-1-ylmethylphenyl)-2,4-dioxobutyric acid,
(23) 4-[5-Benzyl-2-(3-N,N-dimethylaminopropoxy)-3-methoxyphenyl]-2,4-dioxobutyric acid,
(24) 4-[3-(Phenyldifluoromethyl)phenyl]-2,4-dioxobutyric acid,
(25) 4-(5-Benzyl-2-cyclopropyloxyphenyl)-2,4-dioxobutyric acid,
(26) 4-[5-Benzyl-2-isopropoxy-3-(1-piperidinylmethyl)phenyl]-2,4-dioxo-butyric acid,
(27) 4-[5-Benzyl-2-(2-dimethylamino-1-methylethoxy)phenyl]-2,4-dioxo-butyric acid,
(28) 4-[5-Benzyl-2-(1-methylpiperidin-4-yloxy)phenyl]-2,4-dioxo-butyric acid,
(29) 4-[3-Benzyl-5-(4-benzylpiperazin-1-yl)phenyl]-2,4-dioxo-butyric acid, and
(30) 4-[5-Benzyl-2-isopropoxy-3-(pyridin-2-ylaminomethyl) phenyl]-2,4-dioxo-butyric acid;

and tautomers and pharmaceutically acceptable salts thereof.

One class of compounds of the present invention is represented by the structural formula below:

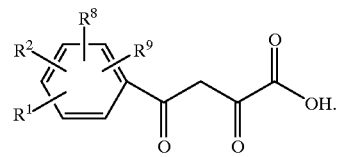

Another class of compounds of the present invention is represented by the structural formula below:

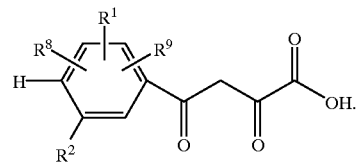

Another class of compounds of the present invention is represented by the following structural formula:

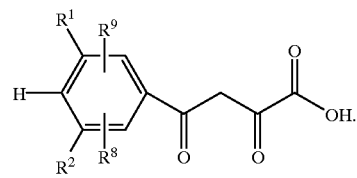

Still another class of compounds of the present invention is represented by the formula below:

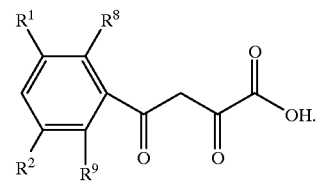

Another class of compounds of the present invention is represented by the following structural formula:

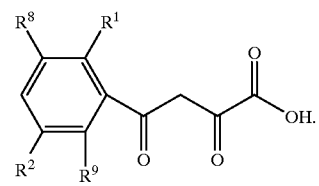

Yet another class of compounds of the present invention is represented by the following structural formula:

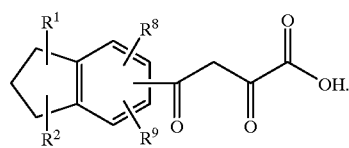

Still another class of compounds of the present invention is represented by the following structural formula:

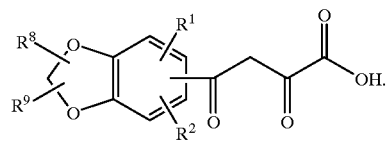

Another class of compounds of the present invention is represented by the following structural formula:

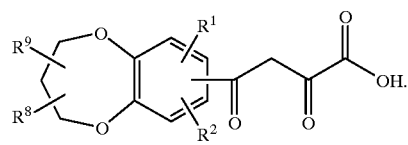

Yet another class of compounds of the present invention is represented by the following structural formula:

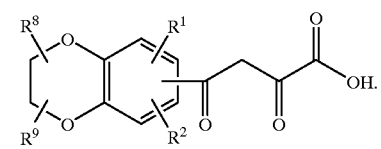

Still another class of compounds of the present invention is represented by the following structural formula:

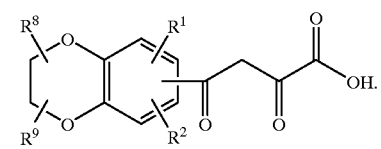

Another class of compounds of the present invention is represented by the following structural formula:

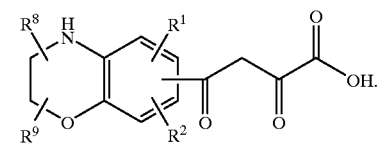

Yet another class of compounds of the present invention is represented by the following structural formula:

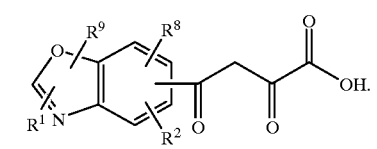

Still another class of compounds of the present invention is represented by the following structural formula:

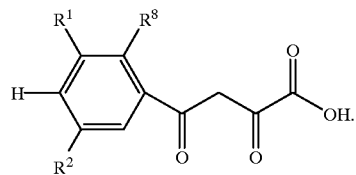

Another class of compounds of the present invention is represented by the following structural formula:

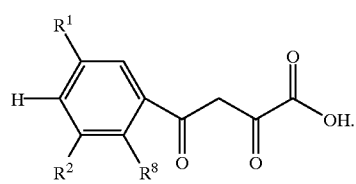

Still another class of compounds of the present invention is represented by the following structural formula:

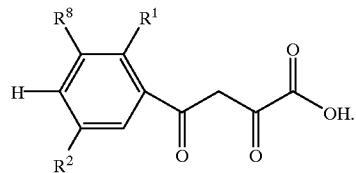

One class of compounds of the present invention is represented by the structural formula below:

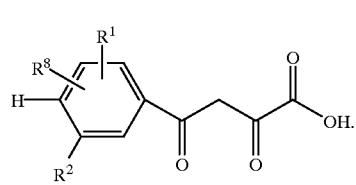

Another class of compounds of the present invention is represented by the following structural formula:

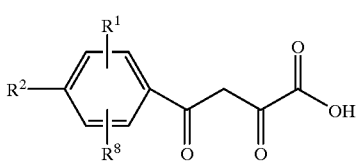

Still another class of compounds of the present invention is represented by the formula below:

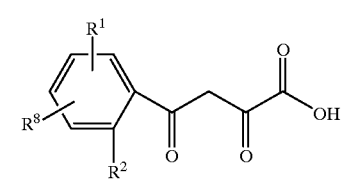

Another class of compounds of the present invention is represented by the following structural formula:

(10)
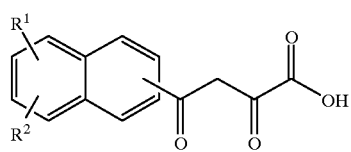

Another class of compounds of the present invention is represented by the following structural formula:

(11)
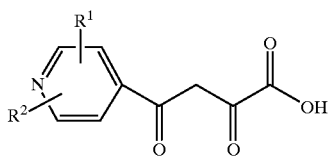

Another class of compounds of the present invention is represented by the following structural formula:

(12)
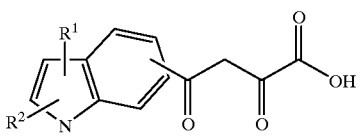

In one embodiment of the present invention, A is selected from:

(1) phenyl,
(2) pyridyl,
(3) naphthyl,
(4) indolyl, provided that the aryl ring is substituted by the dioxobutyric acid/ester moiety in structural formula (I), (5)
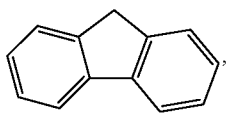

(6)
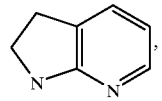

(7)
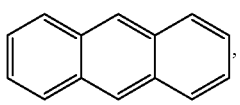

(8)
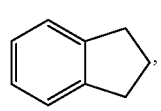

(9)
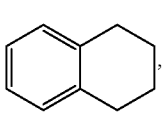

(10)
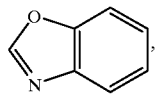

(11)
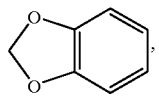

(12)
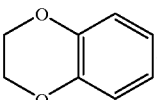

(13)
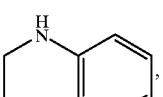

(14)
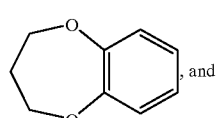, and

(15)
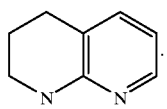.

In another embodiment of the present invention, A is selected from:

(1) phenyl,
(2) pyridinyl,
(3) indolyl, provided that 6-membered aromatic ring is substituted by the dioxobutyric moiety in structural formula (I);

(4)
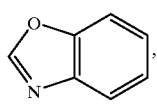

(5)
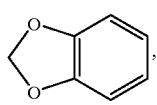

(6)
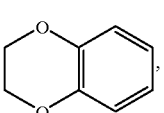

(7)
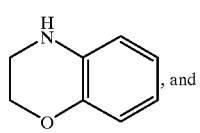, and (8)

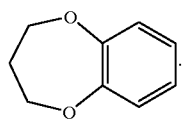

In still another embodiment of the present invention, A is phenyl.

In one embodiment of the present invention, $R^1$ is selected from:
(1) —H,
(2) —$C_{1-5}$ alkyl,
(3) —$C_{1-6}$ alkyl-$OR^7$;
(4) —O—$C_{1-6}$ alkyl-$OR^7$,
(5) —O—$C_{1-6}$ alkyl-$SR^7$,
(6) —$CF_3$ or —$CH_2CF_3$,
(7) —F, Cl, or Br,
(8) —$NO_2$,
(9) —$C_{0-3}$ alkyl-$N(R^4)(R^5)$,
(10) -phenyl,
(11) substituted phenyl substituted with 1 or 2 substituents independently selected from:
 (a) halogen,
 (b) $C_{1-6}$ alkyl,
 (c) $C_{1-6}$ alkyloxy-,
 (d) phenyl,
 (e) —$CF_3$,
 (f) —$OCF_3$,
 (g) —CN,
 (h) hydroxy,
 (i) phenyloxy, and
 (j) substituted phenyloxy with 1, 2, or 3 substituents selected from:
  (i) halogen,
  (ii) $C_{1-6}$ alkyl,
  (iii) —$CF_3$, and
  (iv) hydroxy;
(12) phenyl $C_{1-3}$ alkyl-, wherein the phenyl group may be unsubstituted or substituted with 1 to four substituents independently selected from:
 (a) halogen,
 (b) $C_{1-6}$ alkyl,
 (c) $C_{1-6}$ alkyloxy- wherein one or more of the hydrogen atoms may be replaced with a fluorine atom,
 (d) phenyl,
 (e) —$CF_3$,
 (f) —$SCH_3$,
 (g) —CN,
 (h) hydroxy,
 (i) phenyloxy,
 (j) —$C_{0-6}$ alkyl-$N(R^7)_2$, (k)

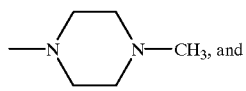

(l) substituted phenyloxy with 1, 2, or 3 substituents selected from:
 (i) halogen,
 (ii) $C_{1-6}$ alkyl,
 (iii) —$CF_3$, and
 (iv) hydroxy;
(13) —O—$R^6$,
(14) —O—$C_{1-6}$ alkyl, unsubstituted or substituted with one to three fluorine atoms,
(15) —O—$C_{1-6}$ alkyl-NH—C(O)—$OR^7$;
(16) —O—$C_{2-6}$ alkyl-$N(R^4)(R^5)$;
(17) —S—$C_{1-3}$ alkyl;
(18) —$C(O)CH_2C(O)C(O)OR^7$;
(19) —$CH_2$—CH(OH)—$CH_2$—O—$R^7$; and
(20) —$C(OH)(CH_3)$—$CH_2N(R^4)(R^5)$.

In another embodiment of the present invention, $R^1$ is selected from:
(1) —H,
(2) —$CH_3$,
(3) —$C_{1-6}$ alkyl-$OR^7$;
(4) —O—$C_{1-6}$ alkyl-$OR^7$,
(5) —O—$C_{1-6}$ alkyl-$SR^7$,
(6) —$CF_3$ or —$CH_2CF_3$,
(7) —Cl,
(8) —F,
(9) —$C_{0-3}$ alkyl-$N(R^4)(R^5)$,
(10) -phenyl,
(11) phenyl $C_{1-3}$ alkyl-, wherein the phenyl group may be unsubstituted or substituted with 1 to four substituents independently selected from:
 (a) —F, —Cl, or —Br,
 (b) $CH_3$,
 (c) —$OCH_3$, $OCH_2CH_3$, $OCF_3$, or $OCH_2CF_3$,
 (d) —$CF_3$,
 (e) —$SCH_3$,
 (f) —CN,
 (g) hydroxy,
 (h) —$C_{0-6}$ alkyl-$N(R^7)_2$,
(12) —O—$CH_2$-phenyl, wherein the phenyl group may be unsubstituted or substituted with 1 to four substituents independently selected from:
 (a) —F, —Cl, or —Br,
 (b) —$CH_3$,
 (c) —$OCH_3$, $OCH_2CH_3$, $OCF_3$, or $OCH_2CF_3$,
 (d) —$CF_3$,
 (e) —$SCH_3$,
 (f) —CN,
 (g) hydroxy,
 (h) —$C_{0-6}$ alkyl-$N(R^7)_2$,
(13) —O—$C_{1-6}$ alkyl, unsubstituted or substituted with one to three fluorine atoms, and
(14) —$C(O)CH_2C(O)C(O)OH$;
(15) —O—$C_{1-6}$ alkyl-NH—C(O)—$OR^7$;
(16) —O—$CH_2CH_2\ N(CH_3)_2$,
(17) —O—$CH(CH_3)CH_2N(CH_3)_2$,
(18) —O—$CH_2CH_2\ NH_2$,
(19) —O—$CH(CH_3)CH_2NH_2$,
(20) —S—$CH_3$,
(21) —$C(O)CH_2C(O)C(O)OH$,
(22) —$CH_2$—CH(OH)—$CH_2$—O—$R^7$, and
(23) —$C(OH)(CH_3)$—$CH_2N(R^4)(R^5)$.

In yet another embodiment of the present invention, $R^1$ is selected from:
(1) —H,
(2) —$CH_3$,
(3) —$CH_2OCH_3$, (4) —OCH$_2$CH$_2$OH,
(5) —OCH$_2$CH$_2$OCH$_3$,
(6) —(CH$_2$)$_6$—OH,
(7) —CF$_3$,
(8) —F,
(9) —Cl,
(10) —C$_{0-3}$ alkyl-N(R$^4$)(R$^5$),
(11) -phenyl,
(12) phenyl C$_{1-3}$ alkyl-, wherein the phenyl group may be unsubstituted or substituted with 1 to four substituents independently selected from:
 (a) —F, —Cl, or —Br,
 (b) CH$_3$,
 (c) —OCH$_3$, OCH$_2$CH$_3$, OCF$_3$, or OCH$_2$CF$_3$,
 (d) —CF$_3$,
 (e) —CN,
 (f) hydroxy,
 (g) —C$_{0-6}$ alkyl-N(R$^7$)$_2$,
(13) —O—CH$_2$-phenyl, wherein the phenyl group may be unsubstituted or substituted with 1 to four substituents independently selected from:
 (a) —F, —Cl, or —Br,
 (b) —CH$_3$,
 (c) —OCH$_3$, OCH$_2$CH$_3$, OCF$_3$, or OCH$_2$CF$_3$,
 (d) —CF$_3$,
 (e) —CN,
 (f) hydroxy,
 (g) —C$_{0-6}$ alkyl-N(R$^7$)$_2$,
(14) —O—CH$_3$,
(15) —OCH$_2$CH$_3$,
(16) —OCH$_2$CF$_3$,
(17) —OCF$_3$,
(18) —OCH(CH$_3$)$_2$,
(19) —C(O)CH$_2$C(O)C(O)OH,
(20) —O—C$_{1-6}$ alkyl-NH—C(O)—OR$^7$,
(21) —O—CH$_2$CH$_2$N(CH$_3$)$_2$,
(22) —O—CH(CH$_3$)CH$_2$N(CH$_3$)$_2$,
(23) —O—CH$_2$CH$_2$ NH$_2$,
(24) —O—CH(CH$_3$)CH$_2$NH$_2$,
(25) —S—CH$_3$,
(26) —C(O)CH$_2$C(O)C(O)OH,
(27) —CH$_2$—CH(OH)—CH$_2$—O—R$^7$, and
(28) —C(OH)(CH$_3$)—CH$_2$N(R$^4$)(R$^5$).

In another embodiment of the present invention, R$^1$ is selected from:
(1) —H,
(2) -phenyl,
(3) substituted phenyl substituted with 1 or 2 substituents independently selected from:
 (a) halo, selected from —F, —Br, —Cl,
 (b) methyl, and
 (c) methoxy,
(4) phenyl C$_{1-3}$ alkyl-,
(5) —O—R$^6$,
(6) —O—CH$_3$, and
(7) —C(O)CH$_2$C(O)C(O)OR$^7$.

In one embodiment of the present invention, R$^2$ is selected from:
(1) —H,
(2) —R$^3$,
(3) —C$_{1-6}$ alkyl,
(4) —C$_{1-6}$ alkyl substituted with R$^3$, wherein one or more of the hydrogen atoms on C$_{1-6}$ alkyl may be replaced with a fluorine atom,
(5) —O—R$^6$,
(6) —S—R$^6$,
(7) —O—C$_{1-6}$ alkyl-SR$^6$;
(8) —C$_{1-6}$ alkyl (OR$^6$)(R$^4$),
(9) —C$_{0-6}$ alkyl-N(R$^4$)(R$^6$),
(10) —C$_{1-6}$ alkyl-S—R$^6$,
(11) —C$_{0-6}$ alkyl-C(O)—R$^6$,
(12) —C$_{0-6}$ alkyl-C(O)CH$_2$—C(O)—OH,
(13) —C$_{1-6}$ alkyl NR$^4$C(O)—R$^6$,
(14) —C$_{1-6}$ alkyl-C(O)N(R$^4$)(R$^5$), and
(15) —CH$_2$(OR$^7$)—R$^6$.

In another embodiment of the present invention, R$^2$ is selected from:
(1) —H,
(2) —R$^3$,
(3) —CH$_3$,
(4) —C$_{1-6}$ alkyl substituted with R$^3$, wherein one or more of the hydrogen atoms on C$_{1-6}$ alkyl may be replaced with a fluorine atom,
(5) —O—R$^6$,
(6) —S—R$^6$,
(7) —O—C$_{1-6}$ alkyl-SR$^6$;
(8) —C$_{1-6}$ alkyl (OR$^6$)(R$^4$),
(9) —C$_{0-6}$ alkyl-N(R$^4$)(R$^6$),
(10) —C$_{0-6}$ alkyl C(O)—R$^6$,
(11) —C$_{0-6}$ alkyl C(O)CH$_2$—C(O)—OH,
(12) —C$_{1-6}$ alkyl NR$^4$C(O)—R$^6$,
(13) —C$_{1-6}$ alkyl-C(O)N(R$^4$)(R$^5$), and
(14) —CH$_2$(OR$^7$)—R$^6$.

In yet another embodiment of the present invention, R$^2$ is selected from:
(1) —H,
(2) —R$^3$,
(3) —CH$_2$—R$^3$,
(4) —CH$_2$CH$_2$—R$^3$,
(5) —CF$_2$—R$^3$,
(6) —CH(CH$_3$)—R$^3$,
(7) —O—R$^6$,
(8) —S-phenyl,
(9) —C$_{1-6}$ alkyl (OR$^6$)(R$^4$),
(10) —C$_{0-6}$ alkyl-N(R$^4$)(R$^6$),
(11) —C(O)—R$^3$,
(12) —C$_{0-6}$ alkyl C(O)CH$_2$—C(O)—OH,
(13) —C$_{1-6}$ alkyl NR$^4$C(O)—R$^6$,
(14) —CH(OCH$_3$)R$^3$, and
(15) —CH(OH)R$^3$.

In another embodiment of the present invention, R$^2$ is selected from:
(1) —R$^3$,
(2) —C$_{1-6}$ alkyl substituted with R$^3$,
(3) —O—R$^6$,
(4) —S(O)$_n$—R$^6$,
(5) —C$_{1-6}$ alkyl (OR$^6$)(R$^4$),
(6) —C$_{0-6}$ alkyl-N(R$^4$)(R$^6$), and
(7) —C$_{1-6}$ alkyl-C(O)N(R$^4$)(R$^5$).

In one embodiment of the present invention, $R^3$ is selected from:
(1) phenyl;
(2) substituted phenyl with 1, 2, 3 or 4 substituents independently selected from:
  (a) halogen,
  (b) $C_{1-6}$ alkyl, wherein one or more of the hydrogen atoms may be replaced with a fluorine atom,
  (c) $C_{1-6}$ alkyloxy- wherein one or more of the hydrogen atoms may be replaced with a fluorine atom,
  (d) phenyl,
  (e) —S—$C_{1-6}$ alkyl,
  (f) —CN,
  (g) hydroxy,
  (h) phenyloxy,
  (i) —$C_{0-6}$ alkyl-N$(R^7)_2$,
  (j)

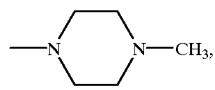

(k) oxo, and
  (l) substituted phenyloxy with 1, 2, or 3 substituents selected from:
    (i) halogen,
    (ii) $C_{1-6}$ alkyl,
    (iii) —$CF_3$, and
    (iv) hydroxy;
(3) thienyl,
(4) substituted thienyl substituted on carbon with one or two substituents independently selected from:
  (a) halogen,
  (b) $C_{1-6}$ alkyl, wherein one or more of the hydrogen atoms may be replaced with a fluorine atom,
  (c) $C_{1-6}$ alkyloxy- wherein one or more of the hydrogen atoms may be replaced with a fluorine atom,
  (d) phenyl,
  (e) —S—$C_{1-6}$ alkyl,
  (f) —CN,
  (g) hydroxy,
  (h) phenyloxy,
  (i) —$C_{0-6}$ alkyl-N$(R^7)_2$,
  (j)

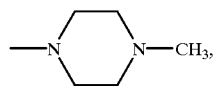

(k) oxo, and
  (l) substituted phenyloxy with 1, 2, or 3 substituents selected from:
    (i) halogen,
    (ii) $C_{1-6}$ alkyl,
    (iii) —$CF_3$, and
    (iv) hydroxy;
(5) pyridyl,
(6) substituted pyridyl substituted on carbon with one or two substituents independently selected from:
  (a) halogen,
  (b) $C_{1-6}$ alkyl, wherein one or more of the hydrogen atoms may be replaced with a fluorine atom,
  (c) $C_{1-6}$ alkyloxy- wherein one or more of the hydrogen atoms may be replaced with a fluorine atom,
  (d) phenyl,
  (e) —S—$C_{1-6}$ alkyl,
  (f) —CN,
  (g) hydroxy,
  (h) phenyloxy,
  (i) —$C_{0-6}$ alkyl-N$(R^7)_2$,
  (j)

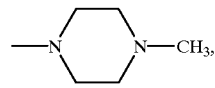

(k) oxo, and
  (l) substituted phenyloxy with 1, 2, or 3 substituents selected from:
    (i) halogen,
    (ii) $C_{1-6}$ alkyl,
    (iii) —$CF_3$, and
    (iv) hydroxy;
(7) imidazolyl,
(8) substituted imidazolyl substituted on carbon with one or two substituents independently selected from:
  (a) halogen,
  (b) $C_{1-6}$ alkyl, wherein one or more of the hydrogen atoms may be replaced with a fluorine atom,
  (c) $C_{1-6}$ alkyloxy- wherein one or more of the hydrogen atoms may be replaced with a fluorine atom,
  (d) phenyl,
  (e) —S—$C_{1-6}$ alkyl,
  (f) —CN,
  (g) hydroxy,
  (h) phenyloxy,
  (i) —$C_{0-6}$ alkyl-N$(R^7)_2$,
  (j)

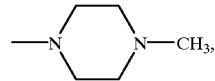

(k) oxo, and
  (l) substituted phenyloxy with 1, 2, or 3 substituents selected from:
    (i) halogen,
    (ii) $C_{1-6}$ alkyl,
    (iii) —$CF_3$, and
    (iv) hydroxy;
(9) pyrrolyl,
(10) substituted pyrrolyl substituted on carbon with one or two substituents independently selected from:
  (a) halogen,
  (b) $C_{1-6}$ alkyl, wherein one or more of the hydrogen atoms may be replaced with a fluorine atom,
  (c) $C_{1-6}$ alkyloxy- wherein one or more of the hydrogen atoms may be replaced with a fluorine atom,
  (d) phenyl,
  (e) —S—$C_{1-6}$ alkyl,
  (f) —CN,
  (g) hydroxy, (h) phenyloxy,
(i) —$C_{0-6}$ alkyl-N($R^7$)$_2$, (j)

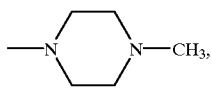

(k) oxo, and
(l) substituted phenyloxy with 1, 2, or 3 substituents selected from:
  (i) halogen,
  (ii) $C_{1-6}$ alkyl,
  (iii) —$CF_3$, and
  (iv) hydroxy;
(11) pyrazolyl,
(12) substituted pyrazolyl substituted on carbon with one or two substituents independently selected from:
  (a) halogen,
  (b) $C_{1-6}$ alkyl, wherein one or more of the hydrogen atoms may be replaced with a fluorine atom,
  (c) $C_{1-6}$ alkyloxy- wherein one or more of the hydrogen atoms may be replaced with a fluorine atom,
  (d) phenyl,
  (e) —S—$C_{1-6}$ alkyl,
  (f) —CN,
  (g) hydroxy,
  (h) phenyloxy,
  (i) —$C_{0-6}$ alkyl-N($R^7$)$_2$, (j)

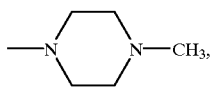

(k) oxo, and
(l) substituted phenyloxy with 1, 2, or 3 substituents selected from:
  (i) halogen,
  (ii) $C_{1-6}$ alkyl,
  (iii) —$CF_3$, and
  (iv) hydroxy;
(15) piperidinyl,
(16) substituted piperidinyl substituted on carbon with one or two substituents independently selected from:
  (a) halogen,
  (b) $C_{1-6}$ alkyl,
  (c) $C_{1-6}$ alkyloxy-,
  (d) —$CF_3$,
  (e) —$OCF_3$,
  (f) —CN,
  (g) =O,
  (h) benzyl, and
  (i) hydroxy;
(17) morpholinyl,
(18) substituted morpholinyl substituted at a carbon or nitrogen atom with 1 or 2 substituents independently selected from:
  (a) halogen,
  (b) $C_{1-6}$ alkyl,
  (c) $C_{1-6}$ alkyloxy-,
  (d) —$CF_3$,
  (e) —$OCF_3$,
  (f) —CN,
  (g) =O,
  (h) benzyl, and
  (i) hydroxy;
(19) hexahydrothieno[3,4-d]imidazolyl,
(20) substituted hexahydrothieno[3,4-d]substituted hexahydrothieno[3,4-d]imidazolyl with one or two substituents independently selected from:
  (a) oxo,
  (b) halogen,
  (c) $C_{1-6}$ alkyl,
  (d) $C_{1-6}$ alkyloxy-,
  (e) —$CF_3$,
  (f) —$OCF_3$,
  (g) —CN, and
  (h) hydroxy,
(21) naphthyl,
(22) substituted naphthyl with 1, 2, or 3 substituents independently selected from:
  (a) -halogen,
  (b) —$C_{1-6}$ alkyl,
  (C) —$C_{1-6}$ alkyloxy-,
  (d) —$CF_3$,
  (e) —$OCF_3$,
  (f) —CN, and
  (g) -hydroxy,
(23) indolyl,
(24) substituted indolyl substituted on a carbon atom with one or two substituents independently selected from:
  (a) -halogen,
  (b) —$C_{1-6}$ alkyl,
  (c) $C_{1-6}$ alkyloxy-,
  (d) —$CF_3$,
  (e) —$OCF_3$,
  (f) —CN, and
  (g) -hydroxy;
(25) $C_{3-6}$ cycloalkyl fused with a phenyl ring;
(26) substituted $C_{3-6}$ cycloalkyl fused with a phenyl ring substituted on carbon with one or two substituents independently selected from:
  (a) halogen,
  (b) $C_{1-6}$ alkyl,
  (c) $C_{1-6}$ alkyloxy-,
  (d) —$CF_3$,
  (e) —$OCF_3$,
  (f) —CN,
  (g) =O, and
  (h) hydroxy;
(27) pyrazinyl;
(28) substituted pyrazinyl substituted on nitrogen or carbon with one or two substituents independently selected from:
  (a) halogen,
  (b) $C_{1-6}$ alkyl, wherein one or more of the hydrogen atoms may be replaced with a fluorine atom,
  (c) $C_{1-6}$ alkyloxy- wherein one or more of the hydrogen atoms may be replaced with a fluorine atom,
  (d) phenyl,
  (e) —S—$C_{1-6}$ alkyl,
  (f) —CN,
  (g) hydroxy, (h) phenyloxy,
(i) —$C_{0-6}$ alkyl-N($R^7$)$_2$, (j)

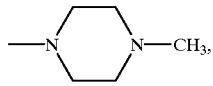

(k) oxo, and
(l) substituted phenyloxy with 1, 2, or 3 substituents selected from:
  (i) halogen,
  (ii) $C_{1-6}$ alkyl,
  (iii) —$CF_3$, and
  (iv) hydroxy;
(29) pyrimidinyl;
(30) substituted pyrimidinyl substituted on nitrogen or carbon with one or two substituents independently selected from:
  (a) halogen,
  (b) $C_{1-6}$ alkyl, wherein one or more of the hydrogen atoms may be replaced with a fluorine atom,
  (c) $C_{1-6}$ alkyloxy- wherein one or more of the hydrogen atoms may be replaced with a fluorine atom,
  (d) phenyl,
  (e) —S—$C_{1-6}$ alkyl,
  (f) —CN,
  (g) hydroxy,
  (h) phenyloxy,
  (i) —$C_{0-6}$ alkyl-N($R^7$)$_2$, (j)

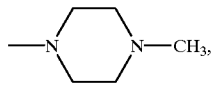

(k) oxo, and
(l) substituted phenyloxy with 1, 2, or 3 substituents selected from:
  (i) halogen,
  (ii) $C_{1-6}$ alkyl,
  (iii) —$CF_3$, and
  (iv) hydroxy;
(31) triazolyl;
(32) substituted triazolyl with one or two substituents independently selected from:
  (a) halogen,
  (b) $C_{1-6}$ alkyl, wherein one or more of the hydrogen atoms may be replaced with a fluorine atom,
  (c) $C_{1-6}$ alkyloxy- wherein one or more of the hydrogen atoms may be replaced with a fluorine atom,
  (d) phenyl,
  (e) —S—$C_{1-6}$ alkyl,
  (f) —CN,
  (g) hydroxy,
  (h) phenyloxy,
  (i) —$C_{0-6}$ alkyl-N($R^7$)$_2$, (j)

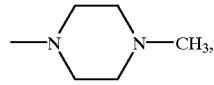

(k) oxo, and
(l) substituted phenyloxy with 1, 2, or 3 substituents selected from:
  (i) halogen,
  (ii) $C_{1-6}$ alkyl,
  (iii) —$CF_3$, and
  (iv) hydroxy;
(33) tetrazolyl;
(34) substituted tetrazolyl with a substituent selected from:
  (a) halogen,
  (b) $C_{1-6}$ alkyl, wherein one or more of the hydrogen atoms may be replaced with a fluorine atom,
  (c) $C_{1-6}$ alkyloxy- wherein one or more of the hydrogen atoms may be replaced with a fluorine atom,
  (d) phenyl,
  (e) —S—$C_{1-6}$ alkyl,
  (f) —CN,
  (g) hydroxy,
  (h) phenyloxy,
  (i) —$C_{0-6}$ alkyl-N($R^7$)$_2$, (j)

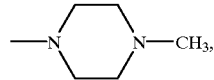

(k) oxo, and
(l) substituted phenyloxy with 1, 2, or 3 substituents selected from:
  (i) halogen,
  (ii) $C_{1-6}$ alkyl,
  (iii) —$CF_3$, and
  (iv) hydroxy;
(35) $C_{3-6}$ cycloalkyl;
(36) substituted $C_{3-6}$ cycloalkyl substituted with one or two substituents independently selected from:
  (a) halogen,
  (b) $C_{1-6}$ alkyl,
  (c) $C_{1-6}$ alkyloxy-,
  (d) —$CF_3$,
  (e) —$OCF_3$,
  (f) —CN,
  (g) =O,
  (h) benzyl, and
  (i) hydroxy;
(37) tetrahydrofuran;
(38) substituted tetrahydrofuran substituted with one or two substituents independently selected from:
  (a) halogen,
  (b) $C_{1-6}$ alkyl,
  (c) $C_{1-6}$ alkyloxy-,
  (d) —$CF_3$,
  (e) —$OCF_3$,
  (f) —CN,
  (g) =O, (h) benzyl, and
(i) hydroxy;
(39) piperazinyl;
(40) substituted piperazinyl substituted with one or two substituents independently selected from:
(a) halogen,
(b) $C_{1-6}$ alkyl,
(c) $C_{1-6}$ alkyloxy-,
(d) —$CF_3$,
(e) —$OCF_3$,
(f) —CN,
(g) =O,
(h) benzyl, and
(i) hydroxy;
(41) benzotriazolyl,
(42) substituted benzotriazolyl substituted on a carbon atom with one or two substituents independently selected from:
(a) -halogen,
(b) —$C_{1-6}$ alkyl,
(c) —$C_{1-6}$ alkyloxy-,
(d) —$CF_3$,
(e) —$OCF_3$,
(f) —CN, and
(g) -hydroxy;
(43) benzoimidazolyl,
(44) substituted benzoimidazolyl substituted on a carbon atom with one or two substituents independently selected from:
(a) -halogen,
(b) —$C_{1-6}$ alkyl,
(c) —$C_{1-6}$ alkyloxy-,
(d) —$CF_3$,
(e) —$OCF_3$,
(f) —CN, and
(g) -hydroxy.

In another embodiment of the present invention, $R^3$ is selected from:
(1) phenyl;
(2) substituted phenyl with 1, 2, 3 or 4 substituents independently selected from:
(a) halogen, selected from —F, —Cl, —Br,
(b) $C_{1-6}$ alkyl, wherein one or more of the hydrogen atoms may be replaced with a fluorine atom
(c) $C_{1-6}$ alkyloxy- wherein one or more of the hydrogen atoms may be replaced with a fluorine atom,
(d) —CN,
(e) hydroxy, and
(f) oxo;
(3) thienyl,
(4) substituted thienyl substituted on carbon with one or two substituents independently selected from:
(a) halogen, selected from F, Cl, and Br,
(b) $C_{1-6}$ alkyl, wherein one or more of the hydrogen atoms may be replaced with a fluorine atom, and
(c) $C_{1-6}$ alkyloxy- wherein one or more of the hydrogen atoms may be replaced with a fluorine atom;
(5) pyridyl,
(6) substituted pyridyl substituted on carbon with one or two substituents independently selected from:
(a) halogen, selected from —F, —Cl, and —Br;
(b) $C_{1-6}$ alkyl, wherein one or more of the hydrogen atoms may be replaced with a fluorine atom,
(c) $C_{1-6}$ alkyloxy- wherein one or more of the hydrogen atoms may be replaced with a fluorine atom,
(d) hydroxy, and
(e) oxo;
(7) imidazolyl,
(8) pyrrolyl,
(9) pyrazolyl
(10) substituted pyrazolyl substituted on carbon with one or two substituents independently selected from:
(a) halogen, selected from —F, —Cl, and —Br;
(b) —$CH_3$,
(c) —$CF_3$,
(d) —$OCH_3$,
(e) —$OCF_3$, and
(f) hydroxy;
(11) $C_{3-6}$ cycloalkyl,
(12) substituted $C_{3-6}$ cycloalkyl with 1 or 2 substituents independently selected from:
(a) halogen, selected from —F, —Cl, and —Br,
(b) $CH_3$,
(c) methyloxy-,
(d) —$CF_3$,
(e) —$OCF_3$,
(f) —CN,
(g) =O, and
(h) hydroxy;
(13) piperidinyl,
(14) substituted piperidinyl substituted on carbon with one or two substituents independently selected from:
(a) halogen selected from —F, —Cl, and —Br,
(b) methyl,
(c) methoxy-,
(d) —$CF_3$,
(e) —$OCF_3$,
(f) =O, and
(g) hydroxy;
(15) morpholinyl,
(16) substituted morpholinyl substituted on carbon or nitrogen with 1 or 2 substituents independently selected from:
(a) halogen, selected from —F, —Cl, and —Br,
(b) methyl,
(c) methoxy-,
(d) —$CF_3$,
(e) —$OCF_3$, and
(f) hydroxy,
(17) hexahydrothieno[3,4-d]imidazolyl,
(18) naphthyl,
(19) substituted naphthyl with 1, 2, or 3 substituents independently selected from:
(a) -halogen, selected from —F, —Cl, and —Br,
(b) methyl,
(c) methoxy-,
(d) —$CF_3$,
(e) —$OCF_3$,
(f) —CN, and
(g) -hydroxy,
(20) indolyl,
(21) 1,2,3,4-tetrahydronaphthalenyl,
(22) substituted 1,2,3,4-tetrahydronaphthalenyl substituted on carbon with a substituent selected from:
(a) halogen, selected from —F, —Cl, and —Br,
(b) methyl,
(c) methoxy-,
(d) —$CF_3$,
(e) —$OCF_3$, (f) —CN,
(g) =O, and
(h) hydroxy;
(23) pyrazinyl;
(24) substituted pyrazinyl substituted on nitrogen or carbon with one or two substituents independently selected from:
(a) halogen, selected from —F, —Cl, and —Br,
(b) $C_{1-6}$ alkyl, wherein one or more of the hydrogen atoms may be replaced with a fluorine atom,
(c) $C_{1-6}$ alkyloxy- wherein one or more of the hydrogen atoms may be replaced with a fluorine atom,
(d) hydroxy,
(e) phenyloxy,
(f) —$C_{0-6}$ alkyl-N($R^7$)$_2$, and
(g)

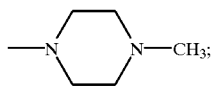

(25) pyrimidinyl;
(26) substituted pyrimidinyl substituted on nitrogen or carbon with a substituent selected from:
(a) halogen, selected from —F, —Cl, and —Br,
(b) methyl,
(c) methoxy-, and
(d) phenyl,
(27) triazolyl;
(28) substituted triazolyl with a substituent selected from:
(a) halogen, selected from —F, —Cl, and —Br,
(b) methyl,
(c) methoxy-, and
(d) hydroxy,
(29) tetrazolyl;
(30) substituted tetrazolyl with a substituent selected from:
(a) halogen, selected from —F, —Cl, and —Br,
(b) methyl,
(c) methoxy-, and
(d) hydroxy,
(31) $C_{3-6}$ cycloalkyl;
(32) substituted $C_{3-6}$ cycloalkyl substituted with one or two substituents independently selected from:
(a) halogen, selected from —F, —Cl, and —Br,
(b) methyl,
(c) methoxy-,
(d) —$CF_3$, and
(e) —$OCF_3$,
(33) tetrahydrofuran;
(34) substituted tetrahydrofuran substituted with one or two substituents independently selected from:
(a) halogen, selected from —F, —Cl, and —Br,
(b) methyl,
(c) methoxy-,
(d) —$CF_3$, and
(e) —$OCF_3$,
(35) piperazinyl;
(36) substituted piperazinyl substituted with one or two substituents independently selected from:
(a) halogen, selected from —F, —Cl, and —Br,
(b) $C_{1-6}$ alkyl,
(c) $C_{1-6}$ alkyloxy-,
(d) —$CF_3$,
(e) —$OCF_3$,
(f) benzyl, and
(g) hydroxy;
(37) benzotriazolyl,
(38) substituted benzotriazolyl substituted on carbon with one or two substituents independently selected from:
(a) -halogen, selected from —F, —Cl. and —Br,
(b) -methyl,
(c) methoxy-,
(d) —$CF_3$, and
(e) —$OCF_3$,
(39) benzoimidazolyl, and
(40) substituted benzoimidazolyl substituted on carbon with one or two substituents independently selected from:
(a) -halogen, selected from —F, —Cl. and —Br,
(b) -methyl,
(c) methoxy-,
(d) —$CF_3$, and
(e) —$OCF_3$.

In yet another embodiment of the present invention, each $R^3$ is independently selected from:
(1) phenyl,
(2) substituted phenyl with 1, 2, or 3 substituents independently selected from:
(a) halogen, selected from —F, —Cl, —Br,
(b) —$CH_3$,
(c) methyloxy-,
(d) ethyloxy-,
(e) —$OCH_2CF_3$,
(f) —$OCF_2CH_3$,
(g) —$CF_3$,
(h) —$CH_2CF_3$,
(i) —$CF_2CH_3$,
(j) —$OCF_3$,
(k) —CN, and
(l) hydroxy;
(3) thienyl,
(4) substituted thienyl substituted on a carbon atom with a substituent selected from:
(a) F,
(b) Cl, and
(c) methyl;
(5) pyridyl,
(6) substituted pyridyl substituted on a carbon with a substituent selected from:
(a) —F,
(b) —Cl,
(c) —$CH_3$,
(d) —$CF_3$,
(e) —$OCH_3$,
(f) —$OCF_3$,
(g) hydroxy, and
(h) oxo;
(7) pyrazolyl
(8) substituted pyrazolyl substituted on carbon with one or two substituents independently selected from:
(a) —F,
(b) —Cl,
(c) —$CH_3$, and
(d) —$CF_3$;
(9) $C_{3-6}$ cycloalkyl,
(10) piperidinyl,
(11) substituted piperidinyl substituted on carbon with a substituent selected from:

(a) methoxy-,
(b) —OCF$_3$,
(c) =O, and
(d) hydroxy;
(12) morpholinyl,
(13) naphthyl,
(14) 1,2,3,4-tetrahydronaphthalenyl,
(15) pyrazinyl;
(16) substituted pyrazinyl substituted on nitrogen or carbon with a substituent selected from:
  (a) halogen, selected from —F, —Cl, and —Br,
  (b) methyl,
  (c) —CF$_3$,
  (d) methoxy-,
  (e) —N(CH$_3$)$_2$, and (f)

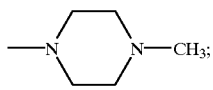

(17) pyrimidinyl,
(18) [1,2,3]-triazolyl,
(19) [1,2,4]-triazolyl,
(20) tetrazolyl;
(21) cyclopropyl,
(22) cyclobutyl,
(23) cyclopentyl,
(24) cyclohexyl,
(25) tetrahydrofuran,
(26) piperazinyl;
(27) substituted piperazinyl substituted with a substituent selected from:
  (a) —F,
  (b) —Cl,
  (c) methyl,
  (d) —CF$_3$, and
  (e) benzyl,
(28) benzotriazolyl, and
(29) benzoimidazolyl.

In still another embodiment of the present invention, R$^3$ is selected from:
(1) phenyl;
(2) substituted phenyl with 1, 2, or 3 substituents independently selected from:
  (a) halogen, selected from —F, —Cl, —Br,
  (b) —CH$_3$,
  (c) methyloxy-,
  (d) phenyl,
  (e) —CF$_3$,
  (f) —OCF$_3$,
  (g) —CN,
  (h) hydroxy,
  (i) phenyloxy, and
  (j) substituted phenyloxy with 1, 2, or 3 substituents selected from:
    (i) halogen, selected from —F, —Cl, —Br,
    (ii) —CH$_3$,
    (iii) —CF$_3$, and
    (iv) hydroxy.

In one embodiment of the present invention, each R$^4$ is independently selected from:
(1) —H,
(2) —C$_{1-4}$ alkyl,
(3) —CF$_3$,
(4) —R$^3$,
(5) —C$_{2-3}$ alkenyl,
(6) —C$_{1-3}$ alkyl-R$^3$,
(7) —C$_{2-3}$ alkenyl-R$^3$, and
(8) —C(O)—R$^3$.

In another embodiment of the present invention, each R$^4$ is independently selected from:
(1) —H,
(2) —C$_{1-4}$ alkyl,
(3) —CF$_3$,
(4) —R$^3$,
(5) —C$_{1-3}$ alkyl-R$^3$, and
(6) —C(O)—R$^3$.

In one embodiment of the present invention, each R$^5$ is independently selected from:
(1) —H,
(2) —C$_{1-3}$ alkyl,
(3) —CF$_3$,
(4) —R$^3$,
(5) —C$_{2-3}$ alkenyl,
(6) —C$_{1-3}$ alkyl-R$^3$,
(7) —S(O)$_n$—R$^3$,
(8) —C(O)—R$^3$,
(9) —C(O)OR$^4$, and
(10) —C(O)C(O)OH;

In another embodiment of the present invention, each R$^5$ is independently selected from:
(1) —H,
(2) —C$_{1-3}$ alkyl,
(3) —CF$_3$,
(4) —R$^3$,
(5) —C$_{1-3}$ alkyl-R$^3$,
(6) —C(O)—R$^3$,
(7) —C(O)OR$^4$, and
(8) —C(O)C(O)OH.

In another embodiment of the present invention, each R$^5$ is independently selected from:
(1) —H,
(2) —CH$_3$,
(3) —CF$_3$,
(4) phenyl,
(5) -benzyl,
(6) —C(O)OR$^4$, and
(7) —C(O)C(O)OH;

In one embodiment of the present invention, R$^7$ is independently selected from H, and —C$_{1-6}$ alkyl.

In one embodiment of the present invention, R$^8$ is selected from hydrogen, methyl and —O—C$_{1-6}$ alkyl.

In yet another embodiment of the present invention, R$^8$ is hydrogen.

In one embodiment of the present invention, R$^9$ is selected from:
(1) —H,
(2) —O—C$_{1-3}$ alkyl,
(3) —OH, and
(4) oxo.

Also included within the present invention are pharmaceutical compositions useful for inhibiting HIV integrase, comprising an effective amount of a compound of this invention, and a pharmaceutically acceptable carrier. Pharmaceutical compositions useful for treating infection by HIV, or for treating AIDS or ARC, are also encompassed by the present invention, as well as a method of inhibiting HIV integrase, and a method of treating infection by HIV, or of treating AIDS or ARC. Additionally, the present invention is directed to a pharmaceutical composition comprising a therapeutically effective amount of a compound of the present invention in combination with a therapeutically effective amount of an AIDS treatment agent selected from:

(1) an AIDS antiviral agent, (2) an anti-infective agent, and (3) an immunomodulator.

The compounds of the present invention may have asymmetric centers and may occur, except when specifically noted, as mixtures of stereoisomers or as individual diastereomers, or enantiomers, with all isomeric forms being included in the present invention.

As is recognized by one of ordinary skill in the art, the diketo-acid/ester compounds of the present invention exist as tautomers, and thus by using the phrase "and tautomers thereof" in describing compounds of structural formula (I), Applicants also intend the following tautomeric forms of the same compound (IA) and (IB):

compounds of this invention are useful in treating infection by HIV after suspected past exposure to HIV by e.g., blood transfusion, exchange of body fluids, bites, accidental needle stick, or exposure to patient blood during surgery.

The compounds of this invention are useful in the preparation and execution of screening assays for antiviral compounds. For example, the compounds of this invention are useful for isolating enzyme mutants, which are excellent screening tools for more powerful antiviral compounds. Furthermore, the compounds of this invention are useful in establishing or determining the binding site of other antivirals to HIV integrase, e.g., by competitive inhibition. Thus the compounds of this invention are commercial products to be sold for these purposes.

The present invention also provides for the use of a compound of structural formula (I) to make a pharmaceutical composition useful for inhibiting HIV integrase and in the treatment of AIDS or ARC.

Schemes AI, AII, and AVI illustrate the preparation of compounds wherein A is di-aryloxy/alkyloxy substituted phenyl. Scheme AIII illustrates the preparation of the compounds of the present invention wherein A is arylalkyl substituted phenyl. Schemes AIV and AV describe the synthesis of compounds wherein A is amino substituted phenyl.

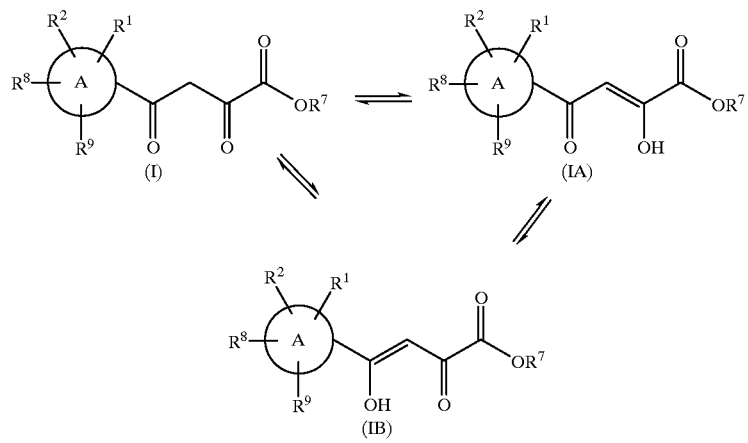

By naming or referring to compound (I) and tautomers thereof, it is understood for the purposes of the present application that the tautomers (IA) and (IB) are also intended. Similarly, by referring to compound (IA), it is understood for the purposes of the present application that the tautomers (I) and (IB) are also intended. The same holds true for references to tautomer (IB).

When any variable (e.g., $R^3$, $R^4$, etc.) occurs more than one time in any constituent or in formula I, its definition on each occurrence is independent of its definition at every other occurrence. Also, combinations of substituents and/or variables are permissible only if such combinations result in stable compounds.

The compounds of the present inventions are useful in the inhibition of HIV integrase, the prevention or treatment of infection by human immunodeficiency virus (HIV) and the treatment of consequent pathological conditions such as AIDS. Treating AIDS or preventing or treating infection by HIV is defined as including, but not limited to, treating a wide range of states of HIV infection: AIDS, ARC (AIDS related complex), both symptomatic and asymptomatic, and actual or potential exposure to HIV. For example, the Scheme AVII describes the synthesis of compounds wherein A is indolyl. Scheme IX illustrates the synthesis of pyridyl compounds.

SCHEME AI

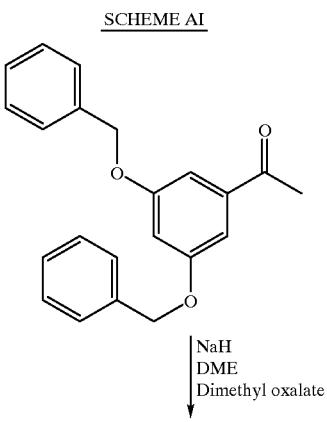

41
-continued
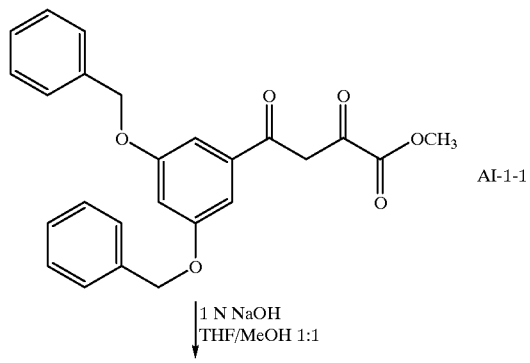
AI-1-1
42
-continued
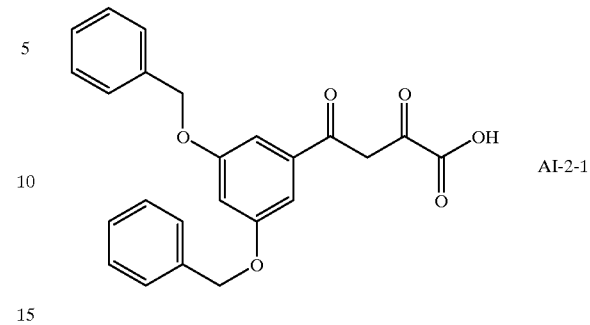
AI-2-1
SCHEME AII
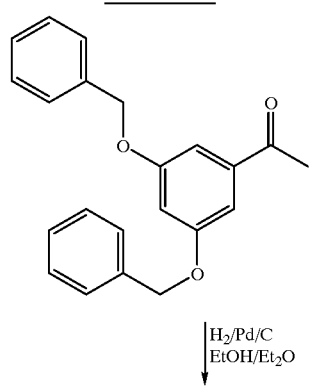
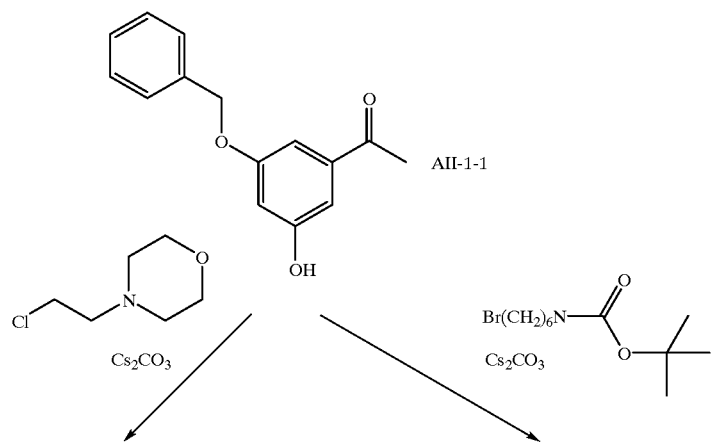
AII-1-1

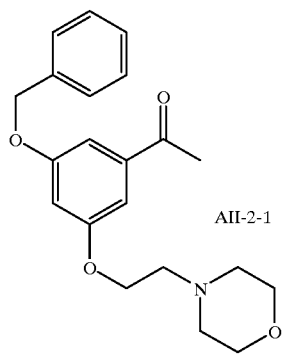 AII-2-1
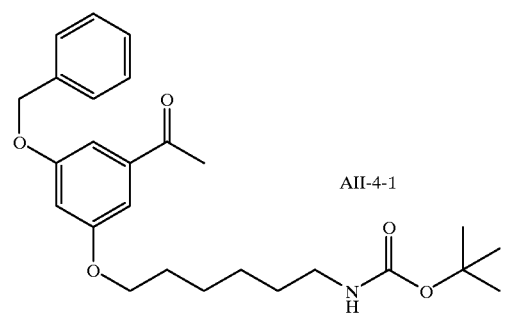 AII-4-1
1) NaH
   DME
   dimethyl oxalate
2) NaOH
NaH
DME
dimethyl oxalate
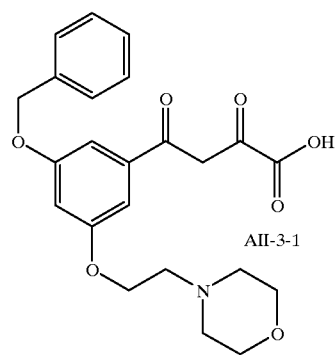 AII-3-1
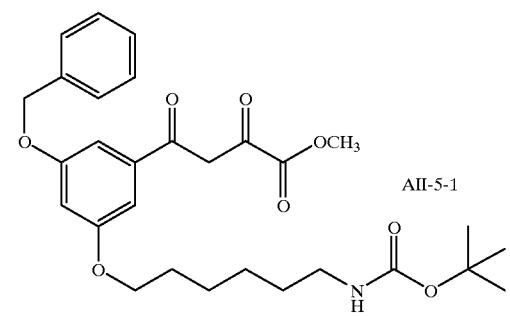 AII-5-1
NaOH
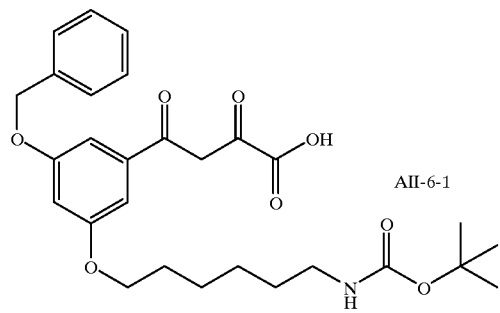 AII-6-1
Scheme AIII
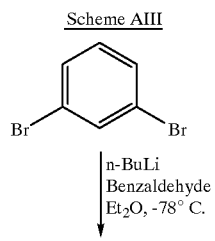
n-BuLi
Benzaldehyde
Et$_2$O, -78° C.
-continued
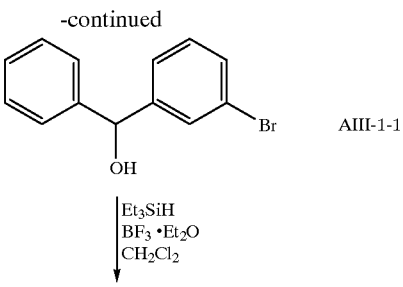 AIII-1-1
Et$_3$SiH
BF$_3$·Et$_2$O
CH$_2$Cl$_2$

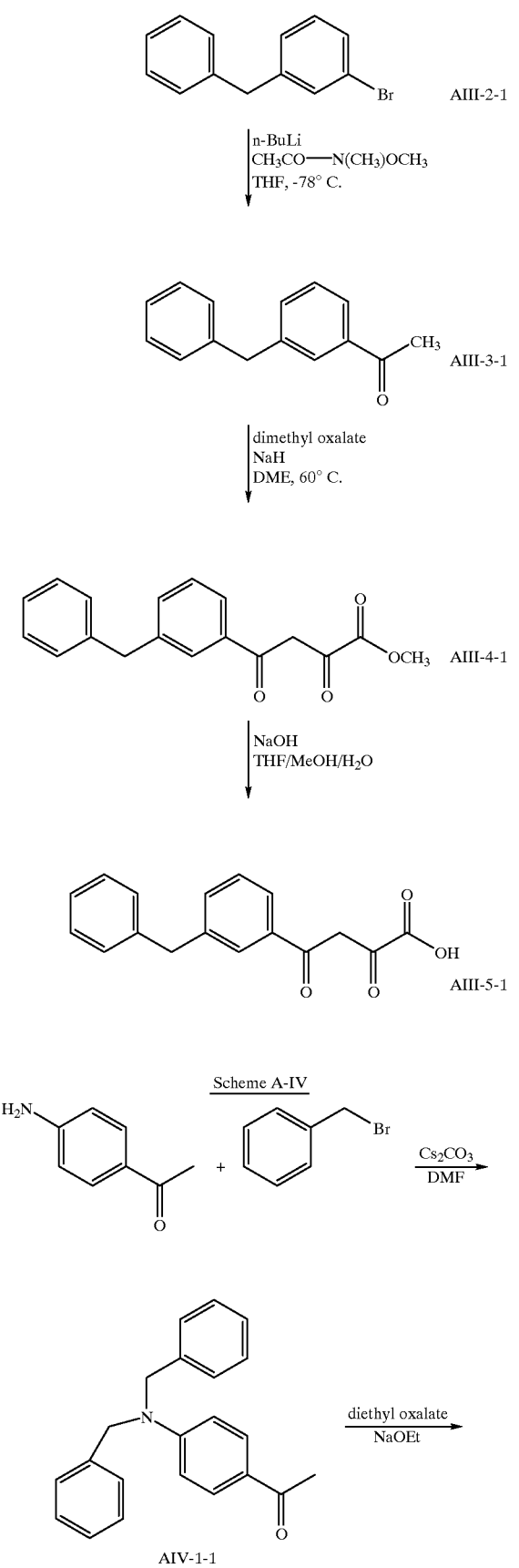
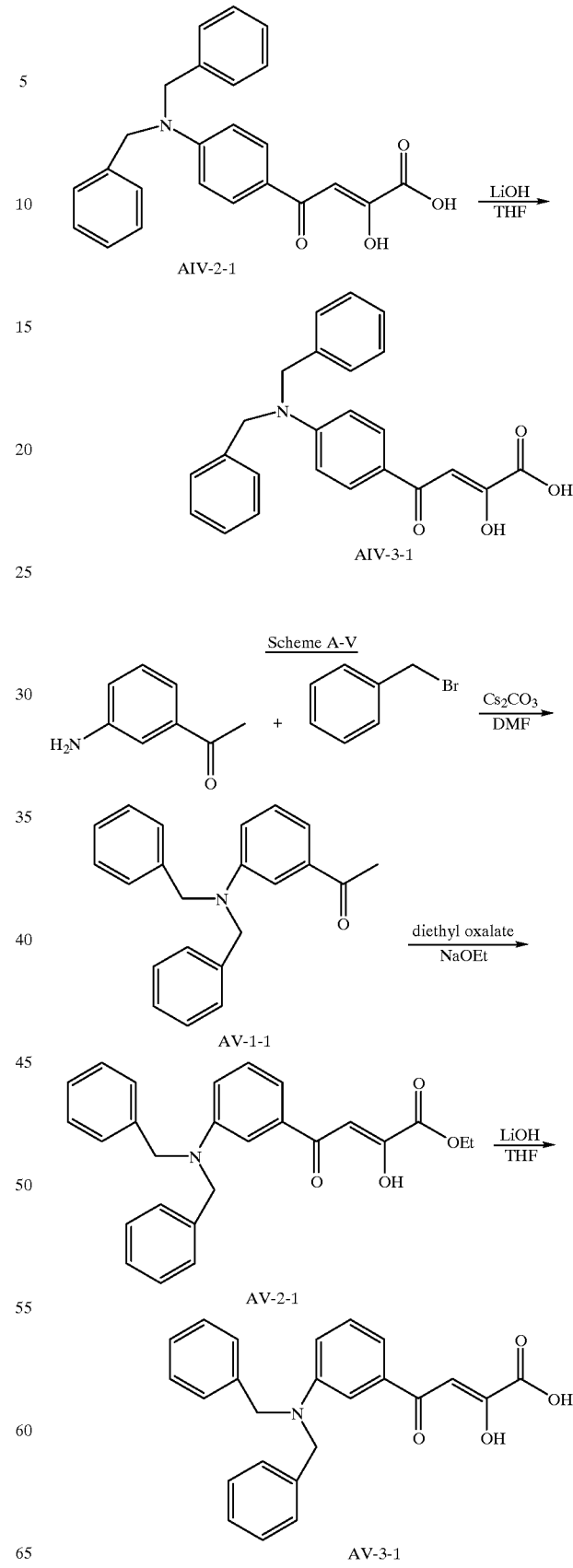

Scheme AVI
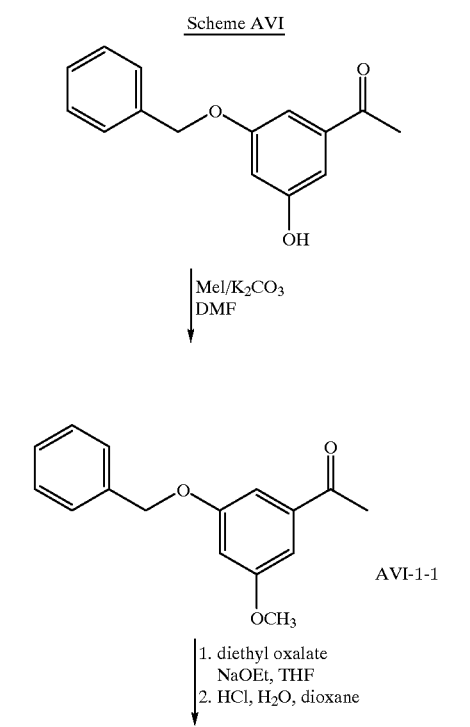
Scheme AVII
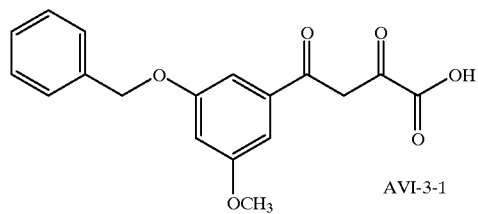
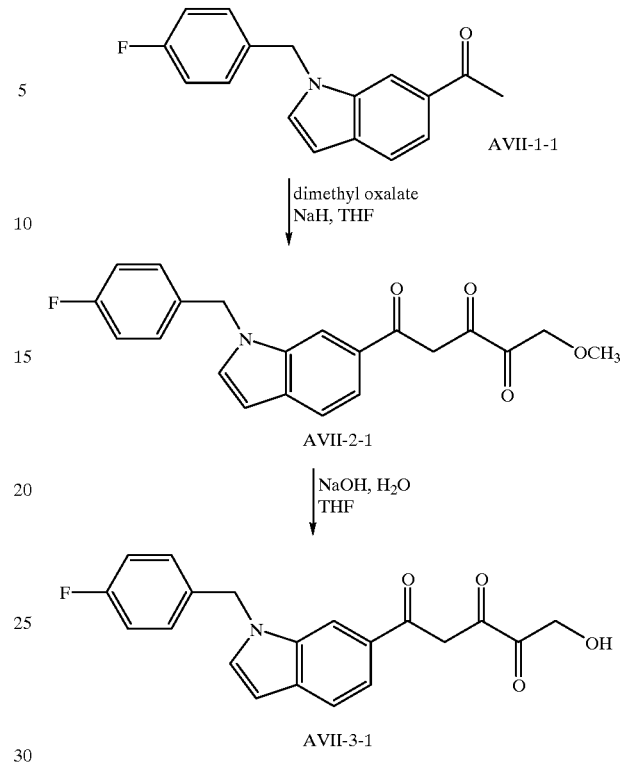
Scheme IX
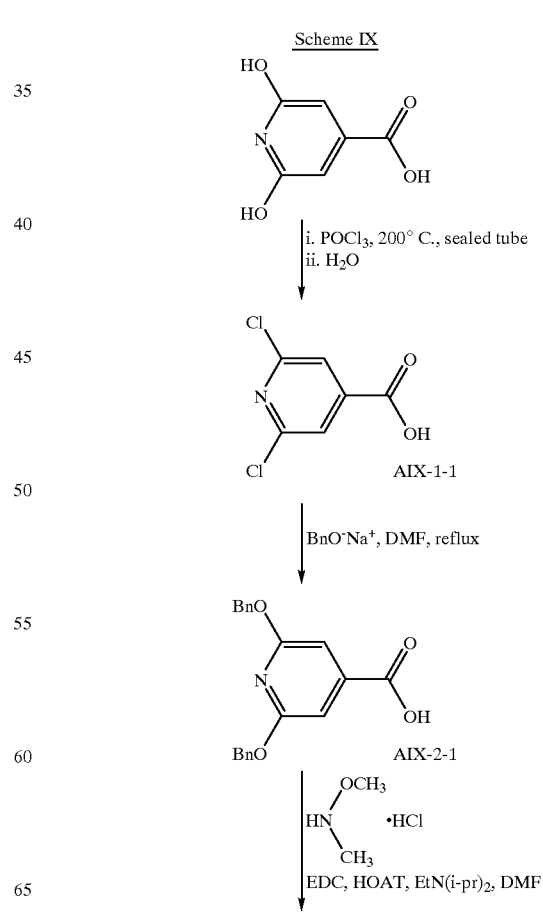

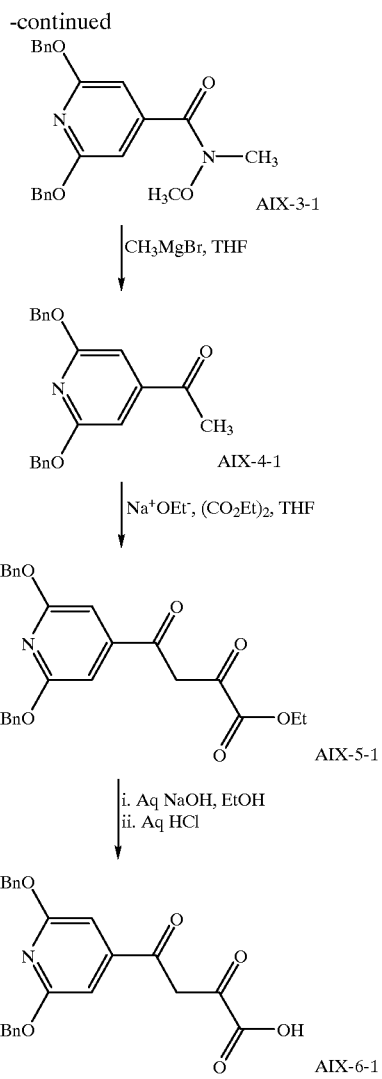

arginine, ornithine, choline, N,N'-dibenzylethylenediamine, chloroprocaine, diethanolamine, procaine, N-benzylphenethylamine, diethylamine, piperazine, tris (hydroxymethyl)aminomethane, and tetramethylammonium hydroxide. These salts may be prepared by standard procedures, e.g. by reacting a free acid with a suitable organic or inorganic base. Where a basic group is present, such as amino, an acidic salt, i.e. hydrochloride, hydrobromide, acetate, pamoate, and the like, can be used as the dosage form.

Also, in the case of an acid (—COOH) or alcohol group being present, pharmaceutically acceptable esters can be employed, e.g. acetate, maleate, pivaloyloxymethyl, and the like, and those esters known in the art for modifying solubility or hydrolysis characteristics for use as sustained release or prodrug formulations.

For these purposes, the compounds of the present invention may be administered orally, parenterally (including subcutaneous injections, intravenous, intramuscular, intrasternal injection or infusion techniques), by inhalation spray, or rectally, in dosage unit formulations containing conventional non-toxic pharmaceutically-acceptable carriers, adjuvants and vehicles.

The terms "administration of" and or "administering a" compound should be understood to mean providing a compound of the invention or a prodrug of a compound of the invention to the individual in need of treatment.

Thus, in accordance with the present invention there is further provided a method of treating and a pharmaceutical composition for treating HIV infection and AIDS. The treatment involves administering to a patient in need of such treatment a pharmaceutical composition comprising a pharmaceutical carrier and a therapeutically-effective amount of a compound of the present invention.

As used herein, the term "composition" is intended to encompass a product comprising the specified ingredients in the specified amounts, as well as any product which results, directly or indirectly, from combination of the specified ingredients in the specified amounts.

By "pharmaceutically acceptable" it is meant the carrier, diluent or excipient must be compatible with the other ingredients of the formulation and not deleterious to the recipient thereof.

These pharmaceutical compositions may be in the form of orally-administrable suspensions or tablets, nasal sprays, sterile injectible preparations, for example, as sterile injectible aqueous or oleagenous suspensions or suppositories.

When administered orally as a suspension, these compositions are prepared according to techniques well-known in the art of pharmaceutical formulation and may contain microcrystalline cellulose for imparting bulk, alginic acid or sodium alginate as a suspending agent, methylcellulose as a viscosity enhancer, and sweeteners/flavoring agents known in the art. As immediate release tablets, these compositions may contain microcrystalline cellulose, dicalcium phosphate, starch, magnesium stearate and lactose and/or other excipients, binders, extenders, disintegrants, diluents and lubricants known in the art.

When administered by nasal aerosol or inhalation, these compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art.

The injectible solutions or suspensions may be formulated according to known art, using suitable non-toxic, The compounds of the present invention may be administered in the form of pharmaceutically acceptable salts. The term "pharmaceutically acceptable salt" is intended to include all acceptable salts such as acetate, lactobionate, benzenesulfonate, laurate, benzoate, malate, bicarbonate, maleate, bisulfate, mandelate, bitartrate, mesylate, borate, methylbromide, bromide, methylnitrate, calcium edetate, methylsulfate, mucate, carbonate, napsylate, chloride, nitrate, clavulanate, N-methylglucamine, citrate, ammonium salt, dihydrochloride, oleate, edetate, oxalate, edisylate, pamoate (embonate), estolate, palmitate, esylate, pantothenate, fumarate, phosphate/diphosphate, gluceptate, polygalacturonate, gluconate, salicylate, glutamate, stearate, glycollylarsanilate, sulfate, hexylresorcinate, subacetate, hydrabamine, succinate, hydrobromide, tannate, hydrochloride, tartrate, hydroxynaphthoate, teoclate, iodide, tosylate, isothionate, triethiodide, lactate, panoate, valerate, and the like which can be used as a dosage form for modifying the solubility or hydrolysis characteristics or can be used in sustained release or pro-drug formulations. Depending on the particular functionality of the compound of the present invention, pharmaceutically acceptable salts of the compounds of this invention include those formed from cations such as sodium, potassium, aluminum, calcium, lithium, magnesium, zinc, and from bases such as ammonia, ethylenediamine, N-methylglutamine, lysine, parenterally-acceptable diluents or solvents, such as mannitol, 1,3-butanediol, water, Ringer's solution or isotonic sodium chloride solution, or suitable dispersing or wetting and suspending agents, such as sterile, bland, fixed oils, including synthetic mono- or diglycerides, and fatty acids, including oleic acid.

When rectally administered in the form of suppositories, these compositions may be prepared by mixing the drug with a suitable non-irritating excipient, such as cocoa butter, synthetic glyceride esters of polyethylene glycols, which are solid at ordinary temperatures, but liquefy and/or dissolve in the rectal cavity to release the drug.

The compounds of this invention can be administered orally to humans in a dosage range of 1 to 1000 mg/kg body weight in divided doses. One preferred dosage range is 0.1 to 200 mg/kg body weight orally in divided doses. Another preferred dosage range is 0.5 to 100 mg/kg body weight orally in divided doses. For oral administration, the compositions are preferably provided in the form of tablets containing 1.0 to 1000 milligrams of the active ingredient, particularly 1.0, 5.0, 10.0, 15.0. 20.0, 25.0, 50.0, 75.0, 100.0, 150.0, 200.0, 250.0, 300.0, 400.0, 500.0, 600.0, 750.0, 800.0, 900.0, and 1000.0 milligrams of the active ingredient for the symptomatic adjustment of the dosage to the patient to be treated. It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

The present invention is also directed to combinations of the HIV integrase inhibitor compounds with one or more agents useful in the treatment of AIDS. For example, the compounds of this invention may be effectively administered, whether at periods of pre-exposure and/or post-exposure, in combination with effective amounts of the AIDS antivirals, imunomodulators, antiinfectives, or vaccines, such as those in the following table.

| Drug Name | Manufacturer | Indication |
|---|---|---|
| ANTIVIRALS | | |
| 097 | Hoechst/Bayer | HIV infection, AIDS, ARC (non-nucleoside reverse transcriptase (RT) inhibitor) |
| Amprenivir 141 W94 GW 141 | Glaxo Wellcome | HIV infection, AIDS, ARC (protease inhibitor) |
| Abacavir (1592U89) GW 1592 | Glaxo Wellcome | HIV infection, AIDS, ARC (RT inhibitor) |
| Acemannan | Carrington Labs (Irving, TX) | ARC |
| Acyclovir | Burroughs Wellcome | HIV infection, AIDS, ARC, in combination with AZT |
| AD-439 | Tanox Biosystems | HIV infection, AIDS, ARC |
| AD-519 | Tanox Biosystems | HIV infection, AIDS, ARC |
| Adefovir dipivoxil AL-721 | Gilead Sciences Ethigen (Los Angeles, CA) | HIV infection ARC, PGL HIV positive, AIDS |
| Alpha Interferon | Glaxo Wellcome | Kaposi's sarcoma, HIV in combination w/Retrovir |
| Ansamycin LM 427 | Adria Laboratories (Dublin, OH) Erbamont (Stamford, CT) | ARC |
| Antibody which neutralizes pH labile alpha aberrant Interferon | Advanced Biotherapy Concepts (Rockville, MD) | AIDS, ARC |
| AR177 | Aronex Pharm | HIV infection, AIDS, ARC |
| beta-fluoro-ddA | Nat'l Cancer Institute | AIDS-associated diseases |
| BMS-232623 (CGP-73547) | Bristol-Myers Squibb/ Novartis | HIV infection, AIDS, ARC (protease inhibitor) |
| BMS-234475 (CGP-61755) | Bristol-Myers Squibb/ Novartis | HIV infection, AIDS, ARC (protease inhibitor) |
| CI-1012 | Warner-Lambert | HIV-1 infection |
| Cidofovir | Gilead Science | CMV retinitis, herpes, papillomavirus |
| Curdlan sulfate | AJI Pharma USA | HIV infection |
| Cytomegalovirus immune globin | Med Immune | CMV retinitis |
| Cytovene Ganciclovir | Syntex | sight threatening CMV peripheral CMV retinitis |
| Delaviridine | Pharmacia-Upjohn | HIV infection, AIDS, ARC (RT inhibitor) |
| Dextran Sulfate | Ueno Fine Chem. Ind. Ltd. (Osaka, Japan) | AIDS, ARC, HIV positive asymptomatic |
| ddC Dideoxycytidine | Hoffman-La Roche | HIV infection, AIDS, ARC |
| ddI Dideoxyinosine | Bristol-Myers Squibb | HIV infection, AIDS, ARC; combination with AZT/d4T |
| DMP-450 | AVID (Camden, NJ) | HIV infection, AIDS, ARC (protease inhibitor) |
| Efavirenz (DMP 266) (-) 6-Chloro-4(S)-cyclopropylethynyl-4(S)-trifluoro-methyl-1,4-dihydro-2H-3,1-benzoxazin-2-one, STOCRINE | DuPont Merck | HIV infection, AIDS, ARC (non-nucleoside RT inhibitor) |
| EL10 | Elan Corp, PLC (Gainesville, GA) | HIV infection |
| Famciclovir | Smith Kline | herpes zoster, herpes simplex |
| FTC | Emory University | HIV infection, AIDS, ARC (reverse transcriptase inhibitor) |
| GS 840 | Gilead | HIV infection, AIDS, ARC (reverse transcriptase inhibitor) |
| HBY097 | Hoechst Marion Roussel | HIV infection, AIDS, ARC (non-nucleoside reverse transcriptase inhibitor) |
| Hypericin | VIMRx Pharm | HIV infection, AIDS, ARC |
| Recombinant Human Interferon Beta | Triton Biosciences (Almeda, CA) | AIDS, Kaposi's sarcoma, ARC |

-continued

| Drug Name | Manufacturer | Indication |
|---|---|---|
| Interferon alfa-n3 | Interferon Sciences | ARC, AIDS |
| Indinavir | Merck | HIV infection, AIDS, ARC, asymptomatic HIV positive, also in combination with AZT/ddI/ddC |
| ISIS 2922 | ISIS Pharmaceuticals | CMV retinitis |
| KNI-272 | Nat'l Cancer Institute | HIV-assoc. diseases |
| Lamivudine, 3TC | Glaxo Wellcome | HIV infection, AIDS, ARC (reverse transcriptase inhibitor); also with AZT |
| Lobucavir | Bristol-Myers Squibb | CMV infection |
| Nelfinavir | Agouron Pharmaceuticals | HIV infection, AIDS, ARC (protease inhibitor) |
| Nevirapine | Boeheringer Ingleheim | HIV infection, AIDS, ARC (RT inhibitor) |
| Novapren | Novaferon Labs, Inc. (Akron, OH) | HIV inhibitor |
| Peptide T Octapeptide Sequence | Peninsula Labs (Belmont, CA) | AIDS |
| Trisodium Phosphonoformate | Astra Pharm. Products, Inc | CMV retinitis, HIV infection, other CMV infections |
| PNU-140690 | Pharmacia Upjohn | HIV infection, AIDS, ARC (protease inhibitor) |
| Probucol | Vyrex | HIV infection, AIDS |
| RBC-CD4 | Sheffield Med. Tech (Houston TX) | HIV infection, AIDS, ARC |
| Ritonavir | Abbott | HIV infection, AIDS, ARC (protease inhibitor) |
| Saquinavir | Hoffmann-LaRoche | HIV infection, AIDS, ARC (protease inhibitor) |
| Stavudine; d4T Didehydrodeoxy-thymidine | Bristol-Myers Squibb | HIV infection, AIDS, ARC |
| Valaciclovir | Glaxo Wellcome | genital HSV & CMV infections |
| Virazole Ribavirin | Viratek/ICN (Costa Mesa, CA) | asymptomatic HIV positive, LAS, ARC |
| VX-478 | Vertex | HIV infection, AIDS, ARC |
| Zalcitabine | Hoffmann-La Roche | HIV infection, AIDS, ARC, with AZT |
| Zidovudine; AZT | Glaxo Wellcome | HIV infection, AIDS, ABC, Kaposi's sarcoma, in combination with other therapies |
| IMMUNO-MODULATORS ||||
| AS-101 | Wyeth-Ayerst | AIDS |
| Bropirimine | Pharmacia Upjohn | advanced AIDS |
| Acemannan | Carrington Labs, Inc. (Irving, TX) | AIDS, ARC |
| CL246,738 | American Cyanamid Lederle Labs | AIDS, Kaposi's sarcoma |
| EL10 | Elan Corp, PLC (Gainesville, GA) | HIV infection |
| FP-21399 | Fuki ImmunoPharm | blocks HIV fusion with CD4+ cells |
| Gamma Interferon | Genentech | ARC, in combination w/TNF (tumor necrosis factor) |
| Granulocyte Macrophage Colony Stimulating Factor | Genetics Institute Sandoz | AIDS |

-continued

| Drug Name | Manufacturer | Indication |
|---|---|---|
| Granulocyte Macrophage Colony Stimulating Factor | Hoeschst-Roussel Immunex | AIDS |
| Granulocyte Macrophage Colony Stimulating Factor | Schering-Plough | AIDS, combination w/AZT |
| HIV Core Particle Immunostimulant | Rorer | seropositive HIV |
| IL-2 Interleukin-2 | Cetus | AIDS, in combination w/AZT |
| IL-2 Interleukin-2 | Hoffman-La Roche Immunex | AIDS, ARC, HIV, in combination w/AZT |
| IL-2 Interleukin-2 (aldesluken) | Chiron | AIDS, increase in CD4 cell counts |
| Immune Globulin Intravenous (human) | Cutter Biological (Berkeley, CA) | pediatric AIDS, in combination w/AZT |
| IMREG-1 | Imreg (New Orleans, LA) | AIDS, Kaposi's sarcoma, ARC, PGL |
| IMREG-2 | Imreg (New Orleans, LA) | AIDS, Kaposi's sarcoma, ARC, PGL |
| Imuthiol Diethyl Dithio Carbamate | Merieux Institute | AIDS, ARC |
| Alpha-2 Interferon | Schering Plough | Kaposi's sarcoma w/AZT, AIDS |
| Methionine-Enkephalin | TNI Pharmaceutical (Chicago, IL) | AIDS, ARC |
| MTP-PE Muramyl-Tripeptide | Ciba-Geigy Corp. | Kaposi's sarcoma |
| Granulocyte Colony Stimulating Factor | Amgen | AIDS, in combination w/AZT |
| Remune | Immune Response Corp. | immunotherapeutic |
| rCD4 Recombinant Soluble Human CD4 | Genentech | AIDS, ARC |
| rCD4-IgG hybrids | | AIDS, ARC |
| Recombinant Soluble Human CD4 | Biogen | AIDS, ARC |
| Interferon Alfa 2a | Hoffman-La Roche | Kaposi's sarcoma AIDS, ARC, in combination w/AZT |
| SK&F106528 Soluble T4 | Smith Kline | HIV infection |
| Thymopentin | Immunobiology Research Institute (Annandale, NJ) | HIV infection |
| Tumor Necrosis Factor; TNF | Genentech | ARC, in combination w/gamma Interferon |
| ANTI-INFECTIVES ||||
| Clindamycin with Primaquine | Pharmacia Upjohn | PCP |
| Fluconazole | Pfizer | cryptococcal meningitis, candidiasis |
| Pastille Nystatin Pastille | Squibb Corp. | prevention of oral candidiasis |
| Ornidyl Eflornthine | Merrell Dow | PCP |
| Pentamidine Isethionate (IM & IV) | LyphoMed (Rosemont, IL) | PCP treatment |
| Trimethoprim | | antibacterial |
| Trimethoprim/sulfa | | antibacterial |
| Piritrexim | Burroughs Wellcome | PCP treatment |
| Pentamidine isethionate for inhalation | Fisons Corporation | PCP prophylaxis |
| Spiramycin | Rhone-Poulenc | cryptosporidial diarrhea |

-continued

| Drug Name | Manufacturer | Indication |
|---|---|---|
| Intraconazole-R51211 | Janssen Pharm. | histoplasmosis; cryptococcal meningitis |
| Trimetrexate | Warner-Lambert | PCP |

OTHER

| | | |
|---|---|---|
| Daunorubicin | NeXstar, Sequus | Karposi's sarcoma |
| Recombinant Human Erythropoietin | Ortho Pharm. Corp. | severe anemia assoc. with AZT therapy |
| Recombinant Human Growth Hormone | Serono | AIDS-related wasting, cachexia |
| Megestrol Acetate | Bristol-Myers Squibb | treatment of anorexia assoc. w/AIDS |
| Testosterone | Alza, Smith Kline | AIDS-related wasting |
| Total Enteral Nutrition | Norwich Eaton Pharmaceuticals | diarrhea and malabsorption related to AIDS |

It will be understood that the scope of combinations of the compounds of this invention with AIDS antivirals, immunomodulators, anti-infectives or vaccines is not limited to the list in the above Table, but includes in principle any combination with any pharmaceutical composition useful for the treatment of AIDS.

Preferred combinations are simultaneous or alternating treatments of with a compound of the present invention and an inhibitor of HIV protease and/or a non-nucleoside inhibitor of HIV reverse transcriptase. An optional fourth component in the combination is a nucleoside inhibitor of HIV reverse transcriptase, such as AZT, 3TC, ddC or ddI. A preferred inhibitor of HIV protease is indinavir, which is the sulfate salt of N-(2(R)-hydroxy-1(S)-indanyl)-2(R)-phenylmethyl-4-(S)-hydroxy-5-(1-(4-(3-pyridyl-methyl)-2(S)-N'-(t-butylcarboxamido)piperazinyl))-pentaneamide ethanolate, and is synthesized according to U.S. Pat. No. 5,413,999. Indinavir is generally administered at a dosage of 800 mg three times a day. Other preferred protease inhibitors are nelfinavir and ritonavir. Another preferred inhibitor of HIV protease is saquinavir which is administered in a dosage of 600 or 1200 mg tid. Preferred non-nucleoside inhibitors of HIV reverse transcriptase include efavirenz. The preparation of ddC, ddI and AZT are also described in EPO 0,484,071. These combinations may have unexpected effects on limiting the spread and degree of infection of HIV. Preferred combinations include those with the following (1) indinavir with efavirenz, and, optionally, AZT and/or 3TC and/or ddI and/or ddC; (2) indinavir, and any of AZT and/or ddI and/or ddC and/or 3TC, in particular, indinavir and AZT and 3TC; (3) stavudine and 3TC and/or zidovudine; (4) zidovudine and lamivudine and 141W94 and 1592U89; (5) zidovudine and lamivudine.

In such combinations the compound of the present invention and other active agents may be administered separately or in conjunction. In addition, the administration of one element may be prior to, concurrent to, or subsequent to the administration of other agent(s).

It will be understood that the scope of combinations of the compounds of this invention with AIDS antivirals, immunomodulators, anti-infectives or vaccines is not limited to the list in the above Table, but includes in principle any combination with any pharmaceutical composition useful for the treatment of AIDS.

Indinavir is an inhibitor of HIV protease and is the sulfate salt of N-(2(R)-hydroxy-1(S)-indanyl)-2(R)-phenylmethyl-4-(S)-hydroxy-5-(1-(4-(3-pyridyl-methyl)-2(S)-N'-(t-butylcarboxamido)-piperazinyl))-pentaneamide ethanolate, and is synthesized according to U.S. Pat. No. 5,413,999. Indinavir is generally administered at a dosage of 800 mg three times a day.

The following examples are provided to further illustrate details for the preparation and use of the compounds of the present invention. The examples are not intended to be limitations on the scope of the instant invention in any way, and they should not be so construed. Furthermore, the compounds described in the following examples are not to be construed as forming the only genus that is considered as the invention, and any combination of the compounds or their moieties may itself form a genus. Those skilled in the art will readily understand that known variations of the conditions and processes of the following preparative procedures can be used to prepare these compounds. All temperatures are in degrees Celsius unless noted otherwise.

Abbreviations: Ac represents acetyl; ACN is acetonitrile; Bn represents benzyl; Bu represents butyl; Calc'd represents calculated; DEAD is diethylazido-carboxylate; DME is dimethoxyethane; DMF is dimethyl formamide; DMSO is dimethylsulfoxide; EI represents electron impact; ES represents electrospray; Et represents ethyl; FAB represents fast atom bombardment; IPA is isopropyl alcohol; LDA is lithium diisopropylamide; L-Selectride® is lithium tri-sec-butylborohydride; MEK is methyl ethyl ketone; Me represents methyl; NMP is 1-methyl-2-pyrrolidinone; PDA is photodiode array; rt and RT represent room temperature; THF is tetrahydrofuran; TLC is thin layer (SiO$_2$) chromatography.

EXAMPLE 1

4-(3,5-Bis-benzyloxy-phenyl)-2,4-dioxobutanoic Acid AI-2-1

Step 1: 4-(3,5-Bis-benzyloxy-phenyl)-2,4-dioxobutanoic acid methyl ester AI-1-1

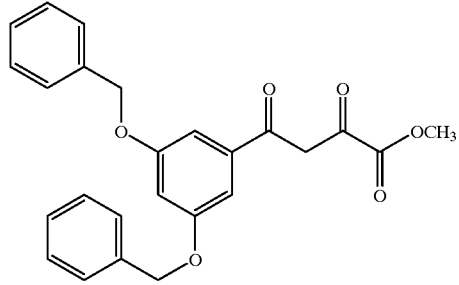

AI-1-1

A solution of 1-(3,5-bis-benzyloxy-phenyl)ethanone (3g, 9.0 mmole) in DME (20 mL) was treated with sodium hydride (0.54 g, 60% dispersion in oil, 13.5 mmole) followed by dimethyl oxalate (1.3, 9.0 mmole) and a drop of methanol and the solution was warmed to 110° C. After 0.5 hours the reaction became dark brown and homogeneous. The reaction mixture was poured into into 1N HCl and extracted with EtOAc three times, the combined organic layers were dried over MgSO$_4$, filtered and evaporated to give a yellow solid. The residue was dissolved in THF and absorbed to silica gel and added to the top of a pad of silica gel. The pad was eluted with CH$_2$Cl$_2$, which removed non-polar impurities, then with 20% MeOH/CH$_2$Cl$_2$, which eluted the product. The product was further purified by crystallization from EtOAc/Hexanes/Et$_2$O to give AI-1-1 as a orange foam. Rf=0.3 (97:3:1 CH$_2$Cl$_3$/MeOH/HOAc). $^1$H NMR (400 MHz, CDCl$_3$) δ7.4 (m, 10H), 7.24 (m, 2H), 7.01 (s, 1H), 6.84 (m, 1H), 5.1 (s, 4H), 3.94, (s, 3H).

Step 2: 4-(3,5-Bis-benzyloxy-phenyl)-2,4-dioxobutanoic acid AI-2-1

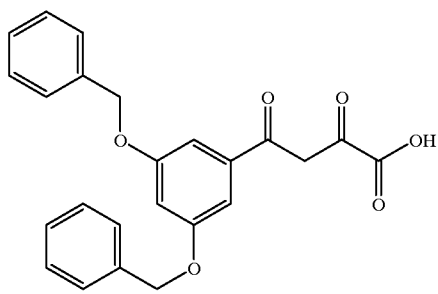

AI-2-1

A solution of AI-1-1 (1.5 g, 3.47 mmole) was dissolved in 1:1 THF/MeOH (20 mL) and treated with 1 N NaOH (10 mL, 10 m mole) and stirred for one hour. The reaction mixture was washed with dilute ether, then acidified to pH2 with 1N HCl and extracted three times with EtOAc. The organic layers were combined, washed with 1 N HCl, dried over MgSO$_4$, filtered through a pad of CELITE diatomaceous earth and evaporated to dryness. The residue was triturated with ether to give AI-2-1 as bright yellow powder. $^1$H NMR (400 MHz, CDCl$_3$) δ7.43–7.31 (m, 10H), 7.22 (s, 1H), 7.21 (s, 1H), 7.10 (s, 1H), 6.86 (m, 1H). mass spec (FAB, m+1) 405.13.

EXAMPLE 2

4-[3-Benzyloxy-5-(2-morpholin-4-yl-ethoxy)-phenyl]-2,4-dioxobutanoic acid AII-3-1

Step 1: 1-(3-Benzyloxy-5-hydroxyphenyl)ethanone AII-1-1

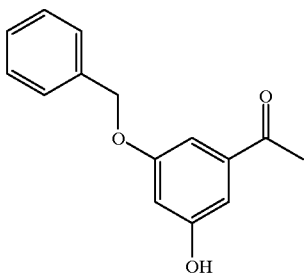

AII-1-1

A solution of 1-(3,5-bis-benzyloxyphenyl)ethanone (10 g, 3.0 mmole) in 1:1 EtOH/Et$_2$O (200 mL) was treated with 10% palladium on carbon (3.4 g) and hydrogen gas at balloon pressure for one hour with vigorous stirring. The solvent was evaporated and the residue chromatographed on silica gel eluting with 20% acetone/hexanes to give AII-1-1 as a white solid. Rf=0.27 (30% acetone/hexanes). $^1$H NMR (400 MHz, CDCl$_3$) δ7.4 (m, 5H), 7.16 (s, 1H), 7.05 (s, 1H), 6.7 (m, 1H), 5.82 (s, 1H), 5.08 (s, 2H), 2.55 (s, 3H).

Step 2: 4-[2-(3-Acetyl-5-benzyloxy-phenoxy)-ethyl] morpholin-4-ium AII-2-1

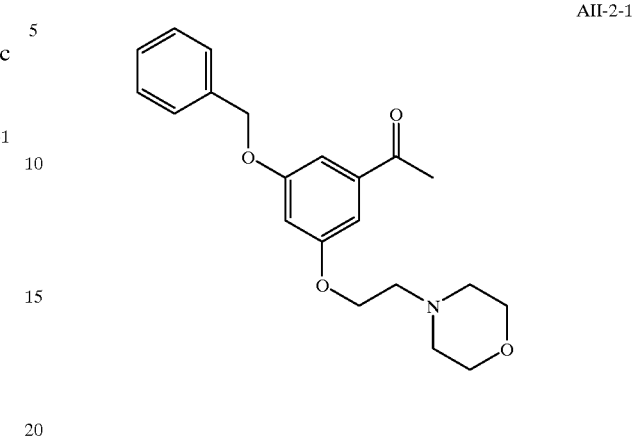

AII-2-1

The free base of 4-(2-chloroethyl)morpholine hydrochloride (1.85 g, 10 mmole) was formed and then combined with AII-1-1 (0.8 g, 3.3 mmole), cesium carbonate (3.25 g, 10 mmole) and dioxane (40 mL) and heated to 80° C. for 4.5 hours. The solution was filtered, washed with EtOAc and concentrated. Column chromatography with 10–30% acetone/hexanes gave AII-2-1 as a brown syrup. Rf=0.39 (30% acetone/hexanes). $^1$H NMR (400 MHz, CDCl$_3$) δ7.4 (m, 5H), 7.2 (s, 1H), 7.18 (s, 1H), 6.74 (m, 1H), 5.1 (s, 2H), 4.13 (t, J=5.6 Hz, 2H), 3.74 (t, J=4.5 Hz, 4H), 2.8 (t, J=5.6 Hz, 2H), 2.58 (m, 4H), 2.55 (s, 3H).

Step 3: 4-[3-Benzyloxy-5-(2-morpholin-4-yl-ethoxy) phenyl]-2,4-dioxobutanoic acid AII-3-1

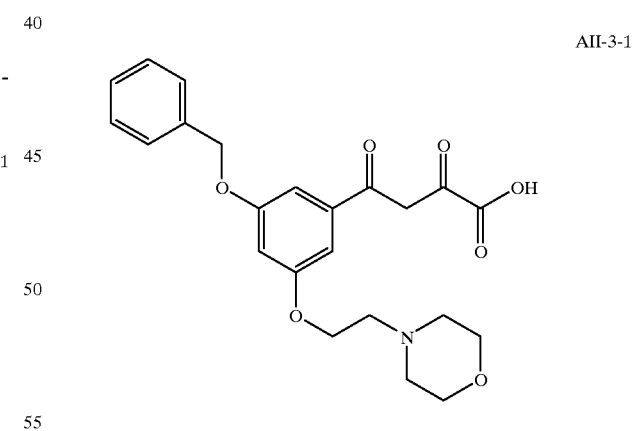

AII-3-1

In a manner similar to that discribed for AI-1-1, AII-2-1 was treated with NaH and dimethyloxate in DME to give a mixture of AII-3-1 and its methyl ester. The mixture was treated with NaOH as described for AI-2-1 to give AII-3-1 as a yellow solid. $^1$H NMR (400 MHz, D$_2$O) δ7.4 (m, 5H), 6.97 (s, 1H), 6.86 (s, 1H), 6.56 (s, 1H), 5.05 (s, 2H), 4.05 (m, 2H), 3.6 (m, 5H), 2.7 (s, 2H), 2.5 (s, 4H). mass spec (m+1)=428.

EXAMPLE 3

4-[3-Benzyloxy-5-(6-tert-butoxycarbonylamino-hexyloxy)-phenyl]-2,4-dioxobutanoic Acid AII-6-1

Step 1: [6-(3-Acetyl-5-benzyloxy-phenoxy)-hexyl] carbamic acid-tert-butyl ester AII-4-1

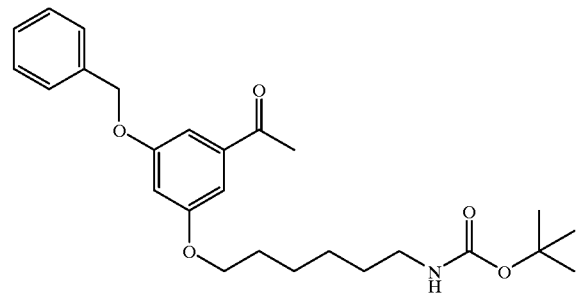

AII-4-1

In a manner similar to that described for AII-2-1, AII-1-1 was treated with (6-bromo-hexyl)-carbamic acid-tert-butyl ester (J. Med. Chem. 1994, 37, 2537–2551) to give AII-4-1. Rf=0.41 (80% acetone/hexanes); $^1$H NMR (400 MHz, CDCl$_3$) δ7.4 (m, 5H), 7.15 (s, 1H), 7.10 (s, 1H), 6.72 (m, 1h), 5.1 (s, 2H), 3.98 (t, J=6.4 Hz, 2H), 3.12 (m, 2H), 2.56 (s, 3H), 1.8 (m, 2H), 1.5 (m, 6H), 1.45 (s, 9H), 1.40 (m, 2H).

Step 2: 4-[3-Benzyloxy-5-(6-tert-butoxycarbonylamino-hexyloxy) phenyl]-2,4-dioxobutanoic acid methyl ester AII-5-1

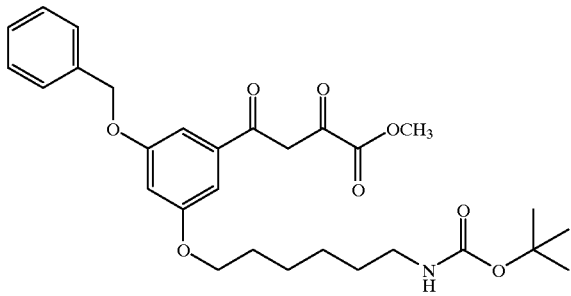

AII-5-1

Freshly prepared sodium methoxide (from 0.25 g sodium metal in MeOH) was suspended in toluene (5 mL) and a solution of AII-4-1 (0.8 g, 1.8 mmole) and dimethyloxalate (0.21 g, 1.8 mmole) in toluene (5 mL) was added. The mixture was stirred for 2 hours, then quenched with 3 N HCl and extracted with EtOAc. The organic layer was dried with Na$_2$SO$_4$, filtered and evaporated. The residue was passed through a plug of silica gel as described for AI-1-1 and the resulting oil crystallized from ether to give AII-5-1 as a red solid. $^1$H NMR (400 MHz, CDCl$_3$) δ7.4 (m, 5H), 7.2 (s, 1H), 7.12 (s, 1H), 7.02 (s, 1H), 6.75 (m, 1H), 5.10 (s, 2H), 4.5 (bs, 1H), 4.0 (t, J=6.4 Hz, 2H), 3.95 (s, 3H), 3.13 (m, 2H), 1.8 (m, 2H), 1.5 (m, 6H), 1.45 (s, 9H), 1.4 (m, 2H).

Step 3: 4-[3-Benzyloxy-5-(6-tert-butoxycarbonylaminohexyloxy) phenyl]-2,4-dioxobutanoic acid AII-6-1

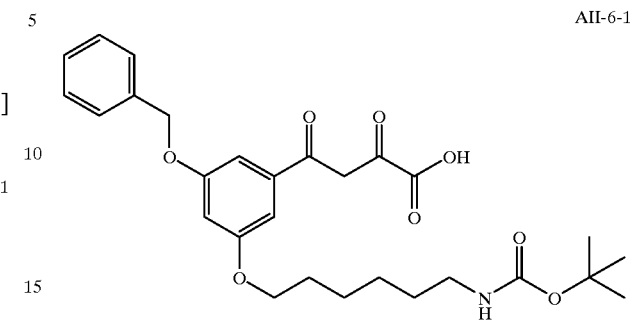

AII-6-1

In a manner similar to that described for AI-2-1, AII-5-1 was treated with NaOH to give AII-6-1 as a foamy yellow solid. $^1$H NMR (400 MHz, CDCl$_3$) δ7.4 (m, 5H), 7.18 (s, 1H), 7.12 (s, 1H), 7.08 (s, 1H), 6.72 (s, 1H), 5.08 (s, 2H), 4.5 (bs, 1H), 4.0 (m, 2H), 3.13 (m, 2H), 1.8 (m, 2H), 1.6–1.3 (m, 17H.

EXAMPLE 4

4-(3-Benzylphenyl)-2,4-dioxobutanoic acid A-III-5-1

Step 1: (3-Bromophenyl)phenylmethanol AIII-1-1

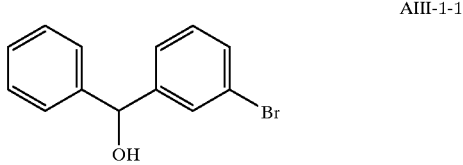

AIII-1-1

To an oven dried 500 ml 3-neck flask fitted with temperature probe, magnetic stir bar, and argon inlet was added a solution of 2.5M n-butyl lithium in hexanes (20.8 ml, 0.052 mole) chilled to −78° C. then diluted with diethyl ether (90 ml). To this was added dropwise by syringe over 30 minutes 1,3-dibromobenzene (11.80 g, 6.043 ml, 0.05 mole; activated basic alumina pretreatment) keeping the internal temperature between −74° C. and −78° C. The reaction was aged at −78° C. for 2.5 h before adding neat benzaldehyde (5.52 g, 5.29 ml, 0.052 mole) over 15 minutes then allowing the reaction mixture to slowly warm to room temperature as the bath discharged overnight. The reaction was quenched with 20 mL H$_2$O then acidified with 5.4 ml conc. HCl and extracted with EtOAc three times. The combined organic layers were washed with NaHCO$_3$, brine and dried over NaSO$_4$, filtered and evaporated in vacuo to give a clear yellow oil AIII-1-1 which crystallized to afford a white solid after washing with pet ether. Rf=0.14 (10% EtOAc/Hexanes). $^1$H NMR (300 MHz, CDCl$_3$) δ7.56 (s, 1H), 7.36–7.40 (m, 3H), 7.32–7.35 (m, 2H), 7.25–7.31 (m, 2H), 7.19 (m, 1H), 5.79 (s, 1H), 2.25 (s, 1H).

Step 2: (3-Benzyl)phenyl bromide AIII-2-1

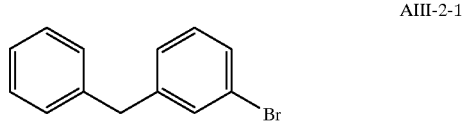

AIII-2-1

A solution of AIII-1-1 (4.10 g, 0.0156 mole) and triethylsilane (2.72 g, 3.71 ml, 0.0234 mole) in methylene chloride (40 ml) was chilled to 0° C. under argon with stirring followed by addition of neat boron trifluoride etherate (3.32 g, 2.96 ml, 23.4 mmol). The reaction stirred at room temprature overnight. The reaction mixture was poured into 160 ml saturated NaHCO$_3$ and extracted with EtOAc three times, the combined organic layers were washed with brine and dried over Na$_2$SO$_4$, filtered and evaporated to afford colorless oil. Chromatographic purification using 5% EtOAc/hexanes afforded pure AIII-2-1; RF=0.44 (5% EtOAc/Hexanes) $^1$H NMR (400 MHz, CDCl$_3$) δ7.27–7.33 (m, 4H), 7.09–7.23 (m, 5H),3.93 (s, 2H).

Step 3: 1-(3-Benzylphenyl)ethanone AIII-3-1

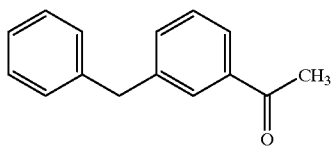

AIII-3-1

To an oven-dried 100 ml 3-neck flask fitted with temperature probe, magnetic stir bar, and argon inlet was added 1.10 g AIII2-1 in 26 ml THF and cooled to –78° C. Following dropwise addition of 1.6 M n-butyl lithium in hexanes (4.90 ml, 49 mmole) over 15 minutes, the reaction was stirred for 1 h at –78° C. before adding neat N-methoxy-N-methylacetamide (551 mg, 53.4 mmole) over 20 minutes. The reaction mixture warmed slowly to room temperature as the bath discharged overnight. The reaction was quenched with 60 ml 10% KHSO$_4$ and extracted with Et$_2$O three times. The combined organic layers were washed with NaHCO$_3$, brine and dried over Na$_2$SO$_4$, filtered and evaporated in vacuo to give a clear yellow oil. Chromatographic purification using EtOAc/hexanes afforded pure AIII-3-1. Rf=0.10 (5% EtOAc/hexanes); 0.40 (30 acetone, 70 hexane, 1.5 HOAc); $^1$H NMR (400 MHz, CDCl$_3$) δ7.80 (m, 2H), 7.39 (m, 2H),7.29 (m, 2H), 7.19 (m, 3H), 4.05 (s, 2H), 2.6 (s, 3H).

Step 4: 4-(3-Benzylphenyl)-2,4-dioxobutanoic acid methyl ester AIII-4-1

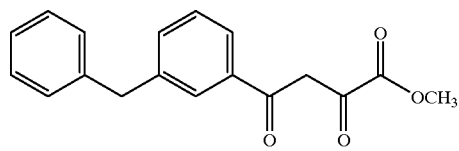

AIII-4-1

To an oven dried 100 ml flask fitted with magnetic stir bar, and argon inlet was added freshly prepared NaOMe (485 mg, 9.2 mmole) in 10 ml toluene and cooled to 0° C. Dimethyl oxalate (951 mg, 8.1 mmole) and AIII-3-1 (770 mg) were dissolved in dry dimethoxyethane (10 ml) and added by syringe at 0° C. over 5 minutes. The flask was removed from ice bath and heated to 60° C. overnight. The reaction was quenched with 60 ml saturated NH$_4$Cl and extracted with EtOAc three times. The combined organic layers were washed with H$_2$O, brine and dried over Na$_2$SO$_4$, filtered and evaporated in vacuo to give an orange oil AIII-4-1.

Rf=0.26 (30 acetone, 70 hexane+1.5 HOAc); $^1$H NMR (400 MHz, CDCl$_3$) δ7.83 (m, 2H), 7.40 (m, 2H), 7.30 (m, 2H), 7.24 (m, 1H), 7.18 (m, 2H), 7.16 (s, 1H), 4.04 (s, 2H) 3.90 (m, 3H).

Step 5: 4-(3-Benzylphenyl)-2,4-dioxobutanoic acid AIII-5-1

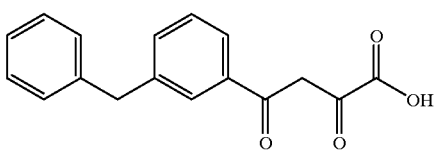

AIII-5-1

A solution of AIII-4-1 (900 mg, 2.9 mmole) was dissolved in 1:1 THF/MeOH (20 ml) and treated with 1 N NaOH (14.6 mL, 0.0146 mole) and stirred 1 h. The reaction mixture was extracted with diethyl ether (2×), then acidified to pH 1–2 with 2N HCl (7.5 ml) and extracted three times with EtOAc. The organic layers were combined, washed with H$_2$O, brine and dried over Na$_2$SO$_4$, filtered and evaporated to afford a waxy solid. The residue was recrystallized from toluene-hexane to give a light yellow solid AIII-5-1. mp 118–119° C. (uncorrected). Rf=0.12 (5 MeOH, 95 CH$_2$Cl$_2$, 5 HOAc). $^1$H NMR (400 MHz, CDCl$_3$) δ7.84 (m, 2H), 7.45 (m, 2H), 7.31 (m, 2H), 7.24 (m, 1H), 7.18 (m, 2H), 7.14 (s, 1H), 4.06 (s, 2H). mass spec (FAB, M+1) 283 m/e

EXAMPLE 5

In a manner similar to that described for AIII-5-1, the following compound was prepared:

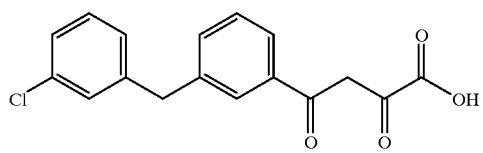

AIII-5-2 mp 102–103° C. (uncorrected). Rf=0.18 (5 MeOH, 95 CH$_2$Cl$_2$, 5 HOAc) $^1$H NMR (400 MHz, CDCl$_3$) δ7.85 (m, 2H), 7.44 (m, 2H), 7.25 (m, 2H), 7.15 (m, 2H), 7.06 (m, 1H), 4.03 (s, 2H). mass spec (FAB, M+1) 317 m/e

EXAMPLE 6

4-(4-Dibenzylaminophenyl)-2,4-dioxobutanoic acid AIV-3-1

Step 1: 1-(4-Dibenzylaminophenyl)ethanone AIV-1-1

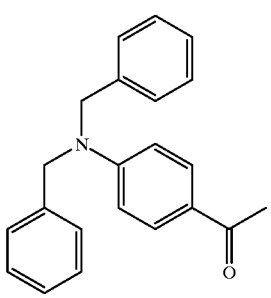

AIV-1-1

A mixture of 4-aminoacetophenone (0.027 g, 2 mmol), benzyl bromide (1.71 g, 0.19 ml, 10 mmol), and cesium carbonate (1.63 g, 5 mmol) were combined in 20 ml DMF and heated to 60° C. for 8 hr. The solvent was then removed and the residue partitioned between ethyl acetate/H₂O and extracted. The combined organic extracts were washed with H₂O, brine, dried over Na₂SO₄, filtered and the solvent removed. Purification by radial disc chromatography (4:1 hexane/EtOAc) yielded 0.238 g (38%) of AIV-1-1 as a clear oil. $^1$H NMR (400 MHz, CDCl$_3$) δ2.51 (s, 3H), 4.76 (s, 4H), 6.77 (d, 2H, J=8.97 Hz), 7.26 (d, 4H, J=6.96 Hz), 7.32 (t, 2H, J=7.14 Hz), 7.37 (t, 4H, J=7.51 Hz), 7.86 (d, 2H, J=9.16 Hz).

Step 2: 4-(4-Dibenzylaminophenyl)-2,4-dioxobutanoic acid ethyl ester AIV-2-1

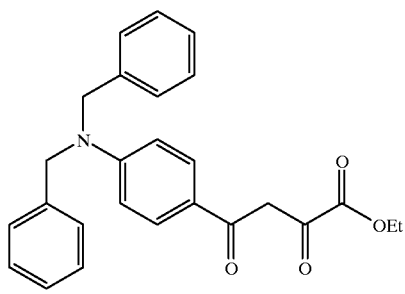

AIV-2-1

In a similar manner to example AI-1-1, 1-(4-dibenzylaminophenyl)-ethanone (0.238 g, 0.75 mmol) was reacted with diethyl oxalate (0.22 g, 0.2 ml, 1.5 mmol) and sodium ethoxide (0.1 g, 1.5 mmol) in 3 ml THF to yield 0.29 g (93%) of AIV-2-1 as a yellow solid. $^1$H NMR (400 MHz, CDCl$_3$) δ1.39 (t, 3H, J=7.14 Hz), 4.36 (q, 2H, J=7.14 Hz), 4.75 (s, 4H), 6.77 (d, 2H, J=9.15 Hz), 6.95 (s, 1H), 7.21 (d, 4H, J=6.96 Hz), 7.29 (t, 2H, J=6.95 Hz), 7.35 (t, 4H, J=7.69 Hz), 7.86 (d, 2H, J=9.15 Hz).

Step 3: 4-(4-Dibenzylaminophenyl)-2,4-dioxobutanoic acid AIV-3-1

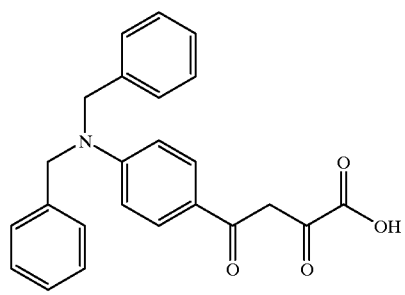

AIV-3-1

In a manner similar to example AI-2-1, 4-(4-dibenzylaminophenyl)-2,4-dioxobutanoic acid ethyl ester (0.29 g, 0.7 mmol) was hydrolyzed using 0.58 ml 1N LiOH in 5 ml THF to afford 0.237 g (87%) of AIV-3-1 as an orange solid. MP=161–162° C. $^1$H NMR (400 MHz, CDCl$_3$) δ4.76 (s, 4H), 6.79 (d, 2H, J=9.34 Hz), 6.99 (s, 1H), 7.20 (d, 4H, J=6.78 Hz), 7.30 (t, 2H, J=7.14 Hz), 7.35 (t, 4H, J=7.33 Hz), 7.86 (d, 2H, J=9.15 Hz).

EXAMPLE 7

4-(3-Dibenzylaminophenyl)-2,4-dioxobutanoic acid AV-3-1

Step 1: 1-(3-Dibenzylaminophenyl)ethanone AV-1-1

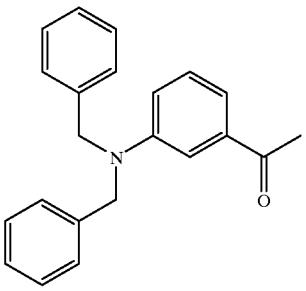

AV-1-1

In a similar manner to example AIV-1-1, 3-aminoacetophenone (0.27 g, 2 mmol) was reacted with benzyl bromide (1.71 g, 1.19 ml, 10 mmol) and cesium carbonate (1.63 g, 5 mmol) in 20 ml DMF at 60° C. for 4 hr to give 0.346 g (55%) of AV-1-1 as a clear oil after purification by radial disc chromatography (4:1 hexane/CH₂Cl₂). $^1$H NMR (400 MHz, CDCl$_3$) δ2.44 (s, 3H), 4.66 (s, 4H), 6.88 (ddd, 1H, J=8.06, 2.75, 1.10 Hz), 7.18–7.26 (m, 7H), 7.26–7.33 (m, 3H), 7.37 (dd, 1H, J=2.74, 1.47 Hz).

Step 2: 4-(3-Dibenzylaminophenyl)-2,4-dioxobutanoic acid ethyl ester AV-2-1

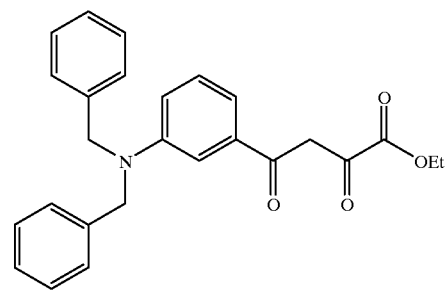

AV-2-1

In a manner similar to example AIV-1-1, 1-(3-dibenzylaminophenyl)-ethanone (0.346 g, 1.1 mmol) was reacted with diethyl oxalate (0.32 g, 0.3 ml, 2.2 mmol) and sodium ethoxide (0.15 g, 2.2 mmol) in 5 ml THF for 1 hr to give 0.48 g (100%) of AV-2-1 as a yellow oil. $^1$H NMR (400 MHz, CDCl$_3$) δ1.37 (t, 3H, J=7.14 Hz), 4.37 (q, 2H, J=7.14 Hz), 4.71 (s, 4H), 6.93 (s, 1H), 6.95 (dd, 1H, J=2.75, 1.47 Hz), 7.21–7.30 (m, 7H), 7.30–7.36 (m, 4H), 7.37–7.41 (m, 1H).

Step 3: 4-(3-Dibenzylaminophenyl)-2,4-dioxobutanoic acid AV-3-1

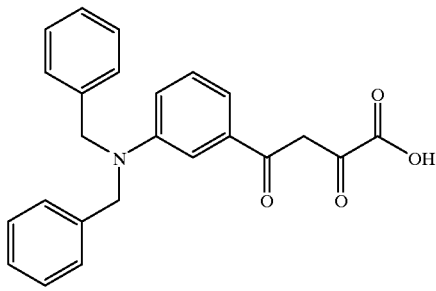

AV-3-1

In a similar manner to example AI-2-1, 4-(3-dibenzylaminophenyl)-2,4-dioxobutanoic acid ethyl ester (0.489 g, 1.1 mmol) was reacted with 3 ml 1N LiOH in 10 ml THF to yield 0.4 g (94%) of AV-3-1 as an orange resin. $^1$H NMR (400 MHz, CDCl$_3$) δ4.71 (s, 4H), 6.96 (dt, 1H, J=7.33, 2.20 Hz).

EXAMPLE 8

1-(3-benzyloxy-5-methoxyphenyl)-2,4-dioxobutanoic acid AVI-3-1

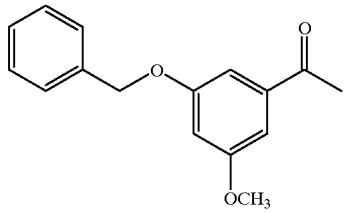

AVI-1-1

Step 1: 1-(3-Benzyloxy-5-methoxyphenyl)-ethanone AVI-1-1

To a solution of 5-hydroxy-3-benzyloxyacetophenone (740 mg, 3.06 mmol) in DMF (10 mL) was added K$_2$CO$_3$ (845 mg, 6.12 mmol) followed by methyl iodide (0.38 mL, 6.10 mmol). After stirring at rt for 3 h, the reaction mixture was poured onto water (20 mL) and extracted with Et$_2$O (3×20 mL). The combined organic extracts were washed with water (20 mL), sat. NaCl (20 mL) and dried (MgSO$_4$). Concentration followed by medium-pressure liquid chromatography on silica gel, eluting with 9:1/hexanes:EtOAc, afforded 0.550 g (70%) of product as a clear oil. $^1$H NMR (400 MHz, CDCl$_3$) δ7.45–7.33 (m, 5H), 7.18 (t, J=1.6 Hz, 1H), 7.11 (t, J=1.4 Hz, 1H), 6.74 (t, J=2.2 Hz, 1H), 5.09 (s, 2H), 3.83 (s, 3H), 2.57 (s, 3H). mass spec (EI, M+) 256

Step 2: 1-(3-Benzyloxy-5-methoxyphenyl)-2,4-dioxobutanoic acid AVI-3-1

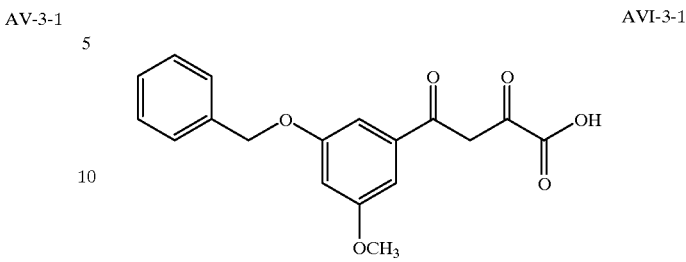

AVI-3-1

AI-1-1 was treated with NaOEt and diethyl oxalate to give the ethyl ester which was treated with aqueous HCl in dioxane to give AVI-3-1. mp 101–102° C. (uncorrected) $^1$H NMR (400 MHz, d$_6$-DMSO) δ7.48–7.44 (m, 2H), 7.39 (m, 2H), 7.34 (m, 1H), 7.25 (s, 1H), 7.14 (s, 1H), 7.06 (s, 1H), 6.89 (s, 1H), 5.19 (s, 2H), 3.81 (s, 3H). mass spec (FAB, M+H) 329.

EXAMPLE 9

1-(3-Benzyloxyphenyl)-2,4-dioxobutanoic acid AVI-3-2

Step 1: 1-(3-Benzyloxyphenyl)-ethanone AVI-1-2

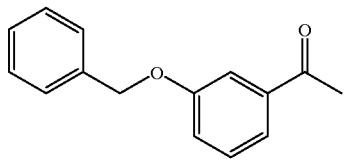

AVI-1-2

To a solution of benzyl alcohol (Aldrich, 1.08 g, 10.0 mmol) in benzene (40 mL) at rt was added 3-hydroxyacetophenone (Aldrich, 1.36 g, 10.0 mmol) followed by PPh$_3$ (2.62 g, 10.0 mmol). After cooling to 0° C., DEAD (1.60 mL, 10.0 mmol) was added and the resulting mixture was stirred at rt. After 4 h, the reaction mixture was poured onto hexanes (50 mL) and filtered through a pad of CELITE diatomaceous earth. The filtrate was concentrated and chromatographed on silica gel, eluting with 9:1/hexanes:EtOAc, to provide 2.01 g (89%) of product as a clear oil. $^1$H NMR (400 MHz, CDCl$_3$) δ7.60–7.54 (m, 2H), 7.47–7.32 (m, 6H), 7.21–7.17 (m, 1H), 5.12 (s, 2H), 2.59 (s, 3H). mass spec (E1, M+) 226.

Step 2: 1-(3-Benzyloxyphenyl)-2,4-dioxobutanoic acid AVI-3-2

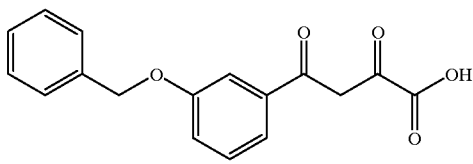

AVI-3-2

AVI-1-2 was treated with NaOEt and diethyl oxalate to give the ethyl ester which was treated with aqueous HCl in dioxane to give AVI-3-2. mp 109–114° C. (uncorrected) $^1$H NMR (400 MHz, d$_6$-DMSO) δ7.66 (dt, J=1.4, 8.0 Hz, 1H), 7.63 (dd, J=1.8, 2.3 Hz, 1H), 7.52–7.47 (m, 3H), 7.43–7.38 (m, 2H), 7.09 (s, 1H), 5.22 (s, 2H).

EXAMPLE 10

1-(2-Benzyloxyphenyl)-2,4-dioxobutanoic acid AVI-3-3

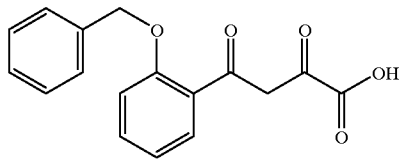

AVI-3-3

2-benzyloxyacetophenone (Chem Service) was treated with NaOEt and diethyl oxalate to give the ethyl ester which was treated with aqueous HCl in dioxane to give AVI-3-3. mp 136–138° C. (uncorrected). $^1$H NMR (400 MHz, $d_6$-DMSO) δ7.81 (dd, J=1.8, 8.4 Hz, 1H), 7.62 (ddd, J=1.8, 7.4, 8.4 Hz, 1H), 7.52 (m, 1H), 7.41–7.31 (m, 4H), 7.27 (s, 1H), 7.12 (t, J=7.4 Hz, 1H), 5.23 (s, 2H). mass spec (FAB, M+H) 299.

EXAMPLE 11

1-[3-(4-Fluorobenzyloxy)phenyl]-2,4-dioxobutanoic acid AVI-3-5

Step 1: 1-[3-(4-Fluorobenzyloxy)phenyl]-ethanone AVI-1-5

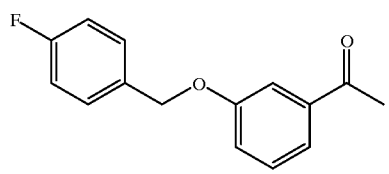

AVI-1-5

To a solution of 3-hydroxyacetophenone (Aldrich, 680 mg, 5.00 mmol) in DMF (10 mL) at rt was added $K_2CO_3$ (1.38 g, 10.0 mmol) and 4-fluorobenzyl bromide (897 mg, 4.75 mmol). After 3 h, the reaction mixture was poured onto water (20 mL) and extracted with $Et_2O$ (3×25 mL). The combined organic extracts were washed with 2.5 N NaOH (25 mL), sat. NaCl (25 mL) and dried (MgSO$_4$). Concentration followed by medium-pressure liquid chromatography on silica gel, eluting with 9:1/hexanes:EtOAc, yielded 1.08 g (93%) of product as a clear oil. $^1$H NMR (400 MHz, CDCl$_3$) δ7.58–7.55 (m, 2H), 7.44–7.36 (m, 3H), 7.19–7.15 (m, 1H), 7.09 (m, 2H), 5.08 (s, 2H), 2.60 (s, 3H). mass spec (EI, M+) 244.

Step 2: 1-[3-(4-Fluorobenzyloxy)phenyl]-2,4-dioxobutanoic acid AVI-3-5

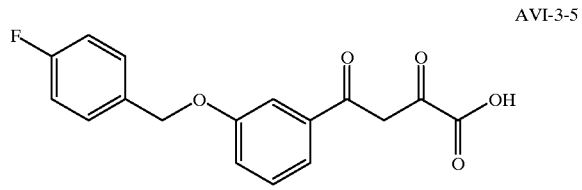

AVI-3-5

AVI-1-5 was treated with NaOEt and diethyl oxalate to give the ethyl ester which was treated with aqueous HCl in dioxane to give AVI-3-5. mp 157–158° C. (uncorrected) $^1$H NMR (400 MHz, $d_6$-DMSO) δ7.66 (d, J=7.7 Hz, 1H), 7.62 (t, J=1.9 Hz, 1H), 7.56–7.47 (m, 4H), 7.33 (dd, J=1.9, 7.7 Hz, 1H), 7.23 (m, 2H), 7.08 (s, 1H), 5.20 (s, 2H). mass spec (FAB, M+H) 317.

EXAMPLE 12

1-[3-(3,4-Difluorobenzyloxy)phenyl]-2,4-dioxobutanoic acid AVI-3-6

Step 1: 1-[3-(3,4-Difluorobenzyloxy)phenyl]-2,4-dioxobutanoic acid AVI-3-6

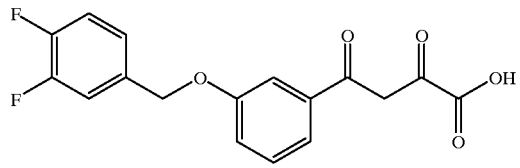

AVI-3-6

AVI-3-6 was prepared in a manner similar to that described for AVI-3-5 by replacing 4-fluorobenzyl bromide with 3,4-difluorobenzyl bromide. mp 181–182° C. (uncorrected). $^1$H NMR (400 MHz, $d_6$-DMSO) δ7.68 (d, J=7.7 Hz, 1H), 7.63 (m, 1H), 7.60–7.55 (m, 1H), 7.53–7.43 (m, 2H), 7.36–7.33 (m, 2H), 7.09 (s, 1H), 5.21 (s, 2H). mass spec (negative mode electrospray, M–H) 333.

EXAMPLE 13

4-[3-(5-methyl-thiophen-2-ylmethyl)-phenyl]-2,4-dioxo-butyric acid E1

Step 1: (3-bromo-phenyl)-(5-methyl-thiophen-2-yl)-methanol E1-A

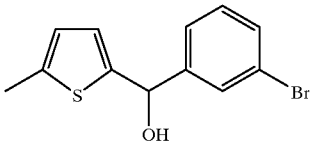

E1-A

To an oven dried 3-neck 250 mL round bottom flask equipped with argon inlet and digital thermometer was added 2.5M nBuLi in hexanes (15.24 ML, 0.0381 mole) at −78° C. 1,3-Dibromobenzene (4.60 mL, 0.0381 mole) was then added dropwise via syringe to the solution, and this was allowed to stir for 2 hours. 5-methyl-2-thiophenecarboxaldehyde (5 g, 4.27 mL, 0.0396 mole) was added over one hour. After an additional hour, 50 mL of water was poured into the reaction which was then acidified with conc. HCl. Extraction with EtOAc three times followed by drying over NaSO$_4$, filtration and removal of solvent gave E1-A as a brown oil that was taken on to the next step.

Step 2: 2-(3-bromobenzyl)-5-methylthiophene E1-B

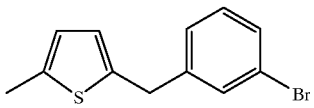

E1-B

A solution of crude E1-A (7.0 g, 0.0247 mole) and triethylsilane (5.9 mL, 0.0371 mole) in methylene chloride (30 mL) was chilled to 0° C. under argon with stirring followed by addition of boron trifluoride etherate (4.67 mL, 0.0371 mole). The reaction was stirred at room temperature for two hours. The reaction mixture was poured into 150 mL of saturated sodium bicarbonate and extracted with methylene chloride 2 times. The combined organic layers were dried over sodium sulfate. Filtration and removal of solvent afforded a brown oil. Chromatographic purification using 100% hexanes afforded E1-B as a clear oil.

Rf=0.52 (100% Hexanes) $^1$H NMR (400MHz, CDCl$_3$) δ7.37–7.38 (m, 1H), 7.33–7.34 (m, 1H), 7.16 (s, 1H), 7.14–7.15 (m, 1H), 6.56 (m, 7.56), 4.02 (s, 2H), 2.41 (s, 3H).

Step 3: 1-[3-(5-methylthiophen-2-ylmethyl)-phenyl]-ethanone E1-C

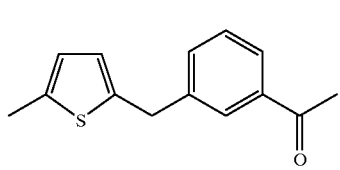

E1-C

To an oven dried 3-neck flask fitted with temperature probe and argon inlet was added E1-B (4 g, 0.0150 mole) in 40 mL of THF. The reaction was cooled to –78° C. and 2.5M nBuLi in hexanes (9.0 mL 0.0225 mole) was added over one hour. The lithium salt of compound precipitated out of solution. Neat N-methoxy-N-methylacetamide (2.3 g, 2.3 mL 0.0225 mole) was added slowly which caused rxn to become homogenous. Once addition was complete the reaction was allowed to stir at room temperture for two hours. The reaction was poured into 20 mL of water and acidified with concentrated HCl. Extraction with EtOAc three times followed by drying over sodium sulfate, and subsequent removal of solvent gave a brown oil. Chromatographic purification using a 88:12 mixture of Hexanes/EtOAc afforded E1-C as a clear oil.

Rf=0.42 (10% EtOAc/Hexanes) $^1$H NMR (400 MHz, CDCl$_3$) δ7.84 (s, 1H), 7.82,7.80 (d, 1H), 7.37–7.45 (m, 2H), 6.58–6.55 (m, 2H), 4.12 (s, 2H), 2.58 (s, 3H), 2.41 (s, 3H).

Step 4: 4-[3-(5-methylthiophen-2-ylmethyl)-phenyl]-2,4-dioxo-butyric acid E1

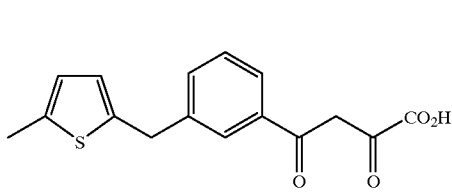

E-1

To a solution of E1-C (1 g, 0.00446 mole) and diethyloxylate (0.67 mL, 0.00491 mole) in THF (8 mL) was added NaOEt (0.46 g, 0.00669 mole) under an atmosphere of Argon. After two hours the reaction was poured into an aqueous solution of potassium hydrogen sulfate, extracted with EtOAc three times, dried over sodium sulfate, and the solvent removed to give the ethyl ester. Immediately following workup the ester was submitted to 3N NaOH (7.4 mL, 0.0223 mole) in a 5:2 mixture of THF/MeOH (20 mL). After one hour the reaction was poured into saturated sodium bicarbonate solution and extracted two times with ether. The aqueous layer was acidified with a solution of 10% KHSO$_4$ which caused a large amount of solids to crash out. The aqeuous layer was extracted with EtOAc eight times, the organic layer was dried over NaSO$_4$, filtered and concentrated to give a solid which was crystallized from CH$_2$Cl$_2$ and pet. ether. Collected pure E1 as a yellow solid by filtration. $^1$H NMR (400MHz, CDCl$_3$) δ7.88–7.85 (m, 2H), 7.50–7.44 (m, 2H), 7.15 (s, 1H), 6.60–6.57 (m, 2H), 4.14 (s, 2H), 2.42, (s, 3H). Exact mass (M+NH$_4$)=320.0951.

EXAMPLE 14

4-{3-[(methyl-phenyl-amino)-methyl]-phenyl}-2,4-dioxo-butyric acid E2

Step 1: (3-bromo-benzyl)-phenyl-amine E2-A

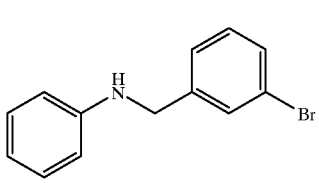

E2-A

To a solution of aniline (1.26 g. 1.23 mL, 0.0135 mole) and 3-bromobenzaldehyde (2.5 g, 1.58 mL, 0.0135 mole) in MeOH (20 mL) under argon was added HOAc to adjust pH to 5.5. After 45 minutes sodium cyanoborohydride (1.11 g, 0.0176 mole) was added and pH readjusted to 5.5. After 16 hours the reaction was poured into saturated aqueous sodium bicarbonate solution, extracted 3 times with EtOAc, dried over NaSO$_4$, filtered and concentrated. Chromatographic purification with 95:5 Hexanes/EtOAc afforded E2-A as an oil.

Rf=0.28 (5% EtOAc/Hexanes) $^1$H NMR (400MHz, CDCl$_3$) δ7.52 (s, 1H), 7.40–7.38 (d, 1H, j=7.33 Hz), 7.28, 7.30 (d, 1H, j=7.69 Hz), 7.21–7.14 (m, 3H), 6.75–6.71 (t, 1H, j=7.42 Hz), 6.62–6.59 (d, 2H, j=7.87 Hz) 4.31 (s, 2H), 4.06 (broad, 1H).

Step 2: (3-bromo-benzyl) methyl-phenyl-amine E2-B

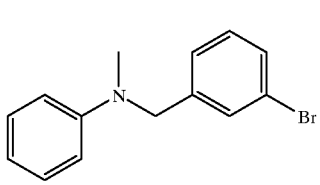

E2-B

To a solution of E2-A (1.5 g, 0.00572 mole) in DMF (25 mL) and under argon at 0° C. was added NaH (0.15 g, 0.00629 mole) and this was stirred for 15 minutes followed by addition of iodomethane (0.40 mL, 0.00629 mole) which was passed through basic alumina. Reaction required an additional 1 equivalent each of NaH and iodomethane. After 24 hours poured into 50 mL of saturated sodium bicarbonate solution, extracted with EtOAc 3 times, dried over sodium sulfate, filtered, and concentrated. Chromatographic purification using 90:10 Hexanes/Ethyl acetate afforded E2-B.

Rf=0.45 (5% EtOAc/Hexanes) $^1$H NMR (400MHz, CDCl$_3$) δ7.40–7.36 (m, 2H), 7.26–7.15 (m, 4H), 6.76–6.72 (m, 3H), 4.49 (s,2H), 3.02 (s, 3H).

71

Step 3: 1-{3-[(methyl-phenyl-amino)-methyl]-phenyl}-ethanone E2-C

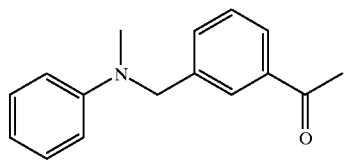

E2-C

Product from E2-B (1 g, 0.00361 mole), triethylamine (2 mL, 0.0144 mole), thallium acetate (1.05 g, 0.00937 mole), palladium acetate (0.2 g, 0.000903 mole), butyl vinyl ether (1.81 mL, 0.0181 mole), and 1,3-Bis(diphenylphosphino)-propane (0.4 g, 0.000975 mole) were combined in a pressure tube in anhydrous DMF (8 mL) under argon at 100° C. overnight. Passed mixture through a pad of CELITE diatomaceous earth which was washed several times with EtOAc. Solvent was then removed and the residue dissolved in THF to which 1N HCl was added (14 mL, 0.0144 mole). After one hour poured into 20 mL of saturated sodium bicarbonate solution and extraced with EtOAc dried over $NaSO_4$, filtered and concentrated. Chromatographic purification with 80:20 Hexanes/EtOAc afforded purified E2-C.

Rf=0.29 (10% EtOAc/Hexanes) $^1$H NMR (400MHz, $CDCl_3$) δ7.91–7.87 (m, 2H), 7.48–7.44 (m, 2H), 7.3–7.25 (m, 2H), 6.82–6.76 (m, 3H), 4.61 (s, 2H), 3.07 (s, 3H), 2.61 (s, 3H.

Step 4: 4-{3-[(methyl-phenyl-amino)-methyl]-phenyl}-2,4-dioxobutyric acid E2

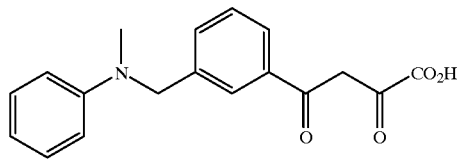

E2

To a solution of E2-C (0.4 g, 0.00167 mole) and dimethyloxylate (0.22 g 0.00184 mole) in THF (5mL) was added NaOMe (0.4 g, 0.00334 mole) under an atmosphere of Argon. After two hours the reaction was poured into an aqueous solution of potassium hydrogen sulfate, extracted with EtOAc three times, dried over sodium sulfate, and the solvent removed to give the methyl ester. Immediately following workup the ester was submitted to 1N NaOH (7.0 mL, 0.00167 mole) in THF (20 mL). After 1 hour the reaction was poured into saturated sodium bicarbonate solution and extracted two times with ether. The aqeuous was with 3N HCl, extracted with EtOAc three times, and the organic layers dried over $NaSO_4$, filtered and concentrated to give solid pure E2. $^1$H NMR (400MHz, $CDCl_3$) δ7.91–7.81 (m, 2H), 7.48–7.44 (m, 2H), 7.28–7.22 (m, 2H), 7.16 (s, 1H), 6.81–6.77 (m, 3H), 4.59 (s, 2H), 3.09 (s, 3H). Exact mass found (m+H)=312.1230.

72

EXAMPLE 15

4-(3-benzyl-5-pyrazin-2-yl-phenyl)2,4-dioxo-butyric acid E3

Step 1: (3,5-dibromo-phenyl)-phenyl-methanol E3-A

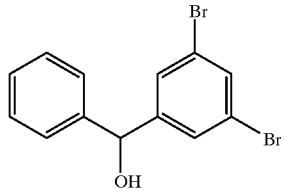

E3-A

To a solution of 1,3,5-tribromobenzene (10 g, 0.0318 mole) in ether (500 g), under argon was added nBuLi in hexanes (13.4 mL, 0.0318 mole) dropwise at –78° C. During the intial cooling of the tribrombenzene in ether some solids crashed out of solution. After addition of nBuLi was complete the reaction was allowed to stir for 0.5 hours at which time neat benzaldehyde (3.55 mL, 0.035 mole) was added dropwise to the vigorously stirred reaction mixture. Once addition was complete the reaction was allowed to reach 0° C. and 100 mL of HCl was added to the mixture. This was extracted with ether two times, dried with brine and over sodium sulfate and concentrated to give an oil. The crude product was purified by chromatography with 5% EtOAc/Hexanes to afford E3-A as a colorless oil that solidified on the bench. Rf=0.44 (5%EtOAc/Hexanes) $^1$H NMR (400MHz, $CDCl_3$) δ7.56–7.55 (m, 1H), 7.48–7.47 (m, 2H), 7.39–7.29 (m, 5H), 5.75 (d, 1H, j=3.48 Hz), 2.28–2.27 (d, 1H, j=3.48 Hz).

Step 2: 3-bromo-5-benzyl-bromobenzene E3-B

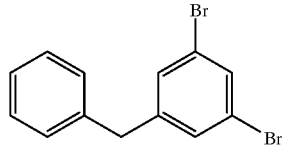

E3-B

A solution of E3-A (2.0 g, 0.00548 mole) and triethylsilane (1.39 mL, 0.00877 mole) in methylene chloride (20 mL) was chilled to 0° C. under argon with stirring followed by addition of boron trifluoride etherate (1.10 mL, 0.00877 mole). The reaction was stirred at room temperature overnight. The reaction mixture was poured into 75 mL of saturated sodium bicarbonate and extracted with methylene chloride two times. The combined organic layers were dried over sodium sulfate, filtered and the solvent removed. Chromatographic purification using 1% EtOAc/Hexanes afforded E3-B. Rf=0.72 (5%EtOAc/hexanes) $^1$H NMR (400 MHz, $CDCl_3$) δ7.50 (s, 1H), 7.37–7.21 (m, 5H), 7.16–7.14 (m, 2H), 3.91 (s, 2H).

Step 3: 2-(3-benzyl-5-bromo-phenyl)-pyrazine E3-C

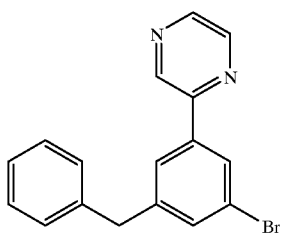

E3-C

To a solution of E3-B (1 g, 0.00307 mole) in THF (20 mL) under argon at −78° C. was added 2.4M nBuLi in hexanes (1.4 mL, 0.00337 mole) dropwise. After 45 minutes of stirring, the solution was treated with 0.5m ZnCl₂ in THF (6.14 mL 0.00337 mole) and this was warmed to 0° C. To the reaction was added a cold mixture of chloropyrazine (0.35 mL, 0.00307 mole) and tetrakistriphenylphosphine palladium (18 mg, 0.0000154 mole) in THF (5 mL) and the reaction was heated to reflux for two hours. The reaction was then cooled, concentrated and treated with EtOAc and washed with 6% aqueous solution of diaminotetraacetic acid disodium salt dihydrate two times. The EtOAc layer was dried over sodium sulfate, filtered and concentrated. Chromatographic purification with 15% EtOAc/hexanes afforded a clear oil E3-C. Rf=0.17 (20%EtOAc/hexanes) $^1$H NMR (400MHz, CDCl₃ ) δ8.95 (s, 1H), 8.62–8.61 (m, 1H), 8.52 (m, 1H), 8.02 (s, 1H), 7.77 (s, 1H), 7.43 (s, 1H), 7.32–7.20 (m, 5H), 4.04 (s, 2H).

Step 4: 1-(3-benzyl-5-pyrazin-2-yl-phenyl)-ethanone E3-D

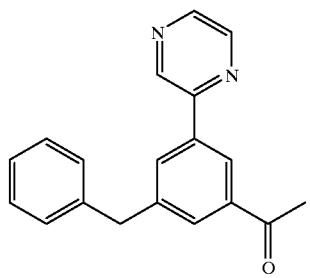

E3-D

E3-C (0.29 g, 0.000926 mole), triethylamine (0.52 mL, 0.00370 mole), thallium acetate (0.27 g, 0.00102 mole), palladium acetate (52 mg, 0.000232 mole), butyl vinyl ether (0.60 mL, 0.00463 mole), and 1,3-bis(diphenylphosphino)-propane (0.1 g, 0.000242 mole) were combined in a pressure tube in anhydrous DMF (4 mL) under argon at 100° C. overnight. The mixture was passed through a pad of CELITE diatomaceous earth which was washed several times with EtOAc. The solvent was then removed and the residue dissolved in THF to which 1N HCl was added (3.70 mL, 0.00370 mole). After one hour the reaction was poured into 15 mL of saturated sodium bicarbonate solution and extraced with EtOAc. The organic layers were dried over NaSO₄, filtered and concentrated. Chromatographic purification with 70:30 Hexanes/EtOAc afforded purified E3-D as a clear oil. Rf=$^1$H NMR (400MHz, CDCl₃ ) δ9.04 (s, 1H), 8.65–8.64 (m, 1H), 8.55–8.54 (m, 1H), 8.44 (s, 1H), 8.06 (s, 1H), 7.91 (s, 1H), 7.33–7.22 (m, 5H), 4.14 (s, 2H), 2.65 (s, 3H).

Step 5: 4-(3-benzyl-5-pyrazin-2-yl-phenyl)-2,4-dioxo-butyric acid E3

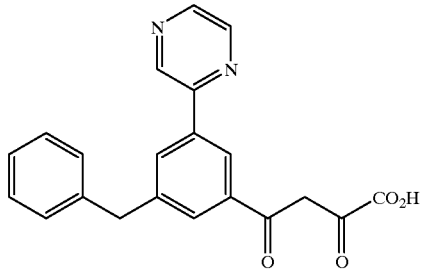

E3

To a solution of E3-D (0.17 g, 0.000590 mole) and dimethyloxylate (76 mg 0.000650 mole) in THF (7mL) was added NaOMe (50 mg, 0.000884 mole) under an atmosphere of Argon. After one hour the reaction was poured into an aqueous solution of potassium hydrogen sulfate, extracted with EtOAc three times, dried over sodium sulfate, and the solvent removed to give the methyl ester. Immediately following workup the ester was submitted to 1N NaOH (1.48 mL, 0.00148 mole) in THF (10 mL). After 1 hour the reaction was poured into saturated sodium bicarbonate solution and extracted three times with ether. The aqueous layer was acidified with 3N HCl, extracted with EtOAc three times, the organic layers were dried over NaSO₄, filtered and concentrated to give E3 as a pure white solid. $^1$H NMR (400MHz, DMSO ) δ9.41 (m, 1H), 8.76–8.75 (m, 1H), 8.67 (m, 1H), 8.60 (s, 1H), 8.36 (s, 1H), 8.08 (s, 1H), 7.36–7.29 (m, 4H), 7.22–7.19 (m, 2H), 4.17 (s, 2H). Exact mass found (m+H)=361.1196.

EXAMPLE 16

2,4-dioxo-4-[3-(1,2,3,4-tetrahydronaphthalen-1-yl)-phenyl]butyric acid (isomers A and B) (G1 and G2)

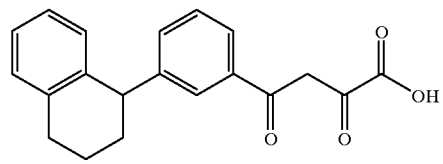

Step 1: Synthesis of 1-(3-bromophenyl)-1,2,3,4-tetrahydronaphthalen-1-ol

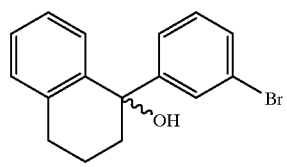

To a solution of 1 g (4.2 mmol) 1,3-dibromobenzene in 10 mL diethyl ether was added 0.096 g (4 mmol) magnesium metal turnings. This mixture was stirred until all of the magnesium was consumed, at which time 0.29 g (2 mmol) 1-tetralone was added dropwise in 2 mL diethyl ether. The reaction was then heated to reflux for 30 min, after which the cooled reaction was quenched with a 10% HCl solution and extracted three times with ethyl acetate. The combined organic layers were washed with water, brine, dried over anhydrous sodium sulphate, filtered, and the solvent removed in vacuo to afford the crude product which was used without further purification.

Step 2. Synthesis of 1-(3-bromophenyl)-1,2,3,4-tetrahydronaphthalene and 4-(3-bromophenyl)-1,2-dihydronaphthalene.

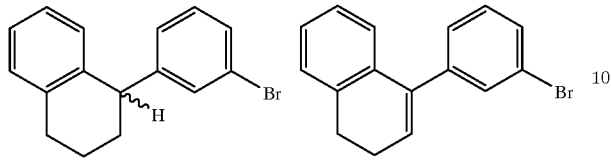

Into an ice cooled solution of 0.671 g (2.2 mmol) of 1-(3-bromophenyl)-1,2,3,4-tetrahydronaphthalen-1-ol and and 0.386 g (3.3 mmol) triethylsilane in 5 mL methylene chloride was added 0.471 g (3.3 mmol) boron trifluoride diethyl etherate dropwise. After stirring the reaction for 6 hr, the solution was slowly poured into 10 mL 10% sodium carbonate solution and extracted three times with methylene chloride. The combined organic layers were washed with water, brine, dried over anhydrous sodium sulphate, filtered, and the solvent removed in vacuo. Purification by radial chromatography (5:1 hexane/ethyl acetate) followed by a second purification (7:1 hexane/methylene chloride) a 2.5:1 mixture of 1-(3-bromophenyl)-1,2,3,4-tetrahydronaphthalene and 4-(3-bromophenyl)-1,2-dihydronaphthalene which was used without further purification.

Step 3. Synthesis of 1-[3-(1,2,3,4-tetrahydronaphthalen-1-yl)-phenyl]-ethanone and 1-[3-(1,2-dihydronaphthalen-1-yl)-phenyl]-ethanone

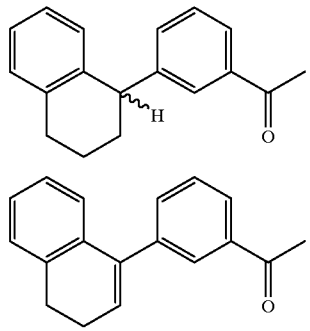

To a solution of 0.276 g of the above mixture dissolved in 10 mL of a 1:1 mixture of diethyl ether/tetrahydrofuran and cooled to −76° C. was slowly added 0.42 mL of a 2.5M solution of n-butyllithium in hexanes so the temperature did not exceed −70° C. After the addition, the reaction was stirred for an addition 30 min, after which time 0.118 mL N-methoxy-N-methyl acetamide was added. This mixture was allowed to stir for 15 min, then warmed to ambient temperature and stirred for 18 hr. The reaction was then quenched by the addition of 50 mL water and extracted three times with ethyl acetate. The combined ethyl acetate extracts were washed with water, brine, dried over anhydrous sodium sulphate, filtered, and the solvent removed in vacuo. Subsequent purification by preparative HPLC afforded three compounds: the olefin, enantiomer A and enantiomer B. The absolute stereochemistry of the enantiomers was not determined.

Step 4: Synthesis of 2,4-dioxo-4-[3-(1,2,3,4-tetrahydronaphthalen-1-yl)-phenyl]butyric acid ethyl ester (isomers A and B)

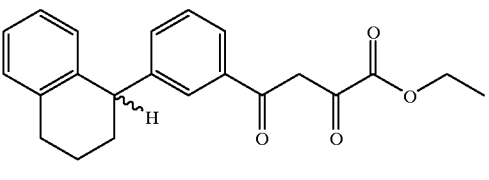

Isomer A: Into 1 mL distilled tetrahydrofuran was placed 0.046 g (0.18 mmol) of 1-[3-(1,2,3,4-tetrahydronaphthalen-1-yl)-phenyl]-ethanone (isomer A), 0.054 g (0.37 mmol) diethyl oxalate, and 0.025 g (0.37 mmol) sodium ethoxide. After stirring for 1.5 hr, excess 10% citric acid solution was added and the THF removed in vacuo. The residue was partitioned between water and ethyl acetate and extracted. The combined organic extracts were washed with water, brine, dried over anhydrous sodium sulphate, filtered, and the solvent removed in vacuo to afford the title compound which was used without further purification.

Isomer B: As described above, 0.048 g (0.19 mmol) of 1-[3-(1,2,3,4-tetrahydronaphthalen-1-yl)-phenyl]-ethanone (isomer B), 0.056 g (0.38 mmol) diethyl oxalate, and 0.026 g (0.38 mmol) sodium ethoxide were reacted to give the title compound which was used without further purification.

Step 5: Synthesis of 2,4-dioxo-4-[3-(1,2,3,4-tetrahydronaphthalen-1-yl)-phenyl]butyric acid (isomers A and B)

Isomer A: 2,4-dioxo-4-[3-(1,2,3,4-tetrahydronaphthalen-1-yl)-phenyl]butyric acid ethyl ester (isomer A from above) was dissolved in 2 mLs methanol, and to it was added 1 mL of a 1M solution of sodium hydroxide in water. After stirring for 4 hr, the reaction was poured into 5 mL sodium hydroxide and extracted three times with diethyl ether. The aqueous layer was then acidified via the addition of excess 10% citric acid and extracted three times with ethyl acetate. The ethyl acetate extracts were combined and washed with water, brine, dried over anhydrous sodium sulfate, filtered, and the solvent removed in vacuo. The residue was triturated in 3:1 hexane/diethyl ether, filtered and the solvent removed in vacuo to yield the title compound as a yellow solid. $^1$H NMR (CDCl$_3$) δ1.72–1.91(3H,m), 2.20(1H,m), 2.80–3.00(2H,m), 4.22(1H, t, J=7.14Hz), 6.77(1H, d, J=7.69 Hz), 7.03(1H, t, J=7.42Hz), 7.11–7.19(3H,m), 7.31(1H, d, J=7.69Hz), 7.41 (1H, t, J=7.69Hz), 7.80(1H,s), 7.84(1H, d, J=7.88Hz).

CHN Calc. (C$_{20}$H$_{18}$O$_4$.0.1EtOAc) 73.98, 5.72; Fnd. 73.68, 6.04

Isomer B: In a similar manner to the above, 2,4-dioxo-4-[3-(1,2,3,4-tetrahydronaphthalen-1-yl)-phenyl]butyric acid ethyl ester (isomer B from above) was reacted in 2 mL methanol with 1 mL 1M sodium hydroxide to afford the title compound as a yellow solid.

$^1$H NMR (CDCl$_3$) δ1.72–1.91(3H,m), 2.20(1H,m), 2.80–3.00(2H,m), 4.22(1H, t, J=7.14Hz), 6.77(1H, d, J=7.69Hz), 7.03(1H, t, J=7.42Hz), 7.11–7.19(3H,m), 7.31 (1H, d, J=7.69Hz), 7.41(1H, t, J=7.69Hz), 7.80(1H,s), 7.84 (1H, d, J=7.88Hz).

CHN Calc. (C$_{20}$H$_{18}$O$_4$.0.1EtOAc) 73.98, 5.72; Fnd. 73.68, 5.90.

EXAMPLE 17

2,4-Dioxo-4-(3-phenylsulfanyl-phenyl)-butyric acid L1

Step 1: 1-(3-Phenylsulfanyl-phenyl)-ethanone L1-A

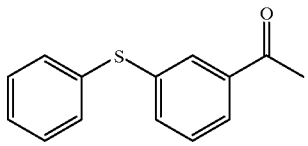

L1-A

A mixture of potassium carbonate (1.20 g, 9.08 mmol), 0.17 M Ni(II)Br$_2$ (2.12 mL, 0.36 mmol), 1,1'-bis(diphenylphosphino)ferrocene (dppf, 403 mg, 0.73 mmol), zinc powder (119 mg, 1.82 mmol), and N-methyl-2-pyrrolidinone (NMP, 10 mL) was stirred at room temperature for one hour in dried glassware under argon. Thiophenol (932 µL, 9.08 mmol) and 3'-iodoacetophenone (1.88 mL, 13.6 mmol) were then introduced and the mixture was stirred for three hours. The resulting mixture was directly chromatographed using 5% EtOAc/hexane as the elutant. Pure fractions were combined and concentrated to afford L1-A as a yellow oil. Rf=0.49 (10% EtOAc/hexane). $^1$H NMR (400 MHz, CDCl$_3$) δ7.89 (m, 1H), 7.79 (m, 1H), 7.56 (m, 1H), 7.29–7.40 (m, 6H), 2.58 (s, 3H).

Step 2: 2,4-Dioxo-4-(3-phenylsulfanyl-phenyl)-butyric acid L1

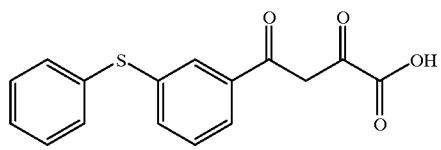

L1

In a manner similar to example AIV-2-1, 2,4-dioxo-4-(3-phenylsulfanyl-phenyl)-butyric acid ethyl ester was formed and the crude material was hydrolyzed in a manner similar to example AIV-3-1 using 1N NaOH to afford L-1 as a yellow solid. Rf=0.32 (6:6:94 MeOH/AcOH/CH$_2$Cl$_2$).

$^1$H NMR (400 MHz, CDCl$_3$) δ7.91 (m, 1H), 7.81 (m, 1H), 7.48 (m, 1H), 7.43 (m, 1H), 7.33–7.43 (m, 5H), 7.09 (s, 1H). mass spec (FAB, M+1) 301 m/e.

EXAMPLE 18

4-[3-(2,4-Difluoro-benzyl)-phenyl]-2,4-dioxo-butyric acid L2

Step 1: 1-[3-(2,4-Difluoro-benzyl)-phenyl]-ethanone L2-A

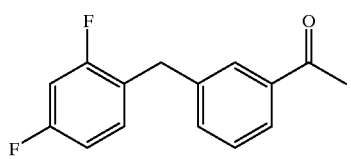

L2-A

To an oven dried three-necked 100 mL round bottom flask fitted with argon inlet, temperature probe and stir bar was added zinc powder (793 mg, 12.2 mmol), 1,2-dibromoethane (21 µL, 0.24 mmol), and THF (2 mL). The mixture was brought to reflux two times using a heat gun then cooled to 0° C. at which time α-bromo-2,4-difluorotoluene (781 µL, 6.10 mL) in THF (3 mL) was added slowly keeping the temperature <3° C. To another 3-necked round bottom flask fitted as above was added bis(dibenzylideneacetone)palladium (Pd(dba)$_2$, 234 mg, 0.41 mmol), tris(2-furyl)phosphine (tfp, 189 mg, 0.81 mmol), and THF (5 mL). The mixture was stirred 10 minutes at room temperature then cooled to 0° C. at which time 3'-iodoacetophenone (562 µL, 4.06 mmol) in THF (1 mL) was added. The flask was flushed with argon and the zinc mixture was pipetted in. After stirring 5 minutes at 0° C., the reaction was left to stir over night at room temperature. The next morning the reaction was quenched with sat. NH$_4$Cl solution and extracted three times with EtOAc. The combined organic layers were washed with brine, dried over Na$_2$SO$_4$, filtered, and concentrated to a brown oil. The crude product was chromatographed on silica gel using 5% EtOAc/hexane as elutant. Pure product fractions were combined and concentrated to afford L2-A as a yellow oil. Rf=0.22 (5% EtOAc/hexane). $^1$H NMR (400 MHz, CDCl$_3$) δ7.81 (m, 2H), 7.39 (m, 2H), 7.11 (m, 1H), 6.81 (m, 2H), 4.02 (s, 2H), 2.56 (s, 3H).

Step 2: 4-[3-(2,4-Difluoro-benzyl)-phenyl]-2,4-dioxo-butyric acid L2

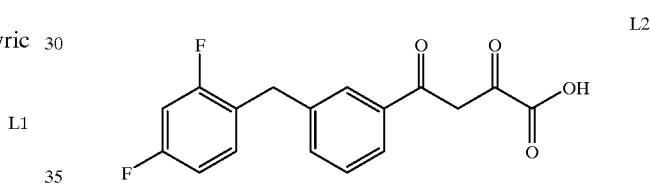

L2

In a manner similar to example AIV-2-1, 4-[3-(2,4-difluoro-benzyl)-phenyl]-2,4-dioxo-butyric acid ethyl ester was formed and the crude material was hydrolyzed in a manner similar to example AIV-3-1 using 1N NaOH to afford L2 as a yellow solid. Rf=0.60 (6:6:94 MeOH/AcOH/CH$_2$Cl$_2$). $^1$H NMR (400 MHz, CDCl$_3$) δ7.85 (m, 2H), 7.45 (m, 2H), 7.13 (m, 2H), 6.82 (m, 2H), 4.03 (s, 2H). mass spec (FAB, M+1) 319 m/e.

EXAMPLE 19

4-[5-(4-Fluoro-benzyl)-2,3-dimethoxy-phenyl]-2,4-dioxo-butyric acid L3

Step 1: (3-Bromo-4,5-dimethoxy-phenyl)-(4-fluoro-phenyl)-methanol L3-A

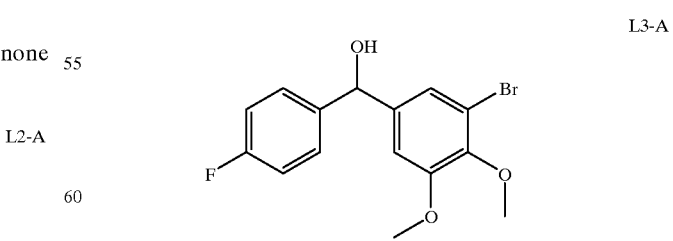

L3-A

In a dried round bottom flask under argon, 1.0 M 4-fluorophenyl-magnesium bromide in THF (25.5 mL, 25.5 mmol) was slowly added to 5-bromoveratraldehyde (2.5 g, 10.2 mmol) in dry THF (150 mL) at 0° C. The resulting solution was stirred for 15 minutes then allowed to stir at room temperature for 2 hours. The solvent was then removed in vacuo and the residue was partitioned between 10% KHSO$_4$ solution and EtOAc. The aqueous layer was extracted three times with EtOAc and the combined organic extracts were washed with brine, dried over Na$_2$SO$_4$, filtered and concentrated to a yellow oil. The crude product was taken on without further purification. $^1$H NMR (400 MHz, CDCl$_3$) δ7.33 (m, 2H), 7.05 (m, 3H), 6.86 (m, 1H), 5.74 (s, 1H), 3.83 (s, 6H).

Step 2: Preparation of L3-B

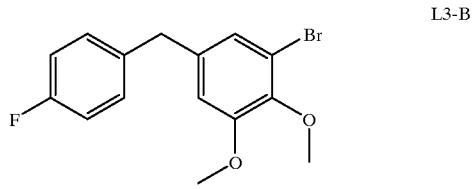

L3-B

To (3-bromo-4,5-dimethoxy-phenyl)-(4-fluoro-phenyl)-methanol (2.95 g, 8.65 mmol) in dry CH$_2$Cl$_2$ at 0° C. was added triethylsilane (3.54 mL, 22.2 mmol) and borontrifluoride diethyl etherate (2.27 mL, 22.2 mmol). The solution was allowed to stir overnight at room temperature. The solvent was then removed in vacuo and the residue was partitioned between sat. NaHCO$_3$ solution and CH$_2$Cl$_2$. The aqueous layer was extracted three times with CH$_2$Cl$_2$ and the combined organic extracts were washed with brine, dried over Na$_2$SO$_4$, filtered and concentrated to a clear oil. The crude product was chromatographed on silica gel using 10% EtOAc/hexane as the elutant. Collected and concentrated pure product fractions to give afford L3-B as a clear oil. Rf=0.41(10% EtOAc/hexane). $^1$H NMR (400 MHz, CDCl$_3$) δ7.13 (m, 2H), 6.97 (m, 3H), 6.62 (m, 1H), 3.86 (s, 2H), 3.83 (s, 3H), 3.81 (s, 3H).

Step 3: 1-[5-(4-Fluoro-benzyl)-2,3-dimethoxy-phenyl]-ethanone L3-C

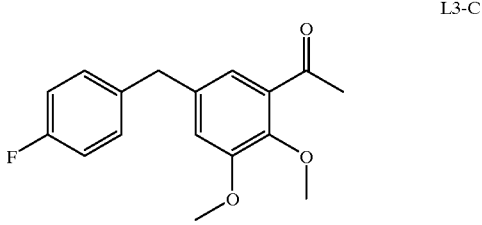

L3-C

In dried glassware under argon, slowly added 2.5 M n-BuLi in hexane to L3-B (2.50 g, 7.69 mmol) in distilled THF (45 mL) at −78° C. Aged solution 10 minutes then added N-methoxy-N-methylacetamide (1.11 mL, 10.8 mmol) dropwise. The reaction was stirred for 30 minutes then allowed to slowly warm to room temperature over 2 hours. The reaction was quenched with sat. NH$_4$Cl solution and extracted three times with EtOAc. The combined organic layers were washed with brine, dried over Na$_2$SO$_4$, filtered, and concentrated to a yellow oil. The crude product was chromatographed on silica gel using 5% EtOAc/hexane as elutant. Collected and concentrated product fractions to afford L3-C as a clear oil. Rf=0.27 (10% EtOAc/hexane).

$^1$H NMR (400 MHz, CDCl$_3$) δ7.12 (m, 2H), 7.05 (m, 1H), 6.97 (m, 2H), 6.80 (m, 1H), 3.90 (s, 2H), 3.88 (s, 3H), 3.83 (s, 3H), 2.61 (s, 3H).

Step 4: 4-[5-(4-Fluoro-benzyl)-2,3-dimethoxy-phenyl]-2,4-dioxo-butyric acid L3

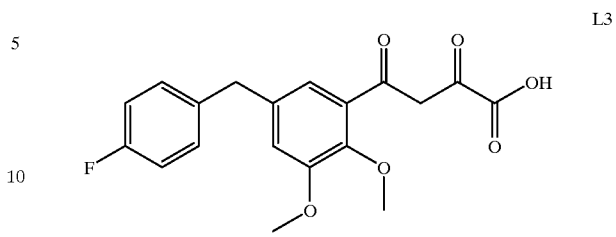

L3

In a manner similar to example AIV-2-1, 4-[5-(4-fluoro-benzyl)-2,3-dimethoxy-phenyl]-2,4-dioxo-butyric acid ethyl ester was formed and the crude material was hydrolyzed in a manner similar to example AIV-3-1 using 1N NaOH to afford L3 as a yellow solid. Rf=0.67 (6:6:94 MeOH/AcOH/CH$_2$Cl$_2$). $^1$H NMR (400 MHz, CDCl$_3$) δ7.38 (s, 1H), 7.25 (m, 1H), 7.14 (m, 2H), 7.00 (m, 2H), 6.88 (m, 1H), 3.94 (s, 2H), 3.90 (s, 3H), 3.85 (s, 3H). mass spec (FAB, M+1) 361 m/e.

EXAMPLE 20

4-(5-Benzyl-2-isopropoxyphenyl)-2,4-dioxobutyric acid W1

Step 1: (3-Bromo-4-fluorophenyl)phenylmethanol W1-A

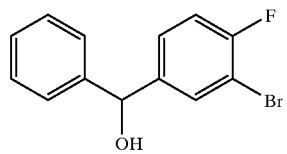

To a cold (0° C.) solution of 3-bromo-4-fluorobenzaldehyde (25.5 g) in THF (300 mL) under an atmosphere of argon, a solution of phenylmagnesium bromide in diethyl ether (3 M, 45 mL) was added. The resultant solution was stirred at room temp. for 2.5 h, and treated with aq. HCl. The resultant mixture was diluted with ethyl acetate, and neutralized with aq. HCl. The organic extract was dried over magnesium sulfate, filtered, and concentrated under vacuum to provide the title alcohol.

Step 2: 1-Benzyl-3-bromo-4-fluorobenzene W1-B

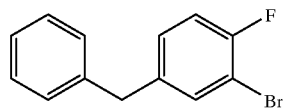

To a cold (0° C.) solution of (3-bromo-4-fluorophenyl)phenylmethanol (35 g) and triethylsilane (100 g) in dichloromethane (400 mL), boron trifluoride diethyl etherate (24 mL) was added dropwise over a period of 45 min. The resultant mixture was stirred at 0° C. for 1 hr, diluted with dichloromethane, and neutralized with saturated aq. sodium bicarbonate. The organic extract was washed with brine, dried over magnesium sulfate, filtered, and concentrated under vacuum. The residue was subjected to column chromatography on silica gel eluted with hexane. Collection and concentration of appropriate fractions provided the title bromide.

Step 3: 5-Benzyl-2-fluorobenzonitrile W1-C

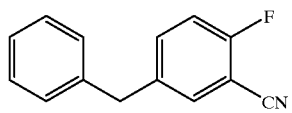

To a mixture of 1-benzyl-3-bromo-4-fluorobenzene (14.7 g) and zinc cyanide (38.7 g) in dimethylformamide (55 mL), purged with a steady stream of argon for 45 min., tetrakis(triphenylphosphine)palladium(0) (7 g) was added. The resultant mixture was stirred at 95° C. for 2 days under an atmosphere of argon. The resultant mixture was diluted with ethyl acetate, washed successively with water, aq. HCl, and brine. The organic extract was dried over magnesium sulfate, filtered, and concentrated under vacuum. The residue was subjected to column chromatography on silica gel eluted with 5–25% ethyl acetate-hexane gradient. Collection and concentration of appropriate fractions provided the title nitrile.

Step 4: 5-Benzyl-2-isopropoxybenzonitrile W1-D

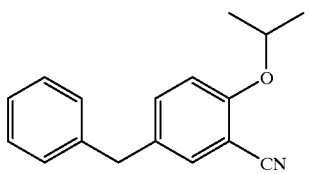

To a mixture of 5-benzyl-2-fluorobenzonitrile (0.55 g) and isopropyl alcohol (0.22 mL) in THF (15 mL) at room temp., a solution of potassium bis(trimethyl-sily)amide (0.5 M, 7 mL) in toluene was added. The resultant mixture was stirred at room temp. for 2 days under an atmosphere of argon. The resultant mixture was diluted with ethyl acetate, washed successively with aq. NH$_4$Cl, and brine. The organic extract was dried over magnesium sulfate, filtered, and concentrated under vacuum. The residue was subjected to column chromatography on silica gel eluted with 10% ethyl acetate in hexane. Collection and concentration of appropriate fractions provided the title nitrile.

Step 5: 5-Benzyl-2-isopropoxyacetophenone W1-E

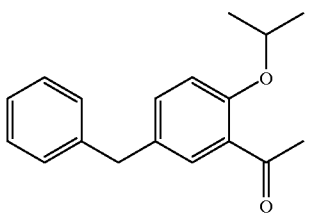

To a solution of 5-benzyl-2-isopropoxybenzonitrile (0.6 g) in benzene (15 mL), a solution of methylmagnesium iodide (3 M, 1.45 mL) in ether was added. The resultant mixture was heated at 80° C. overnight under an atmosphere of argon. The resultant mixture was treated with aq. HCl and washed with brine. The organic extract was dried over magnesium sulfate, filtered, and concentrated under vacuum. The residue was subjected to column chromatography on silica gel eluted with 10% ethyl acetate in hexane. Collection and concentration of appropriate fractions provided the title ketone.

Step 6: 4-(5-Benzyl-2-isopropoxyphenyl)-2,4-dioxobutyric acid W1

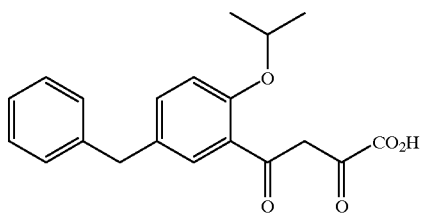

To a solution of 5-benzyl-2-isopropoxyacetophenone (0.268 g) and dimethyl oxalate (0.315 g) in THF (10 mL) at room temp., sodium methoxide (85 mg) was added. The resultant mixture was stirred at room temp. for 2 hr. under an atmosphere of argon. The resultant mixture was treated with aq. NaOH (1M, 5.5 mL) and stirred at room temp for 1 hr. The product solution was diluted with ethyl acetate, washed successively with aq. HCl and brine. The organic extract was dried over magnesium sulfate, filtered, and concentrated under vacuum. The residual oil was triturated with a mixture of ether and hexane. The yellow solid precipitated was filtered to provide the title product. $^1$H NMR (CDCl$_3$) δ7.8–6.8 (m, 9H), 4.6 (m, 1H), 3.95 (s, 2H), 1.43 (d, 6H).

EXAMPLE 21

4-[5-Benzyl-2-(2-N,N-dimethylaminoethoxy)phenyl]-2,4-dioxobutyric acid W2

Step 1: 5-Benzyl-2-(2-N,N-dimethylaminoethoxy)benzonitrile W2-A

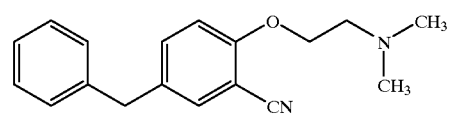

To a mixture of 5-benzyl-2-fluorobenzonitrile (0.60 g) and N,N-dimethylethanolamine (0.32 mL) in THF (20 mL) at room temp., a solution of potassium bis(trimethylsily)amide (0.5 M, 6.25 mL) in toluene was added. The resultant mixture was heated at 60° C. overnight under an atmosphere of argon. The resultant mixture was diluted with ethyl acetate, washed with brine. The organic extract was dried over sodium sulfate, filtered, and concentrated under vacuum. The residue was subjected to column chromatography on silica gel eluted with 5% methanol in chloroform. Collection and concentration of appropriate fractions provided the title nitrile.

Step 2: 4-[5-Benzyl-2-(2-N,N-dimethylaminoethoxy)phenyl]-2,4-dioxo-butyric acid W2

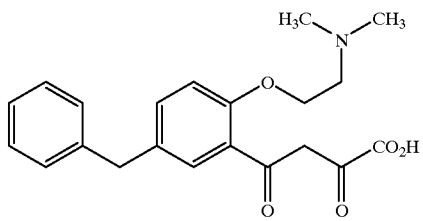

The title compound was prepared using the protocol described in Example W1, Step 5–6 substituting 5-benzyl-2-isopropoxybenzonitrile with 5-Benzyl-2-(2-N,N- dimethylaminoethoxy)benzonitrile in Step 5. $^1$H NMR (DMSO-d$_6$) δ7.7–6.9 (m, 9H), 4.45 (br s, 2H), 3.98 (s, 2H), 3.5 (br s, 2H), 2.85 (s, 6H).

EXAMPLE 22

4-[5-Benzyl-2-(pyridin-2-yloxy)phenyl]-2,4-dioxo-butyric acid W3

Step 1: 4-Benzyl-2-bromophenol W3-A

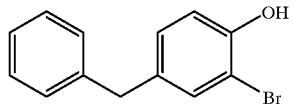

To a solution of 4-hydroxydiphenylmethane (10 g) in chloroform (60 mL) at room temp., a solution of bromine (2.9 mL) in chloroform (20 mL) was added dropwise over a period of 2 hr. The resultant mixture was stirred at room temp. overnight, diluted with chloroform, and washed successively with sat. aq. sodium bicarbonate and brine. The organic extract was dried over magnesium sulfate, filtered, and concentrated under vacuum to provide the title compound.

Step 2: 6-Benzyl-2-(pyridin-2-yloxy)phenyl bromide W3-B

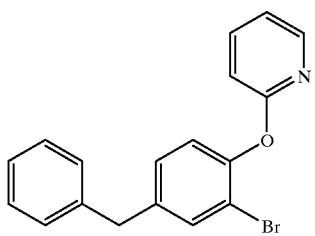

A mixture of 4-benzyl-2-bromophenol (3 g) and sodium hydride (0.3 g) in DMSO (60 mL) was stirred at room temp. until evolution of gas subsided. The resultant mixture was treated with 2-fluoropyridine (2 mL) and stirred at 150° C. under an atmosphere of argon overnight. The product mixture was partitioned between chloroform and water. The organic extract was washed successively with water and brine, dried over sodium sulfate, filtered, and concentrated under vacuum. The residue was subjected to column chromatography on silica gel eluting with chloroform. Collection and concentration of appropriate fractions provide the title bromide.

Step 3: 5-Benzyl-2-(pyridin-2-yloxy)acetophenone W3-C

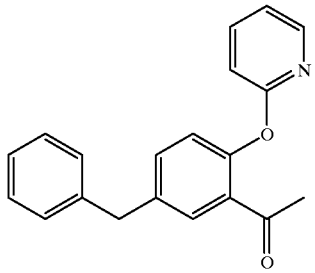

To a cold (−78° C.) solution of 5-benzyl-2-(pyridin-2-yloxy)phenyl bromide (1.68 g) in diethyl ether (40 mL), a solution of n-BuLi in hexanes (2.5 M, 2.12 mL) was added. The resultant mixture was stirred at −78° C. for 1 h and was treated with N-methoxy-N-methylacetamide (0.6 mL). The reaction mixture was allowed to warm up slowly to room temp. and was stirred at room temp. overnight. The product mixture was diluted with ether and partitioned with aq. HCl. The organic extract was washed with brine, dried over sodium sulfate, filtered, and concentrated under vacuum. The residue was subjected to column chromatography on silica gel eluting with chloroform. Collection and concentration of appropriate fractions provide the title ketone.

Step 4: Methyl 4-[5-benzyl-2-(pyridin-2-yloxy)phenyl]-2,4-dioxo-butyrate W3-D

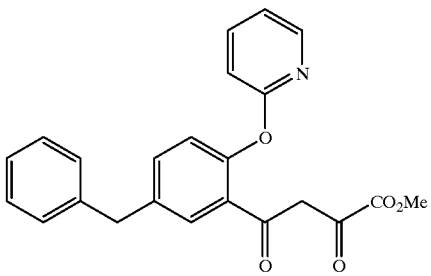

To a cold (−78° C.) solution of 5-benzyl-2-(pyridin-2-yloxy) acetophenone (0.3 g) in THF (15 mL), a solution of LDA in heptane and THF (2 M, 0.56 mL) was added. The resultant mixture was stirred at −78° C. for 1 h and was treated with a solution of dimethyl oxalate (0.213 g) in THF. The reaction mixture was allowed to warm up slowly to room temp. and was stirred at room temp. overnight. The product mixture was diluted with ethyl acetate and partitioned with aq. HCl. The organic extract was washed with brine, dried over sodium sulfate, filtered, and concentrated under vacuum. The residual oil was triturated with diethyl ether. The resultant ethereal solution was isolated and concentrated under vacuum to provide the title ester.

Step 5: 4-[5-Benzyl-2-(pyridin-2-yloxy)phenyl]-2,4-dioxo-butyric acid W3

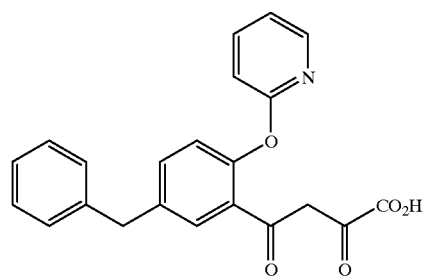

To a solution of methyl 4-[5-benzyl-2-(pyridin-2-yloxy) phenyl]-2,4-dioxo-butyrate (0.14 g) in THF (10 mL) at room temp., aq. NaOH (1 M, 0.44 mL) was added. The resultant mixture was stirred at room temp for 6 h. The product mixture was diluted with chloroform and partitioned with aq. HCl. The organic extract was washed with brine, dried over sodium sulfate, filtered, and concentrated under vacuum. The residue was triturated with a mixture of diethyl ether and hexane. Filtration of the resultant solid provided the title acid. $^1$H NMR (CDCl$_3$) δ8.25 (m, 1H), 7.8–6.8 (m, 12H), 4.05 (s, 2H).

EXAMPLE 23

4-(5-Benzyl-2-isopropoxy-3-methoxyphenyl)-2,4-dioxo-butyric acid W4

Step 1: 5-Benzyl-2-isopropoxy-3-methoxy-1-bromobenzene W4-A

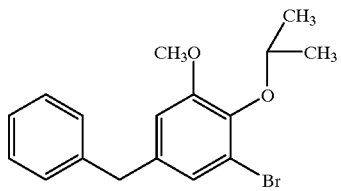

A mixture of 4-benzyl-2-bromo-6-methoxyphenol (0.5 g), cesium carbonate (0.84 g), and isopropyl iodide (0.51 mL) in DMF (2 mL) was stirred at room temp. overnight. The reaction mixture was diluted with ether, and washed with aq. ammonium chloride. The organic extract was dried over magnesium sulfate, filtered, and concentrated under vacuum. The residue was subjected to column chromatography on silica gel eluting with 5% ethyl acetate in hexane. Collection and concentration of appropriate fractions provide the title bromide.

Step 2: 5-Benzyl-2-isopropoxy-3-methoxy-acetophenone W4-B

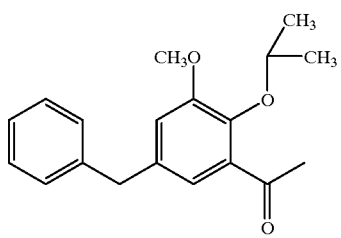

To a mixture of 5-benzyl-2-isopropoxy-3-methoxy-1-bromobenzene (0.4 g), thallium acetate (0.41 g), 1,3-bis(diphenylphosphino)propane (0.138 g) and triethylamine (0.67 mL) in DMF (3 mL) in a pressure tube, purged with argon for a period of 5 minute, palladium acetate (67.2 mg) and n-butyl vinyl ether (0.77 mL) was added. The reaction tube was sealed and stirred at 100° C. overnight. The reaction mixture was filtered through a bed of CELITE diatomaceous earth, and the filtrate concentrated under vacuum. The residue was dissolved in THF (5 mL) and treated with aq. HCl (1M, 2.5 mL). The resultant mixture was stirred at rt for 1 hr., diluted with ether, and washed with brine. The organic extract was dried over magnesium sulfate, filtered, and concentrated under vacuum. The residue was subjected to column chromatography on silica gel eluting with 10% ethyl acetate in hexane. Collection and concentration of appropriate fractions provide the title ketone.

Step 3: 4-(5-Benzyl-2-isopropoxy-3-methoxyphenyl)-2,4-dioxo-butyric acid W4

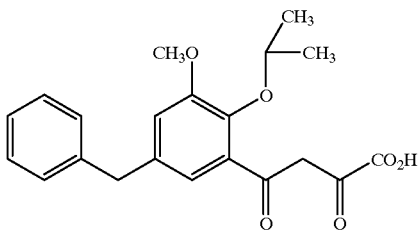

To a solution of 5-benzyl-2-isopropoxy-3-methoxy-acetophenone (79 mg) and dimethyl oxalate (125 mg) in THF (2 mL), sodium methoxide (30 mg) was added. The resultant mixture was stirred at room temp. for 0.5 h under an atmosphere of argon. The resultant mixture was diluted with THF (3 mL) and methanol (0.5 mL), and treated with aq. NaOH (1M, 3 mL) and stirred at room temp for 1 hr. The product solution was adjusted to pH 2 with addition of aq. HCl. The resultant mixture was concentrated under vacuum. The residue was subjected to HPLC purification on reverse phase stationary phase. Collection and lyophilization of appropriate fractions provide the title product as light yellow solid. $^1$H NMR (CDCl$_3$) $\delta$7.58–6.89 (m, 8H), 4.53 (m, 1H), 3.97 (s, 2H), 3.81 (s, 3H), 1.26 (d, 6H).

EXAMPLE 24

4-(5-Benzyl-2,3-dimethoxyphenyl)-2,4-dioxobutyric acid W5

Step 1: (3-Bromo-4,5-dimethoxyphenyl)phenylmethanol W5-A

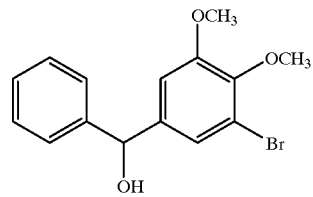

To a cold (0° C.) solution of 3-bromo-4,5-dimethoxybenzaldehyde (5.42 g) in THF (25 mL) under an atmosphere of argon, a solution of phenylmagnesium bromide in THF (1 M, 25 mL) was added. The resultant solution was stirred at room temp. for 1 h, and treated with aq. HCl. The resultant mixture was diluted with ether, and neutralized with aq. HCl. The organic extract was washed with brine, dried over magnesium sulfate, filtered, and concentrated under vacuum to provide the title alcohol.

Step 2: 5-Benzyl-2,3-dimethoxy-1-bromobenzene W5-B

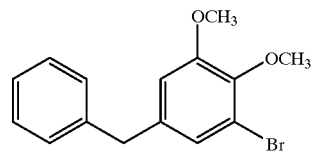

To a cold (0° C.) solution of the (3-Bromo-4,5-dimethoxyphenyl)phenyl-methanol (5 g) and triethylsilane (3.7 g) in dichloromethane (80 mL), boron trifluoride diethyl etherate (3 mL) was added dropwise over a period of 5 min. The resultant mixture was stirred at room temp. for 1 hr, diluted with dichloromethane, and neutralized with saturated aq. sodium bicarbonate. The organic extract was washed with brine, dried over magnesium sulfate, filtered, and concentrated under vacuum. The residue was subjected to column chromatography on silica gel. Collection and concentration of appropriate fractions provided the title bromide.

Step 3: 5-Benzyl-2,3-dimethoxyacetophenone W5-C

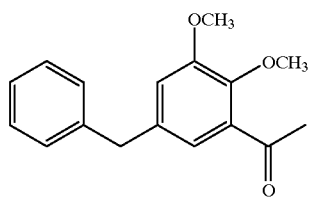

To a cold (−78° C.) solution of 5-benzyl-2,3-dimethoxy-1-bromobenzene (3.1 g) in THF (46 mL), a solution of n-BuLi in hexanes (2.5 M, 4.2 mL) was added. The resultant mixture was stirred at −78° C. for 1 h and was treated with N-methoxy-N-methylacetamide (1.1 g). The reaction mixture was allowed to warm up slowly to room temp. and was stirred at room temp. 1 h. The product mixture was diluted with ethyl acetate and partitioned with aq. HCl. The organic extract was washed with brine, dried over magnesium sulfate, filtered, and concentrated under vacuum. The residue was subjected to column chromatography on silica gel eluting with a 5–20% ethyl acetate gradient. Collection and concentration of appropriate fractions provide the title ketone.

Step 4: Ethyl 4-(5-benzyl-2,3-dimethoxyphenyl)-2,4-dioxobutyrate W5-D

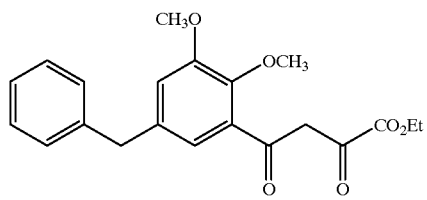

To a solution of 5-benzyl-2,3-dimethoxyacetophenone (0.55 g) and diethyl oxalate (0.48 g) in THF (8 mL), sodium ethoxide (0.22 g) was added. The resultant mixture was stirred at room temp. for 1 hr under an atmosphere of argon. The reaction mixture was quenched with aq. KHSO$_4$, and diluted with ethyl acetate. The organic extract was washed with brine, dried over magnesium sulfate, filtered, and concentrated under vacuum to provide the title ester.

Step 5: 4-(5-Benzyl-2,3-dimethoxyphenyl)-2,4-dioxobutyric acid W5

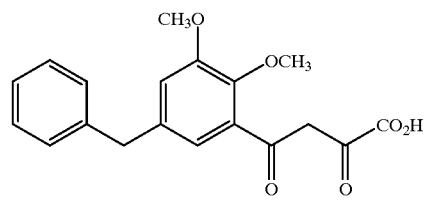

To a solution of ethyl 4-(5-benzyl-2,3-dimethoxyphenyl)-2,4-dioxobutyrate (0.59 g) in ethanol (8 mL), aq. NaOH (1 M, 6.4 mL) was added. The resultant mixture was stirred at room temp for 2 h. The product mixture was concentrated under vacuum. The residue was partitioned between ethyl acetate and aq. HCl. The organic extract was washed with brine, dried over magnesium sulfate, filtered, and concentrated under vacuum. The residue was triturated with a mixture of diethyl ether and hexane. Filtration of the resultant solid provided the title acid. $^1$H NMR (CDCl$_3$) δ7.4–7.2 (m, 7H), 6.92 (br s, 1H), 3.97 (s, 2H), 3.89 (s, 3H), 3.84 (s, 3H).

EXAMPLE 25

4-(5-Benzyl-3-dimethylamino-2-methoxyphenyl)-2,4-dioxobutyric acid W6

Step 1: 4-benzyl-2-bromo-6-nitrophenol W6-A

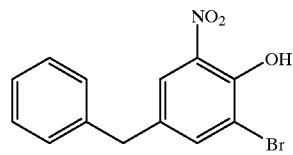

To a solution of 4-benzyl-2-bromophenol (7.2 g) in glacial acetic acid (65 mL) at room temp., a solution of conc. nitric acid (15.8 M, 1.7 mL) in glacial acetic acid (10 mL) was added dropwise over a period of 1 hr. The resultant solution was stirred at room temp. for 2 hr., poured into ice-water, and neutralized with aq. ammonia. The mixture was extracted with ethyl acetate. The organic extract was washed with brine, dried over magnesium sulfate, filtered, and concentrated under vacuum. The residue was subjected to column chromatography on silica gel eluting with a gradient of 5–7% ethyl acetate in hexane. Collection and concentration of appropriate fractions provided the title phenol.

Step 2: 5-Benzyl-2-methoxy-3-nitro-1-bromobenzene W6-B

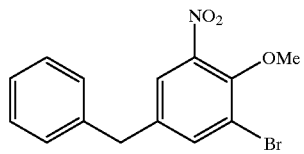

To a cold (0° C.) solution of 4-benzyl-2-bromo-6-nitrophenol (1.3 g) in diethyl ether (50 mL), a solution of diazomethane in diethyl ether was added over a period of 15 minute. The diazomethane solution was prepared by addition of 1-methyl-3-nitro-1-nitrosoguanidine (2.0 g) portionwise into a mixture of 40% aq. KOH (50 mL) and ether (50 mL) at 0° C. over a period of 15 min. The resultant solution was stirred at room temp. overnight, and concentrated under vacuum. The residue was subjected to column chromatography on silica gel eluting with 4% ethyl acetate in hexane. Collection and concentration of appropriate fractions provide the title bromide.

Step 3: 5-Benzyl-2-methoxy-3-bromoaniline W6-C

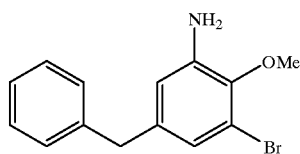

A mixture of 5-benzyl-2-methoxy-3-nitro-1-bromobenzene (2.0 g) and 5% Pt on charcoal (0.2 g) in a mixture of ethanol (100 mL) and acetic acid (5 mL) was shaken in a Parr hydrogenator under an atmosphere of hydrogen gas (56 psi) at room temp. for 45 min. The resultant mixture was filtered through a plug of CELITE diatomaceous earth. The filtrate was concentrated under vacuum to provide the title aniline.

Step 4: 5-Benzyl-2-methoxy-3-bromo-N,N-dimethylaniline W6-D

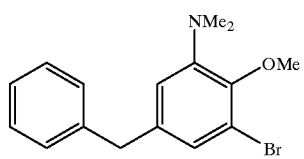

To a solution of 5-benzyl-2-methoxy-3-bromoaniline (1.9 g), formaldehyde (37%, 5.3 g), and sodium cyanoborohydride (1.25 g) in acetonitrile (40 mL) at room temp, glacial acetic acid (2 mL) was added dropwise over a period of 3 hr. The reaction mixture was stirred at room temp. overnight. The resultant solution was adjusted to pH ~6 with addition of aq sodium bicarbonate and partitioned with ethyl acetate. The organic extract was washed with brine, dried over magnesium sulfate, filtered, and concentrated under vacuum. The residue was subjected to column chromatography on silica gel eluting with 3% ethyl acetate in hexane. Collection and concentration of appropriate fractions provide the title bromide.

Step 5: 5-Benzyl-2-methoxy-3-N,N-dimethylaminoacetophenone W6-E

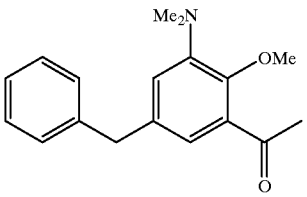

To a mixture of 5-benzyl-2-methoxy-3-bromo-N,N-dimethylaniline (0.33 g), thallium acetate (0.3 g), 1,3-bis(diphenylphosphino)propane (0.106 g) and triethylamine (0.42 mL) in DMF (2.5 mL) in a pressure tube, purged with argon for a period of 5 minute, palladium acetate (56 mg) and n-butyl vinyl ether (0.67 mL) was added. The reaction tube was sealed and stirred at 100° C. for 1 hr. The reaction mixture was filtered through a bed of CELITE diatomaceous earth, and the filtrate concentrated under vacuum. The residue was dissolved in THF (10 mL) and treated with aq. HCl (1M, 3 mL). The resultant mixture was stirred at rt for 1 hr., diluted with ether, basified with aq. sodium bicarbonate. The organic extract was dried over magnesium sulfate, filtered, and concentrated under vacuum. The residue was subjected to column chromatography on silica gel eluting with 4% ethyl acetate in hexane. Collection and concentration of appropriate fractions provide the title ketone.

Step 6: 4-(5-Benzyl-3-dimethylamino-2-methoxyphenyl)-2,4-dioxobutyric acid W6

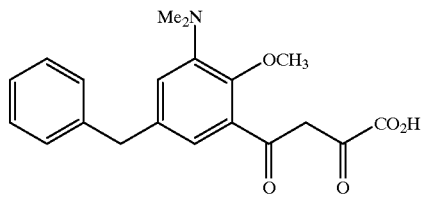

To a solution of 5-benzyl-2-methoxy-3-N,N-dimethylaminoacetophenone (75 mg) and diethyl oxalate (57 mg) in THF (2 mL), sodium ethoxide (36 mg) was added. The resultant mixture was stirred at room temp. for 1 hr. under an atmosphere of argon. The reaction mixture was diluted with ethyl acetate and partitioned with 5% aq. KHSO4. The organic extract was washed with brine, dried over magnesium sulfate, filtered, and concentrated under vacuum. The residue was dissolved in ethanol (3 mL) and treated with aq. NaOH (1M, 1 mL) and stirred at room temp for 1 hr. The product solution was concentrated under vacuum. The residue was dissolved in acetonitrile and acidified with aq TFA, and subjected to HPLC purification on reverse phase. Collection and lyophilization of appropriate fractions provided the title acid. $^1$H NMR (CDCl$_3$) δ7.6–7.0 (m, 8H), 4.00 (s, 2H), 3.89 (s, 3H), 3.21 (s, 6H).

EXAMPLE 26

4-[5-Benzyl-2-N,N-dimethylaminobenzoxazol-7-yl]-2,4-dioxo-butyric acid W7

Step 1: 3-Benzyl-5-bromo-6-hydroxyaniline W7-A

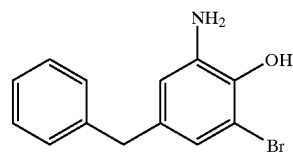

To a solution of 4-benzyl-2-bromo-6-nitrophenol (8.65 g) and 5% Pt on charcoal (0.15 g) in a mixture of ethanol (100 mL) and acetic acid (8 mL) was shaken in a Parr hydrogenator under an atmosphere of hydrogen gas (43 psi) at room temp. for 1 hr. The resultant mixture was filtered through a plug of. CELITE diatomaceous earth. The filtrate was concentrated under vacuum to provide the title aniline.

Step 2: 5-Benzyl-7-bromo-2-N,N-dimethylaminobenzoxazole W7-B

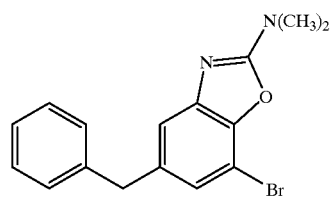

A mixture of 3-benzyl-5-bromo-6-hydroxyaniline (1.0 g) and anhydrous (dichloromethylene)dimethylammonium chloride (0.6 g; dried by repetitive concentration from toluene under vacuum) in anhydrous chloroform (30 mL) was heated under reflux overnight under an atmosphere of argon. The reaction mixture was diluted with chloroform, and washed successively with aq. KOH and brine. The organic extract was dried over sodium sulfate, filtered, and concentrated under vacuum. The residue was subjected to column chromatography on silica gel eluting with 40% ethyl acetate in hexane. Collection and concentration of appropriate fractions provided the title benzoxazole.

Step 3: 7-Acetyl-5-benzyl-2-N,N-dimethylaminobenzoxazole W7-C

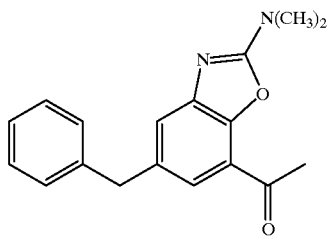

To a mixture of 5-benzyl-7-bromo-2-N,N-dimethylaminobenzoxazole (0.8 g), thallium acetate (0.695 g), 1,3-bis(diphenylphosphino)propane (0.25 g) and triethylamine (0.98 mL) in DMF (5 mL) in a pressure tube, purged with argon for a period of 15 minute, palladium acetate (130 mg) and n-butyl vinyl ether (1.55 mL) was added. The reaction tube was sealed and stirred at 100° C. overnight. The reaction mixture was filtered through a bed of CELITE diatomaceous earth, and the filtrate concentrated under vacuum. The residue was dissolved in THF (20 mL) and treated with aq. HCl (1M, 6 mL). The resultant mixture was stirred at rt for 1 hr., diluted with ether, basified with aq. sodium bicarbonate. The organic extract was dried over magnesium sulfate, filtered, and concentrated under vacuum. The residue was subjected to column chromatography on silica gel eluting with 50% ethyl acetate in hexane. Collection and concentration of appropriate fractions provided the title ketone.

Step 4: 4-[5-Benzyl-2-N,N-dimethylaminobenzoxazol-7-yl]-2,4-dioxo-butyric acid W7

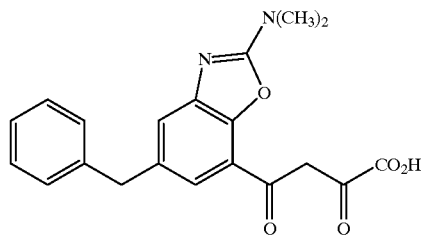

To a solution of 7-acetyl-5-benzyl-2-N,N-dimethylaminobenzoxazole (200 mg) and diethyl oxalate (150 mg) in THF (7 mL), sodium ethoxide (138 mg) was added. The resultant mixture was stirred at room temp. for 3 hr. under an atmosphere of argon. The reaction mixture was diluted with ethyl acetate and partitioned with aq. HCl. The organic extract was washed with brine, dried over magnesium sulfate, filtered, and concentrated under vacuum. The residue was triturated with diethyl ether, and the solid precipitated was obtained by filtration. A solution of this intermediate ester (125 mg) in THF (4 mL) was treated with aq. NaOH (1M, 2.7 mL) and stirred at room temp for 1 hr. The product mixture was partitioned between ethyl acetate and aq. HCl. The organic extract was washed with brine, dried over magnesium sulfate, filtered, and concentrated under vacuum. The residue was triturated with ether. The yellow solid precipitated was filtered to provide the title acid. $^1$H NMR (CDCl$_3$) δ7.54–7.16 (m, 8H), 4.05 (s, 2H), 3.25 (s, 6H).

EXAMPLE 27

4-(3-Benzyl-5-pyrazin-2-ylmethylphenyl)-2,4-dioxobutyric acid W8

Step 1: (3,5-dibromophenyl)phenylmethanol W8-A

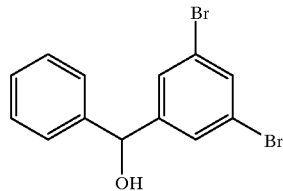

To a cold (−78° C.) solution of 1,3,5-tribromobenzene (30 g) in diethyl ether (500 mL), a solution of n-BuLi in hexanes (2.5 M, 38.1 mL) was added. The resultant mixture was stirred at −78° C. for 1 h and was treated with benzaldehyde (10.2 mL). The reaction mixture was allowed to warm up slowly to 0° C. and was stirred at that temp. for 1.5 hr. The product mixture was diluted with ethyl acetate and partitioned with aq. HCl (1M, 95 mL). The organic extract was washed with brine, dried over magnesium sulfate, filtered, and concentrated under vacuum to provide the title alcohol.

Step 2: 1-Benzyl-3,5-dibromobenzene W8-B

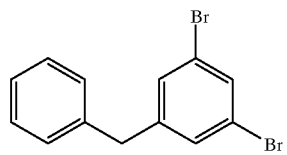

To a cold (0° C.) solution of (3,5-dibromophenyl)phenylmethanol (32.5 g) and triethylsilane (27.7 g) in dichloromethane (500 mL), boron trifluoride diethyl etherate (30 mL) was added dropwise over a period of 45 min. The resultant mixture was stirred at 0° C. for 1 hr, and at room temp. overnight. The product mixture was diluted with dichloromethane, and neutralized with saturated aq. sodium bicarbonate. The organic extract was washed with brine, dried over magnesium sulfate, filtered, and concentrated under vacuum. The residue was subjected to column chromatography on silica gel eluted with hexane. Collection and concentration of appropriate fractions provided the title dibromide.

Step 3: (3-benzyl-5-bromophenyl) pyrazin-2-yl ketone W8-C

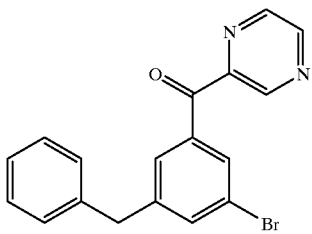

To a cold (−78° C.) solution of 1-benzyl-3,5-dibromobenzene (1.5 g) in diethyl ether (20 mL), a solution of n-BuLi in hexanes (2.5 M, 2 mL) was added. The resultant mixture was stirred at −78° C. for 1 h and was treated with a solution of N-methoxy-N-methylpyrazinecarboxamide (0.84 g) in diethyl ether (5 mL). The reaction mixture was allowed to warm up slowly to room temp. and was stirred at that temp. overnight. The product mixture was diluted with ethyl acetate and partitioned with aq. HCl. The organic extract was washed with brine, dried over magnesium sulfate, filtered, and concentrated under vacuum. The residue was subjected to column chromatography on silica gel eluting with 20% ethyl acetate in hexane. Collection and concentration of appropriate fractions provided the title pyrazine.

Step 4: 3-Benzyl-5-pyrazin-2-ylmethyl-1-bromobenzene W8-D

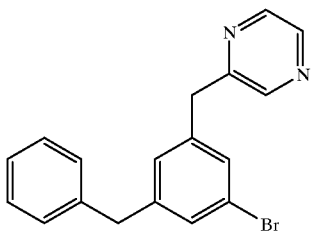

A mixture of (3-benzyl-5-bromophenyl) pyrazin-2-yl ketone (0.97 g) and anhydrous hydrazine (2 mL) in ethylene glycol (6 mL) was heated at 110° C. for 4 hr. Excess hydrazine was removed under reduced pressure. The residue ethylene glycol solution was treated with powdered solid KOH (0.4 g) and heated under an atmosphere of argon for 4 h. The product mixture was partitioned between benzene and water. The organic extract was washed with brine, dried over magnesium sulfate, filtered, and concentrated under vacuum. The residue was subjected to column chromatography on silica gel eluting with 20–30% ethyl acetate in hexane gradient. Collection and concentration of appropriate fractions provided the title bromide.

Step 5: 3-Benzyl-5-1-pyrazin-2-ylmethylacetophenone W8-E

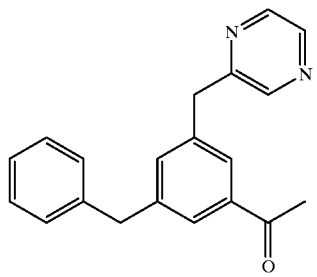

To a mixture of 3-benzyl-5-pyrazin-2-ylmethyl-1-bromobenzene (0.77 g), thallium acetate (0.66 g), 1,3-bis(diphenylphosphino)propane (0.263 g) and triethylamine (1.27 mL) in DMF (5 mL) in a pressure tube, purged with argon for a period of 10 minute, palladium acetate (128 mg) and n-butyl vinyl ether (1.5 mL) was added. The reaction tube was sealed and stirred at 100° C. overnight. The reaction mixture was filtered through a bed of CELITE diatomaceous earth, and the filtrate concentrated under vacuum. The residue was dissolved in THF (5 mL) and treated with aq. HCl (3M, 4 mL). The resultant mixture was stirred at rt for 3 hr., diluted with ethyl acetate, basified with aq. sodium bicarbonate. The organic extract was dried over magnesium sulfate, filtered, and concentrated under vacuum. The residue was subjected to column chromatography on silica gel eluting with 50% ethyl acetate in hexane. Collection and concentration of appropriate fractions provided the title ketone.

Step 6: 4-(3-Benzyl-5-pyrazin-2-ylmethylphenyl)-2,4-dioxobutyric acid W8

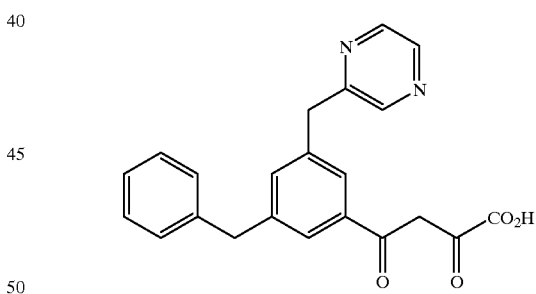

To a cold (−78° C.) solution of 3-benzyl-5-pyrazin-2-ylmethylacetophenone (0.595 g) in THF (4 mL), a solution of lithium bis(trimethylsilyl)amide in THF (1 M, 1.2 mL) was added. The resultant mixture was stirred at −78° C. for 1 h and was treated with diethyl oxalate (0.18 mL). The reaction mixture was allowed to warm up slowly to room temp. and was stirred at room temp. overnight. The product mixture was treated with aq. NaOH (1 M, 2 mL) and stirred at room temp for 4 h. The product solution was concentrated under vacuum. The residue was dissolved in acetonitrile and acidified with aq TFA, and subjected to HPLC purification on reverse phase. Collection and lyophilization of appropriate fractions provided the title acid. $^1$H NMR (CDCl$_3$) δ8.7–7.0 (m, 12H), 4.22 (s, 2H), 4.02 (s, 2H).

EXAMPLE 28

4-(3-Benzyl-5-[1,2,3]triazol-2-ylmethylphenyl)-2,4-dioxobutyric acid W9

Step 1: 3-Benzyl-5-bromobenzaldehyde W9-A

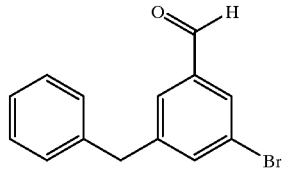

To a cold (−78° C.) solution of 1-benzyl-3,5-dibromobenzene (1.15 g) in THF (30 mL), a solution of n-BuLi in hexanes (2.5 M, 2 mL) was added. The resultant mixture was stirred at −78° C. for 1 h and was treated with anhydrous DMF (0.3 mL). The reaction mixture was allowed to warm up slowly to room temp. and was stirred at that temp. overnight. The product mixture was diluted with ethyl acetate and partitioned with aq. HCl. The organic extract was washed with brine, dried over magnesium sulfate, filtered, and concentrated under vacuum. The residue was subjected to column chromatography on silica gel eluting with 10% ethyl acetate in hexane. Collection and concentration of appropriate fractions provided the title benzaldehyde.

Step 2: 3-Benzyl-5-bromobenzyl alcohol W9-B

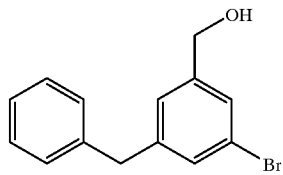

To a cold (0° C.) solution of 3-benzyl-5-bromobenzaldehyde (0.465 g) in methanol (5 mL), sodium borohydride (0.123 g) was added. The reaction mixture was stirred at room temp. for 3 hr. The product mixture was concentrated, and the residue partitioned between ethyl acetate and aq. HCl. The organic extract was washed with brine, dried over magnesium sulfate, filtered, and concentrated under vacuum to provide the title alcohol.

Step 3: 3-Benzyl-5-bromobenzyl bromide W9-C

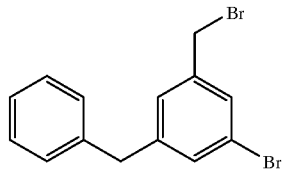

To a cold (0° C.) solution of 3-benzyl-5-bromobenzyl alcohol (0.32 g) and carbon tetrabromide (0.57 g) in dichloromethane (6 mL), a solution of triphenylphosphine (0.45 g) in dichloromethane (4 mL) was added dropwise. The reaction mixture was stirred at room temp. for 2 hr. The product mixture was concentrated, and the residue was subjected to column chromatography on silica gel eluting with 15% ethyl acetate in hexane. Collection and concentration of appropriate fractions provided the title dibromide.

Step 4: 3-Benzyl-5-[1,2,3]triazol-2-ylmethyl-1-bromobenzene W9-D

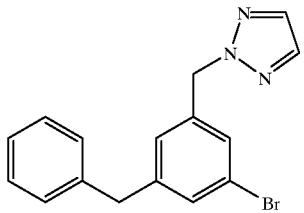

A mixture of sodium hydride (28 mg, 60% dispersion in mineral oil, washed with hexane) and 1,2,3-triazole (0.38 mL) in DMF was stirred at room temp. for 10 min. The resultant mixture was treated with a solution of 3-benzyl-5-bromobenzyl bromide in DMF. The reaction mixture was stirred at room temp. overnight. The product mixture was concentrated, and the residue partitioned between ethyl acetate and aq. ammonium chloride. The organic extract was washed with brine, dried over magnesium sulfate, filtered, and concentrated under vacuum. The residue was subjected to column chromatography on silica gel eluting with 50% ethyl acetate in hexane. Collection and concentration of earlier fractions (Rf=0.8, slica gel, eluted with 50% ethyl acetate in hexane) provided the title triazole bromide [$^1$H NMR (CDCl$_3$) δ7.63 (s, 2H)], and later fractions (Rf=0.2) provided the isomeric 3-benzyl-5-[1,2,3]triazol-1-ylmethyl-1-bromo-benzene analog [$^1$H NMR (CDCl$_3$) δ7.76 (br s, 1H), 7.73 (br s, 1H)].

Step 5: 3-Benzyl-5-[1,2,3]triazol-2-ylmethylacetophenone W9-E

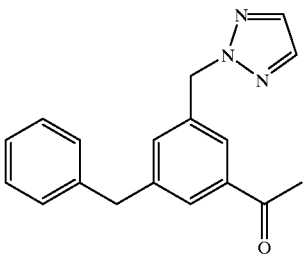

To a mixture of 3-benzyl-5-[1,2,3]triazol-2-ylmethyl-1-bromobenzene (0.4 g), thallium acetate (0.35 g), 1,3-bis(diphenylphosphino)propane (0.13 g) and triethylamine (0.68 mL) in DMF (4 mL) in a pressure tube, purged with argon for a period of 10 minute, palladium acetate (55 mg) and n-butyl vinyl ether (0.8 mL) was added. The reaction tube was sealed and stirred at 100° C. overnight. The reaction mixture was filtered through a bed of CELITE diatomaceous earth, and the filtrate concentrated under vacuum. The residue was dissolved in THF (5 mL) and treated with aq. HCl (3M, 4 mL). The resultant mixture was stirred at rt for 3 hr., diluted with ethyl acetate, basified with aq. sodium bicarbonate. The organic extract was dried over magnesium sulfate, filtered, and concentrated under vacuum. The residue was subjected to column chromatography on silica gel eluting with 50% ethyl acetate in hexane. Collection and concentration of appropriate fractions provided the title ketone.

Step 6: 4-(3-Benzyl-5-[1,2,3]triazol-2-ylmethylphenyl)-2,4-dioxobutyric acid W9

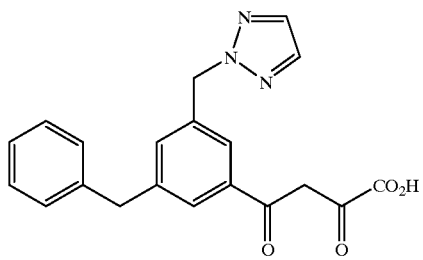

To a solution of 3-benzyl-5-[1,2,3]triazol-2-ylmethylacetophenone (60 mg) and diethyl oxalate (89 mg) in THF (3 mL), sodium ethoxide (21 mg) was added. The resultant mixture was stirred at room temp. for 1 hr. under an atmosphere of argon. The reaction mixture was diluted with ethyl acetate and partitioned with aq. HCl. The organic extract was washed with brine, dried over magnesium sulfate, filtered, and concentrated under vacuum. The residue was dissolved in THF (1 mL) and treated with aq. NaOH (1M, 1 mL) and stirred at room temp for 3 hr. The product mixture was diluted with ethyl acetate and partitioned with aq. HCl. The organic extract was washed with brine, dried over magnesium sulfate, filtered, and concentrated under vacuum. The residue was triturated with hexane/ethyl acetate. Filtration and collection of the solid provided the title acid. $^1$H NMR (CDCl$_3$) δ7.78–7.10 (m, 11H), 5.64 (s, 2H), 4.03 (s, 2H).

EXAMPLE 29

4-[3-(3-Chloropyridin-2-ylmethyl)phenyl]-2,4-dioxobutyric acid W10

Step 1: 3-Chloropyridin-2-yl 3-bromophenyl ketone W10-A

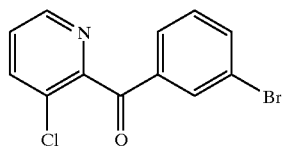

To a cold (−78° C.) solution of 1,3-dibromobenzene (0.8 mL) in THF (4 mL), a solution of n-BuLi in hexanes (2.5 M, 3.2 mL) was added. The resultant mixture was stirred at −78° C. for 1 h and was treated with a solution of N-methoxy-N-methyl-3-chloropyridine-2-carboxyamide in THF (4 mL). The reaction mixture was allowed to warm up slowly to room temp. and was stirred at that temp. overnight. The product mixture was diluted with ethyl acetate and partitioned with aq. HCl. The organic extract was washed with brine, dried over magnesium sulfate, filtered, and concentrated under vacuum. The residue was subjected to column chromatography on silica gel eluting with 50% ethyl acetate in hexane. Collection and concentration of appropriate fractions provided the title ketone.

Step 2: 3-(3-Chloropyridin-2-ylmethyl)-1-bromobenzene W10-B

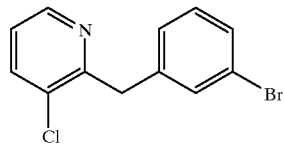

A mixture of 3-chloropyridin-2-yl 3-bromophenyl ketone (0.2 g) and anhydrous hydrazine (1 mL) in ethylene glycol (2.5 mL) was heated at 110° C. for 4 hr. Excess hydrazine was removed under reduced pressure. The residue ethylene glycol solution was treated with powdered solid KOH (0.1 g) and heated under an atmosphere of argon for 1 h. The product mixture was partitioned between benzene and water. The organic extract was washed with brine, dried over magnesium sulfate, filtered, and concentrated under vacuum. The residue was subjected to column chromatography on silica gel eluting with 25% ethyl acetate Collection and concentration of appropriate fractions provided the title bromide. $^1$H NMR (CDCl$_3$) δ8.47 (br dd, 1H), 7.66 (br dd, 1 H), 7.44 (br s, 1H), 7.35 (br d, 1 H), 7.22 (br d, 1H), 7.16–7.12 (m 2 H), 4.28 (s, 2H).

Step 3: 3-(3-Chloropyridin-2-ylmethyl)acetophenone W10-C

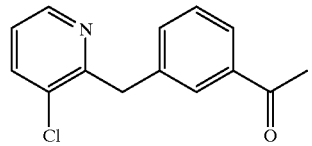

To a mixture of 3-(3-chloropyridin-2-ylmethyl)-1-bromobenzene (0.76 g), thallium acetate (0.87 g), 1,3-bis(diphenylphosphino)propane (0.27 g) and triethylamine (1.67 mL) in DMF (6 mL) in a pressure tube, purged with argon for a period of 10 minute, palladium acetate (134 mg) and n-butyl vinyl ether (1.96 mL) was added. The reaction tube was sealed and stirred at 100° C. for 2 days. The reaction mixture was filtered through a bed of CELITE diatomaceous earth, and the filtrate concentrated under vacuum. The residue was dissolved in THF (3 mL) and treated with aq. HCl (3M, 3 mL). The resultant mixture was stirred at room temp. overnight, diluted with ethyl acetate, basified with aq. sodium bicarbonate. The organic extract was dried over magnesium sulfate, filtered, and concentrated under vacuum. The residue was subjected to column chromatography on silica gel eluting with 25% ethyl acetate in hexane. Collection and concentration of appropriate fractions provided the title ketone.

Step 4: 4-[3-(3-Chloropyridin-2-ylmethyl)phenyl]-2,4-dioxobutyric acid W10

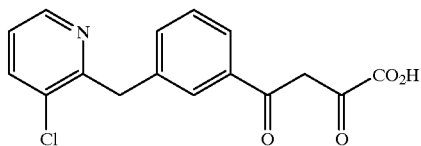

To a cold (−78° C.) solution of 3-(3-chloropyridin-2-ylmethyl)acetophenone (0.19 g) in THF (3 mL), a solution of lithium bis(trimethylsilyl)amide in hexane (1 M, 1.54 mL) was added. The resultant mixture was stirred at −78° C. for 1 h and was treated with diethyl oxalate (0.22 mL). The reaction mixture was allowed to warm up slowly to room temp. and was stirred at room temp. for 1.5 hr. The product mixture was treated with aq. NaOH (1 M, 3.2 mL) and stirred at room temp overnight. The product solution was concentrated under vacuum. The residue was dissolved in acetonitrile and acidified with aq TFA, and subjected to HPLC purification on reverse phase. Collection and lyophilization of appropriate fractions provided the title acid. $^1$H NMR (DMSO-$d_6$) δ8.48 (br d, 1H), 7.92–7.0 (m, 7H), 4.35 (s, 2H).

EXAMPLE 30

4-[5-Benzyl-2-methoxy-3-(N,N-dimethylaminomethyl)phenyl]-2,4-dioxo-butyric acid W11

Step 1: 4-Benzyl-2,6-dibromophenol W11-A

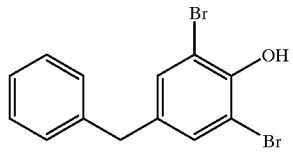

To a solution of 4-hydroxydiphenylmethane (15.3 g) in glacial acetic acid (200 mL) at room temp., a solution of bromine (8.6 mL) in acetic acid (20 mL) was added dropwise over a period of half an hour. The resultant mixture was stirred at room temp. for 3 hr, poured into ice water, and partitioned with toluene. The organic extract was washed successively with 10% aq. sodium hydrogensulfite and brine, dried over sodium sulfate, filtered, and concentrated under vacuum. The residue was subjected to column chromatography on silica gel eluting with 7% ethyl acetate in hexane. Collection and concentration of appropriate fractions provided the title dibromophenol.

Step 2: 4-Benzyl-2,6dibromo-1-methoxybenzene W11-B

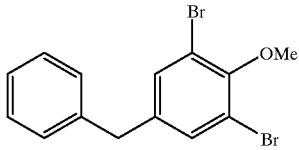

To a cold (0° C.) solution of 4-benzyl-2,6-dibromophenol (10 g) in diethyl ether (100 mL), a solution of diazomethane in diethyl ether was over a period of 20 minute. The diazomethane solution was prepared by addition of 1-methyl-3-nitro-1-nitrosoguanidine (8.5 g) portionwise into a mixture of 40% aq. KOH (100 mL) and ether (50 mL) at 0° C. over a period of 15 min. The resultant solution was stirred at room temp. for two days, and concentrated under vacuum. The residue was subjected to column chromatography on silica gel eluting with 1–2% ethyl acetate in hexane gradient. Collection and concentration of appropriate fractions provided the title dibromide.

Step 3: 3-Benzyl-5-bromo-6-methoxybenzyl bromide W11-C

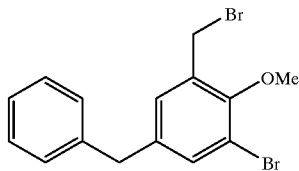

The title compound was prepared using the protocol described in Example W9, Step 1-3 substituting 1-benzyl-3,5-dibromobenzene with 4-benzyl-2,6-dibromo-1-methoxybenzene in Step 1.

Step 4: 3-Benzyl-1-bromo-5-N,N,-dimethylaminomethyl-6-methoxybenzene W11-D

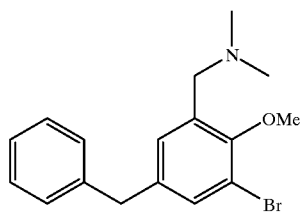

A solution of 3-benzyl-5-bromo-6-methoxybenzyl bromide (0.65 g), dimethylamine hydrochloride (0.29 g), and diisopropylethylamine (0.61 mL) in acetonitrile (8 mL) was heated at 60° C. overnight. The resultant solution was concentrated under vacuum. The residue was subjected to column chromatography on silica gel eluting with 4% methanol in chloroform. Collection and concentration of appropriate fractions provided the title bromide.

Step 5: 5-Benzyl-2-methoxy-3-(N,N-dimethylaminomethyl)-acetophenone W11-E

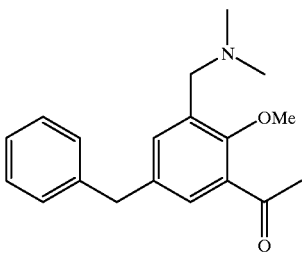

To a mixture of 3-benzyl-1-bromo-5-N,N,-dimethylaminomethyl-6-methoxybenzene (0.30 g), thallium acetate (0.28 g), 1,3-bis(diphenyl-phosphino)propane (0.80 g) and triethylamine (0.39 mL) in DMF (2 mL) in a pressure tube, purged with argon for a period of 5 minute, palladium acetate (43 mg) and n-butyl vinyl ether (0.62 mL) was added. The reaction tube was sealed and stirred at 100° C. overnight. The reaction mixture was filtered through a bed of CELITE diatomaceous earth, and the filtrate concentrated under vacuum. The residue was dissolved in THF (10 mL) and treated with aq. HCl (1M, 3 mL). The resultant mixture was stirred at room temp. for 1 h, diluted with ethyl acetate, basified with aq. sodium bicarbonate. The organic extract was dried over magnesium sulfate, filtered, and concentrated under vacuum. The residue was subjected to column chromatography on silica gel eluting with 7% methanol in chloroform. Collection and concentration of appropriate fractions provided the title ketone.

Step 6: 4-[5-Benzyl-2-methoxy-3-(N,N-dimethylaminomethyl)-phenyl]-2,4-dioxo-butyric acid W11

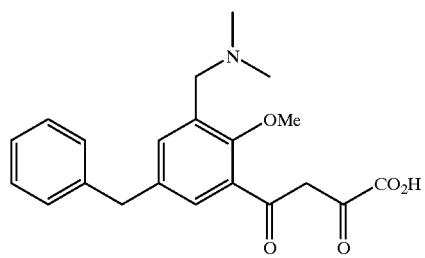

To a solution of 5-benzyl-2-methoxy-3-(N,N-dimethylaminomethyl)-acetophenone (0.26 g) and diethyl oxalate (0.19 g) in THF (8 mL), sodium ethoxide (118 mg) was added. The resultant mixture was stirred at room temp. for 1 hr. under an atmosphere of argon. The resultant solution was treated with aq. NaOH (1M, 5 mL) and stirred at room temp for 1 hr. The product solution was neutralized with addition of aq. HCl, and concentrated under vacuum. The residue was dissolved in acetonitrile and acidified with aq TFA, and subjected to HPLC purification on reverse phase. Collection and lyophilization of appropriate fractions provided the title acid. $^1$H NMR (CDCl$_3$) δ7.67–7.11 (m, 8H), 4.26 (s, 2H), 3.97(s, 2H),3.74 (s, 3H), 2.86 (s, 6H).

EXAMPLE 31

4-(5-Benzyl-3-methoxy-2-methoxyethoxyphenyl)2,4-dioxobutyric acid

Y-1

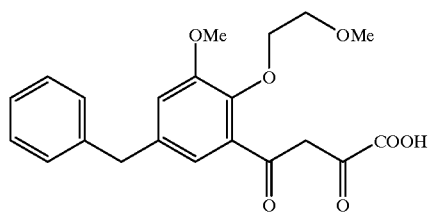

Step 1: 3-Bromo-4-(2-methoxyethoxy)-5-methoxybenzaldehyde

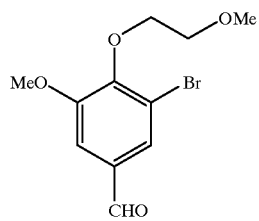

To a 500 mL round bottomed flask with a stirring bar, reflux condenser and an argon inlet was added 5-bromovanillin (10 g, 43.28 mmol), DMF (125 mL), powdered Cs$_2$CO$_3$ (28.2 g, 86.56 mmol) and 2-bromoethylmethyl ether (5.08 mL, 54.10 mmol). This well stirred mixture was heated at 75° C. for 24 h. The cooled mixture was filtered through a frit to remove the cesium salts and the filtrate was concentrated in vacuo. The residue was dissolved in EtOAc and washed with water and brine. Drying (MgSO$_4$), filtration and removal of the solvent in vacuo gave an oil. $^1$H NMR (CDCl$_3$): δ3.44 (s, 3H); 3.77 (t, j=4 Hz, 2H); 3.92 (s, 3H); 4.27 (t, j=4 Hz, 2H); 7.38 (d, j=2 Hz, 1H); 7.65 (d, j=2Hz, 1H); 9.84 (s, 1H).

Step 2: 1-(3-Bromo-4-(2-methoxyethoxy)-5-methoxyphenyl)-1-phenylmethanol.

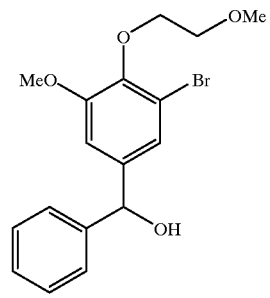

To a 1l round bottomed flask with a stirring bar and an argon inlet was added 3-bromo-4-(2-methoxyethoxy)-5-methoxybenzaldehyde (12.00 g, 41.50 mmol) and dry THF (150 mL). This solution was cooled in an ice bath and phenylmagnesiumbromide in diethyl ether (16.6 mL of a 3.0 M solution, 49.81 mmol) was added with a syringe. The resulting solution was stirred for 1 h at 0° C. The reaction was quenched with aqueous NH$_4$Cl solution. The mixture was diluted with EtOAc and the layers were separated. The organic phase was washed with brine, dried (MgSO$_4$), filtered and concentrated in vacuo. This material was chromatographed on 400g of silica gel using 30/70 EtOAc-hexane as eluant. There was obtained 1-(3-bromo-4-(2-methoxyethoxy)-5-methoxyphenyl)-1-phenylmethanol as an oil. $^1$H NMR (CDCl$_3$): δ2.29 (d, j=4Hz, 1H); 3.44 (s, 3H); 3.74 (t, j=4 Hz, 2H); 3.82 (s, 3H); 4.13 (t, j=4 Hz, 2H); 5.75 (d, j=4Hz, 1H); 6.88 (s, 1H); 7.12 (s, 1H); 7.35 (m, 5H).

Step 3: 1-(3-Bromo-4-(2-methoxyethoxy)-5-methoxyphenyl)-1-phenylmethane.

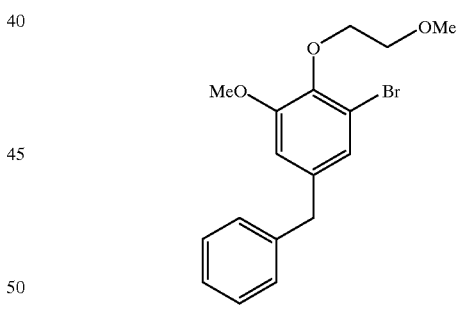

To a 500 mL round bottomed flask with a stirring bar and a nitrogen inlet was added of 1-(3-bromo-4-(2-methoxyethoxy)-5-methoxyphenyl)-1-phenylmethanol (12.83 g, 34.94 mmol), dry methylene chloride (200 mL) and triethylsilane (13.87 mL, 87.34 mmol). This solution was cooled in an ice bath and borontrifluoride etherate (4.43 mL, 34.94 mmol) was added with a syringe over 5 min. The mixture was aged 2 h at 0° C. The reaction was quenched with saturated aqueous sodium bicarbonate solution and the mixture was extracted with chloroform. The chloroform fraction was washed with brine, dried (MgSO$_4$), filtered and concentrated in vacuo. This material was chromatographed on 400 g of silica gel using 20/80 EtOAc-hexane as eluant to give 9.45 g of 1-(3-bromo-4-(2-methoxyethoxy)-5-methoxyphenyl)-1-phenylmethane as an oil. $^1$H NMR (CDCl$_3$): δ3.44 (s, 3H); 3.74 (t, j=4 Hz, 2H); 3.77 (s, 3H); 3.88 (s, 2H); 4.13 (t, j=4 Hz, 2H); 6.64 (d, j=2Hz, 1H); 6.94 (d, j=2Hz, 1H); 7.26 (m, 5H).

Step 4: 1-(2-(2-Methoxyethoxy)-3-methoxy-5-phenylmethyl)-1-ethanone.

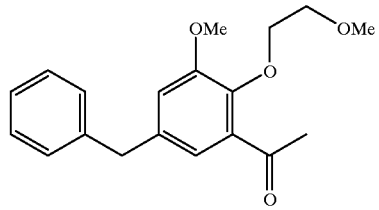

To a 25 mL glass pressure vessel with a stirring bar was added 1-(3-bromo-4-(2-methoxyethoxy)-5-methoxyphenyl)-1-phenylmethane (1.95 g, 5.55 mmol) and 12 mL of DMF. This solution was degassed with a stream of nitrogen for 10 min. Palladium (II) acetate (0.25 g, 1.11 mmol), DPPP (0.50 g, 1.20 mmol), thallium (I) acetate (1.61 g, 6.11 mmol), butylvinyl ether (3.62 mL, 27.75 mmol) and triethylamine (3.09 mL, 22.20 mmol) were added and the mixture was degassed for another 10 min. The vessel was sealed and heated at 100° C. for 18 h with vigorous stirring. The cooled mixture was filtered through a CELITE diatomaceous earth pad and the filtrate was concentrated in vacuo. The residue was dissolved in THF (30 mL) and 1N HCl (30 mL) was added. This solution was stirred at ambient temperature 20 h. The mixture was extracted with two portions of EtOAc. The combined EtOAc extracts were washed with water and brine. Drying (MgSO$_4$), filtration and removal of the solvent in vacuo gave a yellow oil. This material was chromatographed on 90 g of silica gel using 30/70 EtOAc-hexane as eluant. There was obtained 1-(2-(2-methoxyethoxy)-3-methoxy-5-phenylmethyl)-1-ethanone as an oil. $^1$H NMR (CDCl$_3$): δ2.64 (s, 3H);3.37 (s, 3H); 3.63 (t, j=4 Hz, 2H); 3.80 (s, 3H); 3.93 (s, 2H); 4.17 (t, j=4 Hz, 2H); 6.82 (d, j=2Hz, 1H); 7.04 (d, j=2Hz, 1H); 7.26 (m, 5H).

Step 5: Ethyl 4-(benzyl-3-methoxy-2-methoxyethoxyphenyl)-2,4-dioxobutyrate.

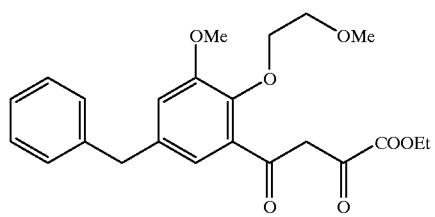

To a 50 mL round bottomed flask with a stirring bar and a nitrogen inlet was added 1-(2-(2-methoxyethoxy)-3-methoxy-5-phenylmethyl)-1-ethanone (1.35 g, 4.29 mmol), THF (30 mL), diethyl oxalate (1.75 mL, 12.88 mmol) and sodium ethoxide (0.41 g, 6.00 mmol). This solution was stirred 2 h at ambient temperature. The reaction was quenched with saturated aqueous NH$_4$Cl solution and extracted with EtOAc. The organic phase was washed with water and brine. Drying (MgSO$_4$), filtration and removal of the solvent in vacuo gave an oil. This material was exposed to high vacuum for 2 days to remove the excess diethyl oxalate giving 1.48 g of ethyl 4-(benzyl-3-methoxy-2-methoxyethoxyphenyl)-2,4-dioxobutyrate as an oil. $^1$H NMR (CDCl$_3$): δ1.38 (t, j=7Hz, 3H), 3.36 (s, 3H); 3.66 (t, j=4 Hz, 2H); 3.82 (s, 3H); 3.96 (s, 2H); 4.16 (t, j=4 Hz, 2H); 4.82 (q, j=7Hz, 2H); 6.87 (d, j=2Hz, 1H); 7.26 (m, 7H).

Step 6: 4-(Benzyl-3-methoxy-2-methoxyethoxyphenyl)-2,4-dioxobutyric acid.

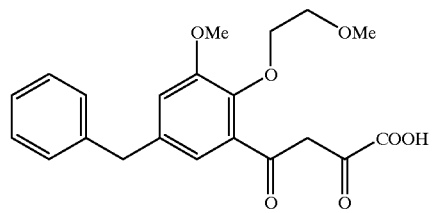

To a 200 mL round bottomed flask with a stirring bar and a nitrogen inlet was added ethyl 4-(benzyl-3-methoxy-2-methoxyethoxyphenyl)-2,4-dioxobutyrate (1.48 g, 3.57 mmol), THF (30 mL), methanol (30 mL), and sodium hydroxide solution (18 mL of a 1 N solution in water, 18 mmol). This mixture was stirred 2 h at ambient temperature. The organic solvents were removed in vacuo and the aqueous residue was diluted with 30 mL of water. This solution was washed with ethyl ether (2×50 mL) then acidified with 1N HCl. This mixture was extracted with ethyl ether (100 mL). The ether solution was washed with water and brine. Drying (MgSO$_4$), filtration and removal of the solvent in vacuo gave a yellow oil. This material was crystallized by dissolving in 1:1 ether-hexane (~5mL) and storing in a freezer over night. The crystalline product was collected by filtration on a frit and dried in vacuo at ambient temperature to give 4-(benzyl-3-methoxy-2-methoxyethoxyphenyl)-2,4-dioxobutyric acid as yellow needles. MP: 83–85° C. Anal. Calc'd for C$_{21}$H$_{22}$O$_7$: C, 65.28; H, 5.74; Found: C, 65.28; H, 6.05. $^1$H NMR (CDCl$_3$): δ3.39 (s, 3H); 3.71 (t, j=4 Hz, 2H); 3.82 (s, 3H); 3.96 (s, 2H); 4.21 (t, j=4 Hz, 2H); 6.90 (d, j=2Hz, 1H); 7.28 (m, 6H); 9.60 (br s, 1H).

EXAMPLES 32–108

The following examples (32–108) may be prepared according to the general procedures outlined in the Schemes and in Examples 1 to 31.

32. 4-(3-Benzyl-4-methoxyphenyl)-2,4-dioxobutyric acid

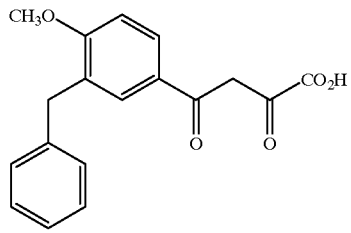

Anal. Calcd for C$_{18}$H$_{16}$O$_5$ 0.30 toluene: C, 71.01; H, 5.46. Found: C, 71.05; H, 5.68.

33. 4-(5-Benzyl-2-methoxyphenyl)-2,4-dioxobutyric acid

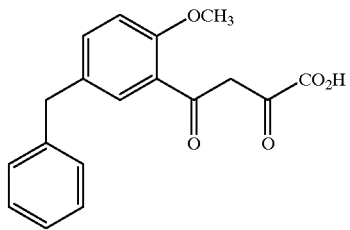

Anal. Calcd for $C_{18}H_{16}O_5$: C, 69.22; H, 5.16. Found: C, 68.89; H, 5.10.

34. 4-(3-Benzyl-4-fluorophenyl)-2,4-dioxobutyric acid

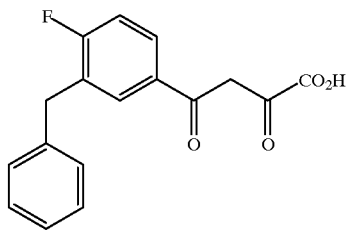

Anal. Calcd for $C_{17}H_{13}FO_4$ 0.15 $H_2O$: C, 67.38; H, 4.42. Found: C, 67.31; H, 4.16.

35. 4-(3-Benzyl-4-N,N-dimethylaminophenyl)-2,4-dioxobutyric acid

Anal. Calcd for $C_{19}H_{19}NO_4$ 1.42 TFA: C, 55.61; H, 4.41; N, 3.03. Found: C, 55.51; H, 4.22; N, 2.95.

36. 4-[5-(2-Methylbenzyl)-2,3-dimethoxyphenyl]-2,4-dioxobutyric acid

Anal. Calcd for $C_{20}H_{20}O_6$: C, 67.41; H, 5.66. Found: C, 67.42; H, 5.57.

37. 2,4-Dioxo-4-(3-pyridin-2-ylmethylphenyl) butyric acid

Anal. Calcd for $C_{16}H_{13}NO_4$ 0.7 TFA: C, 57.55; H, 3.80; N, 3.86. Found: C, 57.73; H, 3.84; N, 3.79.

38. 4-(5-Benzyl-3-N,N-dimethylaminophenyl)-2,4-dioxobutyric acid

Anal. Calcd for $C_{19}H_{19}NO_4$ 1.35 TFA: C, 57.40; H, 4.59; N, 3.19. Found: C, 57.66; H, 4.87; N, 3.03.

39. 4-(5-Benzyl-3-methoxyphenyl)-2,4-dioxobutyric acid

Anal. Calcd for $C_{18}H_{16}O_5$ 0.15 $H_2O$: C, 68.62; H, 5.22. Found: C, 68.59; H, 5.04.

40. 4-(5-Benzyl-2-benzyloxy-3-methoxyphenyl)-2,4-dioxobutyric acid

Anal. Calcd for $C_{25}H_{22}O_6$ 0.30 $H_2O$: C, 70.84; H, 5.37. Found: C, 70.82; H, 5.22.

41. 4-[5-(3-Methylbenzyl)-2,3-dimethoxyphenyl]-2,4-dioxobutyric acid

Anal. Calcd for $C_{20}H_{20}O_6$: C, 67.41; H, 5.66. Found: C, 67.33; H, 5.18.

42. 4-(5-Benzyl-3-benzyloxyphenyl)-2,4-dioxobutyric acid

Anal. Calcd for $C_{24}H_{20}O_5$ 0.15 $H_2O$: C, 73.69; H, 5.23. Found: C, 73.65; H, 5.30.

43. 4-[5-Benzyl-2-(2-hydroxy)ethoxyphenyl]-2,4-dioxo-2-butanoic acid

Anal. Calcd for $C_{19}H_{19}O_6$: C, 66.66; H, 5.30. Found: C, 66.69; H, 5.51.

44. 2,4-Dioxo-4-(3-pyridin-3-ylmethylphenyl) butyric acid

Anal. Calcd for $C_{16}H_{13}NO_4$ 1.1 TFA & 0.35 MECN: C, 53.65; H, 3.61; N, 4.47. Found: C, 53.56; H, 3.79; N, 4.47.

45. 4-[3-(3-Methyl-pyridin-2-ylmethyl)phenyl]-2,4-dioxo-butyric acid

Anal. Calcd for $C_{16}H_{13}NO_4$ 1 TFA: C, 55.48; H, 3.92; N, 3.41. Found: C, 55.20; H, 4.01; N, 3.58.

46. 4-(5-Benzyl-2-methylsulfanylphenyl)-2,4-dioxobutyric acid

Anal. Calcd for $C_{18}H_{16}O_5$ 0.05 $H_2O$ 0.20 HCl: C, 64.23; H, 4.88. Found: C, 64.16; H, 4.76.

47. 4-(5-Benzyl-3-N-morpholinophenyl)-2,4-dioxobutyric acid

Anal. Calcd for $C_{21}H_{21}NO_5$ 1 TFA 0.2 $H_2O$: C, 56.95; H, 4.66; N, 2.89. Found: C, 56.96; H, 5.18; N, 3.00.

48. 4-(8-Benzyl-4-methyl-3,4-dihydro-2h-benzo[1,4]oxazin-6-yl)-2,4-dioxobutyric acid Anal. Calcd for $C_{20}H_{19}NO_5$ 0.15 MeCN 0.1 TFA: C, 66.37; H, 5.31; N, 4.34. Found: C, 66.41; H, 5.58; N, 4.41.

49. 4-[5-(2-Chlorobenzyl)-3-N,N-dimethylaminophenyl]-2,4-dioxobutyric acid

Anal. Calcd for $C_{19}H_{18}ClNO_4$ 0.15 hexane: C, 64.12; H, 5.44; N, 3.76. Found: C, 64.02; H, 5.43; N, 3.56.

50. 4-[5-(3-Chlorobenzyl)-3-N,N-dimethylaminophenyl]-2,4-dioxobutyric acid

Anal. Calcd for $C_{19}H_{18}ClNO_4$ 0.65 $Et_2O$: C, 58.37; H, 5.78; N, 3.15. Found: C, 58.12; H, 5.45; N, 2.77.

51. 4-(5-Benzyl-2,3,4-trimethoxyphenyl)-2,4-dioxobutyric acid

Anal. Calcd for $C_{20}H_{20}O_7$ 0.15 $H_2O$: C, 64.04; H, 5.46. Found: C, 63.98; H, 5.29.

52. 4-(6-Benzylbenzo[1,3]dioxol-4-yl)-2,4-dioxobutyric acid

Anal. Calcd for $C_{18}H_{14}O_6$ 0.3 $H_2O$ 0.1 $Et_2O$: C, 65.16; H, 4.64. Found: C, 65.25; H, 4.65.

53. 4-[3-Benzyl-5-(morpholine-4-carbonyl)phenyl]-2,4-dioxobutyric acid

Anal. Calcd for $C_{22}H_{21}NO_6$ 0.25 $CHCl_3$ 0.15 hexane: C, 63.45; H, 5.37; N, 3.20. Found: C, 63.42; H, 5.30; N, 3.20.

54. 4-(3-Benzyl-5-pyridine-2-ylmethylphenyl)-2,4-dioxobutyric acid

Anal. Calcd for $C_{23}H_{19}NO_4$ 1.0 TFA 0.2 hexane: C, 62.39; H, 4.19; N, 2.46. Found: C, 62.35; H, 4.55; N, 2.78.

55. 4-[3-Benzyl-5-(morpholinomethyl)phenyl]-2,4-dioxobutyric acid

Anal. Calcd for $C_{22}H_{23}NO_5$: C, 58.18; H, 4.88; N, 2.83. Found: C, 58.26; H, 4.76; N, 2.77.

56. 4-(3-Benzyl-5-pyridine-3-ylmethylphenyl)-2,4-dioxobutyric acid

Anal. Calcd for $C_{23}H_{19}NO_4$ 1.0 TFA: C, 61.60; H, 4.14; N, 2.87. Found: C, 61.65; H, 4.43; N, 2.92.

57. 4-[3-Benzyl-5-(2-dimethylamino-1-hydroxy-1-methylethyl)phenyl]-2,4-dioxobutyric acid Anal. Calcd for $C_{22}H_{25}NO_5$ 1.20 $H_2O$: C, 55.53; H, 5.51; N, 2.70. Found: C, 55.55; H, 5.23; N, 2.55.

58. 4-(5-Benzyl-2-N,N-dimethylaminophenyl)-2,4-dioxobutyric acid

Anal. Calcd for $C_{19}H_{19}NO_4$ 1.0 TFA 0.55 $H_2O$: C, 56.13; H, 4.73; N, 3.12. Found: C, 56.11; H, 4.67; N, 3.11.

59. 4-(5-Benzyl-2-fluorophenyl)-2,4-dioxobutyric acid

Anal. Calcd for $C_{17}H_{13}FO_4$ 0.05 $H_2O$ 0.05 $Et_2O$: C, 67.75; H, 4.50. Found: C, 67.83; H, 4.46.

60. 4-(5-Benzyl-3-hydroxymethyl-2-methoxyphenyl)-2,4-dioxobutyric acid

Anal. Calcd for $C_{19}H_{18}O_6$: C, 66.66; H, 5.30. Found: C, 66.91; H, 5.39.

61. 4-[5-Benzyl-2-(pyrazin-2-yloxy)phenyl]-2,4-dioxobutyric acid

Anal. Calcd for $C_{21}H_{16}NO_2O_5$ 0.45 TFA 1.15 $H_2O$: C, 58.66; H, 4.21; N, 6.25. Found: C, 58.67; H, 4.15; N, 6.55.

62. 4-[3-Benzyl-5-(2-oxopiperidin-1-ylmethyl)phenyl]-2,4-dioxobutyric acid

Anal. Calcd for $C_{23}H_{23}NO_5$: C, 70.22; H, 5.89; N, 3.56. Found: C, 69.86; H, 5.55; N, 3.40.

63. 4-[5-Benzyl-2-methoxy-3-(morpholinomethyl)phenyl]-2,4-dioxobutyric acid

Anal. Calcd for $C_{23}H_{25}NO_6$: C, 57.14; H, 4.99; N, 2.67. Found: C, 57.57; H, 5.34; N, 2.47.

64. 4-[3-(2-Chlorobenzyl)-5-pyridin-2-ylmethylphenyl]-2,4-dioxobutyric acid

Anal. Calcd for $C_{23}H_{18}ClNO_4$ 1.0 $H_2O$: C, 64.86; H, 4.73; N, 3.29. Found: C, 64.89; H, 4.37; N, 2.97.

65. 4-[5-Benzyl-2-methoxy-3-(4-methylpiperazin-1-ylmethyl)phenyl]-2,4-dioxobutyric acid Anal. Calcd for $C_{24}H_{28}N_2O_5$ 2.2 TFA: C, 51.01; H, 4.57; N, 4.22. Found: C, 51.03; H, 4.52; N, 4.12.

66. 4-(5-Benzyl-2-methoxymethylphenyl)-2,4-dioxobutyric acid

Anal. Calcd for $C_{19}H_{18}O_5$ 0.10 hexane: C, 70.27; H, 5.84. Found: C, 70.40; H, 5.48.

67. 4-[3-(2-Fluorobenzyl)-5-morpholinomethylphenyl]-2,4-dioxobutyric acid

Anal. Calcd for $C_{22}H_{22}NO_5F$ 2.25 TFA 0.15 $H_2O$: C, 48.32; H, 3.76; N, 2.13. Found: C, 48.30; H, 3.77; N, 1.82.

68. 4-[3-(4-Fluorobenzyl)-5-morpholinomethylphenyl]-2,4-dioxobutyric acid

Anal. Calcd for $C_{22}H_{22}NO_5F$ 1.05 TFA 0.15 $H_2O$: C, 55.46; H, 4.51; N, 2.68. Found: C, 55.48; H, 4.53; N, 2.43.

69. 4-[3-(3-Fluorobenzyl)-5-morpholinomethylphenyl]-2,4-dioxobutyric acid

Anal. Calcd for $C_{22}H_{22}NO_5F$ 1.45 TFA 0.50 $H_2O$: C, 52.12; H, 4.30; N, 2.44. Found: C, 52.11; H, 4.29; N, 2.24.

70. 4-[5-Benzyl-2-methoxy-3-(tert-butylcarbamoyl)phenyl]-2,4-dioxobutyric acid

Anal. Calcd for $C_{23}H_{25}NO_7$ 0.25 EtOAc 0.05 $Et_2O$: C, 64.13; H, 6.12; N, 3.09. Found: C, 64.13; H, 6.10; N, 3.13.

71. 4-(3-Benzyl-5-[1,2,3]triazol-1-ylmethylphenyl)-2,4-dioxobutyric acid

Anal. Calcd for $C_{20}H_{17}N_3O_4$ 0.1 hexane: C, 66.51; H, 4.99; N, 11.30. Found: C, 66.87; H, 4.87; N, 11.65.

72. 4-[5-Benzyl-3-(N'-methyl-N-piperazinyl)phenyl]-2,4-dioxobutyric acid

Anal. Calcd for $C_{22}H_{24}N_3O_4$: C, 63.38; H, 6.04; N, 6.72. Found: C, 63.34; H, 6.12; N, 6.56.

73. 4-(3-Benzyl-5-[1,2,4]triazol-1-ylmethylphenyl)-2,4-dioxobutyric acid

Anal. Calcd for $C_{20}H_{17}N_3O_4$: C, 66.11; H, 4.72; N, 11.56. Found: C, 66.26; H, 4.99; N, 11.59.

74. 4-(6-Benzyl-3-oxo-3,4-dihydro-2-H-benzo[1,4]oxazin-8-yl)-2,4-dioxobutyric acid Anal. Calcd for $C_{19}H_{15}NO_6$ 0.30 $H_2O$: C, 63.61; H, 4.38; N, 3.90. Found: C, 63.69; H, 4.51; N, 3.89.

75. 4-[5-Benzyl-2-(pyrimidin-2-yloxy)phenyl]-2,4-dioxobutyric acid

Anal. Calcd for $C_{21}H_{16}N_2O_5$ 0.40 $H_2O$ 0.45 TFA: C, 60.48; H, 4.00; N, 6.44. Found: C, 60.51; H, 3.96; N, 6.31.

76. 4-(5-Benzyl-3-amino-2-methoxyphenyl)-2,4-dioxobutyric acid

FAB MS M+1=345

77. 4-(5-Benzyl-2-ethoxyphenyl)-2,4-dioxobutyric acid

Anal. Calcd for $C_{18}H_{16}O_5$ 0.15 hexane: C, 70.44; H, 5.97. Found: C, 70.62; H, 5.62.

78. 4-[5-Benzyl-2-(2-morpholin-4-yl-ethoxy)phenyl]-2,4-dioxobutyric acid

Anal. Calcd for $C_{23}H_{25}NO_6$ 0.65 $CH_2Cl_2$ 0.10 $Et_2O$: C, 60.93; H, 5.80; N, 2.95. Found: C, 61.11; H, 5.78; N, 2.75.

79. 4-(5-Benzyl-2-trifluoroethoxyphenyl)-2,4-dioxobutyric acid

Anal. Calcd for $C_{19}H_{15}F_3O_5$ 0.05 $Et_2O$: C, 60.05; H, 4.07. Found: C, 60.00; H, 4.08.

80. 4-(5-Benzyl-2-cyclobutyloxyphenyl)-2,4-dioxobutyric acid

Anal. Calcd for $C_{21}H_{20}O_5$ 0.05 $H_2O$ 0.15 $Et_2O$: C, 71.19; H, 5.97. Found: C, 71.20; H, 5.99.

81. 4-(5-Benzyl-2-cyclopentyloxyphenyl)-2,4-dioxobutyric acid

Anal. Calcd for $C_{22}H_{22}O_5$ 0.20 toluene 0.15 $Et_2O$: C, 72.80; H, 6.39. Found: C, 72.81; H, 6.40.

82. 4-(3-Benzyl-5-tetrazol-2-ylmethylphenyl)-2,4-dioxobutyric acid

Anal. Calcd for $C_{19}H_{16}N_4O_4$: C, 61.99; H, 4.59; N, 14.91. Found: C, 62.00; H, 4.74; N, 14.88.

83. 4-(5-Benzyl-2,3-diisopropoxyphenyl)-2,4-dioxobutyric acid

Anal. Calcd for $C_{23}H_{26}O_6$ 0.2 hexane: C, 69.92; H, 6.98. Found: C, 69.86; H, 6.99.

84. 4-(5-Benzyl-2-isopropoxy-3-N-methylaminophenyl)-2,4-dioxobutyric acid

Anal. Calcd for $C_{21}H_{23}NO_5$ 0.10 TFA 0.90 $H_2O$: C, 55.28; H, 5.20; N, 2.80. Found: C, 55.26; H, 5.12; N, 2.82.

85. 4-(5-Benzyl-2-isopropoxy-3-N,N-dimethylaminophenyl)-2,4-dioxo-butyric acid Anal. Calcd for $C_{22}H_{25}NO_5$ 0.10 TFA: C, 57.95; H, 5.27; N, 2.82. Found: C, 58.09; H, 5.10; N, 2.83.

86. 4-[5-Benzyl-2-isopropoxy-3-(2-N,N-dimethylaminoethoxy)phenyl]-2,4-dioxobutyric acid.

Anal. Calcd for $C_{24}H_{29}NO_6$ 1.70 TFA 0.05 $H_2O$: C, 52.89; H, 4.99; N, 2.25. Found: C, 52.92; H, 5.02; N, 2.01.

87. 4-[5-Benzyl-2-isopropoxy-3-(morpholinomethyl)phenyl]-2,4-dioxo-butyric acid Anal. Calcd for $C_{25}H_{29}NO_6$ 1.0 HCl: C, 63.09; H, 6.35; N, 2.94. Found: C, 63.43; H, 6.46; N, 2.65.

88. 4-(5-Benzyl-2-isopropoxy-3-N,N-dimethylaminomethylphenyl)-2,4-dioxo-butyric acid Anal. Calcd for $C_{23}H_{27}NO_5$ 0.10 TFA: C, 58.70; H, 6.52; N, 2.74. Found: C, 58.42; H, 5.27; N, 2.45.

89. 4-(7-Benzylbenzo[1,3]dioxol-5-yl)-2-hydroxy-4-oxobut-2-enoic acid

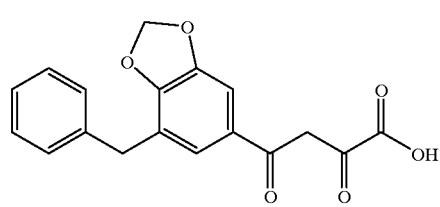

Anal calc for $C_{18}H_{14}O_6$ 0.1 ethylacetate C, 65.94; H, 4.45. Found C, 65.95; H, 4.84.

90. 2-Hydroxy-4-oxo-4-(3-phenylindan-5-yl)but-2-enoic acid

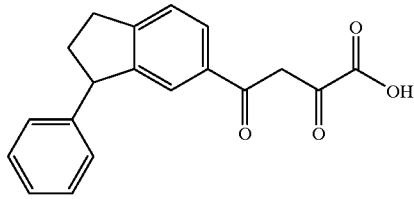

Anal calc for $C_{19}H_{16}O_4$ 0.05 $H_2O$ C, 73.79; H, 5.25. Found C, 73.48; H, 5.33.

91. 4-(Dibenzylaminophenyl)-2-hydroxy-4-oxobut-2-enoic acid

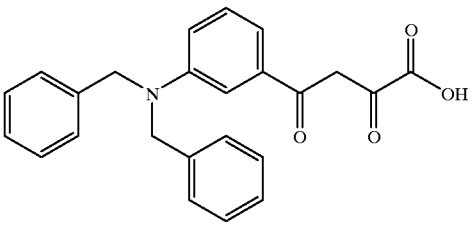

Anal calc for $C_{24}H_{21}NO_4$ 0.1 ethyl acetate C, 73.95; H, 5.55; N, 3.54. Found C, 73.69; H, 5.90; N, 3.22.

92. 3-(3-Benzyl-5-carboxyacetylphenyl)-3-oxopropionic acid

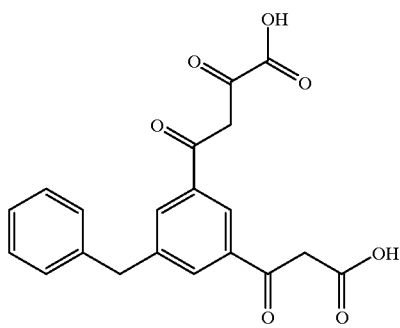

Anal calc for $C_{19}H_{16}O_6$ 1.5 $H_2O$ C, 62.12; H, 5.21. Found C, 61.98; H, 5.28.

93. 4-(4-Dibenzylaminophenyl)-2-hydroxy-4-oxobut-2-enoic acid

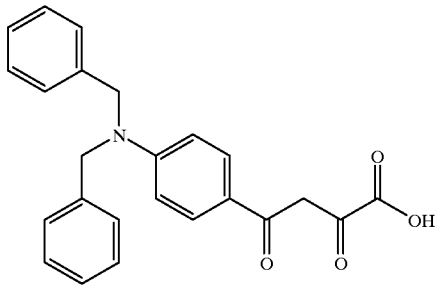

Anal calc for $C_{24}H_{21}NO_4$ 0.05 ethyl acetate C, 7417; H, 5,51; N, 357. Found C, 74.05; H, 5,38; N, 3.29.

94. 4-(5-Benzyl-3-methoxy-2-methylthioethoxyphenyl)-2,4-dioxobutyric acid

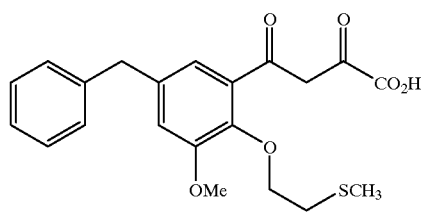

Anal. Calc'd for $C_{21}H_{22}O_6S$: C, 62.67; H, 5.51. Found: C, 62.26; H, 5.65.

mp: 99–100° C.

95. 4-(7-Benzyl-2,3-dihydrobenzo[1,4]dioxin-5-yl)-2,4-dioxobutyric acid

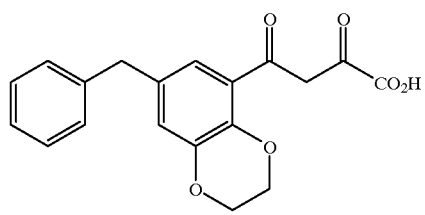

Anal. Calc'd for $C_{19}H_{16}O_6$: C, 67.05; H, 4.74. Found: C, 66.35; H, 4.87.

mp: 154–155° C.

96. (+/−) 4-(8-Benzyl-3-hydroxy-3,4-dihydro-2H-benzo[B][1,4]di-oxepin-6-yl)-2,4-dioxobutyric acid

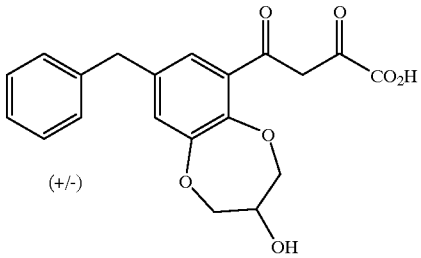

Anal. Calc'd for $C_{20}H_{18}O_7$: C, 64.06; H, 4.90. Found: C, 64.06; H, 5.14.

mp: 182–183° C.

97. 4-(2,3-Dimethoxy-5-pent-4-enylphenyl)-2,4-dioxobutyric acid

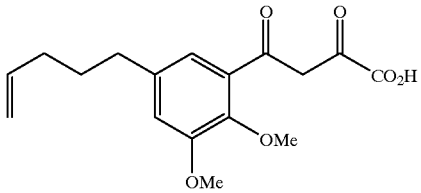

Anal. Calc'd for $C_{17}H_{20}O_6$: C, 63.74; H, 6.29. Found: C, 64.05; H, 6.05.

mp: 75–76° C.

98. 4-(5-Cyclopropylmethyl-2,3-dimethoxyphenyl)-2,4-dioxobutyric acid

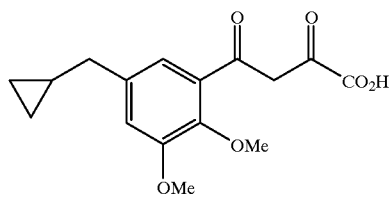

Anal. Calc'd for $C_{16}H_{18}O_6$: C, 62.74; H,5.92. Found: C, 62.75; H,5.79.

mp: 101–103° C.

99. 4-(5-Benzyl-2-isopropoxy-3-[1,2,3]triazol-1-ylmethylphenyl)-2,4-dioxobutyric acid $^1$H NMR (CDCl$_3$) δ7.75 (s, 1H), 7.59 (s, 1H), 7.31–7.12 (m, 7H), 5.63 (s, 2H), 4.19 (m, 1H), 3.92 (s, 2H), 1.29 (d, J=6 Hz, 6H).

100. 4-(5-Benzyl-2-isopropoxy-3-[1,2,4]triazol-1-ylmethylphenyl)-2,4-dioxobutyric acid $^1$H NMR (CDCl$_3$) δ8.42 (s, 1H), 8.02 (s, 1H), 7.58 (s, 1H), 7.34–7.14 (m, 7H), 5.37 (s, 2H), 4.23 (m, 1H), 3.95 (s, 2H), 1.31 (d, J=6 Hz, 6H).

101. 4-[5-Benzyl-2-(3-N,N-dimethylaminopropoxy)-3-methoxyphenyl]-2,4-dioxobutyric acid Anal. Calcd for $C_{23}H_{27}NO_6$ 0.40 HCl 0.25 Et$_2$O: C, 64.54; H, 6.75; N, 3.14. Found: C, 64.42; H, 6.76; N, 3.11.

102. 4-[3-(Phenyldifluoromethy)phenyl]-2,4-dioxobutyric acid

Anal. Calcd for $C_{17}H_{12}F_2O_4$: C, 64.15; H, 3.80. Found: C, 64.29; H, 3.73.

103. 4-(5-Benzyl-2-cyclopropyloxyphenyl)-2,4-dioxobutyric acid

Anal. Calcd for $C_{20}H_{18}O_5$ 0.2 hexane: C, 71.60; H, 5.90. Found: C, 71.78; H, 5.55.

104. 4-[5-Benzyl-2-isopropoxy-3-(1-piperidinylmethyl)phenyl]-2,4-dioxo-butyric acid TFA salt Anal. Calcd for $C_{26}H_{31}NO_5$ 1.15 TFA: C, 59.77; H, 5.70; N, 2.46. Found: C, 59.68; H, 5.70; N, 2.33.

105. 4-[5-Benzyl-2-(2-dimethylamino-1-methylethoxy)phenyl]-2,4-dioxo-butyric acid Anal. Calcd for $C_{22}H_{25}NO_5$ 0.80 $H_2O$ 0.20 EtOAc: C, 65.91; H, 6.84; N, 3.37. Found: C, 65.91; H, 6.91; N, 3.41.

106. 4-[5-Benzyl-2-(1-methylpiperidin-4-yloxy)phenyl]-2,4-dioxo-butyric acid

Anal. Calcd for $C_{23}H_{25}NO_5$ 1.7 $H_2O$ 0.30 EtOAc: C, 64.23; H, 6.86; N, 3.10. Found: C, 64.23; H, 6.62; N, 3.08.

107. 4-[3-Benzyl-5-(4-benzylpiperazin-1-yl)phenyl]-2,4-dioxo-butyric acid

Anal. Calcd for $C_{28}H_{29}N_2O_4$ 0.5 HCl: C, 70.83; H, 6.00; N, 5.62. Found: C, 70.73; H, 6.00; N, 5.62.

108. 4-[5-Benzyl-2-isopropoxy-3-(pyridin-2-ylaminomethyl)phenyl]-2,4-dioxo-butyric acid Anal. Calcd for $C_{26}H_{26}NO_2O_5$ 1.25 $H_2O$ 0.15 methyl t-butyl ether: C, 66.62; H, 6.33; N, 5.81. Found: C, 66.58; H, 6.09; N, 5.43.

EXAMPLE 109

(6-Benzyloxy-1-oxo-indan-2-ylidene)-hydroxyacetic acid AVIII-3-1

Step 1: 6-Benzyloxyindan-1-one AVIII-1-1

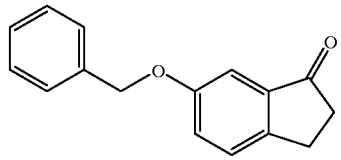

AVIII-1-1

To a solution of 6-hydroxy-indan-1-one (*J. Chem. Soc. Perkin Trans. 1*, 1984, 4, 687–695) (29 g, 196 mmole) in DMF (250 mL), was added under a $N_2$ atmosphere at ambient temperature $K_2CO_3$ (69.1 g, 500 mmole) and benzyl bromide (27.7 mL, 250 mmole). The reaction was set to reflux for 4 hours. The mixture was allowed to cool to room temperature, poured into water, extracted with $CH_2Cl_2$, the organic layer was separated and dried with $MgSO_4$, the solvent evaporated and the product purified by chromatography over silica to obtain AVIII-1-1 as a yellowish solid. $^1$H NMR (400 MHz, $CDCl_3$) δ7.45–7.3 (m, 6H), 7.24 (m, 2H), 5.17 (s, 2H), 3.05 (m, 2H), 2.7 (m, 2H). mass spec EI: m/z (relative abundance) 238 (M+), 91 (100).

Step 2: (6-Benzyloxy-1-oxo-indan-2-ylidene)-hydroxyacetic acid ethyl ester AVIII-2-1

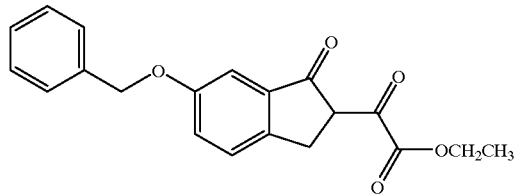

AVIII-2-1

To a solution of AVIII-1-1 (1.9, 8 mmole) and diethyl oxalate (Aldrich, 2.17 mL, 16 mmole) in THF (8 mL) was added in portions NaOEt (Aldrich, 1.088 g, 16 mmole). The reaction was stirred at ambient temperature under a $N_2$ atmosphere for 1.5 hours. The reaction was diluted with $CH_2Cl_2$, quenched with saturated $NaHCO_3$ (aq), the organic layer was separated and dried with $MgSO_4$, the mixture was filtered, the solvent evaporated and the crude purified by preparative silica HPLC eluting with 10:30:60 EtOAc/$CH_2Cl_2$/Hexanes to afford the product as a yellow solid. melting point 118–119° C. (uncorrected). $^1$H NMR (400 MHz, $CDCl_3$) δ7.48–7.30 (m, 8H), 5.12 (s, 2H), 4.41 (q, J=7.24 Hz, 2H), 3.91 (s, 2H), 1.43 (t, J=7.24 Hz, 3H). mass spec EI: m/z (relative abundance) 338 (M+), 91 (100).

Step 3: (6-Benzyloxy-1-oxo-indan-2-ylidene)-hydroxyacetic acid AVIII-3-1

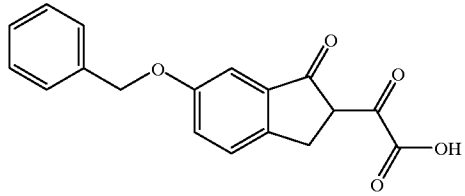

AVIII-3-1

A solution of AVIII-2-1 (500mg, 1.47 mmole) in 1,4-dioxane (3 mL) and 3N HCl (3 mL) was heated in a sealed tube at 70° C. overnight. The reaction was then allowed to cool to ambient temperature and poured into 1N HCl (25 mL), the solid was filtered, dried under vacuum and the product purified by trituration with $Et_2O$/hexanes to afford AVIII-3-1 as a yellow solid. melting point 188–189° C. (uncorrected). $^1$H NMR (400 MHz, DMSO) δ7.56 (d, J=8.4, 1H), 7.47 (m, 2H), 7.42–7.33 (m, 5H), 5.21 (s, 2H), 3.77 (s, 2H). mass spec (FAB, m+1) 311.

EXAMPLE 110

1-[1-(4-Fluorobenzyl)-6-indolyl]-2,4-dioxobutanoic acid AVII-3-1

Step 1: 6-Bromo-1-(4-fluorobenzyl)indole

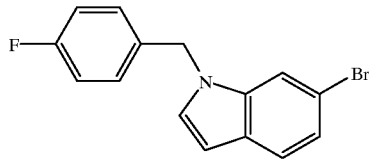

A solution of 6-bromoindole (J. Org. Chem. 1986, 51, 5106) (3.00 g, 15.3 mmol) in DMF (65 mL) was treated with NaH (734 mg of a 60% suspension in mineral oil, 18.4 mmol). After 30 min, 4-fluorobenzyl bromide (1.90 mL, 15.3 mmol) was added. When starting material was consumed, the reaction mixture was poured into 1N HCl and extracted with EtOAc (3×), the combined organic layers were dried (MgSO$_4$) and concentrated. Chromatography of the residue (4:1/hexanes:EtOAc) provided the product.

$^1$H NMR (400 MHz, CDCl$_3$) δ7.49 (d, J=8.4 Hz, 1H), 7.41 (s, 1H), 7.21 (dd, J=8.4, 1.0 Hz, 1H), 7.08–7.04 (m, 3H), 7.15–6.96 (m, 2H), 6.52 (d, J=3.2 Hz, 1H), 5.24 (s, 2H). mass spec (EI, M+) 303, 305.

Step 2: 1-[1-(4-Fluorobenzyl)-6-indolyl]-ethanone AVII-1-1

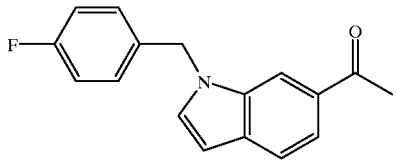

To a solution of 6-bromo-1-(4-fluorobenzyl)indole (2.50 g, 8.20 mmol) in THF (40 mL) at −78° C. was added t-butyllithium (10.6 mL of a 1.7 M solution in pentane, 18.0 mmol) dropwise. After stirring at −78° C. for 30 min, N-methoxy-N-methylacetamide (1.20 g, 12.3 mmol) was added and the mixture was stirred at −78° C. for 2 h and rt for 1 h before adding sat. NH$_4$Cl (5 mL). The reaction mixture was poured onto water and extracted with EtOAc (3×). The combined organic extracts were washed with sat. NaCl and dried (MgSO$_4$). Concentration followed by chromatography of the residue (4:1/hexanes:EtOAc) provided 750 mg (34%) of product.

$^1$H NMR (400 MHz, CDCl$_3$) δ8.00 (s, 1H), 7.74 (dd, J=8.3, 1.5 Hz, 1H), 7.67 (d, J=8.3 Hz; 1H), 7.28 (d, J=3.1 Hz, 1H), 7.12–7.07 (m, 2H), 7.00 (m, 2H), 6.60 (d, J=3.1 Hz, 1H), 5.38 (s, 2H), 2.63 (s, 3H).

Step 3: 1-[1-(4-Fluorobenzyl)-6-indolyl]-2,4-dioxobutanoic acid methyl ester AVII-2-1

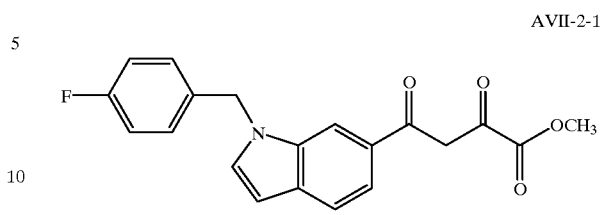

To a solution of AII-1-1 (700 mg, 2.60 mmol) in THF (10 mL) was added dimethyl oxalate (460 mg, 3.90 mmol) followed by NaH (156 mg of a 60% suspension in mineral oil, 3.90 mmol). Methanol (2 drops) was added and the reaction mixture was heated to reflux. After 1 h, 1 N HCl (20 mL) was added and the mixture was extracted with CH$_2$Cl$_2$ (3×15 mL).

The combined organic extracts were washed with sat. NaCl (20 mL) and dried (MgSO$_4$). Concentration followed by medium-pressure liquid chromatography on silica gel, eluting with 5:5:1/CH$_2$Cl$_2$:hexanes:EtOAc, afforded 597 mg (65%) of product. $^1$H NMR (400 MHz, CDCl$_3$) δ8.05 (s, 1H), 7.76 (dt, J=8.4, 1.1 Hz, 1H), 7.71 (d, J=8.4 Hz, 1H), 7.31 (dd, J=3.1, 1.1 Hz, 1H), 7.14 (s, 1H), 7.11 (dd, J=8.4, 5.2 Hz, 2H), 7.01 (t, J=8.4 Hz, 2H), 6.62 (d, J=3.2 Hz, 1H), 5.38 (s, 2H), 3.95 (s, 3H).

Step 4: 1-[1-(4-Fluorobenzyl)-6-indolyl]-2,4-dioxobutanoic acid AVII-3-1

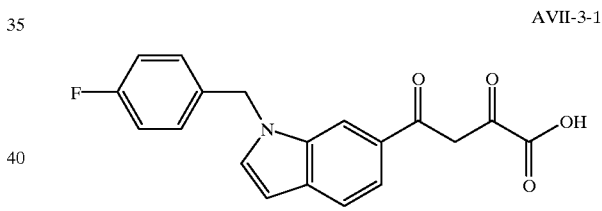

To a solution of AVII-2-1 (597 mg, 1.69 mmol) in THF (10 mL) was added 1 N NaOH (5 mL). After stirring for 14 h at rt, the mixture was poured into 1 N NaOH (20 mL) and extracted with Et$_2$O (3×20 mL). The Et$_2$O extracts were discarded. The aqueous phase was treated with 3 N HCl (30 mL), extracted with CH$_2$Cl$_2$ (3×20 mL) and the combined organic extracts dried (MgSO$_4$). Concentration provided a bright red solid which was triturated with Et$_2$O to provide the product. mp 173–174° C. (uncorrected). $^1$H NMR (400 MHz, d$_6$-DMSO) δ8.37 (s, 1H), 7.79 (d, J=3.0 Hz, 1H), 7.75 (dt, J=8.4, 1.3 Hz, 1H), 7.70 (d, J=8.4 Hz, 1H), 7.28 (dd, J=8.7, 5.6 Hz, 2H), 7.25 (s, 1H), 7.15 (t, J=8.2 Hz, 2H), 6.63 (d, J=3.0 Hz, 1H), 5.62 (s, 2H). mass spec (negative mode electrospray, M−H) 338.

EXAMPLE 111

1-[1-(4-Fluorobenzyl)-4-indolyl]-2,4-dioxobutanoic acid AVII-3-2

Compound AVII-3-2 was prepared in a manner similar to that described for AVII-3-1 by replacing 6-bromoindole with 4-bromoindole (J. Org. Chem. 1986, 51, 5106).

AVII-3-2

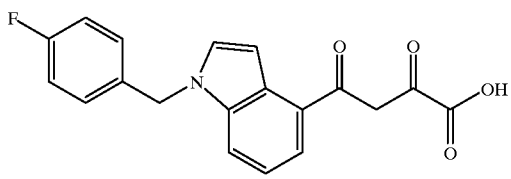

mp 156–157° C. (uncorrected). $^1$H NMR (400 MHz, d$_6$-DMSO) δ7.88 (d, J=8.3 Hz, 1H), 7.85 (d, J=7.7 Hz, 1H), 7.79 (d, J=3.0 Hz, 1H), 7.30–7.25 (m, 1H), 7.17–7.11 (m, 4H), 5.52 (s, 2H). mass spec (negative mode electrospray, M–H) 338.

EXAMPLE 112

4-[1-(2.6-Difluorobenzyl)-1H-indol-6-yl]-2,4-dioxobutyric acid

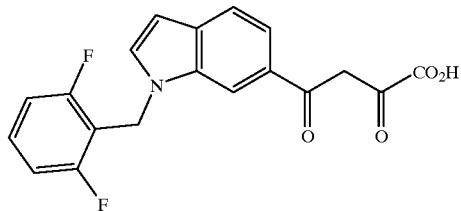

ES MS Exact Mass Calcd. for $C_{19}H_{13}F_2NO_4$+H 358.0885. Found 358.0887.

EXAMPLE 113

4-(1-Benzyl-1H-indol-6-yl)-2,4-dioxobutyric acid

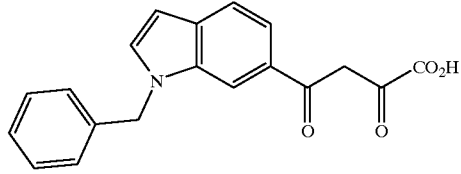

Anal. Calcd for $C_{19}H_{15}NO_4$ 0.75 HCl 0.05 H$_2$O: C, 65.27; H, 4.57; N, 4.01. Found: C, 65.26; H, 4.25; N, 3.87.

EXAMPLE 114

4-(5-Benzyl-2-methoxypyridin-3-yl)-2,4-dioxobutyric acid

Anal. Calcd for $C_{17}H_{15}NO_5$ 0.05 Et$_2$O 0.05 H$_2$O: C, 64.98; H, 4.95; N, 4.41. Found: C, 64.91; H, 4.89; N, 4.15.

EXAMPLE 115

The Compounds in the following Table were made according to the procedures outlined in the Schemes and in Examples 1 to 31.

| COMPOUND NAME | EXACT MASS CALC (m/z): | FOUND (m/z): |
|---|---|---|
| 4-[3-(2,4-difluoro-benzyl)-phenyl]-2,4-dioxo-butyric acid | 319.0776 | 319.0781 |
| 2,4-dioxo-4-[3-(2,6-difluoro-benzyl)-phenyl]-butyric acid | NH$_4$ + 336. 1042 | 336.1063 |
| 2,4-dioxo-4-[3-(2-4-6-difluoro-trifluoro-benzyl)-phenyl]-butyric acid (sodium salt) | 354.0948 | |
| 2,4-dioxo-4-[3-(2-fluoro-3-choro-benzyl)-phenyl]-butyric acid | $C_{17}H_{12}ClFO_4$ NH$_4$ + 352.0746 | 352.0763 |
| 2,4-dioxo-4-[3-(2-methyl-4-fluoro-benzyl)-phenyl]-butyric acid | NH$_4$ + 332.1293 | 332.1307 |
| 4-[3-(2,3-dichloro-benzyl)-phenyl]-2,4-dioxo-butyric acid | $C_{17}H_{12}Cl_2O_{4.NH4}$ + 368.0451 | 368.0443 |
| 4-[3-(2-chloro-3-methylbenzyl)phenyl]-2,4-dioxobutyric acid | $C_{18}H_{15}ClO_4$.NH$_4$ + 348.0997 | 348.1015 |
| 2,4-dioxo-4-[3-(2,6-dichloro-benzyl)-phenyl]-butyric acid | NH$_4$ + 368.0451 | 368.046 |
| 2,4-dioxo-4-[3-(2,3,4,5,6-penta-fluoro-benzyl)-phenyl]-butyric acid | NH$_4$ + 390.0759 | 390.0775 |
| 4-[3-(2-fluorobenzyl)phenyl]-2,4-dioxobutyric acid | $C_{17}H_{13}FO_4$.NH$_4$ 318.1136 | 318.1133 |
| 2,4-dioxo-4-[3-(2-chloro-4-fluoro-benzyl)-phenyl]-butyric acid | NH$_4$ + 352.0746 | 352.0752 |
| 4-[3-(2-methylbenzyl)phenyl]-2,4-dioxobutyric acid | $C_{18}H_{16}O_4$.NH$_4$ + 314.1387 | 314.1395 |
| 2,4-dioxo-4-3-(2-methoxybenzyl)phenyl]butyric acid | NH$_4$ + 330.1336 | 330.135 |
| 4[3-(2-chlorobenzyl)phenyl]-2,4-dioxobutyric acid | $C_{17}H_{13}ClO_4$.NH$_4$ + 334.0841 | 334.0854 |
| 4-[3-(2-bromobenzyl)phenyl]-2,4-dioxobutyric acid | $C_{17}H_{13}BrO_4$.NH$_4$ + 378.0335 | 378.034 |
| 4-[5-(4-fluoro-benzyl-2,3-dimethoxy-phenyl]-2,4-dioxo-butyric acid | 361.1082 | 361.109 |
| 4-[3-(3-chloro-2-methyl-benzyl)phenyl]-2,4-dioxobutyric acid | $C_{18}H_{15}ClO_4$.NH$_4$ + 348.0997 | 348.1013 |
| 4-[3-(2,3-difluoro-benzyl)-phenyl]-2,4-dioxo-butyric acid | $C_{17}H_{12}F_2O_4$.NH$_4$ + 336 1042 | 336.1044 |
| 4-(3,5-dibenzylphenyl)-2,4-dioxo-butyric acid | $C_{24}H_{20}O_4$.NH$_4$ + 390.1700 | 390.171 |
| 2,4-dioxo-4-[3-(2-trifluoromethylbenzyl)phenyl]butyric acid | NH$_4$ + 368.1104 | 368.1111 |
| 4-[3-(4-fluorobenzyl)phenyl]-2,4-dioxobutyric acid | $C_{17}H_{13}FO_4$ 301.0876 | 301.0885 |
| 4-[3-(3-chlorobenzyl)phenyl]-2,4-dioxobutyric acid | $C_{17}H_{13}ClO_4$.NH$_4$ + 334.0841 | 334.0847 |
| 2,4-dioxo-4-[3-(2-bromo-3-chloro-benzyl)-phenyl]-butyric acid | NH$_4$ + 411.9946 | 411.9944 |
| 4-(3-benzylphenyl)-2,4 dioxo-butyric acid | $C_{17}H_{14}O_4$.NH$_4$ + 300.123 | 300.124 |
| 4-[3-(2-fluoro-3-methyl-benzyl)-phenyl]-2,4-dioxo-butyri acid sodium salt | 315.1027 | 315.1034 |
| 4-[3-(3-chloro-4-fluoro-benzyl)-phenyl]-2,4-dioxo-butyric acid | $C_{17}H_{12}ClFO_4$.NH$_4$ + 352.0746 | 352.0733 |

| COMPOUND NAME | EXACT MASS CALC (m/z): | FOUND (m/z): |
|---|---|---|
| 2,4-dioxo-4-[3-(2-bromo-4-fluoro-benzyl)-phenyl]-butyric acid | NH$_4$ + 396.0241 | 396.0247 |
| 4-[3-(3-bromobenzyl)phenyl]-2,4-dioxobutyric acid | C$_{17}$H$_{13}$BrO$_4$ 361.0075 | 361.0101 |
| 4-[3-(2,5-difluoro-benzyl)-phenyl]-2,4-dioxo-butyric acid | C$_{17}$H$_{12}$F$_2$O$_4$.NH$_4$ + 336.1042 | 336.1046 |
| 4-[3-(5-chloro-2-fluoro-nzyl)phenyl]-2,4-dioxobutyric acid | C$_{17}$H$_{12}$ClFO$_4$.NH$_4$ + 352.0746 | 352.0753 |
| 4-[3-(3-methylbenzyl)phenyl]-2,4-dioxobutyric acid | C$_{18}$H$_{16}$O$_4$ 297.1121 | 297.112 |
| 4-(3-benzyl-4-methyl-phenyl)-2,4-dioxo-butyric acid | 297.1121 | 297.1142 |
| 4-[3-(3,4-difluoro-benzyl)phenyl]-2,4-dioxo-butyric acid | 319.0776 | 319.078 |
| 4-[3-(2,5-dichloro-benzyl)phenyl]-2,4-dioxo-butyric acid | C$_{17}$H$_{12}$Cl$_2$O$_4$.NH$_4$ + 368.0451 | 368.0465 |
| 4-[3-(2-chloro-6-methyl-benzyl)phenyl]-2,4-dioxobutyric acid | C$_{18}$H$_{15}$ClO$_4$.NH$_4$ + 348.0997 | 348.1012 |
| 2,4-dioxo-4-[3-(2-trifluoromethyl-4-chloro-benzyl)-phenyl]-butyric acid | NH$_4$ + 386.1010 | 386.1009 |
| 4-[3-(2-bromo-5-chloro-benzyl)-phenyl]-2,4-dioxo-butyric acid | C$_{17}$H$_{12}$BrClO$_4$.NH$_4$ + 411.9947 | 411.9966 |
| 4-(3-naphthalen-1-ylmethyl-phenyl)-2,4-dioxo-butyric acid | 333.1121 | 333.1121 |
| 2,4-dioxo-4-[3-(3-fluorobenzyl)phenyl]butyric acid | NH$_4$ + 318.1136 | 318.114 |
| 2,4-dioxo-4-(3-phenylsulfanyl-phenyl)-butyric acid | 301.0535 | 301.0524 |
| 2,4-dioxo-4-[3-(1-phenylethyl)phenyl]butyric acid | NH$_4$ + 314.1387 | 314.1401 |
| 4-(3-benzyl-4,5-dimethylphenyl)-2,4-dioxo-butyric acid | 311.1278 | 311.1293 |
| 2,4-dioxo-4-[3-(3-methoxybenzyl)phenyl]butyric acid | NH$_4$ + 330.1336 | 330.1341 |
| 4-[3-(5-methyl-thiophen-2-ylmethyl)phenyl]-2,4-dioxo-butyric acid | NH$_4$ + 320.0951 | 320.0967 |
| 4-[3-(5-chloro-thiophen-2-ylmethyl)phenyl]-2,4-dioxo-butyric acid | NH$_4$ + 340.0405 | 340.0418 |
| 4-(3-benzyl-5-methylphenyl)-2,4-dioxo-butyric acid | 297.1121 | 297.1127 |
| 4-[3-(2-cyanobenzyl)phenyl]-2,4-dioxo-butyric acid | NH$_4$ + 325.1183 | 325.1157 |
| Methyl 4-[3-benzylphenyl]-2,-4-dioxobutyrate | C$_{18}$H$_{16}$O$_4$ 297.1121 | 297.113 |
| 4-[3-(3,5-dichloro-benzyl)-phenyl]-2,4-dioxo-butyric acid | 351.0185 | 351.0167 |
| 4-(5-benzyl)-2,4-dimethylphenyl)-2,4-dioxo-butyric acid | 311.1278 | 311.1298 |
| 4-(5-benzyl-2-methylphenyl)-2,4-dioxo-butyric acid | 297.1121 | 297.1123 |
| 4-(3-cyclohexylmethyl-phenyl)-2,4-dioxo-butyric acid | 289.1434 | 289.1449 |
| 4-{(3-[(methyl-phenyl-amino)-methyl]-phenyl}-2,4-dioxo-butyric acid | 312.123 | 312.1235 |
| 4-[3-benzyl-5-(5-hydroxy pentyl)-phenyl]-2,4-dioxo-butyric acid | 369.1696 | 369.1688 |
| 4-(3-benzyl-5-pyrazin-2-yl-phenyl)-2,4-dioxo-butyric acid | NH$_4$ + 378.1448 | 378.1455 |
| 4-[3-(3-tert-butoxy-2-hydroxy-propyl)-5-(2-methyl-benzyl)-phenyl]-2,4-dioxo-butyric acid | 427.2115 | 427.213 |
| 2,4-dioxo-4-[3-(2,3-dimethoxy-benzyl)-phenyl]-butyric acid | NH$_4$ + 360.1442 | 360.1451 |
| 4-[3-(methoxyphenyl-methyl)phenyl]-2,4-dioxobutyric acid | C$_{18}$H$_{16}$O$_5$.NH$_4$ + 330.1336 | 330.1344 |
| 4-[3-[hydroxy-(tetrahydro-furan-3-yl)-methyl]-5-(2-methyl-benzyl)-phenyl]-2,4 dioxo-butyric acid | C$_{23}$H$_{24}$O$_6$.NH$_4$ + 414.1917 | 414.1911 |
| 2,4-dioxo-4-(3-phenoxymethyl-phenyl)-butyric acid | 299.0914 | 299.0924 |
| 2,4-dioxo-4-(3-phenoxymethyl-phenyl)-butyric acid methyl ester | 313.107 | 313.1096 |
| 4-[3-benzyl-5-(cyclopropylcarboxamido)-phenyl]-2,4-dioxobutyric acid | C$_{21}$H$_9$NO$_5$.NH$_4$ + 383.1601 | 383.1601 |
| 4-[3-benzyl-5-(t-butoxycarbamoyl)phenyl]-2,4-dioxobutyric acid | C$_{22}$H$_{23}$NO$_6$.NH$_4$ + 415.1863 | 415.1867 |
| 4-[3-(hydroxy-phenyl-methyl)-phenyl]-2,4-dioxo-butyric acid | C$_{17}$H$_{14}$O$_5$ 299.0919 | 299.0905 |
| 4-(5-benzyl-2,3-dimethylphenyl)-2,4-dioxo-butyric acid sodium salt | 311.1278 | 311.1275 |
| N-[3-(3,5-dibromobenzyl)phenyl]-2,4-dioxo-butyric acid | C$_{17}$H$_{12}$Br$_2$O$_4$ NH$_4$ + 455.9440 | 455.9461 |
| 4-[3-(2-methyl-benzyl)-5-pyrimidin-2-yl-phenyl]-2,4-dioxo-butyric acid methyl ester | 389.1496 | 389.149 |
| 4-[3-benzyl-2-(pyrimidin-2-ylamino)-phenyl]-2,4-dioxo-butyric acid hydrochloride | C$_{21}$H$_2$ON$_3$O$_4$ 376.1306 | 376.1292 |
| 4-[3-benzoimidazol-1-ylmethyl-5-(2-methyl-benzyl)-phenyl]--2,4-dioxo-butyric acid TFA salt | 427.1652 | 427.1648 |
| 2,4-dioxo-4-[3-(3-trifluoromethylbenzyl)phenyl]butyric acid | CHN + 0.75 HCl C:57.24; H: 3.67 | C: 57.38; H, 4.03 |
| 4-(4-phenoxy-phenyl)-2,4-dioxo-butyric acid | 285.0757 | 285.0763 |
| 2,4-dioxo-4-(3-[1,2,3]triazol-2-ylmethyl-phenyl)-butyric acid | C$_{13}$H$_{11}$N$_3$O$_4$.Na 296.0642 | 296.0645 |
| 4-[3-benzyl-5-(6-methoxy-pyridin-2-yl)-phenyl]-2,4-dioxo-butyric acid | 390.1336 | 390.1361 |
| 4-(3-benzotriazol-2-ylmethyl-phenyl)-2,4-dioxo-butyric acid | 324.0984 | 324.0978 |

| COMPOUND NAME | EXACT MASS CALC (m/z): | FOUND (m/z): |
|---|---|---|
| 4-[3-benzyl-5-(2-(4-methylpiperazin-1-yl)-pyrazin-6-yl)phenyl]-2,4-dioxobutyric acid | 459.2027 | 459.2014 |
| 4-[4-(3-phenethyl)phenyl]-2,4-dioxobutyric acid | 297.1121 | 297.1124 |
| 4-[4-(3-chlorobenzyl)phenyl]-2,4-dioxobutyric acid | $C_{17}H_{13}ClO_4NH_4$ + 334.0841 | 334,0854 |
| 4-(3-benzoimidazol-1-ylmethyl-phenyl)-2,4-dioxo-butyric acid trifluoracetic acid salt | 323.1026 | 323.1033 |
| 4-[3-benzyloxy-5-(6-tert-butoxycarbonylamino-hexyloxy)phenyl]-2-hydroxy-4-oxo-but-2-enoic acid methyl ester | 528.2604 | 528.2592 |
| 4-(3-benzotriazol-1-ylmethyl-phenyl)-2,4-dioxo-butyric acid | 274.0822 | 274.0825 |
| 4-[3-(3,5-dimethyl-pyrazol-1-ylmethyl)-phenyl]-2,4-dioxo-butyric acid | $C_{16}H_{16}N_2O_4$ 301.1183 | 301.1196 |
| 4-[3-benzyloxy-5-(2-morphonin-4-yl-ethoxy)phenyl]-2-hydroxy-4-oxo-but-2-enoic acid TFA salt | 428.1704 | 428.1695 |
| 4-(4-methyl-3-phenoxy-phenyl)-2,4-dioxo-butyric acid | 299.0914 | 299.0914 |
| 4-[3-(2-hydroxy-benzyl)-phenyl]-2,4-dioxo-butyric acid | 316.118 | 316.1177 |
| 4-[3-benzyl-5-(6-dimethylamino-pyrazin-2-yl)-phenyl]-2,4-dioxo-butyric acid | 404.1605 | 404.162 |

EXAMPLE 116

HIV Integrase Assay: Strand Transfer Catalyzed by Recombinant Integrase and Preintegration Complexes Assays for the strand transfer activity of integrase were conducted according to Wolfe, A. L. et al., J. Virol. 70, 1424 (1996), and Farnet, C. M. and Bushman F. D. (1997) Cell; 88, 483 for recombinant integrase and preintegration complexes, respectively, hereby incorporated by reference for these purposes.

Representative compounds tested in the integrase assay demonstrated $IC_{50}$'s less than 1 micromolar. Further, representative compounds tested in the preintegration complex assay also demonstrated $IC_{50}$'s of less than 1 micromolar.

EXAMPLE 117

Assay for Inhibition of HIV Replication

Assays for the inhibition of acute HIV infection of T-lymphoid cells was conducted according to Vacca, J. P. et al., (1994), Proc. Natl. Acad. Sci. USA 91, 4906, herein incorporated by reference for these purposes.

Representative compounds tested in the present assay demonstrated $IC_{95}$s of less than 10 micromolar.

EXAMPLE 118

Oral Composition

As a specific embodiment of an oral composition of a compound of this invention, 50 mg of a compound of the present invention is formatted with sufficient finely divided lactose to provide a total amount of 580 to 590 mg to fill a size 0 hard gelatin capsule.

While the foregoing specification teaches the principles of the present invention, with examples provided for the purpose of illustration, it will be understood that the practice of the invention encompasses all of the usual variations, adoptions, or modifications, as come within the scope of the following claims and their equivalents.

What is claimed:

1. A compound of structural formula (I):

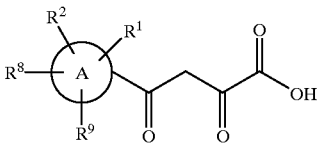

(I)

and tautomers and pharmaceutically acceptable salts thereof, wherein:

A is a six-membered aromatic ring substituted on carbon by $R^1$, $R^2$, $R^8$, and $R^9$, optionally fused with another ring system, and is selected from:
(1) phenyl,
(2) naphthyl, (3)

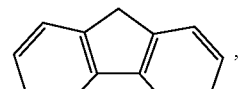

, (4)

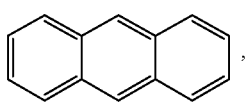

, (5)

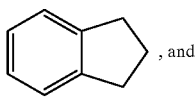

, and (6)

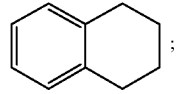

;

$R^1$ is selected from:
(1) —H,
(2) —$C_{1-5}$ alkyl,
(3) —$C_{1-6}$ alkyl-$OR^7$;
(4) —O—$C_{1-6}$ alkyl-$OR^7$,
(5) —O—$C_{1-6}$ alkyl-$SR^7$,
(6) —$CF_3$ or —$CH_2CF_3$,
(7) —F, Cl, or Br,
(8) —$NO_2$,
(9) —$C_{0-3}$ alkyl —$N(R^4)(R^5)$,
(10) -phenyl,
(11) substituted phenyl substituted with 1 or 2 substituents independently selected from:
(a) halogen,
(b) $C_{1-6}$ alkyl,
(c) $C_{1-6}$ alkyloxy-,
(d) phenyl, (e) —CF$_3$,
(f) —OCF$_3$,
(g) —CN,
(h) hydroxy,
(i) phenyloxy, and
(j) substituted phenyloxy with 1, 2, or 3 substituents selected from:
  (i) halogen,
  (ii) C$_{1-6}$ alkyl,
  (iii) —CF$_3$, and
  (iv) hydroxy;
(12) phenyl C$_{1-3}$ alkyl-, wherein the phenyl group may be unsubstituted or substituted with 1 to four substituents independently selected from:
  (a) halogen,
  (b) C$_{1-6}$ alkyl,
  (c) C$_{1-6}$ alkyloxy- wherein one or more of the hydrogen atoms may be replaced with a fluorine atom,
  (d) phenyl,
  (e) —CF$_3$,
  (f) —SCH$_3$,
  (g) —CN,
  (h) hydroxy,
  (i) phenyloxy,
  (j) —C$_{0-6}$ alkyl-N(R$^7$)$_2$, (k)

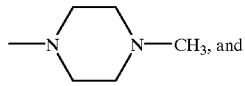

(l) substituted phenyloxy with 1, 2, or 3 substituents selected from:
  (i) halogen,
  (ii) C$_{1-6}$ alkyl,
  (iii) —CF$_3$, and
  (iv) hydroxy;
(13) —O—R$^6$,
(14) —O—C$_{1-6}$ alkyl, unsubstituted or substituted with one to three fluorine atoms,
(15) —O—C$_{1-6}$ alkyl-NH—C(O)—OR$^7$;
(16) —O—C$_{2-6}$ alkyl-N(R$^4$)(R$^5$);
(17) —S—C$_{1-3}$ alkyl;
(18) —C(O)CH$_2$C(O)C(O)OR$^7$;
(19) —CH$_2$—CH(OH)—CH$_2$—O—R$^7$; and
(20) —C(OH)(CH$_3$)—CH$_2$N(R$^4$)(R$^5$);

R$^2$ is selected from:
(1) —R$^3$,
(2) —C$_{1-6}$ alkyl substituted with R$^3$, wherein one or more of the hydrogen atoms on C$_{1-6}$ alkyl may be replaced with a fluorine atom,
(3) —O—C$_{1-6}$ alkyl-SR$^6$;
(4) —C$_{1-6}$ alkyl (OR$^6$)(R$^4$),
(5) —C$_{0-6}$ alkyl-N(R$^4$)(R$^6$),
(6) —C$_{1-6}$ alkyl S—R$^6$,
(7) —C$_{0-6}$ alkyl C(O)—R$^6$,
(8) —C$_{0-6}$ alkyl C(O)CH$_2$—C(O)—OH,
(9) —C$_{1-6}$ alkyl NR$^4$C(O)—R$^6$,
(10) —C$_{1-6}$ alkyl-C(O)N(R$^4$)(R$^5$), and
(11) —CH$_2$(OR$^7$)—R$^6$;

each R$^3$ is independently selected from:
(1) phenyl;
(2) substituted phenyl with 1, 2, 3 or 4 substituents independently selected from:
  (a) halogen,
  (b) C$_{1-6}$ alkyl, wherein one or more of the hydrogen atoms may be replaced with a fluorine atom,
  (c) C$_{1-6}$ alkyloxy- wherein one or more of the hydrogen atoms may be replaced with a fluorine atom,
  (d) phenyl,
  (e) —CN,
  (f) hydroxy,
  (g) phenyloxy,
  (h) —C$_{0-6}$ alkyl-N(R$^7$)$_2$, (i)

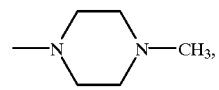

(j) oxo, and
  (k) substituted phenyloxy with 1, 2, or 3 substituents selected from:
    (i) halogen,
    (ii) C$_{1-6}$ alkyl,
    (iii) —CF$_3$, and
    (iv) hydroxy;
(3) thienyl,
(4) substituted thienyl substituted on carbon with one or two substituents independently selected from:
  (a) halogen,
  (b) C$_{1-6}$ alkyl, wherein one or more of the hydrogen atoms may be replaced with a fluorine atom,
  (c) C$_{1-6}$ alkyloxy- wherein one or more of the hydrogen atoms may be replaced with a fluorine atom,
  (d) phenyl,
  (e) —S—C$_{1-6}$ alkyl,
  (f) —CN,
  (g) hydroxy,
  (h) phenyloxy,
  (i) —C$_{0-6}$ alkyl-N(R$^7$)$_2$, (j)

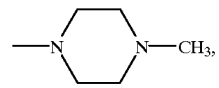

(k) oxo, and
  (l) substituted phenyloxy with 1, 2, or 3 substituents selected from:
    (i) halogen,
    (ii) C$_{1-6}$ alkyl,
    (iii) —CF$_3$, and
    (iv) hydroxy;
(5) pyridyl,
(6) substituted pyridyl substituted on carbon with one or two substituents independently selected from:
  (a) halogen,
  (b) C$_{1-6}$ alkyl, wherein one or more of the hydrogen atoms may be replaced with a fluorine atom,
  (c) C$_{1-6}$ alkyloxy- wherein one or more of the hydrogen atoms may be replaced with a fluorine atom,
  (d) phenyl,
  (e) —S—C$_{1-6}$ alkyl,
  (f) —CN,
  (g) hydroxy, (h) phenyloxy,
(i) —$C_{0-6}$ alkyl-N($R^7$)$_2$, (j)
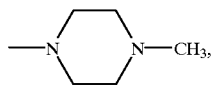

(k) oxo, and
(l) substituted phenyloxy with 1, 2, or 3 substituents selected from:
  (i) halogen,
  (ii) $C_{1-6}$ alkyl,
  (iii) —$CF_3$, and
  (iv) hydroxy;
(7) substituted imidazolyl substituted on carbon with one or two substituents independently selected from:
  (a) halogen,
  (b) $C_{1-6}$ alkyl, wherein one or more of the hydrogen atoms may be replaced with a fluorine atom,
  (c) $C_{1-6}$ alkyloxy- wherein one or more of the hydrogen atoms may be replaced with a fluorine atom,
  (d) phenyl,
  (e) —S—$C_{1-6}$ alkyl,
  (f) —CN,
  (g) hydroxy,
  (h) phenyloxy,
  (i) —$C_{0-6}$ alkyl-N($R^7$)$_2$, (j)
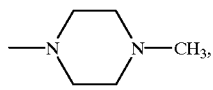

(k) oxo, and
(l) substituted phenyloxy with 1, 2, or 3 substituents selected from:
  (i) halogen,
  (ii) $C_{1-6}$ alkyl,
  (iii) —$CF_3$, and
  (iv) hydroxy;
(8) pyrrolyl,
(9) substituted pyrrolyl substituted on carbon with one or two substituents independently selected from:
  (a) halogen,
  (b) $C_{1-6}$ alkyl, wherein one or more of the hydrogen atoms may be replaced with a fluorine atom,
  (c) $C_{1-6}$ alkyloxy- wherein one or more of the hydrogen atoms may be replaced with a fluorine atom,
  (d) phenyl,
  (e) —S—$C_{1-6}$ alkyl,
  (f) —CN,
  (g) hydroxy,
  (h) phenyloxy,
  (i) —$C_{0-6}$ alkyl-N($R^7$)$_2$, (j)
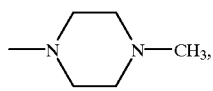

(k) oxo, and
(l) substituted phenyloxy with 1, 2, or 3 substituents selected from:
  (i) halogen,
  (ii) $C_{1-6}$ alkyl,
  (iii) —$CF_3$, and
  (iv) hydroxy;
(10) pyrazolyl,
(11) substituted pyrazolyl substituted on carbon with one or two substituents independently selected from:
  (a) halogen,
  (b) $C_{1-6}$ alkyl, wherein one or more of the hydrogen atoms may be replaced with a fluorine atom,
  (c) $C_{1-6}$ alkyloxy- wherein one or more of the hydrogen atoms may be replaced with a fluorine atom,
  (d) phenyl,
  (e) —S—$C_{1-6}$ alkyl,
  (f) —CN,
  (g) hydroxy,
  (h) phenyloxy,
  (i) —$C_{0-6}$ alkyl-N($R^7$)$_2$, (j)
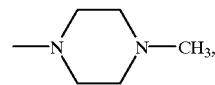

(k) oxo, and
(l) substituted phenyloxy with 1, 2, or 3 substituents selected from:
  (i) halogen,
  (ii) $C_{1-6}$ alkyl,
  (iii) —$CF_3$, and
  (iv) hydroxy;
(12) piperidinyl,
(13) substituted piperidinyl substituted on carbon with one or two substituents independently selected from:
  (a) halogen,
  (b) $C_{1-6}$ alkyl,
  (c) $C_{1-6}$ alkyloxy-,
  (d) —$CF_3$,
  (e) —$OCF_3$,
  (f) —CN,
  (g) =O,
  (h) benzyl, and
  (i) hydroxy;
(14) substituted morpholinyl substituted at a carbon or nitrogen atom with 1 or 2 substituents independently selected from:
  (a) halogen,
  (b) $C_{1-6}$ alkyl,
  (c) $C_{1-6}$ alkyloxy-,
  (d) —$CF_3$,
  (e) —$OCF_3$,
  (f) —CN,
  (g) =O,
  (h) benzyl, and
  (i) hydroxy;
(15) hexahydrothieno[3,4-d]imidazolyl,
(16) substituted hexahydrothieno[3,4-d]substituted hexahydrothieno[3,4-d]imidazolyl with one or two substituents independently selected from:
  (a) oxo,
  (b) halogen,
  (c) $C_{1-6}$ alkyl,
  (d) $C_{1-6}$ alkyloxy-,
  (e) —$CF_3$,
  (f) —$OCF_3$, (g) —CN, and
(h) hydroxy,
(17) naphthyl,
(18) substituted naphthyl with 1, 2, or 3 substituents independently selected from:
  (a) -halogen,
  (b) —$C_{1-6}$ alkyl,
  (c) —$C_{1-6}$ alkyloxy-,
  (d) —$CF_3$,
  (e) —$OCF_3$,
  (f) —CN, and
  (g) -hydroxy,
(19) indolyl,
(20) substituted indolyl substituted on a carbon atom with one or two substituents independently selected from:
  (a) -halogen,
  (b) —$C_{1-6}$ alkyl,
  (c) $C_{1-6}$ alkyloxy-,
  (d) —$CF_3$,
  (e) —$OCF_3$,
  (f) —CN, and
  (g) -hydroxy;
(21) $C_{3-5}$ cycloalkyl fused with a phenyl ring,
(22) substituted $C_{3-6}$ cycloalkyl fused with a phenyl ring substituted on carbon with one or two substituents independently selected from:
  (a) halogen,
  (b) $C_{1-6}$ alkyl,
  (c) $C_{1-6}$ alkyloxy-,
  (d) —$CF_3$,
  (e) —$OCF_3$,
  (f) —CN,
  (g) =O, and
  (h) hydroxy;
(23) pyrazinyl;
(24) substituted pyrazinyl substituted on nitrogen or carbon with one or two substituents independently selected from:
  (a) halogen,
  (b) $C_{1-6}$ alkyl, wherein one or more of the hydrogen atoms may be replaced with a fluorine atom,
  (c) $C_{1-6}$ alkyloxy- wherein one or more of the hydrogen atoms may be replaced with a fluorine atom,
  (d) phenyl,
  (e) —S—$C_{1-6}$ alkyl,
  (f) —CN,
  (g) hydroxy,
  (h) phenyloxy,
  (i) —$C_{0-6}$ alkyl-$N(R^7)_2$,
  (j)

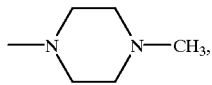

(k) oxo, and
  (l) substituted phenyloxy with 1, 2, or 3 substituents selected from:
    (i) halogen,
    (ii) $C_{1-6}$ alkyl,
    (iii) —$CF_3$, and
    (iv) hydroxy;
(25) pyrimidinyl;
(26) substituted pyrimidinyl substituted on nitrogen or carbon with one or two substituents independently selected from:
  (a) halogen,
  (b) $C_{1-6}$ alkyl, wherein one or more of the hydrogen atoms may be replaced with a fluorine atom,
  (c) $C_{1-6}$ alkyloxy- wherein one or more of the hydrogen atoms may be replaced with a fluorine atom,
  (d) phenyl,
  (e) —S—$C_{1-6}$ alkyl,
  (f) —CN,
  (g) hydroxy,
  (h) phenyloxy,
  (i) —$C_{0-6}$ alkyl-$N(R^7)_2$,
  (j)

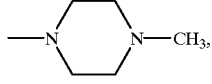

(k) oxo, and
  (l) substituted phenyloxy with 1, 2, or 3 substituents selected from:
    (i) halogen,
    (ii) $C_{1-6}$ alkyl,
    (iii) —$CF_3$, and
    (iv) hydroxy;
(27) triazolyl;
(28) substituted triazolyl with one or two substituents independently selected from:
  (a) halogen,
  (b) $C_{1-6}$ alkyl, wherein one or more of the hydrogen atoms may be replaced with a fluorine atom,
  (c) $C_{1-6}$ alkyloxy- wherein one or more of the hydrogen atoms may be replaced with a fluorine atom,
  (d) phenyl,
  (e) —S—$C_{1-6}$ alkyl,
  (f) —CN,
  (g) hydroxy,
  (h) phenyloxy,
  (i) —$C_{0-6}$ alkyl-$N(R^7)_2$,
  (j)

(k) oxo, and
  (l) substituted phenyloxy with 1, 2, or 3 substituents selected from:
    (i) halogen,
    (ii) $C_{1-6}$ alkyl,
    (iii) —$CF_3$, and
    (iv) hydroxy;
(29) tetrazolyl;
(30) substituted tetrazolyl with a substituent selected from:
  (a) halogen,
  (b) $C_{1-6}$ alkyl, wherein one or more of the hydrogen atoms may be replaced with a fluorine atom,
  (c) $C_{1-6}$ alkyloxy- wherein one or more of the hydrogen atoms may be replaced with a fluorine atom,
  (d) phenyl,
  (e) —S—$C_{1-6}$ alkyl,
  (f) —CN, (g) hydroxy,
(h) phenyloxy,
(i) —$C_{0-6}$ alkyl-N($R^7$)$_2$, (j)
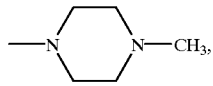

(k) oxo, and
(l) substituted phenyloxy with 1, 2, or 3 substituents selected from:
  (i) halogen,
  (ii) $C_{1-6}$ alkyl,
  (iii) —$CF_3$, and
  (iv) hydroxy;
(31) $C_{3-6}$ cycloalkyl;
(32) substituted $C_{3-6}$ cycloalkyl substituted with one or two substituents independently selected from:
  (a) halogen,
  (b) $C_{1-6}$ alkyl,
  (c) $C_{1-6}$ alkyloxy-,
  (d) —$CF_3$,
  (e) —$OCF_3$,
  (f) —CN,
  (g) =O,
  (h) benzyl, and
  (i) hydroxy;
(33) tetrahydrofuran;
(34) substituted tetrahydrofuran substituted with one or two substituents independently selected from:
  (a) halogen,
  (b) $C_{1-6}$ alkyl,
  (c) $C_{1-6}$ alkyloxy-,
  (d) —$CF_3$,
  (e) —$OCF_3$,
  (f) —CN,
  (g) =O,
  (h) benzyl, and
  (i) hydroxy;
(35) piperazinyl;
(36) substituted piperazinyl substituted with one or two substituents independently selected from:
  (a) halogen,
  (b) $C_{1-6}$ alkyl,
  (c) $C_{1-6}$ alkyloxy-,
  (d) —$CF_3$,
  (e) —$OCF_3$,
  (f) —CN,
  (g) =O,
  (h) benzyl, and
  (i) hydroxy;
(37) benzotriazolyl,
(38) substituted benzotriazolyl substituted on a carbon atom with one or two substituents independently selected from:
  (a) -halogen,
  (b) —$C_{1-6}$ alkyl,
  (c) —$C_{1-6}$ alkyloxy-,
  (d) —$CF_3$,
  (e) —$OCF_3$,
  (f) —CN, and
  (g) -hydroxy;
(39) benzoimidazolyl,
(40) substituted benzoimidazolyl substituted on a carbon atom with one or two substituents independently selected from:
  (a) -halogen,
  (b) —$C_{1-6}$ alkyl,
  (c) —$C_{1-6}$ alkyloxy-,
  (d) —$CF_3$,
  (e) —$OCF_3$,
  (f) —CN, and
  (g) -hydroxy;

each $R^4$ is independently selected from:
  (1) —H,
  (2) —$C_{1-4}$ alkyl,
  (3) —$CF_3$,
  (4) —$R^3$,
  (5) —$C_{2-3}$ alkenyl,
  (6) —$C_{1-3}$ alkyl-$R^3$,
  (7) —$C_{2-3}$ alkenyl-$R^3$, and
  (8) —C(O)—$R^3$;

each $R^5$ is independently selected from:
  (1) —H,
  (2) —$C_{1-3}$ alkyl,
  (3) —$CF_3$,
  (4) —$R^3$,
  (5) —$C_{2-3}$ alkenyl,
  (6) —$C_{1-3}$ alkyl-$R^3$,
  (7) —S(O)$_n$—$R^3$,
  (8) —C(O)—$R^3$,
  (9) —C(O)OR4, and
  (10) —C(O)C(O)OH;

each $R^6$ is independently selected from:
  (1) —$C_{1-3}$ alkyl-$R^3$, and
  (2) —$R^3$;

each $R^7$ is independently selected from:
  (1) —H, and
  (2) —$C_{1-6}$ alkyl;

$R^8$ is selected from hydrogen, methyl and —O—$C_{1-6}$ alkyl;

$R^9$ is selected from:
  (1) —H,
  (2) —O—$C_{1-3}$ alkyl,
  (3) —OH, and
  (4) oxo;

and each n is independently selected from 0, 1 and 2; and

PROVIDED THAT when A is phenyl:
  (1) $R^1$ is not:
    (a) phenyl para to the dioxobutyric acid moiety,
    (b) substituted phenyl para to the dioxobutyric acid moiety,
    (c) —$C_{1-3}$ alkyl phenyl para to the dioxobutyric acid moiety, or
    (d) substituted —$C_{1-3}$ alkyl phenyl para to the dioxobutyric acid moiety; and
  (2) $R^2$ is not selected from:
    (a) phenyl para to the dioxobutyric acid moiety,
    (b) substituted phenyl para to the dioxobutyric acid moiety,
    (c) —$C_{1-6}$ alkyl phenyl para to the dioxobutyric acid moiety, and
    (d) substituted —$C_{1-6}$ alkyl phenyl para to the dioxobutyric acid moiety; and
  (3) at least one of $R^1$, $R^2$, and $R^8$ is not:
    (a) —H,
    (b) $C_{1-6}$ alkyl, or
    (c) $R^3$ wherein $R^3$ is cycloalkyl.

2. The compound according to claim 1, and tautomers and pharmaceutically acceptable salts thereof, wherein:

A is phenyl;
$R^1$ is selected from:
(1) —H,
(2) —$CH_3$,
(3) —$C_{1-6}$ alkyl-$OR^7$;
(4) —O—$C_{1-6}$ alkyl-$OR^7$,
(5) —O—$C_{1-6}$ alkyl-$SR^7$,
(6) —$CF_3$ or —$CH_2CF_3$,
(7) —Cl,
(8) —F,
(9) —$C_{0-3}$ alkyl —$N(R^4)(R^5)$,
(10) -phenyl,
(11) phenyl $C_{1-3}$ alkyl-, wherein the phenyl group may be unsubstituted or substituted with 1 to four substituents independently selected from:
  (a) —F, —Cl, or —Br,
  (b) $CH_3$,
  (c) —$OCH_3$, $OCH_2CH_3$, $OCF_3$, or $OCH_2CF_3$,
  (d) —$CF_3$,
  (e) —$SCH_3$,
  (f) —CN,
  (g) hydroxy, and
  (h) —$C_{0-6}$ alkyl-$N(R^7)_2$,
(12) —O—$CH_2$-phenyl, wherein the phenyl group may be unsubstituted or substituted with 1 to four substituents independently selected from:
  (a) —F, —Cl, or —Br,
  (b) $CH_3$,
  (c) —$OCH_3$, $OCH_2CH_3$, $OCF_3$, or $OCH_2CF_3$,
  (d) —$CF_3$,
  (e) —$SCH_3$,
  (f) —CN,
  (g) hydroxy, and
  (h) —$C_{0-6}$ alkyl-$N(R^7)_2$,
(13) —O—$C_{1-6}$ alkyl, unsubstituted or substituted with one to three fluorine atoms,
(14) —C(O)$CH_2$C(O)C(O)OH;
(15) —O—$C_{1-6}$ alkyl-NH—C(O)—$OR^7$;
(16) —O—$CH_2CH_2N(CH_3)_2$,
(17) —O—$CH(CH_3)CH_2N(CH_3)_2$,
(18) —O—$CH_2CH_2NH_2$,
(19) —O—$CH(CH_3)CH_2NH_2$,
(20) —S—$CH_3$,
(21) —$CH_2$—CH(OH)—$CH_2$—O—$R^7$, and
(22) —C(OH)($CH_3$)—$CH_2N(R^4)(R^5)$;
$R^2$ is selected from:
(1) —$R^3$,
(2) —$C_{1-6}$ alkyl substituted with $R^3$, wherein one or more of the hydrogen atoms on $C_{1-6}$ alkyl may be replaced with a fluorine atom,
(3) —O—$C_{1-6}$ alkyl-$SR^6$;
(4) —$C_{1-6}$ alkyl $(OR^6)(R^4)$,
(5) —$C_{0-6}$ alkyl-$N(R^4)(R^6)$,
(6) —$C_{0-6}$ alkyl C(O)—$R^6$,
(7) —$C_{0-6}$ alkyl C(O)$CH_2$—C(O)—OH,
(8) —$C_{1-6}$ alkyl $NR^4$C(O)—$R^6$,
(9) —$C_{1-6}$ alkyl-C(O)$N(R^4)(R^5)$, and
(10) —$CH_2(OR^7)$—$R^6$;
each $R^3$ is independently selected from:
(1) phenyl;
(2) substituted phenyl with 1, 2, 3 or 4 substituents independently selected from:
  (a) halogen, selected from —F, —Cl, and —Br,
  (b) $C_{1-6}$ alkyl, wherein one or more of the hydrogen atoms may be replaced with a fluorine atom,
  (c) $C_{1-6}$ alkyloxy- wherein one or more of the hydrogen atoms may be replaced with a fluorine atom,
  (d) —CN,
  (e) hydroxy, and
  (f) oxo;
(3) thienyl,
(4) substituted thienyl substituted on carbon with one or two substituents independently selected from:
  (a) halogen, selected from F, Cl, and Br,
  (b) $C_{1-6}$ alkyl, wherein one or more of the hydrogen atoms may be replaced with a fluorine atom, and
  (c) $C_{1-6}$ alkyloxy- wherein one or more of the hydrogen atoms may be replaced with a fluorine atom;
(5) pyridyl,
(6) substituted pyridyl substituted on carbon with one or two substituents independently selected from:
  (a) halogen, selected from —F, —Cl, and —Br;
  (b) $C_{1-6}$ alkyl, wherein one or more of the hydrogen atoms may be replaced with a fluorine atom,
  (c) $C_{1-6}$ alkyloxy- wherein one or more of the hydrogen atoms may be replaced with a fluorine atom,
  (d) hydroxy, and
  (e) oxo;
(7) pyrrolyl,
(8) pyrazolyl
(9) substituted pyrazolyl substituted on carbon with one or two substituents independently selected from:
  (a) halogen, selected from —F, —Cl, and —Br;
  (b) —$CH_3$,
  (c) —$CF_3$,
  (d) —$OCH_3$,
  (e) —$OCF_3$, and
  (f) hydroxy;
(10) $C_{3-5}$ cycloalkyl fused with a phenyl ring,
(11) substituted $C_{3-5}$ cycloalkyl fused with a phenyl ring substituted on carbon with 1 or 2 substituents independently selected from:
  (a) halogen, selected from —F, —Cl, and —Br,
  (b) $CH_3$,
  (c) methyloxy-,
  (d) —$CF_3$,
  (e) —$OCF_3$,
  (f) —CN,
  (g) =O, and
  (h) hydroxy;
(12) piperidinyl,
(13) substituted piperidinyl substituted on carbon with one or two substituents independently selected from:
  (a) halogen selected from —F, —Cl, and —Br,
  (b) methyl,
  (c) methoxy-,
  (d) —$CF_3$,
  (e) —$OCF_3$,
  (f) =O, and
  (g) hydroxy;
(14) substituted morpholinyl substituted on carbon or nitrogen with 1 or 2 substituents independently selected from:
  (a) halogen, selected from —F, —Cl, and —Br,
  (b) methyl,
  (c) methoxy-,
  (d) —$CF_3$,
  (e) —$OCF_3$, and
  (f) hydroxy;
(15) hexahydrothieno[3,4-d]imidazolyl,
(16) naphthyl,
(17) substituted naphthyl with 1, 2, or 3 substituents independently selected from:

(a) -halogen, selected from —F, —Cl, and —Br,
(b) methyl,
(c) methoxy-,
(d) —CF$_3$,
(e) —OCF$_3$,
(f) —CN, and
(g) -hydroxy,
(18) indolyl, and
(19) substituted 1,2,3,4-tetrahydronaphthalenyl substituted on carbon with a substituent selected from:
(a) halogen, selected from —F, —Cl, and —Br,
(b) methyl,
(c) methoxy-,
(d) —CF$_3$,
(e) —OCF$_3$,
(f) —CN,
(g) =O, and
(h) hydroxy;
(20) pyrazinyl;
(21) substituted pyrazinyl substituted on nitrogen or carbon with one or two substituents independently selected from:
(a) halogen, selected from —F, —Cl, and —Br,
(b) C$_{1-6}$ alkyl, wherein one or more of the hydrogen atoms may be replaced with a fluorine atom,
(c) C$_{1-6}$ alkyloxy- wherein one or more of the hydrogen atoms may be replaced with a fluorine atom,
(d) hydroxy,
(e) phenyloxy,
(f) —C$_{0-6}$ alkyl-N(R$^7$)$_2$, and (g)

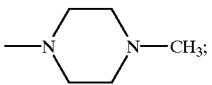

(22) pyrimidinyl;
(23) substituted pyrimidinyl substituted on nitrogen or carbon with a substituent selected from:
(a) halogen, selected from —F, —Cl, and —Br,
(b) methyl,
(c) methoxy-, and
(d) phenyl,
(24) triazolyl;
(25) substituted triazolyl with a substituent selected from:
(a) halogen, selected from —F, —Cl, and —Br,
(b) methyl,
(c) methoxy-, and
(d) hydroxy,
(26) tetrazolyl;
(27) substituted tetrazolyl with a substituent selected from:
(a) halogen, selected from —F, —Cl, and —Br,
(b) methyl,
(c) methoxy-, and
(d) hydroxy,
(28) C$_{3-6}$ cycloalkyl;
(29) substituted C$_{3-6}$ cycloalkyl substituted with one or two substituents independently selected from:
(a) halogen, selected from —F, —Cl, and —Br,
(b) methyl,
(c) methoxy-,
(d) —CF$_3$, and
(e) —OCF$_3$,
(30) tetrahydrofuran;
(31) substituted tetrahydrofuran substituted with one or two substituents independently selected from:
(a) halogen, selected from —F, —Cl, and —Br,
(b) methyl,
(c) methoxy-,
(d) —CF$_3$, and
(e) —OCF$_3$,
(32) piperazinyl;
(33) substituted piperazinyl substituted with one or two substituents independently selected from:
(a) halogen, selected from —F, —Cl, and —Br,
(b) C$_{1-6}$ alkyl,
(c) C$_{1-6}$ alkyloxy-,
(d) —CF$_3$,
(e) —OCF$_3$,
(f) benzyl, and
(g) hydroxy;
(34) benzotriazolyl,
(35) substituted benzotriazolyl substituted on carbon with one or two substituents independently selected from:
(a) -halogen, selected from —F, —Cl, and —Br,
(b) -methyl,
(c) methoxy-,
(d) —CF$_3$, and
(e) —OCF$_3$,
(36) benzoimidazolyl, and
(37) substituted benzoimidazolyl substituted on carbon with one or two substituents independently selected from:
(a) -halogen, selected from —F, —Cl, and —Br,
(b) -methyl,
(c) methoxy-,
(d) —CF$_3$, and
(e) —OCF$_3$;

each R$^4$ is independently selected from:
(1) —H,
(2) —C$_{1-4}$ alkyl,
(3) —CF$_3$,
(4) —R$^3$,
(5) —C$_{1-3}$ alkyl-R$^3$, and
(6) —C(O)—R$^3$;

each R$^5$ is independently selected from:
(1) —H,
(2) —C$_{1-3}$ alkyl,
(3) —CF$_3$,
(4) —R$^3$,
(5) —C$_{1-3}$ alkyl-R$^3$,
(6) —C(O)—R$^3$,
(7) —C(O)OR$^4$, and
(8) —C(O)C(O)OH;

each R$^6$ is independently selected from:
(1) —C$_{1-3}$ alkyl-R$^3$, and
(2) —R$^3$;

each R$^7$ is independently selected from:
(1) —H, and
(2) —C$_{1-6}$ alkyl;

R$^8$ is selected from hydrogen, methyl and —O—C$_{1-6}$ alkyl; and

R$^9$ is selected from:
(1) —H,
(2) —O—C$_{1-3}$ alkyl,
(3) —OH, and
(4) oxo; and PROVIDED THAT:
(1) $R^1$ is not:
  (a) phenyl para to the dioxobutyric acid/ester moiety,
  (b) substituted phenyl para to the dioxobutyric acid moiety,
  (c) $C_{1-3}$ alkyl phenyl para to the dioxobutyric acid moiety, or
  (d) substituted —$C_{1-3}$ alkyl phenyl para to the dioxobutyric acid moiety; and
(2) $R^2$ is not selected from:
  (a) phenyl para to the dioxobutyric acid moiety,
  (b) substituted phenyl para to the dioxobutyric acid moiety,
  (c) —$C_{1-6}$ alkyl phenyl para to the dioxobutyric acid moiety, and
  (d) substituted —$C_{1-6}$ alkyl phenyl para to the dioxobutyric acid moiety; and
(3) at least one of $R^1$, $R^2$, and $R^8$ is not:
  (a) —H,
  (b) $C_{1-6}$ alkyl, or
  (c) $R^3$ wherein $R^3$ is cycloalkyl.

3. The compound according to claim 2, and tautomers and pharmaceutically acceptable salts thereof, wherein:
$R^1$ is selected from:
(1) —H,
(2) —$CH_3$,
(3) —$CH_2OCH_3$,
(4) —$OCH_2CH_2OH$,
(5) —$OCH_2CH_2OCH_3$,
(6) —$(CH_2)_6$—OH,
(7) —$CF_3$,
(8) —F,
(9) —Cl,
(10) —$C_{0-3}$ alkyl-$N(R^4)(R^5)$,
(11) -phenyl,
(12) phenyl $C_{1-3}$ alkyl-, wherein the phenyl group may be unsubstituted or substituted with 1 to four substituents independently selected from:
  (a) —F, —Cl, or —Br,
  (b) $CH_3$,
  (c) —$OCH_3$, $OCH_2CH_3$, $OCF_3$, or $OCH_2CF_3$,
  (d) —$CF_3$,
  (e) —CN,
  (f) hydroxy,
  (g) —$C_{0-6}$ alkyl-$N(R^7)_2$,
(13) —O—$CH_2$-phenyl, wherein the phenyl group may be unsubstituted or substituted with 1 to four substituents independently selected from:
  (a) —F, —Cl, or —Br,
  (b) $CH_3$,
  (c) —$OCH_3$, $OCH_2CH_3$, $OCF_3$, or $OCH_2CF_3$,
  (d) —$CF_3$,
  (e) —CN,
  (f) hydroxy,
  (g) —$C_{0-6}$ alkyl-$N(R^7)_2$,
(14) —O—$CH_3$,
(15) —$OCH_2CH_3$,
(16) —$OCH_2CF_3$,
(17) —$OCF_3$,
(18) —$OCH(CH_3)_2$,
(19) —$C(O)CH_2C(O)C(O)OH$,
(20) —O—$C_{1-6}$ alkyl-NH—C(O)—$OR^7$,
(21) —O—$CH_2CH_2N(CH_3)_2$,
(22) —O—$CH(CH_3)CH_2N(CH_3)_2$,
(23) —O—$CH_2CH_2NH_2$,
(24) —O—$CH(CH_3)CH_2NH_2$,
(25) —S—$CH_3$,
(26) —$CH_2$—CH(OH)—$CH_2$—O—$R^7$, and
(27) —$C(OH)(CH_3)$—$CH_2N(R^4)(R^5)$;
$R^2$ is selected from:
(1) —$R^3$,
(2) —$CH_2$—$R^3$,
(3) —$CH_2CH_2$—$R^3$,
(4) —$CF_2$—$R^3$,
(5) —$CH(CH_3)$—$R^3$,
(6) —$C_{1-6}$ alkyl $(OR^6)(R^4)$,
(7) —$C_{0-6}$ alkyl-$N(R^4)(R^6)$,
(8) —$C(O)$—$R^3$,
(9) —$C_{0-6}$ alkyl $C(O)CH_2$—C(O)—OH,
(10) —$C_{1-6}$ alkyl $NR^4C(O)$—$R^6$,
(11) —$CH(OCH_3)R^3$, and
(12) —$CH(OH)R^3$;
each $R^3$ is independently selected from:
(1) phenyl;
(2) substituted phenyl with 1, 2, or 3 substituents independently selected from:
  (a) halogen, selected from —F, —Cl, and —Br,
  (b) —$CH_3$,
  (c) methyloxy-,
  (d) ethyloxy-,
  (e) —$OCH_2CF_3$,
  (f) —$OCF_2CH_3$,
  (g) —$CF_3$,
  (h) —$CH_2CF_3$,
  (i) —$CF_2CH_3$,
  (j) —$OCF_3$,
  (k) —CN, and
  (l) hydroxy;
(3) thienyl,
(4) substituted thienyl substituted on a carbon atom with a substituent selected from:
  (a) F,
  (b) Cl, and
  (c) methyl;
(5) pyridyl,
(6) substituted pyridyl substituted on a carbon with a substituent selected from:
  (a) —F,
  (b) —Cl,
  (c) —$CH_3$,
  (d) —$CF_3$,
  (e) —$OCH_3$,
  (f) —$OCF_3$,
  (g) hydroxy, and
  (h) oxo;
(7) pyrazolyl
(8) substituted pyrazolyl substituted on carbon with one or two substituents independently selected from:
  (a) —F,
  (b) —Cl,
  (c) —$CH_3$, and
  (d) —$CF_3$;
(9) $C_{3-5}$ cycloalkyl fused with a phenyl ring,
(10) piperidinyl,
(11) substituted piperidinyl substituted on carbon with a substituent selected from:
  (a) methoxy-,
  (b) —$OCF_3$,
  (c) =O, and
  (d) hydroxy;
(12) naphthyl,
(13) pyrazinyl;
(14) substituted pyrazinyl substituted on nitrogen or carbon with a substituent selected from:

(a) halogen, selected from —F, —Cl, and —Br,
(b) methyl,
(c) —CF$_3$,
(d) methoxy-,
(e) —N(CH$_3$)$_2$, and
(f)
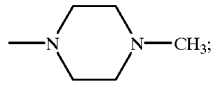

(15) pyrimidinyl,
(16) [1,2,3]-triazolyl,
(17) [1,2,4]-triazolyl,
(18) tetrazolyl;
(19) cyclopropyl,
(20) cyclobutyl,
(21) cyclopentyl,
(22) cyclohexyl,
(23) tetrahydrofuran,
(24) piperazinyl,
(25) substituted piperazinyl substituted with a substituent selected from:
  (a) —F,
  (b) —Cl,
  (c) methyl,
  (d) —CF$_3$, and
  (e) benzyl,
(26) benzotriazolyl, and
(27) benzoimidazolyl;
each R$^4$ is independently selected from:
  (1) —H,
  (2) —C$_{1-4}$ alkyl,
  (3) —CF$_3$,
  (4) —R$^3$,
  (5) —C$_{1-3}$ alkyl-R$^3$, and
  (6) —C(O)—R$^3$;
each R$^5$ is independently selected from:
  (1) —H,
  (2) —CH$_3$,
  (3) —CF$_3$,
  (4) phenyl,
  (5) -benzyl,
  (6) —C(O)OR$^4$, and
  (7) —C(O)C(O)OH;
each R$^6$ is independently selected from:
  (1) —C$_{1-3}$ alkyl-R$^3$, and
  (2) —R$^3$;
each R$^7$ is independently selected from:
  (1) —H, and
  (2) —C$_{1-6}$ alkyl;
R$^8$ is selected from:
  (1) —H,
  (2) methoxy, and
  (3) —C$_{1-6}$ alkyl; and
R$^9$ is selected from:
  (1) —H,
  (2) —O—C$_{1-3}$ alkyl,
  (3) —OH, and
  (4) oxo; and
PROVIDED THAT:
(1) R$^1$ is not:
  (a) phenyl para to the dioxobutyric acid moiety,
  (b) substituted phenyl para to the dioxobutyric acid moiety,
  (c) C$_{1-3}$ alkyl phenyl para to the dioxobutyric acid moiety, or
  (d) substituted —C$_{1-3}$ alkyl phenyl para to the dioxobutyric acid moiety; and
(2) R$^2$ is not selected from:
  (a) phenyl para to the dioxobutyric acid moiety,
  (b) substituted phenyl para to the dioxobutyric acid moiety,
  (c) —C$_{1-6}$ alkyl phenyl para to the dioxobutyric acid moiety, and
  (d) substituted —C$_{1-6}$ alkyl phenyl para to the dioxobutyric acid moiety; and
(3) at least one of R$^1$, R$^2$, R$^8$ and R$^9$ is not:
  (a) —H,
  (b) C1–6 alkyl, or
  (c) R$^3$ wherein R$^3$ is cycloalkyl.

4. The compound according to claim 1 of structural formula:

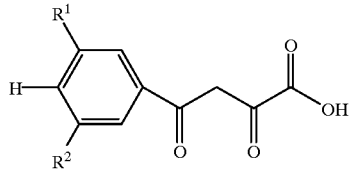

and tautomers and pharmaceutically acceptable salts thereof, wherein:
R$^1$ is selected from:
  (1) —H,
  (2) —CH$_3$,
  (3) —C$_{1-6}$ alkyl-OR$^7$;
  (4) —O—C$_{1-6}$ alkyl-OR$^7$,
  (5) —O—C$_{1-6}$ alkyl-SR$^7$,
  (6) —CF$_3$ or —CH$_2$CF$_3$,
  (7) —Cl,
  (8) —F,
  (9) —C$_{0-3}$ alkyl —N(R$^4$)(R$^5$),
  (10) -phenyl,
  (11) phenyl C$_{1-3}$ alkyl-, wherein the phenyl group may be unsubstituted or substituted with 1 to four substituents independently selected from:
    (a) —F, —Cl, or —Br,
    (b) —CH$_3$,
    (c) —OCH$_3$, OCH$_2$CH$_3$, OCF$_3$, or OCH$_2$CF$_3$,
    (e) —CF$_3$,
    (f) —SCH$_3$,
    (g) —CN,
    (h) hydroxy,
    (i) —C$_{0-6}$ alkyl-N(R$^7$)$_2$,
(12) —O—CH$_2$-phenyl, wherein the phenyl group may be unsubstituted or substituted with 1 to four substituents independently selected from:
    (a) —F, —Cl, or —Br,
    (b) CH$_3$,
    (c) —OCH$_3$, —OCH$_2$CH$_3$, —OCF$_3$, or —OCH$_2$CF$_3$,
    (e) —CF$_3$,
    (f) —SCH$_3$,
    (g) —CN,
    (h) hydroxy,
    (i) —C$_{0-6}$ alkyl-N(R$^7$)$_2$,
(13) —O—C$_{1-6}$ alkyl, unsubstituted or substituted with one to three fluorine atoms,
(14) —C(O)CH$_2$C(O)C(O)OH,
(15) —O—C$_{1-6}$ alkyl-NH—C(O)—OR$^7$,

(16) —O—CH$_2$CH$_2$N(CH$_3$)$_2$,
(17) —O—CH(CH$_3$)CH$_2$N(CH$_3$)$_2$,
(18) —O—CH$_2$CH$_2$NH$_2$,
(19) —O—CH(CH$_3$)CH$_2$NH$_2$,
(20) —S—CH$_3$,
(21) —CH$_2$—CH(OH)—CH$_2$—O—R$^7$, and
(22) —C(OH)(CH$_3$)—CH$_2$N(R$^4$)(R$^5$);

R$^2$ is selected from:
(1) —R$^3$;
(2) —C$_{1-6}$ alkyl substituted with R$^3$, wherein one or more of the hydrogen atoms on C$_{1-6}$ alkyl may be replaced with a fluorine atom,
(3) —O—C$_{1-6}$ alkyl-SR$^6$,
(4) —C$_{1-6}$ alkyl (OR$^6$)(R$^4$),
(5) —C$_{0-6}$ alkyl-N(R$^4$)(R$^6$),
(6) —C$_{0-6}$ alkyl C(O)—R$^6$,
(7) —C$_{0-6}$ alkyl C(O)CH$_2$—C(O)—OH,
(8) —C$_{1-6}$ alkyl NR$^4$C(O)—R$^6$,
(9) —C$_{1-6}$ alkyl-C(O)N(R$^4$)(R$^5$), and
(10) —CH$_2$(OR$^7$)—R$^6$;

each R$^3$ is independently selected from:
(1) phenyl;
(2) substituted phenyl with 1, 2, 3 or 4 substituents independently selected from:
  (a) halogen, selected from —F, —Cl, and —Br,
  (b) C$_{1-6}$ alkyl, wherein one or more of the hydrogen atoms may be replaced with a fluorine atom,
  (c) C$_{1-6}$ alkyloxy- wherein one or more of the hydrogen atoms may be replaced with a fluorine atom,
  (d) —CN,
  (e) hydroxy, and
  (f) oxo;
(3) thienyl,
(4) substituted thienyl substituted on carbon with one or two substituents independently selected from:
  (a) halogen, selected from F, Cl, and Br,
  (b) C$_{1-6}$ alkyl, wherein one or more of the hydrogen atoms may be replaced with a fluorine atom, and
  (c) C$_{1-6}$ alkyloxy- wherein one or more of the hydrogen atoms may be replaced with a fluorine atom;
(5) pyridyl,
(6) substituted pyridyl substituted on carbon with one or two substituents independently selected from:
  (a) halogen, selected from —F, —Cl, and —Br;
  (b) C$_{1-6}$ alkyl, wherein one or more of the hydrogen atoms may be replaced with a fluorine atom,
  (c) C$_{1-6}$ alkyloxy- wherein one or more of the hydrogen atoms may be replaced with a fluorine atom,
  (d) hydroxy, and
  (e) oxo;
(7) pyrrolyl,
(8) pyrazolyl
(9) substituted pyrazolyl substituted on carbon with one or two substituents independently selected from:
  (a) halogen, selected from —F, —Cl, and —Br;
  (b) —CH$_3$,
  (c) —CF$_3$,
  (d) —OCH$_3$,
  (e) —OCF$_3$, and
  (f) hydroxy;
(10) C$_{3-5}$ cycloalkyl fused with a phenyl ring,
(11) substituted C$_{3-5}$ cycloalkyl fused with a phenyl ring substituted on carbon with 1 or 2 substituents independently selected from:
  (a) halogen, selected from —F, —Cl, and —Br,
  (b) CH$_3$,
  (c) methyloxy-,
  (d) —CF$_3$,
  (e) —OCF$_3$,
  (f) —CN,
  (g) =O, and
  (h) hydroxy;
(12) piperidinyl,
(13) substituted piperidinyl substituted on carbon with one or two substituents independently selected from:
  (a) halogen selected from —F, —Cl, and —Br,
  (b) methyl,
  (c) methoxy-,
  (d) —CF$_3$,
  (e) —OCF$_3$,
  (f) =O, and
  (g) hydroxy;
(14) substituted morpholinyl substituted on carbon or nitrogen with 1 or 2 substituents independently selected from:
  (a) halogen, selected from —F, —Cl, and —Br,
  (b) methyl,
  (c) methoxy-,
  (d) —CF$_3$,
  (e) —OCF$_3$, and
  (f) hydroxy;
(15) hexahydrothieno[3,4-d]imidazolyl,
(16) naphthyl,
(17) substituted naphthyl with 1, 2, or 3 substituents independently selected from:
  (a) -halogen, selected from —F, —Cl, and —Br,
  (b) methyl,
  (c) methoxy-,
  (d) —CF$_3$,
  (e) —OCF$_3$,
  (f) —CN, and
  (g) -hydroxy,
(18) indolyl,
(19) substituted 1,2,3,4-tetrahydronaphthalenyl substituted on carbon with a substituent selected from:
  (a) halogen, selected from —F, —Cl, and —Br,
  (b) methyl,
  (c) methoxy-,
  (d) —CF$_3$,
  (e) —OCF$_3$,
  (f) —CN,
  (g) =O, and
  (h) hydroxy;
(20) pyrazinyl;
(21) substituted pyrazinyl substituted on nitrogen or carbon with one or two substituents independently selected from:
  (a) halogen, selected from —F, —Cl, and —Br,
  (b) C$_{1-6}$ alkyl, wherein one or more of the hydrogen atoms may be replaced with a fluorine atom,
  (c) C$_{1-6}$ alkyloxy- wherein one or more of the hydrogen atoms may be replaced with a fluorine atom,
  (d) hydroxy, (e) phenyloxy,
(f) —$C_{0-6}$ alkyl-$N(R^7)_2$, and (g) 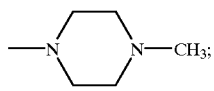

(22) pyrimidinyl;
(23) substituted pyrimidinyl substituted on nitrogen or carbon with a substituent selected from:
  (a) halogen, selected from —F, —Cl, and —Br,
  (b) methyl,
  (c) methoxy-, and
  (d) phenyl,
(24) triazolyl;
(25) substituted triazolyl with a substituent selected from:
  (a) halogen, selected from —F, —Cl, and —Br,
  (b) methyl,
  (c) methoxy-, and
  (d) hydroxy,
(26) tetrazolyl;
(27) substituted tetrazolyl with a substituent selected from:
  (a) halogen, selected from —F, —Cl, and —Br,
  (b) methyl,
  (c) methoxy-, and
  (d) hydroxy,
(28) $C_{3-6}$ cycloalkyl;
(29) substituted $C_{3-6}$ cycloalkyl substituted with one or two substituents independently selected from:
  (a) halogen, selected from —F, —Cl, and —Br,
  (b) methyl,
  (c) methoxy-,
  (d) —$CF_3$, and
  (e) —$OCF_3$,
(30) tetrahydrofuran;
(31) substituted tetrahydrofuran substituted with one or two substituents independently selected from:
  (a) halogen, selected from —F, —Cl, and —Br,
  (b) methyl,
  (c) methoxy-,
  (d) —$CF_3$, and
  (e) —$OCF_3$,
(32) piperazinyl;
(33) substituted piperazinyl substituted with one or two substituents independently selected from:
  (a) halogen, selected from —F, —Cl, and —Br,
  (b) $C_{1-6}$ alkyl,
  (c) $C_{1-6}$ alkyloxy-,
  (d) —$CF_3$,
  (e) —$OCF_3$,
  (f) benzyl, and
  (g) hydroxy;
(34) benzotriazolyl,
(35) substituted benzotriazolyl substituted on carbon with one or two substituents independently selected from:
  (a) -halogen, selected from —F, —Cl, and —Br,
  (b) -methyl,
  (c) methoxy-,
  (d) —$CF_3$, and
  (e) —$OCF_3$,
(36) benzoimidazolyl, and
(37) substituted benzoimidazolyl substituted on carbon with one or two independently selected from:
  (a) -halogen, selected from —F, —Cl, and —Br,
  (b) -methyl,
  (c) methoxy-,
  (d) —$CF_3$, and
  (e) —$OCF_3$;

each $R^4$ is independently selected from:
  (1) —H,
  (2) —$C_{1-4}$ alkyl,
  (3) —$CF_3$,
  (4) —$R^3$,
  (5) —$C_{1-3}$ alkyl-$R^3$, and
  (6) —$C(O)$—$R^3$;

each $R^5$ is independently selected from:
  (1) —H,
  (2) —$C_{1-3}$ alkyl,
  (3) —$CF_3$,
  (4) —$R^3$,
  (5) —$C_{1-3}$ alkyl-$R^3$,
  (6) —$C(O)$—$R^3$,
  (7) —$C(O)OR^4$, and
  (8) —$C(O)C(O)OH$;

each $R^6$ is independently selected from:
  (1) —$C_{1-3}$ alkyl-$R^3$, and
  (2) —$R^3$; and each $R^7$ is independently selected from:
  (1) —H, and
  (2) —$C_{1-6}$ alkyl; and PROVIDED THAT:
  (1) at least one of $R^1$ and $R^2$ is not:
    (a) H,
    (b) $C_{1-6}$ alkyl, or
    (c) $R^3$ wherein $R^3$ is cycloalkyl.

5. The compound according to claim 1 of structural formula:

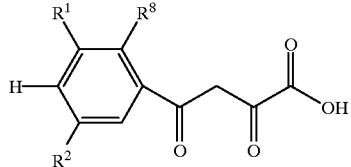

and tautomers and pharmaceutically acceptable salts thereof, wherein:

$R^1$ is selected from:
  (1) —H,
  (2) —$CH_3$,
  (3) —$C_{1-6}$ alkyl-$OR^7$;
  (4) —O—$C_{1-6}$ alkyl-$OR^7$,
  (5) —O—$C_{1-6}$ alkyl-$SR^7$,
  (6) —$CF_3$ or —$CH_2CF_3$,
  (7) —Cl,
  (8) —F,
  (9) —$C_{0-3}$ alkyl —$N(R^4)(R^5)$,
  (10) -phenyl,
  (11) phenyl $C_{1-3}$ alkyl-, wherein the phenyl group may be unsubstituted or substituted with 1 to four substituents independently selected from:
    (a) —F, —Cl, or —Br,
    (b) $CH_3$,
    (c) —$OCH_3$, $OCH_2CH_3$, $OCF_3$, or $OCH_2CF_3$,
    (d) —$CF_3$,
    (e) —$SCH_3$,
    (f) —CN, (g) hydroxy, and
(h) —C$_{0-6}$ alkyl-N(R$^7$)$_2$,
(12) —O—CH$_2$-phenyl, wherein the phenyl group may be unsubstituted or substituted with 1 to four substituents independently selected from:
(a) —F, —Cl, or —Br,
(b) —CH$_3$,
(c) —OCH$_3$, OCH$_2$CH$_3$, OCF$_3$, or OCH$_2$CF$_3$,
(d) —CF$_3$,
(e) —SCH$_3$,
(f) —CN,
(g) hydroxy, and
(h) —C$_{0-6}$ alkyl-N(R$^7$)$_2$,
(13) —O—C$_{1-6}$ alkyl, unsubstituted or substituted with one to three fluorine atoms,
(14) —C(O)CH$_2$C(O)C(O)OH,
(15) —O—C$_{1-6}$ alkyl-NH—C(O)—OR$^7$,
(16) —O—CH$_2$CH$_2$N(CH$_3$)$_2$,
(17) —O—CH(CH$_3$)CH$_2$N(CH$_3$)$_2$,
(18) —O—CH$_2$CH$_2$NH$_2$,
(19) —O—CH(CH$_3$)CH$_2$NH$_2$,
(20) —S—CH$_3$,
(21) —CH$_2$—CH(OH)—CH$_2$—O—R$^7$, and
(22) —C(OH)(CH$_3$)—CH$_2$N(R$^4$)(R$^5$);
R$^2$ is selected from:
(1) —R$^3$,
(2) —C$_{1-6}$ alkyl substituted with R$^3$, wherein one or more of the hydrogen atoms on C$_{1-6}$ alkyl may be replaced with a fluorine atom,
(3) —O—C$_{1-6}$ alkyl-SR$^6$;
(4) —C$_{1-6}$ alkyl (OR$^6$)(R$^4$),
(5) —C$_{0-6}$ alkyl-N(R$^4$)(R$^6$),
(6) —C$_{0-6}$ alkyl C(O)—R$^6$,
(7) —C$_{0-6}$ alkyl C(O)CH$_2$—C(O)—OH,
(8) —C$_{1-6}$ alkyl NR$^4$C(O)—R$^6$,
(9) —C$_{1-6}$ alkyl-C(O)N(R$^4$)(R$^5$), and
(10) —CH$_2$(OR$^7$)—R$^6$;
each R$^3$ is independently selected from:
(1) phenyl,
(2) substituted phenyl with 1, 2, 3 or 4 substituents independently selected from:
(a) halogen, selected from —F, —Cl, and —Br,
(b) C$_{1-6}$ alkyl, wherein one or more of the hydrogen atoms may be replaced with a fluorine atom,
(c) C$_{1-6}$ alkyloxy- wherein one or more of the hydrogen atoms may be replaced with a fluorine atom,
(d) —CN,
(e) hydroxy, and
(f) oxo;
(3) thienyl,
(4) substituted thienyl substituted on carbon with one or two substituents independently selected from:
(a) halogen, selected from F, Cl, and Br,
(b) C$_{1-6}$ alkyl, wherein one or more of the hydrogen atoms may be replaced with a fluorine atom, and
(c) C$_{1-6}$ alkyloxy- wherein one or more of the hydrogen atoms may be replaced with a fluorine atom;
(5) pyridyl,
(6) substituted pyridyl substituted on carbon with one or two substituents independently selected from:
(a) halogen, selected from —F, —Cl, and —Br;
(b) C$_{1-6}$ alkyl, wherein one or more of the hydrogen atoms may be replaced with a fluorine atom,
(c) C$_{1-6}$ alkyloxy- wherein one or more of the hydrogen atoms may be replaced with a fluorine atom,
(d) hydroxy, and
(e) oxo;
(7) pyrrolyl,
(8) pyrazolyl
(9) substituted pyrazolyl substituted on carbon with one or two substituents independently selected from:
(a) halogen, selected from —F, —Cl, and —Br;
(b) —CH$_3$,
(c) —CF$_3$,
(d) —OCH$_3$,
(e) —OCF$_3$, and
(f) hydroxy;
(10) C$_{3-5}$ cycloalkyl fused with a phenyl ring,
(11) substituted C$_{3-5}$ cycloalkyl fused with a phenyl ring substituted on carbon with 1 or 2 substituents independently selected from:
(a) halogen, selected from —F, —Cl, and —Br,
(b) CH$_3$,
(c) methyloxy-,
(d) —CF$_3$,
(e) —OCF$_3$,
(f) —CN,
(g) =O, and
(h) hydroxy;
(12) piperidinyl,
(13) substituted piperidinyl substituted on carbon with one or two substituents independently selected from:
(a) halogen selected from —F, —Cl, and —Br,
(b) methyl,
(c) methoxy-,
(d) —CF$_3$,
(e) —OCF$_3$,
(f) =O, and
(g) hydroxy;
(14) substituted morpholinyl substituted on carbon or nitrogen with 1 or 2 substituents independently selected from:
(a) halogen, selected from —F, —Cl, and —Br,
(b) methyl,
(c) methoxy-,
(d) —CF$_3$,
(e) —OCF$_3$, and
(f) hydroxy;
(15) hexahydrothieno[3,4-d]imidazolyl,
(16) naphthyl,
(17) substituted naphthyl with 1, 2, or 3 substituents independently selected from:
(a) -halogen, selected from —F, —Cl, and —Br,
(b) methyl,
(c) methoxy-,
(d) —CF$_3$,
(e) —OCF$_3$,
(f) —CN, and
(g) -hydroxy,
(18) indolyl,
(19) substituted 1,2,3,4-tetrahydronaphthalenyl substituted on carbon with a substituent selected from:
(a) halogen, selected from —F, —Cl, and —Br,
(b) methyl,
(c) methoxy-,
(d) —CF$_3$,
(e) —OCF$_3$,
(f) —CN,
(g) =O, and
(h) hydroxy;
(20) pyrazinyl;
(21) substituted pyrazinyl substituted on nitrogen or carbon with one or two substituents independently selected from:

(a) halogen, selected from —F, —Cl, and —Br,
(b) $C_{1-6}$ alkyl, wherein one or more of the hydrogen atoms may be replaced with a fluorine atom,
(c) $C_{1-6}$ alkyloxy- wherein one or more of the hydrogen atoms may be replaced with a fluorine atom,
(d) hydroxy,
(e) phenyloxy,
(f) —$C_{0-6}$ alkyl-N($R^7$)$_2$, and
(g)

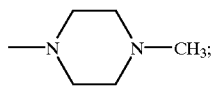

(22) pyrimidinyl;
(23) substituted pyrimidinyl substituted on nitrogen or carbon with a substituent selected from:
(a) halogen, selected from —F, —Cl, and —Br,
(b) methyl,
(c) methoxy-, and
(d) phenyl,
(24) triazolyl;
(25) substituted triazolyl with a substituent selected from:
(a) halogen, selected from —F, —Cl, and —Br,
(b) methyl,
(c) methoxy-, and
(d) hydroxy,
(26) tetrazolyl;
(27) substituted tetrazolyl with a substituent selected from:
(a) halogen, selected from —F, —Cl, and —Br,
(b) methyl,
(c) methoxy-, and
(d) hydroxy,
(28) $C_{3-6}$ cycloalkyl;
(29) substituted $C_{3-6}$ cycloalkyl substituted with one or two substituents independently selected from:
(a) halogen, selected from —F, —Cl, and —Br,
(b) methyl,
(c) methoxy-,
(d) —$CF_3$, and
(e) —$OCF_3$,
(30) tetrahydrofuran;
(31) substituted tetrahydrofuran substituted with one or two substituents independently selected from:
(a) halogen, selected from —F, —Cl, and —Br,
(b) methyl,
(c) methoxy-,
(d) —$CF_3$, and
(e) —$OCF_3$,
(32) piperazinyl;
(33) substituted piperazinyl substituted with one or two substituents independently selected from:
(a) halogen, selected from —F, —Cl, and —Br,
(b) $C_{1-6}$ alkyl,
(c) $C_{1-6}$ alkyloxy-,
(d) —$CF_3$,
(e) —$OCF_3$,
(f) benzyl, and
(g) hydroxy;
(34) benzotriazolyl,
(35) substituted benzotriazolyl substituted on carbon with one or two substituents independently selected from:
(a) -halogen, selected from —F, —Cl, and —Br,
(b) -methyl,
(c) methoxy-,
(d) —$CF_3$, and
(e) —$OCF_3$,
(36) benzoimidazolyl, and
(37) substituted benzoimidazolyl substituted on carbon with one or two substituents independently selected from:
(a) -halogen, selected from —F, —Cl, and —Br,
(b) -methyl,
(c) methoxy-,
(d) —$CF_3$, and
(e) —$OCF_3$;
each $R^4$ is independently selected from:
(1) —H
(2) —$C_{1-4}$ alkyl,
(3) —$CF_3$,
(4) —$R^3$,
(5) —$C_{1-3}$ alkyl-$R^3$, and
(6) —C(O)—$R^3$;
each $R^5$ is independently selected from:
(1) —H,
(2) —$C_{1-3}$ alkyl,
(3) —$CF_3$,
(4) —$R^3$,
(5) —$C_{1-3}$ alkyl-$R^3$,
(6) —C(O)—$R^3$,
(7) —C(O)O$R^4$, and
(8) —C(O)C(O)OH;
each $R^6$ is independently selected from:
(1) —$C_{1-3}$ alkyl-$R^3$, and
(2) —$R^3$;
each $R^7$ is independently selected from:
(1) —H, and
(2) —$C_{1-6}$ alkyl;
$R^8$ is selected from methyl and —O—$C_{1-6}$ alkyl; and
PROVIDED THAT:
(1) at least one of $R^1$, $R^2$, and $R^8$ is not:
(a) $C_{1-6}$ alkyl, or
(b) $R^3$ wherein $R^3$ is cycloalkyl.

6. The compound according to claim 1 of structural formula:

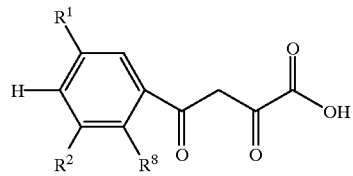

and tautomers and pharmaceutically acceptable salts thereof, wherein:
$R^1$ is selected from:
(1) —H,
(2) —$CH_3$,
(3) —$C_{1-6}$ alkyl-$OR^7$;
(4) —O—$C_{1-6}$ alkyl-$OR^7$,
(5) —O—$C_{1-6}$ alkyl-$SR^7$,
(6) —$CF_3$ or —$CH_2CF_3$,
(7) —Cl,
(8) —F,
(9) —$C_{0-3}$ alkyl-N($R^4$)($R^5$),
(10) -phenyl,
(11) phenyl $C_{1-3}$ alkyl-, wherein the phenyl group may be unsubstituted or substituted with 1 to four substituents independently selected from:

(a) —F, —Cl, or —Br,
(b) CH$_3$,
(c) —OCH$_3$, OCH$_2$CH$_3$, OCF$_3$, or OCH$_2$CF$_3$,
(d) —CF$_3$,
(e) —SCH$_3$,
(f) —CN,
(g) hydroxy,
(h) —C$_{0-6}$ alkyl-N(R$^7$)$_2$,
(12) —O—CH$_2$-phenyl, wherein the phenyl group may be unsubstituted or substituted with 1 to four substituents independently selected from:
(a) —F, —Cl, or —Br,
(b) CH$_3$,
(c) —OCH$_3$, OCH$_2$CH$_3$, OCF$_3$, or OCH$_2$CF$_3$,
(d) —CF$_3$,
(e) —SCH$_3$,
(f) —CN,
(g) hydroxy,
(h) —C$_{0-6}$ alkyl-N(R$^7$)$_2$,
(13) —O—C$_{1-6}$ alkyl, unsubstituted or substituted with one to three fluorine atoms,
(14) —C(O)CH$_2$C(O)C(O)OH,
(15) —O—C$_{1-6}$ alkyl-NH—C(O)—OR$^7$,
(16) —O—CH$_2$CH$_2$N(CH$_3$)$_2$,
(17) —O—CH(CH$_3$)CH$_2$N(CH$_3$)$_2$,
(18) —O—CH$_2$CH$_2$NH$_2$,
(19) —O—CH(CH$_3$)CH$_2$NH$_2$,
(20) —S—CH$_3$,
(21) —CH$_2$—CH(OH)—CH$_2$—O—R$^7$, and
(22) —C(OH)(CH$_3$)—CH$_2$N(R$^4$)(R$^5$);

R$^2$ is selected from:
(1) —R$^3$,
(2) —C$_{1-6}$ alkyl substituted with R$^3$, wherein one or more of the hydrogen atoms on C$_{1-6}$ alkyl may be replaced with a fluorine atom,
(3) —O—C$_{1-6}$ alkyl-SR$^6$,
(4) —C$_{1-6}$ alkyl-(OR$^6$)(R$^4$),
(5) —C$_{0-6}$ alkyl-N(R$^4$)(R$^6$),
(6) —C$_{0-6}$ alkyl-C(O)—R$^6$,
(7) —C$_{0-6}$ alkyl-C(O)CH$_2$—C(O)—OH,
(8) —C$_{1-6}$ alkyl-NR$^4$C(O)—R$^6$,
(9) —C$_{1-6}$ alkyl-C(O)N(R$^4$)(R$^5$), and
(10) —CH$_2$(OR$^7$)—R$^6$;

each R$^3$ is independently selected from:
(1) phenyl,
(2) substituted phenyl with 1, 2, 3 or 4 substituents independently selected from:
(a) halogen, selected from —F, —Cl, and —Br,
(b) C$_{1-6}$ alkyl, wherein one or more of the hydrogen atoms may be replaced with a fluorine atom,
(c) C$_{1-6}$ alkyloxy- wherein one or more of the hydrogen atoms may be replaced with a fluorine atom,
(d) —CN,
(e) hydroxy, and
(f) oxo;
(3) thienyl,
(4) substituted thienyl substituted on carbon with one or two substituents independently selected from:
(a) halogen, selected from F, Cl, and Br,
(b) C$_{1-6}$ alkyl, wherein one or more of the hydrogen atoms may be replaced with a fluorine atom, and
(c) C$_{1-6}$ alkyloxy- wherein one or more of the hydrogen atoms may be replaced with a fluorine atom;
(5) pyridyl,
(6) substituted pyridyl substituted on carbon with one or two substituents independently selected from:
(a) halogen, selected from —F, —Cl, and —Br;
(b) C$_{1-6}$ alkyl, wherein one or more of the hydrogen atoms may be replaced with a fluorine atom,
(c) C$_{1-6}$ alkyloxy- wherein one or more of the hydrogen atoms may be replaced with a fluorine atom,
(d) hydroxy, and
(e) oxo;
(7) pyrrolyl,
(8) pyrazolyl
(9) substituted pyrazolyl substituted on carbon with one or two substituents independently selected from:
(a) halogen, selected from —F, —Cl, and —Br;
(b) —CH$_3$,
(c) —CF$_3$,
(d) —OCH$_3$,
(e) —OCF$_3$, and
(f) hydroxy;
(10) C$_{3-5}$ cycloalkyl fused with a phenyl ring,
(11) substituted C$_{3-5}$ cycloalkyl fused with a phenyl ring substituted on carbon with 1 or 2 substituents independently selected from:
(a) halogen, selected from —F, —Cl, and —Br,
(b) CH$_3$,
(c) methyloxy-,
(d) —CF$_3$,
(e) —OCF$_3$,
(f) —CN,
(g) =O, and
(h) hydroxy;
(12) piperidinyl,
(13) substituted piperidinyl substituted on carbon with one or two substituents independently selected from:
(a) halogen selected from —F, —Cl, and —Br,
(b) methyl,
(c) methoxy-,
(d) —CF$_3$,
(e) —OCF$_3$,
(f) =O, and
(g) hydroxy;
(14) substituted morpholinyl substituted at carbon or nitrogen with 1 or 2 substituents independently selected from:
(a) halogen, selected from —F, —Cl, and —Br,
(b) methyl,
(c) methoxy-,
(d) —CF$_3$,
(e) —OCF$_3$, and
(f) hydroxy;
(15) hexahydrothieno[3,4-d]imidazolyl,
(16) naphthyl,
(17) substituted naphthyl with 1, 2, or 3 substituents independently selected from:
(a) -halogen, selected from —F, —Cl, and —Br,
(b) methyl,
(c) methoxy-,
(d) —CF$_3$,
(e) —OCF$_3$,
(f) —CN, and
(g) -hydroxy,
(18) indolyl, and
(19) substituted 1,2,3,4-tetrahydronaphthalenyl substituted on carbon with a substituent selected from:
(a) halogen, selected from —F, —Cl, and —Br,
(b) methyl,
(c) methoxy-,
(d) —CF$_3$, (e) —OCF$_3$,
(f) —CN,
(g) =O, and
(h) hydroxy;
(20) pyrazinyl;
(21) substituted pyrazinyl substituted on nitrogen or carbon with one or two substituents independently selected from:
 (a) halogen, selected from —F, —Cl, and —Br,
 (b) C$_{1-6}$ alkyl, wherein one or more of the hydrogen atoms may be replaced with a fluorine atom,
 (c) C$_{1-6}$ alkyloxy- wherein one or more of the hydrogen atoms may be replaced with a fluorine atom,
 (d) hydroxy,
 (e) phenyloxy,
 (f) —C$_{0-6}$ alkyl-N(R$^7$)$_2$, and
 (g)

—N◯N—CH$_3$;

(22) pyrimidinyl;
(23) substituted pyrimidinyl substituted on nitrogen or carbon with a substituent selected from:
 (a) halogen, selected from —F, —Cl, and —Br,
 (b) methyl,
 (c) methoxy-, and
 (d) phenyl,
(24) triazolyl;
(25) substituted triazolyl with a substituent selected from:
 (a) halogen, selected from —F, —Cl, and —Br,
 (b) methyl,
 (c) methoxy-, and
 (d) hydroxy,
(26) tetrazolyl;
(27) substituted tetrazolyl with a substituent selected from:
 (a) halogen, selected from —F, —Cl, and —Br,
 (b) methyl,
 (c) methoxy-, and
 (d) hydroxy,
(28) C$_{3-6}$ cycloalkyl;
(29) substituted C$_{3-6}$ cycloalkyl substituted with one or two substituents independently selected from:
 (a) halogen, selected from —F, —Cl, and —Br,
 (b) methyl,
 (c) methoxy-,
 (d) —CF$_3$, and
 (e) —OCF$_3$,
(30) tetrahydrofuran;
(31) substituted tetrahydrofuran substituted with one or two substituents independently selected from:
 (a) halogen, selected from —F, —Cl, and —Br,
 (b) methyl,
 (c) methoxy-,
 (d) —CF$_3$, and
 (e) —OCF$_3$,
(32) piperazinyl;
(33) substituted piperazinyl substituted with one or two substituents independently selected from:
 (a) halogen, selected from —F, —Cl, and —Br,
 (b) C$_{1-6}$ alkyl,
 (c) C$_{1-6}$ alkyloxy-,
 (d) —CF$_3$,
 (e) —OCF$_3$,
 (f) benzyl, and
 (g) hydroxy;
(34) benzotriazolyl,
(35) substituted benzotriazolyl substituted on carbon with one or two substituents independently selected from:
 (a) -halogen, selected from —F, —Cl, and —Br,
 (b) -methyl,
 (c) methoxy-,
 (d) —CF$_3$, and
 (e) —OCF$_3$,
(36) benzoimidazolyl, and
(37) substituted benzoimidazolyl substituted on carbon with one or two substituents independently selected from:
 (a) -halogen, selected from —F, —Cl, and —Br,
 (b) -methyl,
 (c) methoxy-,
 (d) —CF$_3$, and
 (e) —OCF$_3$;
each R$^4$ is independently selected from:
 (1) —H,
 (2) —C$_{1-4}$ alkyl,
 (3) —CF$_3$,
 (4) —R$^3$,
 (5) —C$_{1-3}$ alkyl-R$^3$, and
 (6) —C(O)—R$^3$;
each R$^5$ is independently selected from:
 (1) —H,
 (2) —C$_{1-3}$ alkyl,
 (3) —CF$_3$,
 (4) —R$^3$,
 (5) —C$_{1-3}$ alkyl-R$^3$,
 (6) —C(O)—R$^3$,
 (7) —C(O)OR$^4$, and
 (8) —C(O)C(O)OH;
each R$^6$ is independently selected from:
 (1) —C$_{1-3}$ alkyl-R$^3$, and
 (2) —R$^3$;
each R$^7$ is independently selected from:
 (1) —H, and
 (2) —C$_{1-6}$ alkyl; and
R$^8$ is selected from methyl and —O—C$_{1-6}$ alkyl; and
PROVIDED THAT:
 (1) at least one of R$^1$, R$^2$, and R$^8$ is not:
  (a) C$_{1-6}$ alkyl, or
  (b) R$^3$ wherein R$^3$ is cycloalkyl.
7. The compound according to claim 1 of structural formula:

and tautomers and pharmaceutically acceptable salts thereof, wherein:
R$^1$ is selected from:
 (1) —H,
 (2) —CH$_3$,
 (3) —C$_{1-6}$ alkyl-OR$^7$, (4) —O—$C_{1-6}$ alkyl-$OR^7$,
(5) —O—$C_{1-6}$ alkyl-$SR^7$,
(6) —$CF_3$ or —$CH_2CF_3$,
(7) —Cl,
(8) —F,
(9) —$C_{0-3}$ alkyl —$N(R^4)(R^5)$,
(10) -phenyl,
(11) phenyl $C_{1-3}$ alkyl-, wherein the phenyl group may be unsubstituted or substituted with 1 to four substituents independently selected from:
  (a) —F, —Cl, or —Br,
  (b) $CH_3$,
  (c) —$OCH_3$, $OCH_2CH_3$, $OCF_3$, or $OCH_2CF_3$,
  (d) —$CF_3$,
  (e) —$SCH_3$,
  (f) —CN,
  (g) hydroxy,
  (h) —$C_{0-6}$ alkyl-$N(R^7)_2$,
(12) —O—$CH_2$-phenyl, wherein the phenyl group may be unsubstituted or substituted with 1 to four substituents independently selected from:
  (a) —F, —Cl, or —Br,
  (b) $CH_3$,
  (c) —$OCH_3$, $OCH_2CH_3$, $OCF_3$, or $OCH_2CF_3$,
  (d) —$CF_3$,
  (e) —$SCH_3$,
  (f) —CN,
  (g) hydroxy,
  (h) —$C_{0-6}$ alkyl-$NR^7)_2$,
(13) —O—$C_{1-6}$ alkyl, unsubstituted or substituted with one to three fluorine atoms, and
(14) —C(O)$CH_2$C(O)C(O)OH,
(15) —O—$C_{1-6}$ alkyl-NH—C(O)—$OR^7$,
(16) —O—$CH_2CH_2N(CH_3)_2$,
(17) —O—$CH(CH_3)CH_2N(CH_3)_2$,
(18) —O—$CH_2CH_2NH_2$,
(19) —O—$CH(CH_3)CH_2NH_2$,
(20) —S—$CH_3$,
(21) —$CH_2$—CH(OH)—$CH_2$—O—$R^7$, and
(22) —C(OH)($CH_3$)—$CH_2N(R^4)(R^5)$;

$R^2$ is selected from:
  (1) —$R^3$,
  (2) —$C_{1-6}$ alkyl substituted with $R^3$, wherein one or more of the hydrogen atoms on $C_{1-6}$ alkyl may be replaced with a fluorine atom,
  (3) —O—$C_{1-6}$ alkyl-$SR^6$,
  (4) —$C_{1-6}$ alkyl ($OR^6$)($R^4$),
  (5) —$C_{0-6}$ alkyl-$N(R^4)(R^6)$,
  (6) —$C_{0-6}$ alkyl C(O)—$R^6$,
  (7) —$C_{0-6}$ alkyl C(O)$CH_2$—C(O)—OH,
  (8) —$C_{1-6}$ alkyl $NR^4$C(O)—$R^6$,
  (9) —$C_{1-6}$ alkyl-C(O)$N(R^4)(R^5)$, and
  (10) —$CH_2(OR^7)$—$R^6$;

each $R^3$ is independently selected from:
  (1) phenyl;
  (2) substituted phenyl with 1, 2, 3 or 4 substituents independently selected from:
    (a) halogen, selected from —F, —Cl, and —Br,
    (b) $C_{1-6}$ alkyl, wherein one or more of the hydrogen atoms may be replaced with a fluorine atom,
    (c) $C_{1-6}$ alkyloxy- wherein one or more of the hydrogen atoms may be replaced with a fluorine atom,
    (d) —CN,
    (e) hydroxy, and
    (f) oxo;
  (3) thienyl,
  (4) substituted thienyl substituted on carbon with one or two substituents independently selected from:
    (a) halogen, selected from F, Cl, and Br,
    (b) $C_{1-6}$ alkyl, wherein one or more of the hydrogen atoms may be replaced with a fluorine atom, and
    (c) $C_{1-6}$ alkyloxy- wherein one or more of the hydrogen atoms may be replaced with a fluorine atom;
  (5) pyridyl,
  (6) substituted pyridyl substituted on carbon with one or two substituents independently selected from:
    (a) halogen, selected from —F, —Cl, and —Br;
    (b) $C_{1-6}$ alkyl, wherein one or more of the hydrogen atoms may be replaced with a fluorine atom,
    (c) $C_{1-6}$ alkyloxy- wherein one or more of the hydrogen atoms may be replaced with a fluorine atom,
    (d) hydroxy, and
    (e) oxo;
  (7) pyrrolyl,
  (8) pyrazolyl
  (9) substituted pyrazolyl substituted on carbon with one or two substituents independently selected from:
    (a) halogen, selected from —F, —Cl, and —Br;
    (b) —$CH_3$,
    (c) —$CF_3$,
    (d) —$OCH_3$,
    (e) —$OCF_3$, and
    (f) hydroxy;
  (10) $C_{3-5}$ cycloalkyl fused with a phenyl ring,
  (11) substituted $C_{3-5}$ cycloalkyl fused with a phenyl ring substituted on carbon with 1 or 2 substituents independently selected from:
    (a) halogen, selected from —F, —Cl, and —Br,
    (b) $CH_3$,
    (c) methyloxy-,
    (d) —$CF_3$,
    (e) —$OCF_3$,
    (f) —CN,
    (g) =O, and
    (h) hydroxy;
  (12) piperidinyl,
  (13) substituted piperidinyl substituted on carbon with one or two substituents independently selected from:
    (a) halogen selected from —F, —Cl, and —Br,
    (b) methyl,
    (c) methoxy-,
    (d) —$CF_3$,
    (e) —$OCF_3$,
    (f) =O, and
    (g) hydroxy;
  (14) substituted morpholinyl substituted on carbon or nitrogen with 1 or 2 substituents independently selected from:
    (a) halogen, selected from —F, —Cl, and —Br,
    (b) methyl,
    (c) methoxy-,
    (d) —$CF_3$,
    (e) —$OCF_3$, and
    (f) hydroxy;
  (15) hexahydrothieno[3,4-d]imidazolyl,
  (16) naphthyl,
  (17) substituted naphthyl with 1, 2, or 3 substituents independently selected from:
    (a) -halogen, selected from —F, —Cl, and —Br,
    (b) methyl,
    (c) methoxy-, (d) —CF$_3$,
(e) —OCF$_3$,
(f) —CN, and
(g) -hydroxy,
(18) indolyl, and
(19) substituted 1,2,3,4-tetrahydronaphthalenyl substituted on carbon with a substituent selected from:
   (a) halogen, selected from —F, —Cl, and —Br,
   (b) methyl,
   (c) methoxy-,
   (d) —CF$_3$,
   (e) —OCF$_3$,
   (f) —CN,
   (g) =O, and
   (h) hydroxy;
(20) pyrazinyl;
(21) substituted pyrazinyl substituted on nitrogen or carbon with one or two substituents independently selected from:
   (a) halogen, selected from —F, —Cl, and —Br,
   (b) C$_{1-6}$ alkyl, wherein one or more of the hydrogen atoms may be replaced with a fluorine atom,
   (c) C$_{1-6}$ alkyloxy- wherein one or more of the hydrogen atoms may be replaced with a fluorine atom,
   (d) hydroxy,
   (e) phenyloxy,
   (f) —C$_{0-6}$ alkyl-N(R$^7$)$_2$, and (g)

—N⟨ ⟩N—CH$_3$;

(22) pyrimidinyl;
(23) substituted pyrimidinyl substituted on nitrogen or carbon with a substituent selected from:
   (a) halogen, selected from —F, —Cl, and —Br,
   (b) methyl,
   (c) methoxy-, and
   (d) phenyl,
(24) triazolyl;
(25) substituted triazolyl with a substituent selected from:
   (a) halogen, selected from —F, —Cl, and —Br,
   (b) methyl,
   (c) methoxy-, and
   (d) hydroxy,
(26) tetrazolyl;
(27) substituted tetrazolyl with a substituent selected from:
   (a) halogen, selected from —F, —Cl, and —Br,
   (b) methyl,
   (c) methoxy-, and
   (d) hydroxy,
(28) C$_{3-6}$ cycloalkyl;
(29) substituted C$_{3-6}$ cycloalkyl substituted with one or two substituents independently selected from:
   (a) halogen, selected from —F, —Cl, and —Br,
   (b) methyl,
   (c) methoxy-,
   (d) —CF$_3$, and
   (e) —OCF$_3$,
(30) tetrahydrofuran;
(31) substituted tetrahydrofuran substituted with one or two substituents independently selected from:
   (a) halogen, selected from —F, —Cl, and —Br,
   (b) methyl,
   (c) methoxy-,
   (d) —CF$_3$, and
   (e) —OCF$_3$,
(32) piperazinyl;
(33) substituted piperazinyl substituted with one or two substituents independently selected from:
   (a) halogen, selected from —F, —Cl, and —Br,
   (b) C$_{1-6}$ alkyl,
   (c) C$_{1-6}$ alkyloxy-,
   (d) —CF$_3$,
   (e) —OCF$_3$,
   (f) benzyl, and
   (g) hydroxy;
(34) benzotriazolyl,
(35) substituted benzotriazolyl substituted on carbon with one or two substituents independently selected from:
   (a) -halogen, selected from —F, —Cl, and —Br,
   (b) -methyl,
   (c) methoxy-,
   (d) —CF$_3$, and
   (e) —OCF$_3$,
(36) benzoimidazolyl, and
(37) substituted benzoimidazolyl substituted on carbon with one or two substituents independently selected from:
   (a) -halogen, selected from —F, —Cl, and —Br,
   (b) -methyl,
   (c) methoxy-,
   (d) —CF$_3$, and
   (e) —OCF$_3$;

each R$^4$ is independently selected from:
   (1) —H,
   (2) —C$_{1-4}$ alkyl,
   (3) —CF$_3$,
   (4) —R$^3$,
   (5) —C$_{13}$ alkyl-R$^3$, and
   (6) —C(O)—R$^3$;

each R$^5$ is independently selected from:
   (1) —H,
   (2) —C$_{1-3}$ alkyl,
   (3) —CF$_3$,
   (4) —R$^3$,
   (5) —C$_{1-3}$ alkyl-R$^3$,
   (6) —C(O)—R$^3$,
   (7) —C(O)OR$^4$, and
   (8) —C(O)C(O)OH;

each R$^6$ is independently selected from:
   (1) —C$_{1-3}$ alkyl-R$^3$, and
   (2) —R$^3$;

each R$^7$ is independently selected from:
   (1) —H, and
   (2) —C$_{1-6}$ alkyl; and R$^8$ is selected from methyl and —O—C$_{1-6}$ alkyl; and
PROVIDED THAT:
   (1) at least one of R$^1$, R$^2$, and R$^8$ is not:
      (b) C$_{1-6}$ alkyl, or
      (c) R$^3$ wherein R$^3$ is cycloalkyl.

8. The compound according to claim 1 of structural formula:

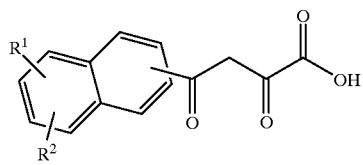

and tautomers and pharmaceutically acceptable salts thereof, wherein:

$R^1$ is selected from:
(1) —H,
(2) —$CH_3$,
(3) —$CH_2OCH_3$,
(4) —$OCH_2CH_2OH$,
(5) —$OCH_2CH_2OCH_3$,
(6) —$(CH_2)_6$—OH,
(7) —$CF_3$,
(8) —F,
(9) —Cl,
(10) —$C_{0-3}$ alkyl-N($R^4$)($R^5$),
(11) -phenyl,
(12) phenyl $C_{1-3}$ alkyl-, wherein the phenyl group may be unsubstituted or substituted with 1 to four substituents independently selected from:
  (a) —F, —Cl, or —Br,
  (b) $CH_3$,
  (c) —$OCH_3$, $OCH_2CH_3$, $OCF_3$, or $OCH_2CF_3$,
  (d) —$CF_3$,
  (e) —CN,
  (f) hydroxy,
  (g) —$C_{0-6}$ alkyl-N$R^7_2$,
(13) —O—$CH_2$-phenyl, wherein the phenyl group may be unsubstituted or substituted with 1 to four substituents independently selected from:
  (a) —F, —Cl, or —Br,
  (b) —$CH_3$,
  (c) —$OCH_3$, $OCH_2CH_3$, $OCF_3$, or $OCH_2CF_3$,
  (d) —$CF_3$,
  (e) —CN,
  (f) hydroxy,
  (g) —$C_{0-6}$ alkyl-N($R^7$)$_2$,
(14) —O—$CH_3$,
(15) —$OCH_2CH_3$,
(16) —$OCH_2CF_3$,
(17) —$OCF_3$,
(18) —$OCH(CH_3)_2$,
(19) —C(O)$CH_2$C(O)C(O)OH,
(20) —O—$C_{1-6}$ alkyl-NH—C(O)—$OR^7$,
(21) —O—$CH_2CH_2$ N($CH_3$)$_2$,
(22) —O—CH($CH_3$)$CH_2$N($CH_3$)$_2$,
(23) —O—$CH_2CH_2NH_2$,
(24) —O—CH($CH_3$)$CH_2NH_2$,
(25) —S—$CH_3$,
(26) —$CH_2$—CH(OH)—$CH_2$—O—$R^7$, and
(27) —C(OH)($CH_3$)—$CH_2$N($R^4$)($R^5$);

$R^2$ is selected from:
(1) —$R^3$,
(2) —$CH_2$—$R^3$,
(3) —$CH_2CH_2$—$R^3$,
(4) —$CF_2$—$R^3$,
(5) —CH($CH_3$)—$R^3$,
(6) —$C_{1-6}$ alkyl (O$R^6$)($R^4$),
(7) —$C_{0-6}$ alkyl-N($R^4$)($R^6$),
(8) —C(O)—$R^3$,
(9) —$C_{0-6}$ alkyl C(O)$CH_2$—C(O)—OH,
(10) —$C_{1-6}$ alkyl N$R^4$C(O)—$R^6$,
(11) —CH(O$CH_3$)$R^3$, and
(12) —CH(OH)$R^3$;

each $R^3$ is independently selected from:
(1) phenyl;
(2) substituted phenyl with 1, 2, or 3 substituents independently selected from:
  (a) halogen, selected from —F, —Cl, and —Br,
  (b) —$CH_3$,
  (c) methyloxy-,
  (d) ethyloxy-,
  (e) —$OCH_2CF_3$,
  (f) —$OCF_2CH_3$,
  (g) —$CF_3$,
  (h) —$CH_2CF_3$,
  (i) —$CF_2CH_3$,
  (j) —$OCF_3$,
  (k) —CN, and
  (l) hydroxy;
(3) thienyl,
(4) substituted thienyl substituted on a carbon atom with a substituent selected from:
  (a) F,
  (b) Cl, and
  (c) methyl;
(5) pyridyl,
(6) substituted pyridyl substituted on a carbon with a substituent selected from:
  (a) —F,
  (b) —Cl,
  (c) —$CH_3$,
  (d) —$CF_3$,
  (e) —$OCH_3$,
  (f) —$OCF_3$,
  (g) hydroxy, and
  (h) oxo;
(7) pyrazolyl
(8) substituted pyrazolyl substituted on carbon with one or two substituents independently selected from:
  (a) —F,
  (b) —Cl,
  (c) —$CH_3$, and
  (d) —$CF_3$;
(9) $C_{3-5}$ cycloalkyl fused with a phenyl ring,
(10) piperidinyl,
(11) substituted piperidinyl substituted on carbon with a substituent selected from:
  (a) methoxy-,
  (b) —$OCF_3$,
  (c) =O, and
  (d) hydroxy;
(12) naphthyl,
(13) pyrazinyl;
(14) substituted pyrazinyl substituted on nitrogen or carbon with a substituent selected from:
  (a) halogen, selected from —F, —Cl, and —Br,
  (b) methyl,
  (c) —$CF_3$, (d) methoxy-,
(e) —N(CH₃)₂, and (f) 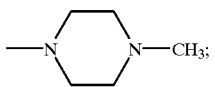

(15) pyrimidinyl,
(16) [1,2,3]-triazolyl,
(17) [1,2,4]-triazolyl,
(18) tetrazolyl;
(19) cyclopropyl,
(20) cyclobutyl,
(21) cyclopentyl,
(22) cyclohexyl,
(23) tetrahydrofuran,
(24) piperazinyl;
(25) substituted piperazinyl substituted with a substituent selected from:
  (a) —F,
  (b) —Cl,
  (c) methyl,
  (d) —CF₃, and
  (e) benzyl,
(26) benzotriazolyl, and
(27) benzoimidazolyl;
each R⁴ is independently selected from:
  (1) —H,
  (2) —C₁₋₄ alkyl,
  (3) —CF₃,
  (4) —R³,
  (5) —C₁₋₃ alkyl-R³, and
  (6) —C(O)—R³;
each R⁵ is independently selected from:
  (1) —H,
  (2) —CH₃,
  (3) —CF₃,
  (4) phenyl,
  (5) -benzyl,
  (6) —C(O)OR⁴, and
  (7) —C(O)C(O)OH;
each R⁶ is independently selected from:
  (1) —C₁₋₃ alkyl-R³, and
  (2) —R³; and
each R⁷ is independently selected from:
  (1) —H, and
  (2) —C₁₋₆ alkyl.

9. A compound according to claim 1, selected from:
(1) 3-biphenyl-4-yl-2,4-dioxobutanoic acid,
(17) 4-(3-dibenzylaminophenyl)-2-hydroxy4-oxobut-2-enoic acid,
(19) 4-(3-benzyl-phenyl)-2,4-dioxo-butanoic acid,
(20) 4-(4-dibenzylaminophenyl)-2-hydroxy-4-oxobut-2-enoic acid,
(21) 4-(4-benzylaminophenyl)-2-hydroxy-4-oxobut-2-enoic acid,
and tautomers and pharmaceutically acceptable salts thereof.

10. A compound selected from the group consisting of:
(3) 4-[3-Benzyloxy-5-(6-tert-butoxycarbonylamino-hexyloxy)-phenyl]-2,4-dioxobutanoic acid,
(4) 4-(3-Benzylphenyl)-2,4-dioxobutanoic acid,
(5) 4-[3-(2-chlorobenzyl)phenyl]-2,4-dioxobutanoic acid,
(6) 4-Dibenzylaminophenyl)-2,4-dioxobutanoic acid,
(7) 4-(3-Dibenzylaminophenyl)-2,4-dioxobutanoic acid,
(9) 1-(3-Benzyloxyphenyl)-2,4-dioxobutanoic acid,
(10) 1-(2-Benzyloxyphenyl)-2,4-dioxobutanoic acid,
(11) 1-[3-(4-Fluorobenzyloxy)phenyl]-2,4-dioxobutanoic acid,
(12) 1-[3-(3,4-Difluorobenzyloxy)phenyl]-2,4-dioxobutanoic acid,
(13) 4-[3-(5-methyl-thiophen-2-ylmethyl)-phenyl]-2,4-dioxo-butyric acid,
(14) 4-{3-[(methyl-phenyl-amino)-methyl]-phenyl}-2,4-dioxo-butyric acid,
(15) 4-(3-benzyl-5-pyrazin-2-yl-phenyl)-2,4-dioxo-butyric acid,
(16) 2,4-dioxo-4-[3-(1,2,3,4-tetrahydronaphthalen-1-yl)-phenyl]butyric acid,
(17) 2,4-Dioxo-4-(3-phenylsulfanyl-phenyl)-butyric acid,
(18) 4-[3-(2,4-Difluoro-benzyl)-phenyl]-2,4-dioxo-butyric acid,
(19) 4-[5-(4-Fluoro-benzyl)-2,3-dimethoxy-phenyl]-2,4-dioxo-butyric acid,
(20) 4-(5-Benzyl-2-isopropoxyphenyl)-2,4-dioxobutyric acid,
(21) 4-[5-Benzyl-2-(2-N,N-dimethylaminoethoxy)phenyl]-2,4-dioxobutyric acid,
(22) 4-[5-Benzyl-2-(pyridin-2-yloxy)phenyl]-2,4-dioxo-butyric acid,
(23) 4-(5-Benzyl-2-isopropoxy-3-methoxyphenyl)-2,4-dioxo-butyric acid,
(24) 4-(5-Benzyl-2,3-dimethoxyphenyl)-2,4-dioxobutyric acid,
(25) 4-(5-Benzyl-3-dimethylamino-2-methoxyphenyl)-2,4-dioxobutyric acid,
(27) 4-(3-Benzyl-5-pyrazin-2-ylmethylphenyl)-2,4-dioxobutyric acid,
(28) 4-(3-Benzyl-5-[1,2,3]triazol-2-ylmethylphenyl)-2,4-dioxobutyric acid,
(29) 4-[3-(3-Chloropyridin-2-ylmethyl)phenyl]-2,4-dioxobutyric acid,
(30) 4-[5-Benzyl-2-methoxy-3-(N,N-dimethylamninomethyl) phenyl]-2,4-dioxo-butyric acid,
(31) 4-(5-benzyl-3-methoxy-2-methoxyethoxyphenyl)-2,4-dioxobutyric acid,
(32) 4-(3-Benzyl-4-methoxyphenyl)-2,4-dioxobutyric acid,
(33) 4-(5-Benzyl-2-methoxyphenyl)-2,4-dioxobutyric acid,
(34) 4-(3-Benzyl-4-fluorophenyl)-2,4-dioxobutyric acid,
(35) 4-(3-Benzyl-4-N,N-dimethylaminophenyl)-2,4-dioxobutyric acid,
(36) 4-[5-(2-Methylbenzyl)-2,3-dimethoxyphenyl]-2,4-dioxobutyric acid,
(37) 2,4-Dioxo-4-(3-pyridin-2-ylmethylphenyl)butyric acid,
(38) 4-(5-Benzyl-3-N,N-dimethylaminophenyl)-2,4-dioxobutyric acid,
(39) 4-(5-Benzyl-3-methoxyphenyl)-2,4-dioxobutyric acid,
(40) 4-(5-Benzyl-2-benzyloxy-3-methoxyphenyl)-2,4-dioxobutyric acid,
(41) 4-[5-(3-Methylbenzyl)-2,3-dimethoxyphenyl]-2,4-dioxobutyric acid,

(42) 4-(5-Benzyl-3-benzyloxyphenyl)-2,4-dioxobutyric acid,
(43) 4-[5-Benzyl-2-(2-hydroxy)ethoxyphenyl]-2,4-dioxo-2-butanoic acid,
(44) 2,4-Dioxo-4-(3-pyridin-3-ylmethylphenyl)butyric acid,
(45) 4-[3-(3-Methyl-pyridin-2-ylmethyl)phenyl]-2,4-dioxo-butyric acid,
(46) 4-(5-Benzyl-2-methylsulfanylphenyl)-2,4-dioxobutyric acid,
(47) 4-(5-Benzyl-3-N-morpholinophenyl)-2,4-dioxobutyric acid,
(48) 4-(8-Benzyl-4-methyl-3,4-dihydro-2h-benzo[1,4]oxazin-6-yl)-2,4-dioxobutyric acid,
(49) 4-[5-(2-Chlorobenzyl)-3-N,N-dimethylaminophenyl]-2,4-dioxobutyric acid,
(50) 4-[5-(3-Chlorobenzyl)-3-N,N-dimethylaminophenyl]-2,4-dioxobutyric acid,
(51) 4-(5-Benzyl-2,3,4-trimethoxyphenyl)-2,4-dioxobutyric acid,
(52) 4-(6-Benzylbenzo[1,3]dioxol-4-yl)-2,4-dioxobutyric acid,
(53) 4-[3-Benzyl-5-(morpholine-4-carbonyl)phenyl]-2,4-dioxobutyric acid,
(54) 4-(3-Benzyl-5-pyridine-2-ylmethylphenyl)-2,4-dioxobutyric acid,
(55) 4-[3-Benzyl-5-(morpholinomethyl)phenyl]-2,4-dioxobutyric acid,
(56) 4-(3-Benzyl-5-pyridine-3-ylmethylphenyl)-2,4-dioxobutyric acid,
(57) 4-[3-Benzyl-5-(2-dimethylamino-1-hydroxy-1-methylethyl)phenyl]-2,4-dioxobutyric acid,
(58) 4-(5-Benzyl-2-N,N-dimethylaminophenyl)-2,4-dioxobutyric acid,
(59) 4-(5-Benzyl-2-fluorophenyl)-2,4-dioxobutyric acid,
(60) 4-(5-Benzyl-3-hydroxymethyl-2-methoxyphenyl)-2,4-dioxobutyric acid,
(61) 4-[5-Benzyl-2-(pyrazin-2-yloxy)phenyl]-2,4-dioxobutyric acid,
(62) 4-[3-Benzyl-5-(2-oxopiperidin-1-ylmethyl)phenyl]-2,4-dioxobutyric acid,
(63) 4-[5-Benzyl-2-methoxy-3-(morpholinomethyl)phenyl]-2,4-dioxo-butyric acid,
(64) 4-[3-(2-Chlorobenzyl)-5-pyridin-2-ylmethylphenyl]-2,4-dioxobutyric acid,
(65) 4-[5-Benzyl-2-methoxy-3-(4-methylpiperazin-1-ylmethyl)phenyl]-2,4-dioxobutyric acid,
(66) 4-(5-Benzyl-2-methoxymethylphenyl)-2,4-dioxobutyric acid,
(67) 4-[3-(2-Fluorobenzyl)-5-morpholinomethylphenyl]-2,4-dioxobutyric acid,
(68) 4-[3-(4-Fluorobenzyl)-5-morpholinomethylphenyl]-2,4-dioxobutyric acid,
(69) 4-[3-(3-Fluorobenzyl)-5-morpholinomethylphenyl]-2,4-dioxobutyric acid,
(70) 4-[5-Benzyl-2-methoxy-3-(tert-butylcarbamoyl)phenyl]-2,4-dioxobutyric acid,
(71) 4-(3-Benzyl-5-[1,2,3]triazol-1-ylmethylphenyl)-2,4-dioxobutyric acid,
(72) 4-[5-Benzyl-3-(N'-methyl-N-piperazinyl)phenyl]-2,4-dioxobutyric acid,
(73) 4-(3-Benzyl-5-[1,2,4]triazol-1-ylmethylphenyl)-2,4-dioxobutyric acid,
(75) 4-[5-Benzyl-2-(pyrimidin-2-yloxy)phenyl]-2,4-dioxobutyric acid,
(76) 4-(5-Benzyl-3-amino-2-methoxyphenyl)-2,4-dioxobutyric acid,
(77) 4-(5-Benzyl-2-ethoxyphenyl)-2,4-dioxobutyric acid,
(78) 4-[5-Benzyl-2-(2-morpholin-4-yl-ethoxy)phenyl]-2,4-dioxobutyric acid,
(79) 4-(5-Benzyl-2-trifluoroethoxyphenyl)-2,4-dioxobutyric acid,
(80) 4-(5-Benzyl-2-cyclobutyloxyphenyl)-2,4-dioxobutyric acid,
(81) 4-(5-Benzyl-2-cyclopentyloxyphenyl)-2,4-dioxobutyric acid,
(82) 4-(3-Benzyl-5-tetrazol-2-ylmethylphenyl)-2,4-dioxobutyric acid,
(83) 4-(5-Benzyl-2,3-diisopropoxyphenyl)-2,4-dioxobutyric acid,
(84) 4-(5-Benzyl-2-isopropoxy-3-N-methylaminophenyl)-2,4-dioxobutyric acid,
(85) 4-(5-Benzyl-2-isopropoxy-3-N,N-dimethylaminophenyl)-2,4-dioxo-butyric acid,
(86) 4-[5-Benzyl-2-isopropoxy-3-(2-N,N-dimethylaminoethoxy)phenyl]-2,4-dioxobutyric acid,
(87) 4-[5-Benzyl-2-isopropoxy-3-(morpholinomethyl)phenyl]-2,4-dioxo-butyric acid,
(88) 4-(5-Benzyl-2-isopropoxy-3-N,N-dimethylaminomethylphenyl)-2,4-dioxo-butyric acid,
(90) 2-Hydroxy-4-oxo-4-(3-phenylindan-5-yl)but-2-enoic acid,
(91) 4-(Dibenzylaminophenyl)-2-hydroxy-4-oxobut-2-enoic acid,
(92) 3-(3-Benzyl-5-carboxyacetylphenyl)-3-oxopropionic acid,
(93) 4-(4-Dibenzylaminophenyl)-2-hydroxy-4-oxobut-2-enoic acid,
(94) 4-(5-Benzyl-3-methoxy-2-methylthioethoxyphenyl)-2,4-dioxobutyric acid,
(97) 4-(2,3-Dimethoxy-5-pent4-enylphenyl)-2,4-dioxobutyric acid,
(98) 4-(5-Cyclopropylmethyl-2,3-dimethoxyphenyl)-2,4-dioxobutyric acid,
(99) (6-Benzyloxy-1-oxo-indan-2-ylidene)-hydroxyacetic acid,
(100) 4-(5-Benzyl-2-isopropoxy-3-[1,2,3]triazol-1-ylmethylphenyl)-2,4-dioxobutyric acid,
(101) 4-(5-Benzyl-2-isopropoxy-3-[1,2,4]triazol-1-ylmethylphenyl)-2,4-dioxobutyric acid,
(102) 4-[5-Benzyl-2-(3-N,N-dimethylaminopropoxy)-3-methoxyphenyl]-2,4-dioxobutyric acid,
(103) 4-[3-(Phenyldifluoromethyl)phenyl]-2,4-dioxobutyric acid,
(104) 4-(5-Benzyl-2-cyclopropyloxyphenyl)-2,4-dioxobutyric acid,
(105) 4-[5-Benzyl-2-isopropoxy-3-(1-piperidinylmethyl)phenyl]-2,4-dioxo-butyric acid,
(106) 4-[5-Benzyl-2-(2-dimethylamino-1-methylethoxy)phenyl]-2,4-dioxo-butyric acid,
(107) 4-[5-Benzyl-2-(1-methylpiperidin-4-yloxy)phenyl]-2,4-dioxo-butyric acid, (108) 4-[3-Benzyl-5-(4-benzylpiperazin-1-yl)phenyl]-2,4-dioxo-butyric acid,
(109) 4-[5-Benzyl-2-isopropoxy-3-(pyridin-2-ylaminomethyl)phenyl]-2,4-dioxo-butyric acid,
(114) 4-[3-(2,4-difluoro-benzyl)-phenyl]-2,4-dioxo-butyric acid,
(115) 2,4-dioxo-4-[3-(2,6-difluoro-benzyl)-phenyl]-butyric acid,
(116) 2,4-dioxo-4-[3-(2-4-6-trifluoro-benzyl)-phenyl]-butyric acid,
(117) 2,4-dioxo-4-[3-(2-fluoro-3-chloro-benzyl)-phenyl]-butyric acid,
(118) 2,4-dioxo4-[3-(2-methyl-4-fluoro-benzyl)-phenyl]-butyric acid,
(119) 4-[3-(2,3-dichloro-benzyl)-phenyl]-2,4-dioxo-butyric acid,
(120) 4-[3-(2-chloro-3-methylbenzyl)phenyl]-2,4-dioxobutyric acid,
(121) 2,4-dioxo4-[3-(2,6-dichloro-benzyl)-phenyl]-butyric acid,
(122) 2,4-dioxo-4-[3-(2,3,4,5,6-penta-fluoro-benzyl)-phenyl]-butyric acid,
(123) 4-[3-(2-fluorobenzyl)phenyl]-2,4-dioxobutyric acid,
(124) 2,4-dioxo4-[3-(2-chloro-4-fluoro-benzyl)-phenyl]-butyric acid,
(125) 4-[3-(2-methylbenzyl)phenyl]-2,4-dioxobutyric acid,
(126) 2,4-dioxo-4-[3-(2-methoxybenzyl)phenyl]butyric acid,
(127) 4-[3-(2-chlorobenzyl)phenyl]-2,4-dioxobutyric acid,
(128) 4-[3-(2-bromobenzyl)phenyl]-2,4-dioxobutyric acid,
(129) 4-[5-(4-fluoro-benzyl)-2,3-dimethoxy-phenyl]-2,4-dioxo-butyric acid,
(130) 4-[3-(3-chloro-2-methyl-benzyl)phenyl]-2,4-dioxobutyric acid,
(131) 4-[3-(2,3-difluoro-benzyl)-phenyl]-2,4-dioxo-butyric acid,
(132) 4-(3,5-dibenzylphenyl)-2,4-dioxo-butyric acid,
(133) 2,4-dioxo4-[3-(2-trifluoromethylbenzyl)phenyl]butyric acid,
(134) 4-[3-(4-fluorobenzyl)phenyl]-2,4-dioxobutyric acid,
(135) 4-[3-(3-chlorobenzyl)phenyl]-2,4-dioxobutyric acid,
(136) 2,4-dioxo-4-[3-(2-bromo-3-chloro-benzyl)-phenyl]-butyric acid,
(137) 4-(3-benzylphenyl)-2,4-dioxo-butyric acid,
(138) 4-[3-(2-fluoro-3-methyl-benzyl)-phenyl]-2,4-dioxo-butyric acid,
(139) 4-[3-(3-chloro-4-fluoro-benzyl)-phenyl]-2,4-dioxo-butyric acid,
(140) 2,4-dioxo-4-[3-(2-bromo4-fluoro-benzyl)-phenyl]-butyric acid,
(141) 4-[3-(3-bromobenzyl)phenyl]-2,4-dioxobutyric acid,
(142) 4-[3-(2,5-difluoro-benzyl)-phenyl]-2,4-dioxo-butyric acid,
(143) 4-[3-(5-chloro-2-fluoro-benzyl)phenyl]-2,4-dioxobutyric acid,
(144) 4-[3-(3-methylbenzyl)phenyl]-2,4-dioxobutyric acid,
(145) 4-(3-benzyl-4-methyl-phenyl)-2,4-dioxo-butyric acid,
(146) 4-[3-(3,4-difluoro-benzyl)-phenyl]-2,4-dioxo-butyric acid,
(147) 4-[3-(2,5-dichloro-benzyl)-phenyl]-2,4-dioxo-butyric acid,
(148) 4-[3-(2-chloro-6-methyl-benzyl)phenyl]-2,4-dioxobutyric acid,
(149) 2,4-dioxo-4-[3-(2-trifluoromethyl-4-chloro-benzyl)-phenyl]-butyric acid,
(150) 4-[3-(2-bromo-5-chloro-benzyl)-phenyl]-2,4-dioxo-butyric acid,
(151) 4-(3-naphthalen-1-ylmethyl-phenyl)-2,4-dioxo-butyric acid,
(152) 2,4-dioxo-4-[3-(3-fluorobenzyl)phenyl]butyric acid,
(153) 2,4-dioxo-4-(3-phenylsulfanyl-phenyl)-butyric acid,
(154) 2,4-dioxo4-[3-(1-phenylethyl)phenyl]butyric acid,
(155) 4-(3-benzyl-4,5-dimethylphenyl)-2,4-dioxo-butyric acid,
(156) 2,4-dioxo-4-[3-(3-methoxybenzyl)phenyl]butyric acid,
(157) 4-[3-(5-methyl-thiophen-2-ylmethyl)phenyl]-2,4-dioxo-butyric acid,
(158) 4-[3-(5-chloro-thiophen-2-ylmethyl)phenyl]-2,4-dioxo-butylic acid,
(159) 4-(3-benzyl-5-methylphenyl)-2,4-dioxo-butyric acid,
(160) 4-[3-(2-cyanobenzyl)phenyl]-2,4-dioxo-butyric acid,
(161) 4-[3-benzylphenyl]-2,4-dioxobutyric acid,
(162) 4-[3-(3,5-dichloro-benzyl)-phenyl]-2,4-dioxo-butyric acid,
(163) 4-(5-benzyl-2,4-dimethylphenyl)-2,4-dioxo-butyric acid,
(164) 4-(5-benzyl-2-methylphenyl)-2,4-dioxo-butyric acid,
(165) 4-(3-cyclohexylmethyl-phenyl)-2,4-dioxo-butyric acid,
(166) 4-{3-[(methyl-phenyl-amino)-methyl]-phenyl}-2,4-dioxo-butyric acid,
(167) 4-[3-benzyl-5-(5-hydroxy-pentyl)-phenyl]-2,4-dioxo-butyric acid,
(168) 4-(3-benzyl-5-pyrazin-2-yl-phenyl)-2,4-dioxo-butyric acid,
(169) 4-[3-(3-tert-butoxy-2-hydroxy-propyl)-5-(2-methyl-benzyl)-phenyl]-2,4-dioxo-butyric acid,
(170) 2,4-dioxo-4-[3-(2,3-dimethoxy-benzyl)-phenyl]-butyric acid,
(171) 4-[3-(methoxyphenylmethyl)phenyl]-2,4-dioxobutyric acid,
(172) 4-[3-[hydroxy-(tetrahydro-furan-3-yl)-methyl]-5-(2-methyl-benzyl)-phenyl]-2,4-dioxo-butyric acid,
(173) 2,4-dioxo-4-(3-phenoxymethyl-phenyl)-butyric acid,
(175) 4-[3-benzyl-5-(cyclopropylcarboxamido)-phenyl]-2,4-dioxobutyric acid,
(176) 4-[3-benzyl-5-(t-butoxycarbamoyl)phenyl]-2,4-dioxobutyric acid, (177) 4-[3-(hydroxy-phenyl-methyl)-phenyl]-2,4-dioxo-butyric acid,
(178) 4-(5-benzyl-2,3-dimethylphenyl)-2,4-dioxo-butyric acid,
(179) 4-[3-(3,5-dibromobenzyl)phenyl]-2,4-dioxo-butyric acid,
(180) 4-[3-(2-methyl-benzyl)-5-pyrimidin-2-yl-phenyl]-2,4-dioxo-butyric acid,
(181) 4-[3-benzyl-2-(pyrimidin-2-ylamino)-phenyl]-2,4-dioxo-butyric acid
(182) 4-[3-benzoimidazol-1-ylmethyl-5-(2-methyl-benzyl)-phenyl]-2,4-dioxo-butyric acid,
(183) 2,4-dioxo-4-[3-(3-trifluoromethylbenzyl)phenyl]butyric acid,
(185) 2,4-dioxo-4-(3-[1,2,3]triazol-2-ylmethyl-phenyl)-butyric acid,
(186) 4-[3-benzyl-5-(6-methoxy-pyridin-2-yl)-phenyl]-2,4-dioxo-butyric acid,
(187) 4-(3-benzotriazol-2-ylmethyl-phenyl)-2,4-dioxo-butyric acid,
(188) 4-[3-benzyl-5-(2-(4-methylpiperazin-1-yl)-pyrazin-6-yl)phenyl]-2,4-dioxobutyric acid,
(189) 4-[4-(3-phenethyl)phenyl]-2,4-dioxobutyric acid,
(190) 4-[4-(3-chlorobenzyl)phenyl]-2,4-dioxobutyric acid,
(191) 4-(3-benzoimidazol-1-ylmethyl-phenyl)-2,4-dioxo-butyric acid,
(192) 4-[3-benzyloxy-5-(6-tert-butoxycarbonylamino-hexyloxy)phenyl]-2-hydroxy-4-oxo-but-2-enoic acid,
(193) 4-(3-benzotriazol-1-ylmethyl-phenyl)-2,4-dioxo-butyric acid,
(194) 4-[3-(3,5-dimethyl-pyrazol-1-ylmethyl)-phenyl]-2,4-dioxo-butylic acid,
(196) 4-(4-methyl-3-phenoxy-phenyl)-2,4-dioxo-butyric acid,
197) 4-[3-(2-hydroxy-benzyl)-phenyl]-2,4-dioxo-butyric acid,
(198) 4-[3-benzyl-5-(6-dimethylamino-pyrazin-2-yl)-phenyl]-2,4-dioxo-butyric acid,
and tautomers and pharmaceutically acceptable salts thereof.

11. The compound according to claim 10 selected from:
(1) 4-(3-Benzylphenyl)-2,4-dioxobutanoic acid,
(2) 4-[3-(5-methyl-thiophen-2-ylmethyl)-phenyl]-2,4-dioxo-butyric acid,
(3) 4-{3-[(methyl-phenyl-amino)-methyl]-phenyl}-2,4-dioxo-butyric acid,
(4) 4-(3-benzyl-5-pyrazin-2-yl-phenyl)-2,4-dioxo-butyric acid,
(5) 2,4-dioxo-4-[3-(1,2,3,4-tetrahydronaphthalen-1-yl)-phenyl]butyric acid,
(6) 2,4-Dioxo-4-(3-phenylsulfanyl-phenyl)-butyric acid,
(7) 4-[3-(2,4-Difluoro-benzyl)-phenyl]-2,4-dioxo-butyric acid,
(8) 4-[5-(4-Fluoro-benzyl)-2,3-dimethoxy-phenyl]-2,4-dioxo-butyric acid,
(9) 4-(5-Benzyl-2-isopropoxyphenyl)-2,4-dioxobutyric acid,
(10) 4-[5-Benzyl-2-(2-N,N-dimethylaminoethoxy)phenyl]-2,4-dioxobutyric acid,
(11) 4-[5-Benzyl-2-(pyridin-2-yloxy)phenyl]-2,4-dioxo-butylic acid,
(12) 4-(5-Benzyl-2-isopropoxy-3-methoxyphenyl)-2,4-dioxo-butyric acid,
(13) 4-(5-Benzyl-2,3-dimethoxyphenyl)-2,4-dioxobutyric acid,
(14) 4-(5-Benzyl-3-dimethylamino-2-methoxyphenyl)-2,4-dioxobutyric acid,
(16) 4-(3-Benzyl-5-pyrazin-2-ylmethylphenyl)-2,4-dioxobutyric acid,
(17) 4-(3-Benzyl-5-[1,2,3]triazol-2-ylmethylphenyl)-2,4-dioxobutyric acid,
(18) 4-[3-(3-Chloropyridin-2-ylmethyl)phenyl]-2,4-dioxobutyric acid,
(19) 4-[5-Benzyl-2-methoxy-3-(N,N-dimethylaminomethyl) phenyl]-2,4-dioxo-butyric acid,
(20) 4-(5-benzyl-3-methoxy-2-methoxyethoxyphenyl)-2,4-dioxobutyric acid,
(21) 4-(5-Benzyl-2-isopropoxy-3-[1,2,3]triazol-1-ylmethylphenyl)-2,4-dioxobutyric acid,
(22) 4-(5-Benzyl-2-isopropoxy-3-[1,2,4]triazol-1-ylmethylphenyl)-2,4-dioxobutyric acid,
(23) 4-[5-Benzyl-2-(3-N,N-dimethylaminopropoxy)-3-methoxyphenyl]-2,4-dioxobutyric acid,
(24) 4-[3-(Phenyldifluoromethyl)phenyl]-2,4-dioxobutyric acid,
(25) 4-(5-Benzyl-2-cyclopropyloxyphenyl)-2,4-dioxobutyric acid,
(26) 4-[5-Benzyl-2-isopropoxy-3-(1-piperidinylmethyl)phenyl]-2,4-dioxo-butyric acid,
(27) 4-[5-Benzyl-2-(2-dimethylamino-1-methylethoxy)phenyl]-2,4-dioxo-butyric acid,
(28) 4-[5-Benzyl-2-(1-methylpiperidin-4-yloxy)phenyl]-2,4-dioxo-butyric acid,
(29) 4-[3-Benzyl-5-(4-benzylpiperazin-1-yl)phenyl]-2,4-dioxo-butyric acid, and
(30) 4-[5-Benzyl-2-isopropoxy-3-(pyridin-2-ylaminomethyl)phenyl]-2,4-dioxo-butyric acid;
and tautomers and pharmaceutically acceptable salts thereof.

12. A pharmaceutical composition, comprising a pharmaceutically acceptable carrier and an effective amount of a compound according to claim 2.

13. The pharmaceutical composition according to claim 12 additionally comprising a therapeutically effective amount of an AIDS treatment agent selected from
(1) an AIDS antiviral agent,
(2) an anti-infective agent, and
(3) an immunomodulator.

14. The composition of claim 13 wherein the antiviral agent is an HIV protease inhibitor.

15. The composition of claim 14 wherein the HIV protease inhibitor is N-(2(R)-hydroxy-1-(S)-indanyl)-2(R)-phenylmethyl-4(S)-hydroxy-5-(1-(4-(3-pyridylmethyl)-2 (S)-N'-(t-butylcarboxamido)-piperazinyl))-pentaneamide or a pharmaceutically acceptable salt thereof.

16. A method of inhibiting HIV integrase, comprising the administration to a mammal in need of such treatment a therapeutically effective amount of a compound of structural formula (I):

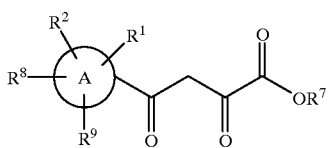

(I)

and tautomers and pharmaceutically acceptable salts thereof, wherein:

A is a six-membered aromatic ring substituted on carbon by $R^1$, $R^2$, $R^8$, and $R^9$; optionally the aromatic ring may be fused with another ring system to form:

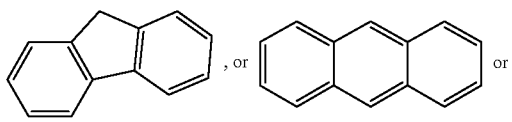

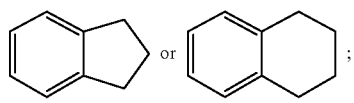

$R^1$ is selected from:
(1) —H,
(2) —$C_{1-5}$ alkyl,
(3) —$C_{1-6}$ alkyl-$OR^7$,
(4) —O—$C_{1-6}$ alkyl-$OR^7$,
(5) —O—$C_{1-6}$ alkyl-$SR^7$,
(6) —$CF_3$ or —$CH_2CF_3$,
(7) -halo,
(8) —$NO_2$,
(9) —$C_{0-3}$ alkyl —$N(R^4)(R^5)$,
(10) —$R^6$,
(11) —$C_{2-5}$ alkenyl-$R^3$,
(12) —$C_{2-5}$ alkynyl-$R^3$,
(13) —O—$R^6$,
(14) —O—$C_{1-6}$ alkyl, wherein one or more of the hydrogen atoms may be replaced with fluorine atoms,
(15) —O—$C_{1-6}$ alkyl-NH—C(O)—$OR^7$;
(16) —O—$C_{2-6}$ alkyl-$N(R^4)(R^5)$;
(17) —S—$C_{1-3}$ alkyl;
(18) —C(O)$CH_2$C(O)C(O)$OR^7$;
(19) —$CH_2$—CH(OH)—$CH_2$—O—$R^7$; and
(20) —C(OH)($CH_3$)—$CH_2N(R^4)(R^5)$;

$R^2$ is selected from:
(1) —H,
(2) —$R^3$,
(3) —$C_{1-6}$ alkyl,
(4) —$C_{1-6}$ alkyl substituted with $R^3$, wherein one or more of the hydrogen atoms on $C_{1-6}$ alkyl may be replaced with a fluorine atom,
(5) —$C_{2-6}$ alkenyl,
(6) —O—$R^6$,
(7) —O—$C_{1-6}$ alkyl-$OR^6$,
(8) —O—$C_{1-6}$ alkyl-$SR^6$,
(9) —S(O)$_n$—$R^6$,
(10) —$C_{1-6}$ alkyl ($OR^6$)($R^4$),
(11) —$C_{0-6}$ alkyl-$N(R^4)(R^6)$,
(12) —$C_{1-6}$ alkyl S(O)n—$R^6$,
(13) —$C_{0-6}$ alkyl C(O)—$R^6$,
(14) —$C_{0-6}$ alkyl C(O)$CH_2$—C(O)—OH,
(15) —$C_{1-6}$ alkyl C(S)—$R^6$,
(16) —$C_{1-6}$ alkyl $NR^4$C(O)—$R^6$,
(17) —$C_{1-6}$ alkyl-C(O)N($R^4$)($R^5$), and
(18) —$CH_2(OR^7)$—$R^6$;

each $R^3$ is independently selected from:
(1) a 5 or 6 membered aromatic or heteroaromatic ring, containing 0, 1, 2, 3, or 4 heteroatoms selected from oxygen, nitrogen and sulfur, unsubstituted or substituted on nitrogen or carbon by 1 to 5 substituents selected from:
(a) halogen,
(b) $C_{1-6}$ alkyl, wherein one or more of the hydrogen atoms may be replaced with a fluorine atom,
(c) $C_{1-6}$ alkyloxy- wherein one or more of the hydrogen atoms may be replaced with a fluorine atom,
(d) phenyl,
(e) —S—$C_{1-6}$ alkyl,
(f) —CN,
(g) hydroxy,
(h) phenyloxy,
(i) —$C_{0-6}$ alkyl-$N(R^7)_2$,
(j)

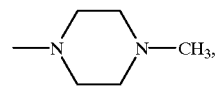

(k) oxo, and
(l) substituted phenyloxy with 1, 2, or 3 substituents selected from:
(i) halogen,
(ii) $C_{1-6}$ alkyl,
(iii) —$CF_3$, and
(iv) hydroxy;
(2) a 3 to 6 membered saturated ring containing 0, 1 or 2 heteroatoms selected from oxygen, nitrogen or sulfur, unsubstituted or substituted with 1 to 5 substituents selected from:
(a) halogen,
(b) $C_{1-6}$ alkyl,
(c) $C_{1-6}$ alkyloxy-,
(d) —$CF_3$,
(e) —$OCF_3$,
(f) —CN,
(g) =O,
(h) benzyl, and
(i) hydroxy;
(3) unsubstituted or substituted hexahydrothieno[3,4-d]imidazolyl with one or two substituents selected from:
(a) oxo,
(b) halogen,
(c) $C_{1-6}$ alkyl,
(d) $C_{1-6}$ alkyloxy-,
(e) —$CF_3$,
(f) —$OCF_3$,
(g) —CN, and
(h) hydroxy;
(4) a 5 or 6 membered aromatic or heteroaromatic ring, containing 0, 1, 2 or 3 heteroatoms selected from oxygen, nitrogen and sulfur, fused with a phenyl ring; wherein the ring system is unsubstituted or substituted on a nitrogen or carbon atom by 1 to 3 substituents selected from:

(a) -halogen,
(b) —C$_{1-6}$ alkyl,
(c) —C$_{1-6}$ alkyloxy-,
(d) —CF$_3$,
(e) —OCF$_3$,
(f) —CN, and
(g) -hydroxy;
(5) a 3 to 6 membered saturated ring containing 0, 1 or 2 heteroatoms selected from oxygen, nitrogen or sulfur, fused with a phenyl ring, unsubstituted or substituted with 1 or 2 substituents selected from:
(a) halogen,
(b) C$_{1-6}$ alkyl,
(c) C$_{1-6}$ alkyloxy-,
(d) —CF$_3$,
(e) —OCF$_3$,
(f) —CN,
(g) =O, and
(h) hydroxy;
(6) a 5 to 6 membered ring containing 0, 1 or 2 heteroatoms selected from oxygen, nitrogen or sulfur, containing 2 or 3 double bonds, unsubstituted or substituted with 1 or 2 substituents selected from:
(a) halogen,
(b) C$_{1-6}$ alkyl,
(c) C$_{1-6}$ alkyloxy-,
(d) —CF$_3$,
(e) —OCF$_3$,
(f) —CN,
(g) =O, and
(h) hydroxy; and
(7) a 5 to 6 membered ring containing 0, 1 or 2 heteroatoms selected from oxygen, nitrogen or sulfur, containing 2 or 3 double bonds, fused with a phenyl ring, unsubstituted or substituted with 1 or 2 substituents selected from:
(a) halogen,
(b) C$_{1-6}$ alkyl,
(c) C$_{1-6}$ alkyloxy-,
(d) —CF$_3$,
(e) —OCF$_3$,
(f) —CN,
(g) =O, and
(h) hydroxy; and
each R$^4$ is independently selected from:
(1) —H,
(2) —C$_{1-4}$ alkyl,
(3) —CF$_3$,
(4) —R$^3$,
(5) —C$_{2-3}$ alkenyl,
(6) —C$_{1-3}$ alkyl-R$^3$,
(7) —C$_{2-3}$ alkenyl-R$^3$,
(8) —S(O)$_n$—R$^3$, and
(9) —C(O)—R$^3$;
each R$^5$ is independently selected from:
(1) —H,
(2) —C$_{1-3}$ alkyl,
(3) —CF$_3$,
(4) —R$^3$,
(5) —C$_{2-3}$ alkenyl,
(6) —C$_{1-3}$ alkyl-R$^3$,
(7) —C$_{2-3}$ alkenyl-R$^3$,
(8) —S(O)$_n$—R$^3$,
(9) —C(O)—R$^3$,
(10) —C(O)OR4, and
(11) —C(O)C(O)OH;

each R$^6$ is independently selected from:
(1) —C$_{1-3}$ alkyl-R$^3$, and
(2) —R$^3$;
each R$^7$ is independently selected from:
(1) —H, and
(2) —C$_{1-6}$ alkyl;
R$^8$ is selected from:
(1) —H,
(2) —O—C$_{1-6}$ alkyl and
(3) C$_{1-6}$ alkyl;
R$^9$ is selected from:
(1) —H,
(2) —O—C$_{1-3}$ alkyl,
(3) —OH, and
(4) oxo; and each n is independently selected from 0, 1 and 2.

17. The method according to claim 16, wherein the compound of structural formula (I) is selected from:
(1) 4-(3-Benzylphenyl)-2,4-dioxobutanoic acid,
(2) 4-[3-(5-methyl-thiophen-2-ylmethyl)-phenyl]-2,4-dioxo-butyric acid,
(3) 4-(3-[(methyl-phenyl-amino)-methyl]-phenyl)-2,4-dioxo-butyric acid,
(4) 4-(3-benzyl-5-pyrazin-2-yl-phenyl)-2,4-dioxo-butyric acid,
(5) 2,4-dioxo-4-[3-(1,2,3,4-tetrahydronaphthalen-1-yl)-phenyl]butyric acid,
(6) 2,4-Dioxo-4-(3-phenylsulfanyl-phenyl)-butyric acid,
(7) 4-[3-(2,4-Difluoro-benzyl)-phenyl]-2,4-dioxo-butyric acid,
(8) 4-[5-(4-Fluoro-benzyl)-2,3-dimethoxy-phenyl]-2,4-dioxo-butyric acid,
(9) 4-(5-Benzyl-2-isopropoxyphenyl)-2,4-dioxobutyric acid,
(10) 4-[5-Benzyl-2-(2-N,N-dimethylaminoethoxy)phenyl]-2,4-dioxobutyric acid,
(11) 4-[5-Benzyl-2-(pyridin-2-yloxy)phenyl]-2,4-dioxo-butyric acid,
(12) 4-(5-Benzyl-2-isopropoxy-3-methoxyphenyl)-2,4-dioxo-butyric acid,
(13) 4-(5-Benzyl-2,3-dimethoxyphenyl)-2,4-dioxobutyric acid,
(14) 4-(5-Benzyl-3-dimethylamino-2-methoxyphenyl)-2,4-dioxobutyric acid,
(16) 4-(3-Benzyl-5-pyrazin-2-ylmethylphenyl)-2,4-dioxobutyric acid,
(17) 4-(3-Benzyl-5-[1,2,3]triazol-2-ylmethylphenyl)-2,4-dioxobutyric acid,
(18) 4-[3-(3-Chloropyridin-2-ylmethyl)phenyl]-2,4-dioxobutyric acid,
(19) 4-[5-Benzyl-2-methoxy-3-(N,N-dimethylaminomethyl) phenyl]-2,4-dioxo-butyric acid,
(20) 4-(5-benzyl-3-methoxy-2-methoxyethoxyphenyl)-2,4-dioxobutyric acid,
(21) 4-(5-Benzyl-2-isopropoxy-3-[1,2,3]triazol-1-ylmethylphenyl)-2,4-dioxobutyric acid,
(22) 4-(5-Benzyl-2-isopropoxy-3-[1,2,4]triazol-1-ylmethylphenyl)-2,4-dioxobutyric acid,
(23) 4-[5-Benzyl-2-(3-N,N-dimethylaminopropoxy)-3-methoxyphenyl]-2,4-dioxobutyric acid,
(24) 4-[3-(Phenyldifluoromethyl)phenyl]-2,4-dioxobutyric acid,

(25) 4-(5-Benzyl-2-cyclopropyloxyphenyl)-2,4-dioxobutyric acid,
(26) 4-[5-Benzyl-2-isopropoxy-3-(1-piperidinylmethyl)phenyl]-2,4-dioxo-butyric acid,
(27) 4-[5-Benzyl-2-(2-dimethylamino-1-methylethoxy)phenyl]-2,4-dioxo-butyric acid,
(28) 4-[5-Benzyl-2-(1-methylpiperidin-4-yloxy)phenyl]-2,4-dioxo-butyric acid,
(29) 4-[3-Benzyl-5-(4-benzylpiperazin-1-yl)phenyl]-2,4-dioxo-butyric acid, and
(30) 4-[5-Benzyl-2-isopropoxy-3-(pyridin-2-ylaminomethyl)phenyl]-2,4-dioxo-butyric acid;

and tautomers and pharmaceutically acceptable salts thereof.

18. A method of treating infection by HIV, or of treating AIDS or ARC, comprising the administration to a human in need of such treatment a therapeutically effective amount of a compound of structural formula (I):

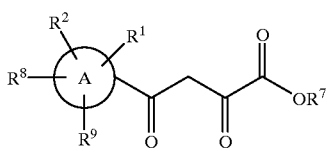
(I)

and tautomers and pharmaceutically acceptable salts thereof, wherein:

A is a six-membered aromatic ring substituted on carbon by $R^1$, $R^2$, $R^8$, and $R^9$; optionally the aromatic ring may be fused with another ring system to form:

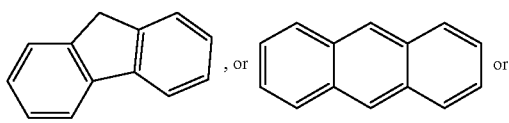

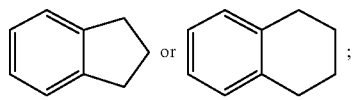

$R^1$ is selected from:
(1) —H,
(2) —$C_{1-5}$ alkyl,
(3) —$C_{1-6}$ alkyl-$OR^7$,
(4) —O—$C_{1-6}$ alkyl-$OR^7$,
(5) —O—$C_{1-6}$ alkyl-$SR^7$,
(6) —$CF_3$ or —$CH_2CF_3$,
(7) -halo,
(8) —$NO_2$,
(9) —$C_{0-3}$ alkyl —$N(R^4)(R^5)$,
(10) —$R^6$,
(11) —$C_{2-5}$ alkenyl-$R^3$,
(12) —$C_{2-5}$ alkynyl-$R^3$,
(13) —O—$R^6$,
(14) —O—$C_{1-6}$ alkyl, wherein one or more of the hydrogen atoms may be replaced with fluorine atoms,
(15) —O—$C_{1-6}$ alkyl-NH—C(O)—$OR^7$,
(16) —O—$C_{2-6}$ alkyl-$N(R^4)(R^5)$,
(17) —S—$C_{1-3}$ alkyl,
(18) —C(O)$CH_2$C(O)C(O)$OR^7$,
(19) —$CH_2$—CH(OH)—$CH_2$—O—$R^7$, and
(20) —C(OH)($CH_3$)—$CH_2N(R^4)(R^5)$;

$R^2$ is selected from:
(1) —H,
(2) —$R^3$,
(3) —$C_{1-6}$ alkyl,
(4) —$C_{1-6}$ alkyl substituted with $R^3$, wherein one or more of the hydrogen atoms on $C_{1-6}$ alkyl may be replaced with a fluorine atom,
(5) —$C_{2-6}$ alkenyl,
(6) —O—$R^6$,
(7) —O—$C_{1-6}$ alkyl-$OR^6$,
(8) —O—$C_{1-6}$ alkyl-$SR^6$,
(9) —S(O)$_n$—$R^6$,
(10) —$C_{1-6}$ alkyl ($OR^6$)($R^4$),
(11) —$C_{0-6}$ alkyl-$N(R^4)(R^6)$,
(12) —$C_{1-6}$ alkyl S(O)$_n$—$R^6$,
(13) —$C_{0-6}$ alkyl C(O)—$R^6$,
(14) —$C_{0-6}$ alkyl C(O)$CH_2$—C(O)—OH,
(15) —$C_{1-6}$ alkyl C(S)—$R^6$,
(16) —$C_{1-6}$ alkyl $NR^4$C(O)—$R^6$,
(17) —$C_{1-6}$ alkyl-C(O)$N(R^4)(R^5)$, and
(18) —$CH_2(OR^7)$—$R^6$;

each $R^3$ is independently selected from:
(1) a 5 or 6 membered aromatic or heteroaromatic ring, containing 0, 1, 2, 3, or 4 heteroatoms selected from oxygen, nitrogen and sulfur, unsubstituted or substituted on nitrogen or carbon by 1 to 5 substituents selected from:
(a) halogen,
(b) $C_{1-6}$ alkyl, wherein one or more of the hydrogen atoms may be replaced with a fluorine atom,
(c) $C_{1-6}$ alkyloxy- wherein one or more of the hydrogen atoms may be replaced with a fluorine atom,
(d) phenyl,
(e) —S—$C_{1-6}$ alkyl,
(f) —CN,
(g) hydroxy,
(h) phenyloxy,
(i) —$C_{0-6}$ alkyl-$N(R^7)_2$, (j)
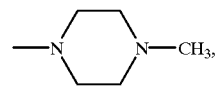

(k) oxo, and
(l) substituted phenyloxy with 1, 2, or 3 substituents selected from:
(i) halogen,
(ii) $C_{1-6}$ alkyl,
(iii) —$CF_3$, and
(iv) hydroxy;
(2) a 3 to 6 membered saturated ring containing 0, 1 or 2 heteroatoms selected from oxygen, nitrogen or sulfur, unsubstituted or substituted with 1 to 5 substituents selected from:
(a) halogen,
(b) $C_{1-6}$ alkyl,
(c) $C_{1-6}$ alkyloxy-,
(d) —$CF_3$,
(e) —$OCF_3$,
(f) —CN,
(g) =O,
(h) benzyl, and
(i) hydroxy;

(3) unsubstituted or substituted hexahydrothieno[3,4-d]imidazolyl with one or two substituents selected from:
  (a) oxo,
  (b) halogen,
  (c) $C_{1-6}$ alkyl,
  (d) $C_{1-6}$ alkyloxy-,
  (e) —$CF_3$,
  (f) —$OCF_3$,
  (g) —CN, and
  (h) hydroxy;
(4) a 5 or 6 membered aromatic or heteroaromatic ring, containing 0, 1, 2 or 3 heteroatoms selected from oxygen, nitrogen and sulfur, fused with a phenyl ring; wherein the ring system is unsubstituted or substituted on a nitrogen or carbon atom by 1 to 3 substituents selected from:
  (a) -halogen,
  (b) —$C_{1-6}$ alkyl,
  (c) —$C_{1-6}$ alkyloxy-,
  (d) —$CF_3$,
  (e) —$OCF_3$,
  (f) —CN, and
  (g) -hydroxy;
(5) a 3 to 6 membered saturated ring containing 0, 1 or 2 heteroatoms selected from oxygen, nitrogen or sulfur, fused with a phenyl ring, unsubstituted or substituted with 1 or 2 substituents selected from:
  (a) halogen,
  (b) $C_{1-6}$ alkyl,
  (c) $C_{1-6}$ alkyloxy-,
  (d) —$CF_3$,
  (e) —$OCF_3$,
  (f) —CN,
  (g) =O, and
  (h) hydroxy;
(6) a 5 to 6 membered ring containing 0, 1 or 2 heteroatoms selected from oxygen, nitrogen or sulfur, containing 2 or 3 double bonds, unsubstituted or substituted with 1 or 2 substituents selected from:
  (a) halogen,
  (b) $C_{1-6}$ alkyl,
  (c) $C_{1-6}$ alkyloxy-,
  (d) —$CF_3$,
  (e) —$OCF_3$,
  (f) —CN,
  (g) =O, and
  (h) hydroxy; and
(7) a 5 to 6 membered ring containing 0, 1 or 2 heteroatoms selected from oxygen, nitrogen or sulfur, containing 2 or 3 double bonds, fused with a phenyl ring, unsubstituted or substituted with 1 or 2 substituents selected from:
  (a) halogen,
  (b) $C_{1-6}$ alkyl,
  (c) $C_{1-6}$ alkyloxy-,
  (d) —$CF_3$,
  (e) —$OCF_3$,
  (f) —CN,
  (g) =O, and
  (h) hydroxy; and
each $R^4$ is independently selected from:
  (1) —H,
  (2) —$C_{1-4}$ alkyl,
  (3) —$CF_3$,
  (4) —$R^3$,
  (5) —$C_{2-3}$ alkenyl,
  (6) —$C_{1-3}$ alkyl-$R^3$,
  (7) —$C_{2-3}$ alkenyl-$R^3$,
  (8) —$S(O)_n$—$R^3$, and
  (9) —C(O)—$R^3$;
each $R^5$ is independently selected from:
  (1) —H,
  (2) —$C_{1-3}$ alkyl,
  (3) —$CF_3$,
  (4) —$R^3$,
  (5) —$C_{2-3}$ alkenyl,
  (6) —$C_{1-3}$ alkyl-$R^3$,
  (7) —$C_{2-3}$ alkenyl-$R^3$,
  (8) —$S(O)_n$—$R^3$,
  (9) —C(O)—$R^3$,
  (10) —C(O)OR4, and
  (11) —C(O)C(O)OH;
each $R^6$ is independently selected from:
  (1) —$C_{1-3}$ alkyl-$R^3$, and
  (2) —$R^3$;
each $R^7$ is independently selected from:
  (1) —H, and
  (2) —$C_{1-6}$ alkyl;
$R^8$ is selected from:
  (1) —H,
  (2) —O—$C_{1-6}$ alkyl and
  (3) $C_{1-6}$ alkyl;
$R^9$ is selected from:
  (1) —H,
  (2) —O—$C_{1-3}$ alkyl,
  (3) —OH, and
  (4) oxo; and
each n is independently selected from 0, 1 and 2.

19. The method according to claim 18 wherein the compound of structural formula (I) is selected from:
(1) 4-(3-Benzylphenyl)-2,4-dioxobutanoic acid,
(2) 4-[3-(5-methyl-thiophen-2-ylmethyl)-phenyl]-2,4-dioxo-butyric acid,
(3) 4-{3-[(methyl-phenyl-amino)-methyl]-phenyl}-2,4-dioxo-butyric acid,
(4) 4-(3-benzyl-5-pyrazin-2-yl-phenyl)-2,4-dioxo-butyric acid,
(5) 2,4-dioxo-4-[3-(1,2,3,4-tetrahydronaphthalen-1-yl)-phenyl]butyric acid,
(6) 2,4-Dioxo-4-(3-phenylsulfanyl-phenyl)-butyric acid,
(7) 4-[3-(2,4-Difluoro-benzyl)-phenyl]-2,4-dioxo-butyric acid,
(8) 4-[5-(4-Fluoro-benzyl)-2,3-dimethoxy-phenyl]-2,4-dioxo-butyric acid,
(9) 4-(5-Benzyl-2-isopropoxyphenyl)-2,4-dioxobutyric acid,
(10) 4-[5-Benzyl-2-(2-N,N-dimethylaminoethoxy)phenyl]-2,4-dioxobutyric acid,
(11) 4-[5-Benzyl-2-(pyzidin-2-yloxy)phenyl]-2,4-dioxo-butyric acid,
(12) 4-(5-Benzyl-2-isopropoxy-3-methoxyphenyl)-2,4-dioxo-butyric acid,
(13) 4-(5-Benzyl-2,3-dimethoxyphenyl)-2,4-dioxobutyric acid,
(14) 4-(5-Benzyl-3-dimethylamino-2-methoxyphenyl)-2,4-dioxobutyric acid,
(15)
(16) 4-(3-Benzyl-5-pyrazin-2-ylmethylphenyl)-2,4-dioxobutyric acid,

(17) 4-(3-Benzyl-5-[1,2,3]triazol-2-ylmethylphenyl)-2,4-dioxobutyric acid,
(18) 4-[3-(3-Chloropyridin-2-ylmethyl)phenyl]-2,4-dioxobutyric acid,
(19) 4-[5-Benzyl-2-methoxy-3-(N,N-dimethylaminomethyl) phenyl]-2,4-dioxo-butyric acid,
(20) 4-(5-benzyl-3-methoxy-2-methoxyethoxyphenyl)-2,4-dioxobutyric acid,
(21) 4-(5-Benzyl-2-isopropoxy-3-[1,2,3]triazol-1-ylmethylphenyl)-2,4-dioxobutyric acid,
(22) 4-(5-Benzyl-2-isopropoxy-3-[1,2,4]triazol-1-ylmethylphenyl)-2,4-dioxobutyric acid,
(23) 4-[5-Benzyl-2-(3-N,N-dimethylaminopropoxy)-3-methoxyphenyl]-2,4-dioxobutyric acid,
(24) 4-[3-(Phenyldifluoromethyl)phenyl]-2,4-dioxobutyric acid,
(25) 4-(5-Benzyl-2-cyclopropyloxyphenyl)-2,4-dioxobutyric acid,
(26) 4-[5-Benzyl-2-isopropoxy-3-(1-piperidinylmethyl)phenyl]-2,4-dioxo-butyric acid,
(27) 4-[5-Benzyl-2-(2-dimethylamino-1-methylethoxy)phenyl]-2,4-dioxo-butyric acid,
(28) 4-[5-Benzyl-2-(1-methylpiperidin-4-yloxy)phenyl]-2,4-dioxo-butyric acid,
(29) 4-[3-Benzyl-5-(4-benzylpiperazin-1-yl)phenyl]-2,4-dioxo-butyric acid, and
(30) 4-[5-Benzyl-2-isopropoxy-3-(pyridin-2-ylaminomethyl)phenyl]-2,4-dioxo-butyric acid;
and tautomers and pharmaceutically acceptable salts thereof.

20. A method of inhibiting HIV integrase which comprises administering to a mammal in need of such treatment a therapeutically effective amount of a compound of claim 1, or a tautomer or pharmaceutically acceptable salt thereof.

21. A method of treating infection by HIV or of treating AIDS or ARC which comprises administering to a mammal in need of such treatment a therapeutically effective amount of a compound of claim 1, a tautomer or pharmaceutically acceptable salt thereof.

* * * * *